(12) United States Patent
Johnson, Jr.

(10) Patent No.: US 6,754,524 B2
(45) Date of Patent: Jun. 22, 2004

(54) METHOD FOR DETECTING DECEPTION

(75) Inventor: Ray Johnson, Jr., Port Washington, NY (US)

(73) Assignee: Research Foundation of the City University of New York, New York, NY (US)

(*) Notice: Subject to any disclaimer, the term of this patent is extended or adjusted under 35 U.S.C. 154(b) by 0 days.

(21) Appl. No.: 09/942,050

(22) Filed: Aug. 28, 2001

(65) Prior Publication Data
US 2002/0062089 A1 May 23, 2002

Related U.S. Application Data

(60) Provisional application No. 60/234,321, filed on Sep. 20, 2000, and provisional application No. 60/228,827, filed on Aug. 28, 2000.

(51) Int. Cl.$^7$ ................................................. A61B 5/04
(52) U.S. Cl. ....................................................... 600/544
(58) Field of Search ................................. 600/544, 545

(56) References Cited

U.S. PATENT DOCUMENTS

| | | | |
|---|---|---|---|
| 4,753,246 A | * 6/1988 | Freeman | 600/544 |
| 5,137,027 A | * 8/1992 | Rosenfeld | 600/544 |
| 5,363,858 A | * 11/1994 | Farwell | 600/544 |
| 5,876,334 A |   3/1999 | Levy | 600/300 |
| 5,957,859 A | * 9/1999 | Rosenfeld | 600/544 |
| 2002/0188217 A1 | 12/2002 | Farwell | 600/544 |
| 2003/0032870 A1 | 2/2003 | Farwell | 600/300 |

* cited by examiner

Primary Examiner—Robert L. Nasser
Assistant Examiner—Patricia Mallari
(74) Attorney, Agent, or Firm—Darby & Darby

(57) ABSTRACT

The present invention provides a novel and reliable method for detecting deception in a subject. Deception as well as confabulation may be characterized by detectable changes in a (ERP) activity and/or behavioral responses to stimuli. These changes occur in one or more measures or markers of brain activity or behavioral activity referred to herein as "the neural and behavioral signature of deception." The method is independent of the intent to commit deception.

43 Claims, 110 Drawing Sheets

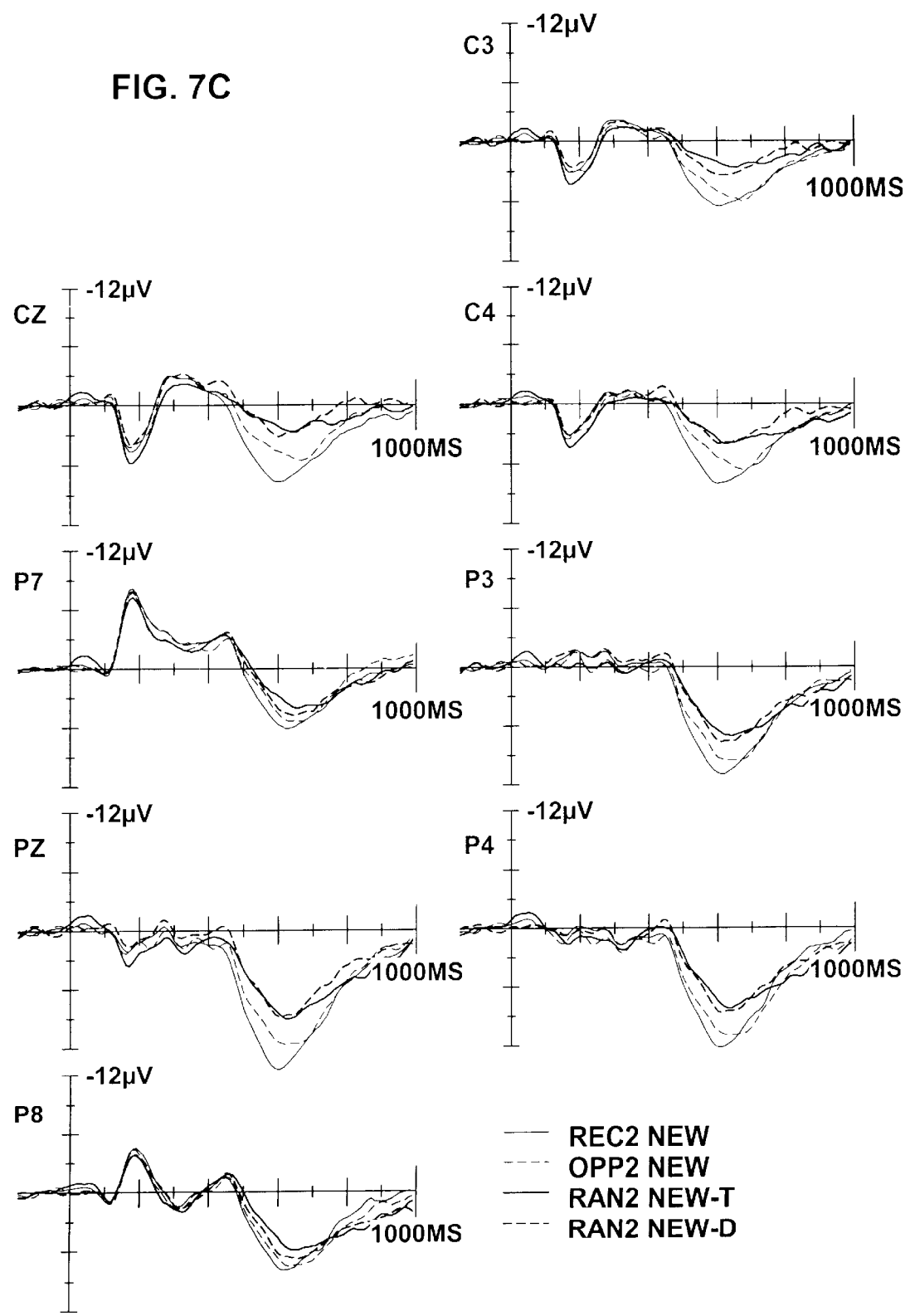

— REC Catch Old
--- OPP Catch Old
— RAN Catch Old

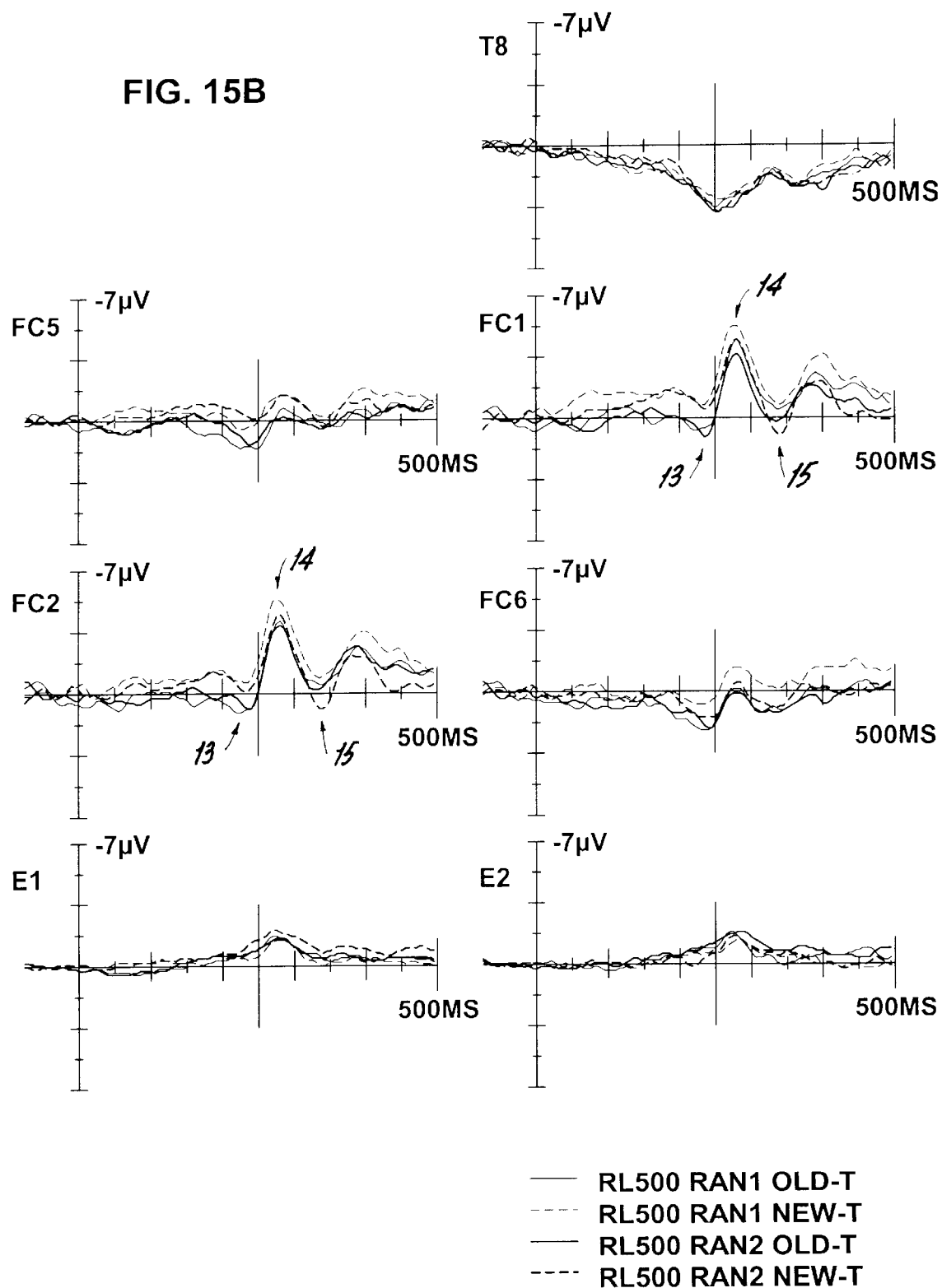

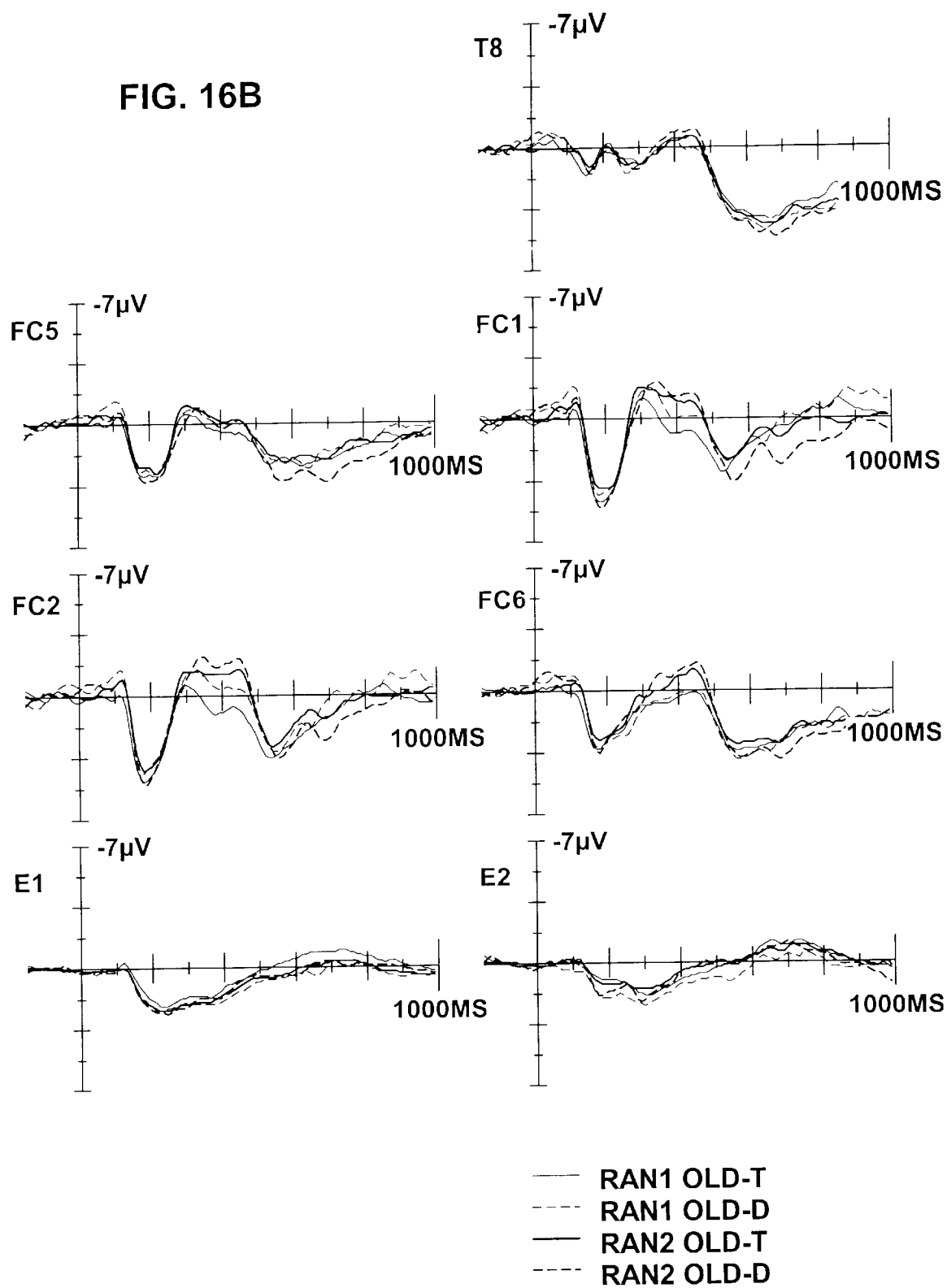

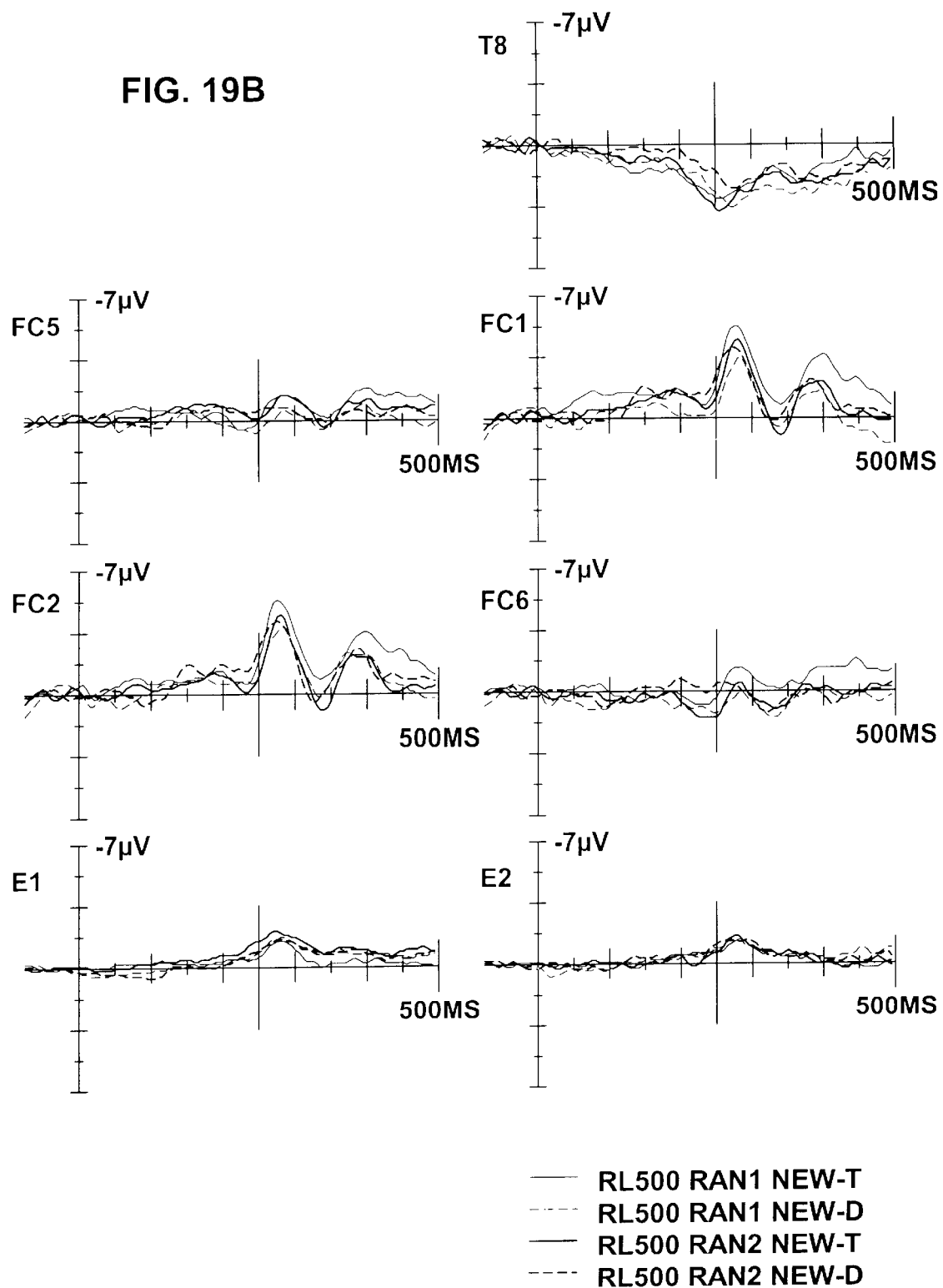

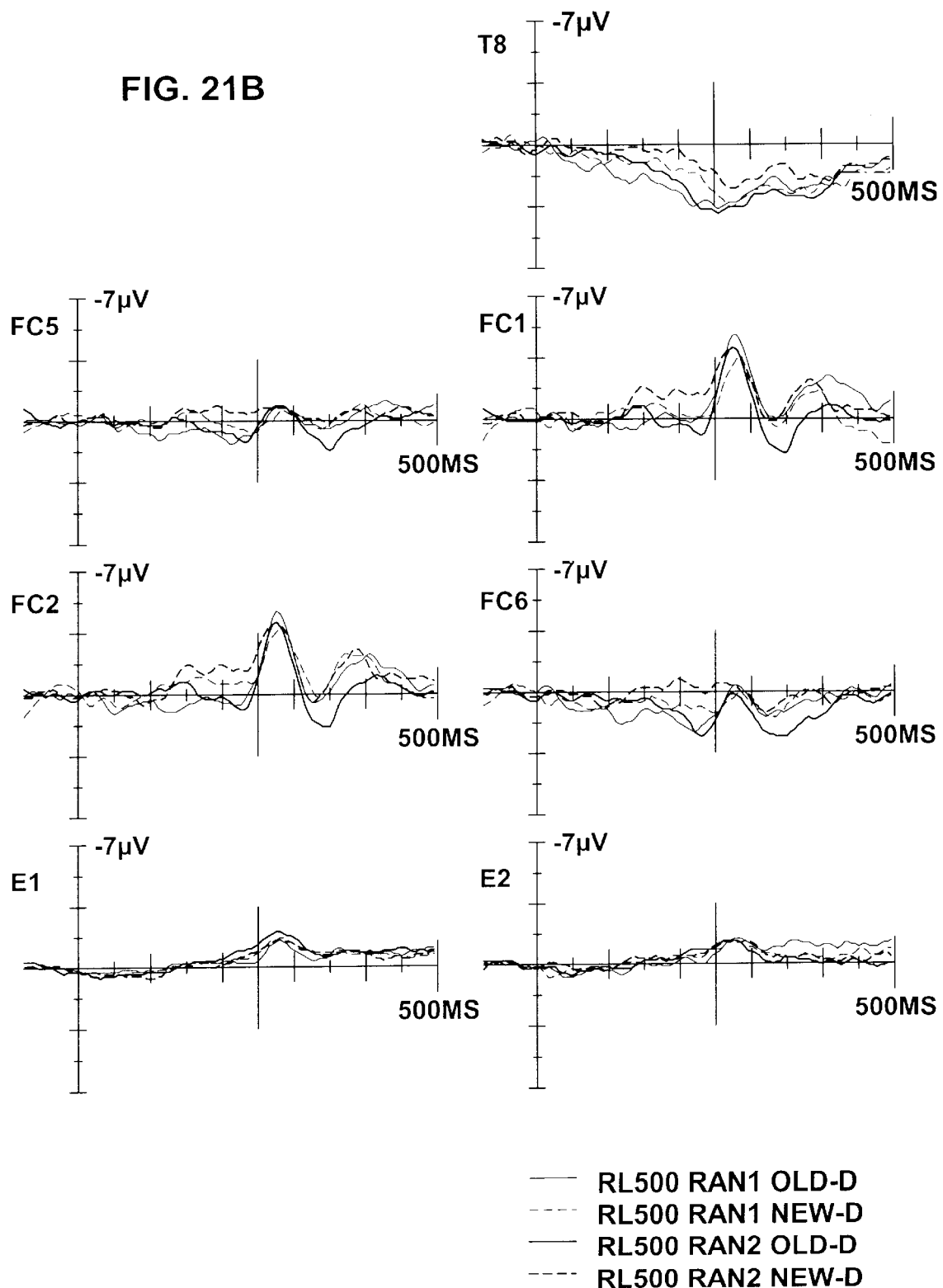

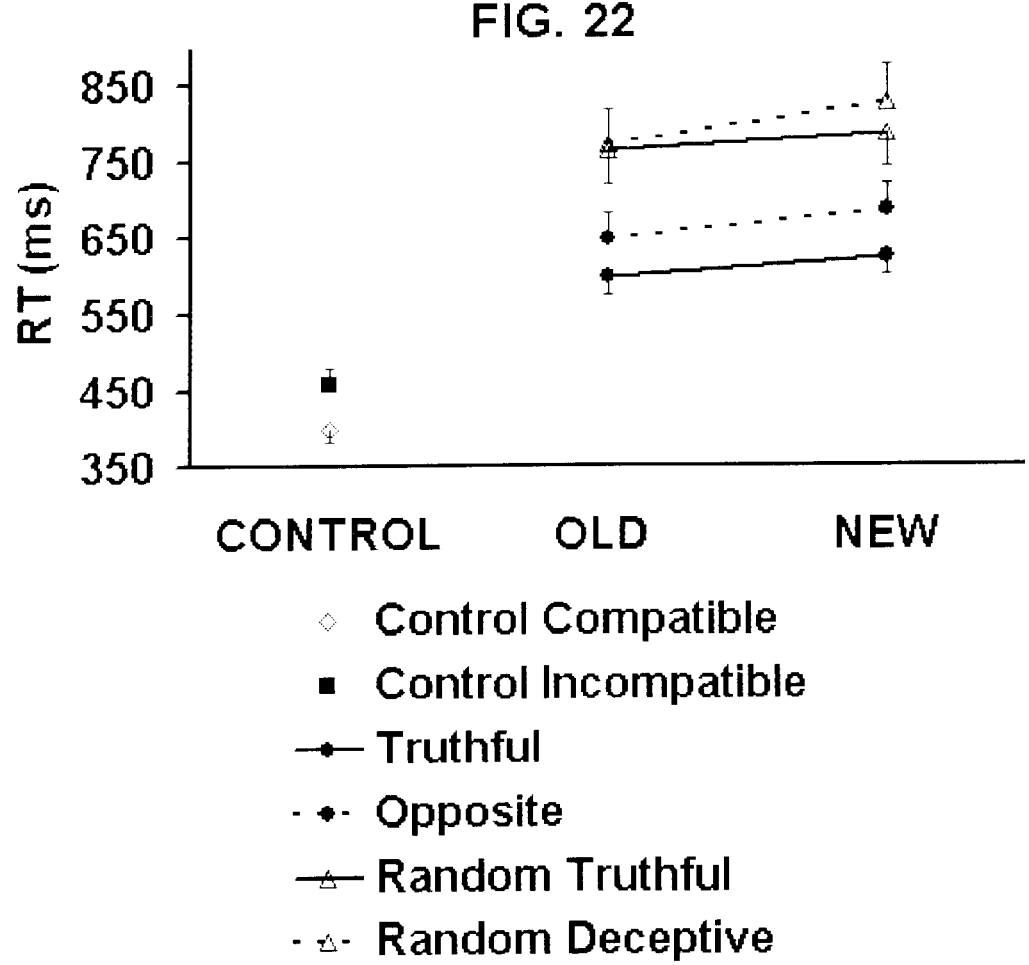

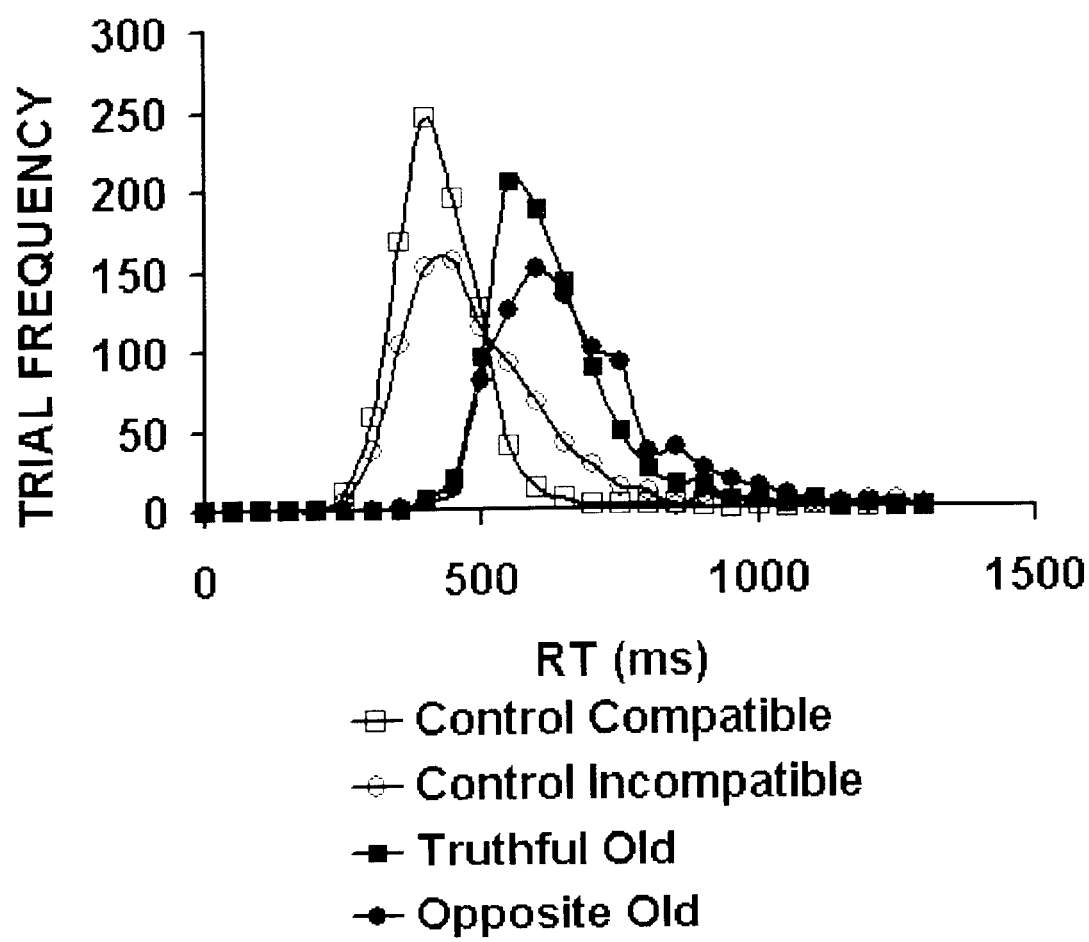

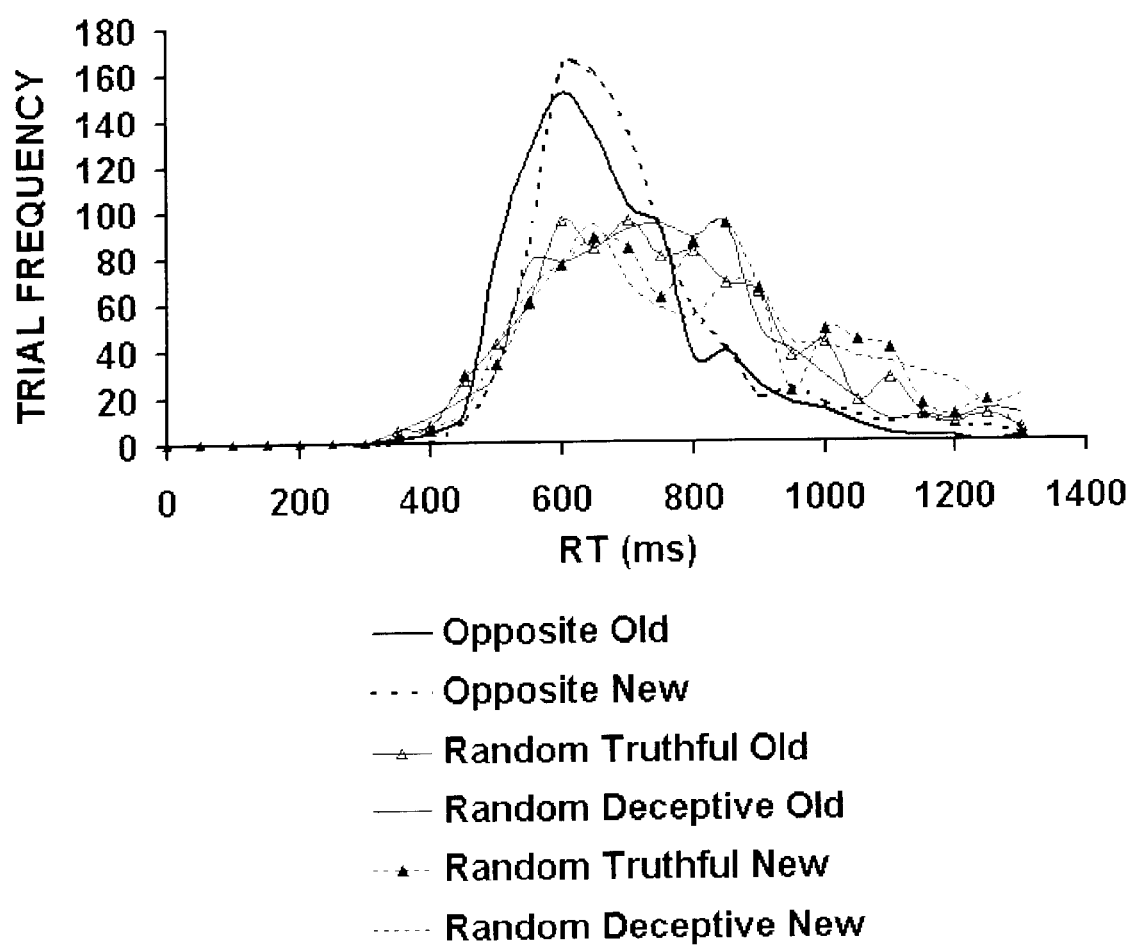

—— RL500 CONTROL-COMPAT
--- RL500 CONTROL-INCOMPAT
—— RL500 REC2 OLD
--- RL500 OPP2 OLD

— RL500 REC2 OLD
- - - RL500 REC2 NEW
— RL500 OPP2 OLD
- - - RL500 OPP2 NEW

—— RL500 OPP2 OLD
--- RL500 OPP2 NEW
—— RL500 RAN2 OLD-D
--- RL500 RAN2 NEW-D

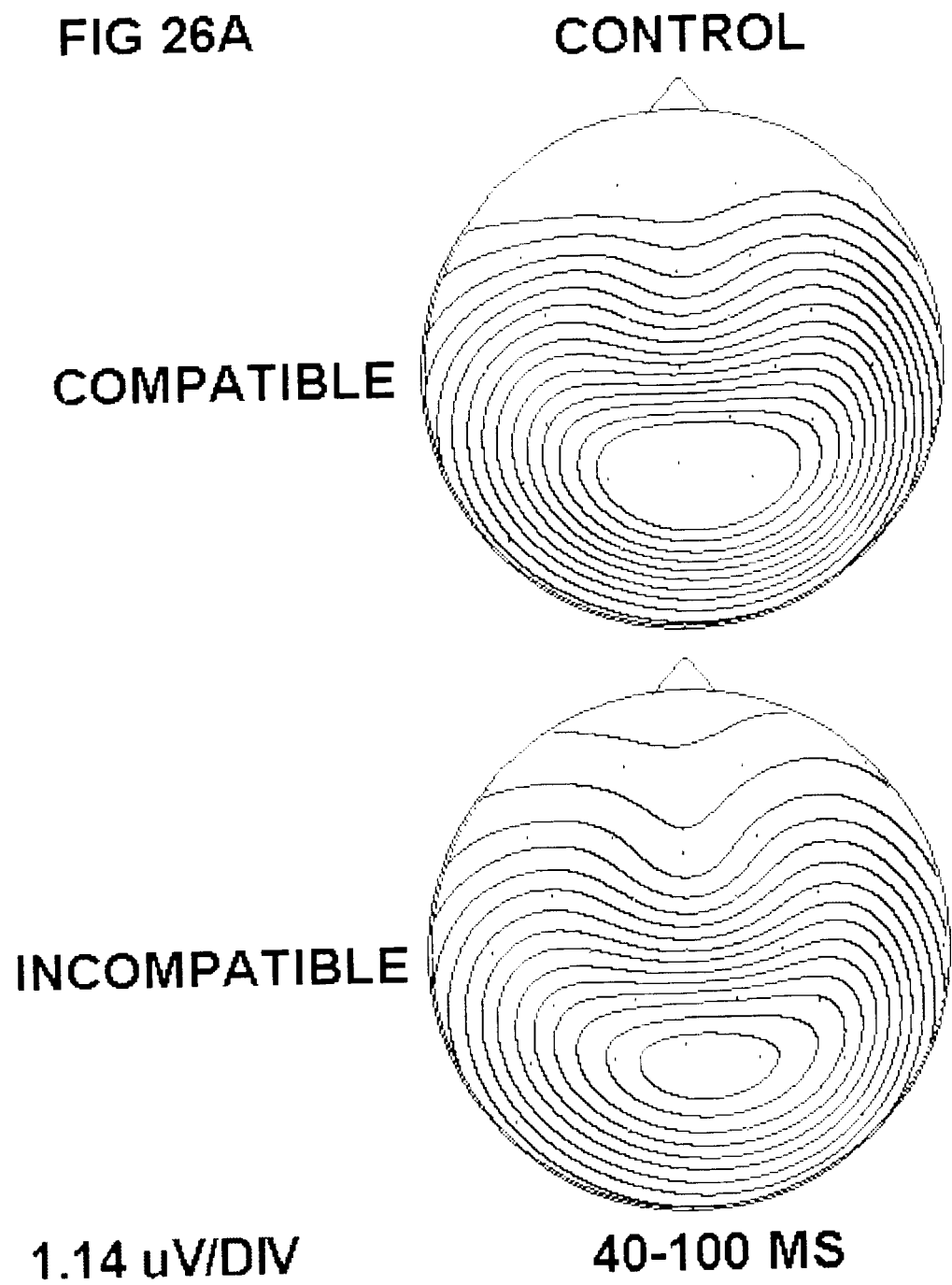

FIG. 26B  RECOGNITION OLD
TRUTHFUL 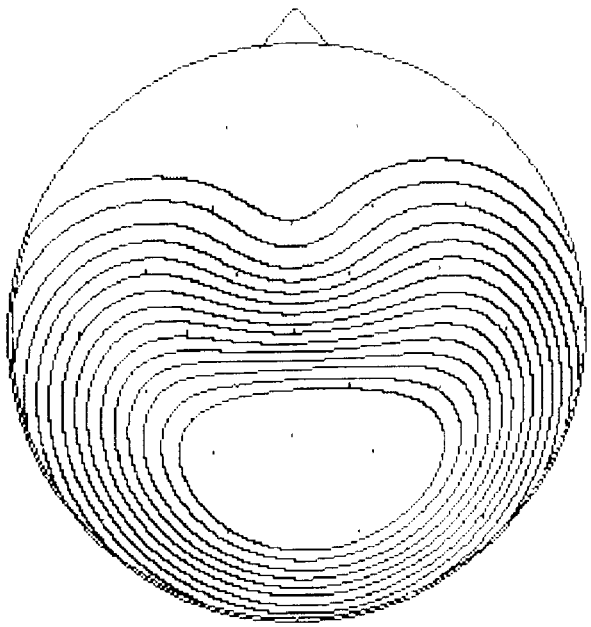
DECEPTIVE 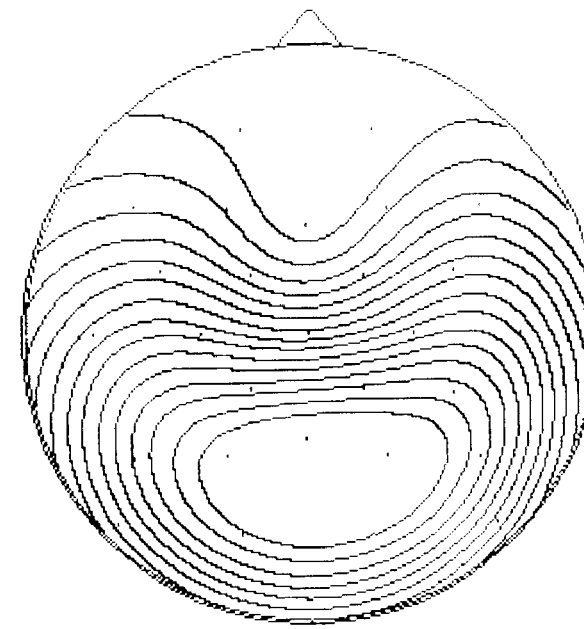
1.14 uV/DIV          40-100 MS FIG. 26C   RANDOM OLD
TRUTHFUL
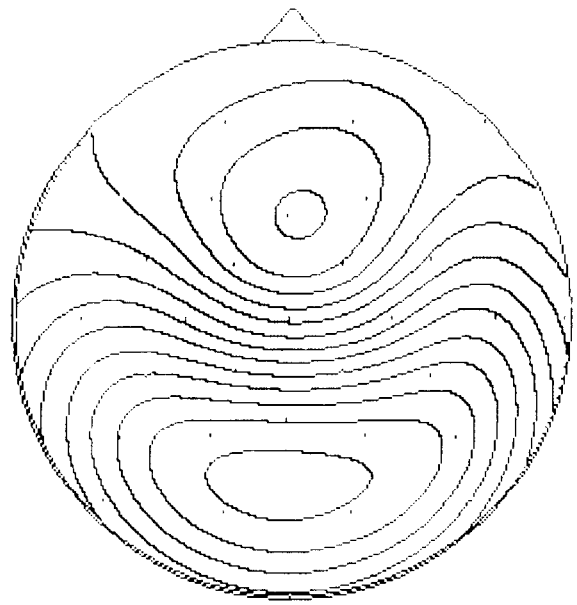
DECEPTIVE
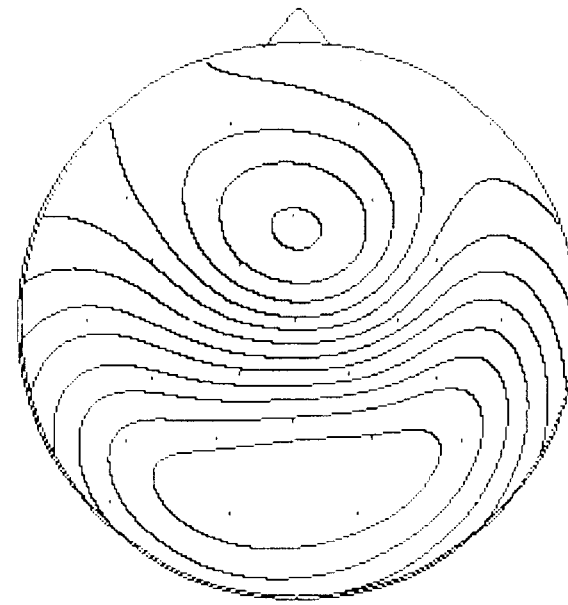
1.14 uV/DIV   40-100 MS FIG. 26D    RANDOM NEW
TRUTHFUL 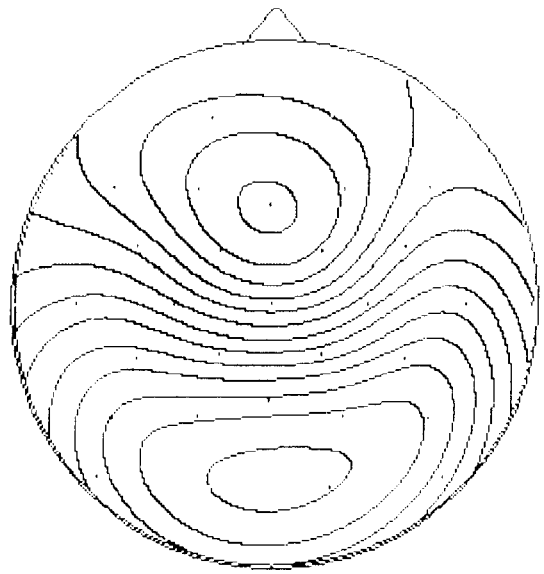
DECEPTIVE 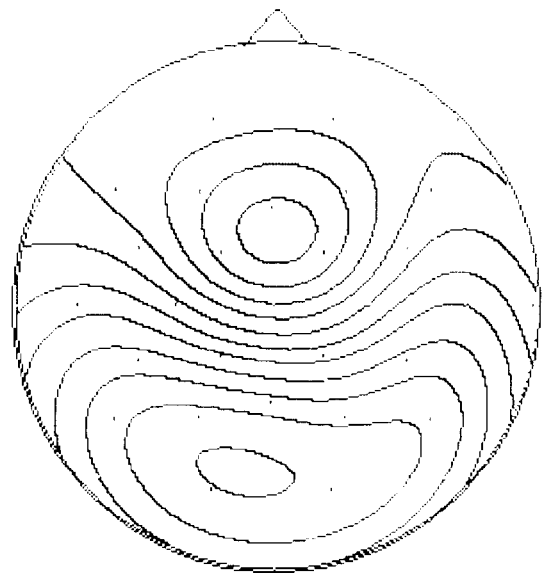
1.14 uV/DIV    40-100 MS

— REC2 OLD
--- REC2 NEW

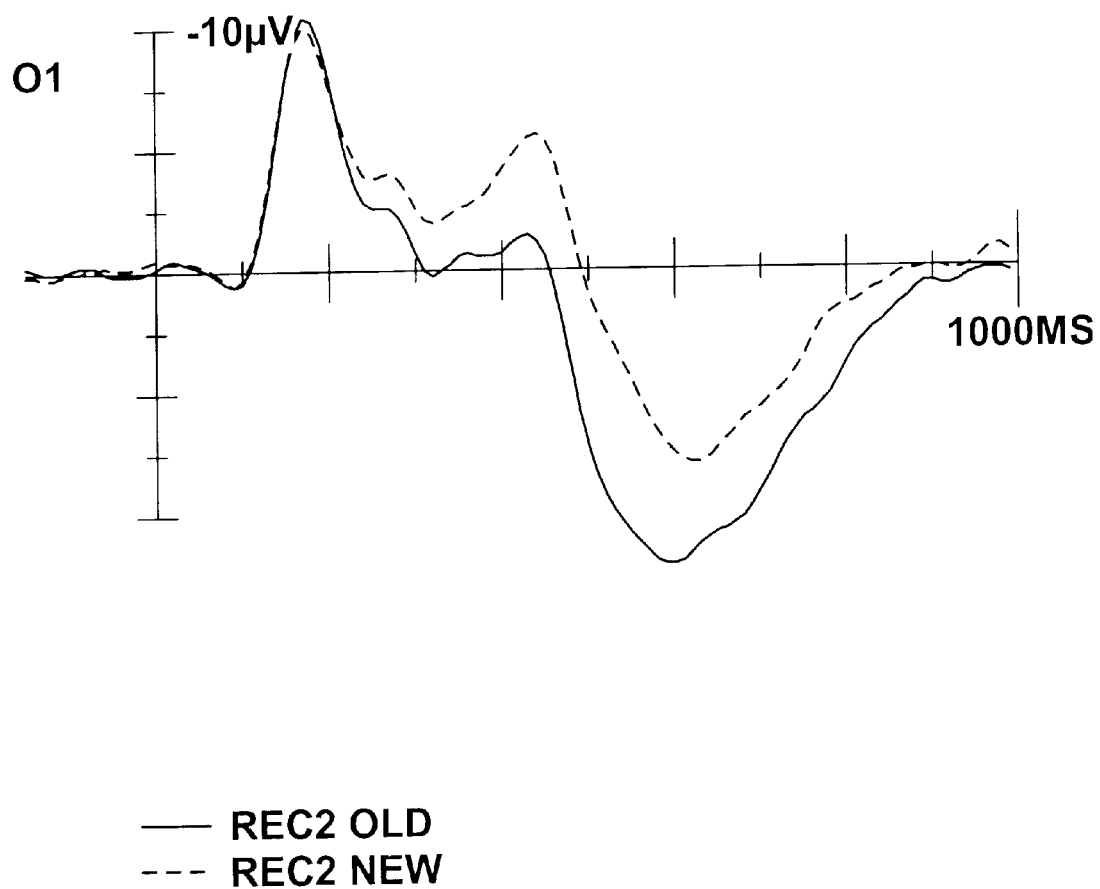

—— RAN2 OLD-T
--- RAN2 NEW-T

—— CONTROL-COMPAT
--- CONTROL-INCOMPAT
—— REC2 OLD
--- OPP2 OLD

— REC2 NEW
--- OPP2 NEW

— OPP2 OLD
--- RAN2 OLD-T
— RAN2 OLD-D

METHOD FOR DETECTING DECEPTION

This application claims the benefit of U.S. Provisional Application No. 60/228,827, filed Aug. 28, 2000, and U.S. Provisional Application No. 60/234,321, filed Sep. 20, 2000.

The present invention provides a novel and reliable method for detecting when a subject responds deceptively.

BACKGROUND OF THE INVENTION

Current technology for detecting deception is typified by the polygraph test which measures the activity of the subject's autonomic nervous system (galvanic skin response, respiration rate, heart rate, etc.) in response to questions. Disadvantages of the polygraph test include that it does not directly measure brain activity associated with deception, and that the test is subject to countermeasures by a trained, knowledgeable and/or determined subject. In addition, the scientific basis and validity of the polygraph test is often challenged and results of polygraph tests are not admissible as evidence in court proceedings. Nevertheless, the polygraph test continues to be administered by various authorities.

Studies have attempted to demonstrate that the event-related brain potential (ERPs) can be used to detect deception in human subjects. These efforts have focused on developing ERPs, specifically the P300, a positive ERP component with a latency of at least 300 ms, as a tool to reveal when subjects possess certain information in their memory. For example the P300 has been used in the Guilty Knowledge Test (GKT), to detect if a subject possesses information related to a crime (U.S. Pat. No. 4,941,477 (Farwell); U.S. Pat. No. 4,932,416 (Rosenfeld)), or as a tool to detect memory deficiency malingering (U.S. Pat. No. 5,846,207 (Rosenfeld). This research however did not directly examine cognitive processes or brain activity related to the deception. A disadvantage of the GKT is that it indirectly assesses the presence of guilty knowledge and thus may be subject to countermeasures by the subject. In addition, because the GKT tests knowledge of a crime, it is not useful in the majority of polygraph tests, such as those used for screening employees or potential employees for security reasons and where commission of a crime is not at issue.

In non-deceptive situations, response conflict is typically induced when one aspect of a stimulus suggests one particular response while another aspect of the same stimulus suggests a different, competing response. Such situations can be classified as perceptually-driven response conflicts. One example is the Stroop test in which subjects see color words printed in different colored inks and are instructed to respond by naming the color of the ink in which a word is printed and to ignore the response indicated by the word itself. Perceptually-driven response conflicts affect task performance by reducing accuracy and slowing responses (Casey et al., 2000, Carter et al., 1998; Scheffers and Coles, 2000).

Studies of brain activity using functional magnetic resonance imaging (fMRI) have shown that the anterior cingulate cortex, an area of the medial frontal lobes, is active in situations when there is uncertainty about the proper response for a stimulus, such as when stimuli produce conflicting response tendencies (Botvinick et al., 1999; Casey et al., 2000; Carter et al., 1998, 2000). Therefore, it is believed that the anterior cingulate plays an important role in monitoring potential conflicts between intended and actual responses and signaling when a correction needs to be made (e.g., in situations when the response being prepared does not match the intended correct response)(Botvinick et al.,1999; Carter et al., 1998).

The error-related negativity (ERN) component of the ERP occurs between 0 to 100 ms after a response and is recorded maximally over medial central-frontal scalp. The ERN has been detected in tests in which the stimuli elicit conflicting response tendencies. While the largest ERNs have been found in error trials (Falkenstein et al., 2000), smaller ERNs are also found in correct trials (Vidal et al., 2000), particularly when degrading stimulus quality created uncertainty about how the stimulus should be categorized (Scheffers and Coles, 2000). Localization studies have placed the neural generator of the ERN in the medial frontal lobes, in or near the anterior cingulate cortex (Miltner et al., 1997) suggesting that the ERN may be linked with the activity measured in the anterior cingulate cortex fMRI studies cited above.

Little is known about the cognitive processes used when subjects are being deceptive and less is known about the brain activity underlying these cognitive processes.

It is thus an object of the invention to compare how the brain processes response conflicts in deceptive situations and non-deceptive situations.

It is an object of the present invention to provide a reliable method for testing deception that is less susceptible to the influence of countermeasures, is not dependent on the intent to deceive and detects long-term strategic deceptive patterns.

SUMMARY OF THE INVENTION

The present invention provides a method for determining whether a subject responds deceptively comprising a) presenting the subject with a test series of stimuli; b) presenting the subject with a control series of stimuli; c) monitoring the subject's electrophysiological activity, behavioral activity, or both, associated with the subject's response to the test series and control series of stimuli; d) comparing the subject's electrophysiological activity, behavioral activity, or both, obtained from the responses to the test series and control series of stimuli; wherein a difference in the activity between the test and control stimuli indicates that the subject is responding deceptively.

The present invention also provides a method for determining whether a subject responds deceptively comprising a) presenting the subject with one or more sets of stimuli, each set comprising a test series of stimuli and a control series of stimuli; b) monitoring the subject's electrophysiological activity, behavioral activity, or both, associated with the subject's response to each set of stimuli; and c) comparing the subject's electrophysiological activity, behavioral activity, or both, obtained from the responses to one set of stimuli to the activity from another set of stimuli; wherein a difference in the activity between the sets of stimuli indicates that the subject is responding deceptively. This embodiment is also known as a Repetition Series.

The present invention further provides a method for determining whether a subject possesses guilty knowledge comprising a) presenting the subject with a test series of stimuli wherein the test series of stimuli comprises an equal number of relevant and irrelevant items; b) presenting the subject with a control series of stimuli wherein the control series of stimuli comprises an equal number of relevant and irrelevant items; c) monitoring the subject's electrophysiological activity, behavioral activity, or both, associated with the subject's response to the test series and control series of stimuli; d) comparing the subject's electrophysiological activity, behavioral activity, or both, obtained from the responses to the test series and control series of stimuli; wherein a difference in the activity between the relevant and irrelevant items indicates that the subject possesses guilty knowledge. This embodiment is also known as the guilty knowledge test.

According to the methods described herein, the electrophysiological activity comprises event-related brain potential (ERP); and behavioral activity comprises speed of response, variability in response speed and accuracy of response. The difference in electrophysiological and behavioral activity is defined by one or more markers, defined below which indicate when a subject is being deceptive or possesses guilty knowledge. The method of detecting deception described herein is suitable for both practiced and unpracticed deceptive responses. The method is independent of the subject's intent to commit deception. The method also differentiates lies (e.g., saying one wasn't in a place when they were there) from confabulations (e.g., saying one was in a place when they were not there).

Figure 1:
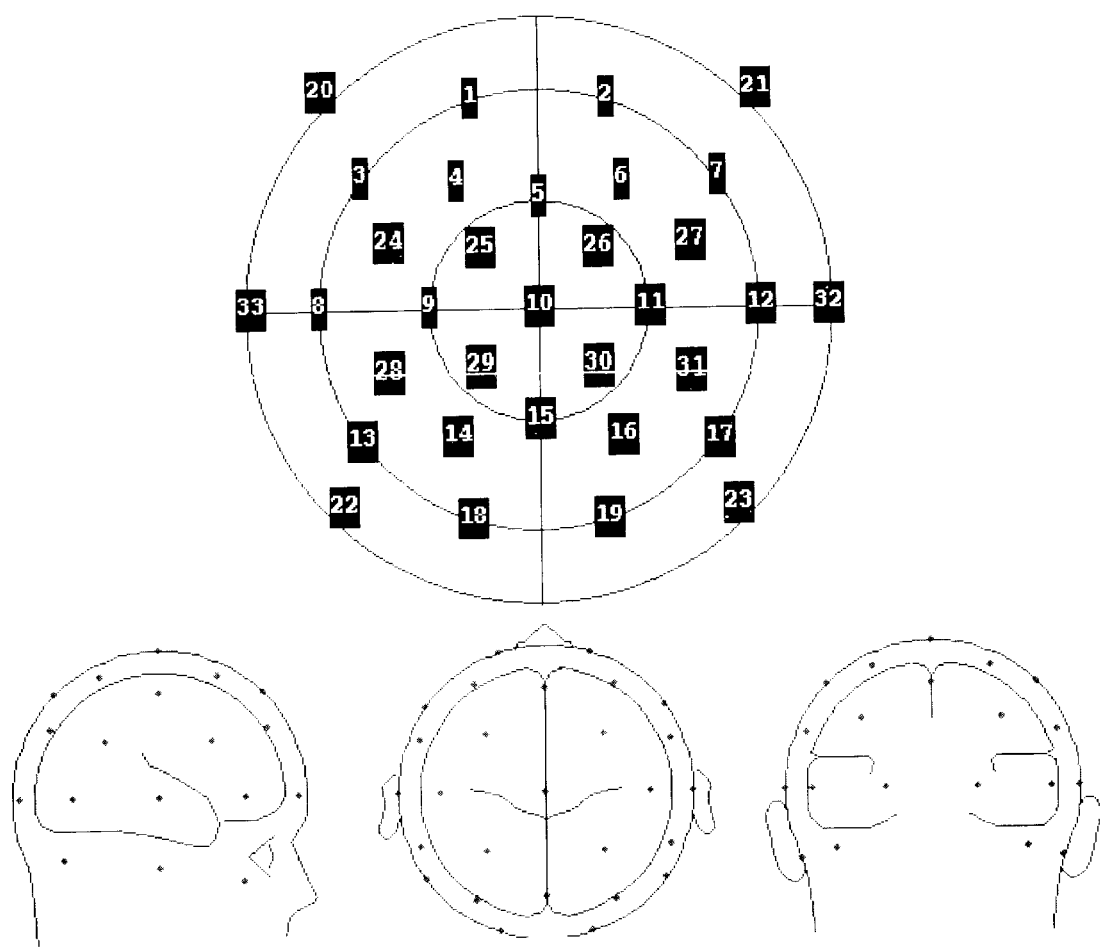
FIG. 1 shows scalp sites for placement of electrodes (channels). ERP activity was recorded from 32 scalp sites. All scalp-recorded activity was referenced to the left canthus (33), and digitally re-referenced to an average of the left (33) and right (32) canthi. EOG artifact trials (any trial with a signal>50 $\mu$V during any six sampling points) were discarded. The data were recorded with a bandpass of 0.01–35 Hz (−3 dB/octave) and sampled at 100 Hz from 150 ms before stimulus onset until 2000 ms after stimulus onset. (Images were adapted from BESA 3.0, Scherg, 1989–1998).
Figure 2A:
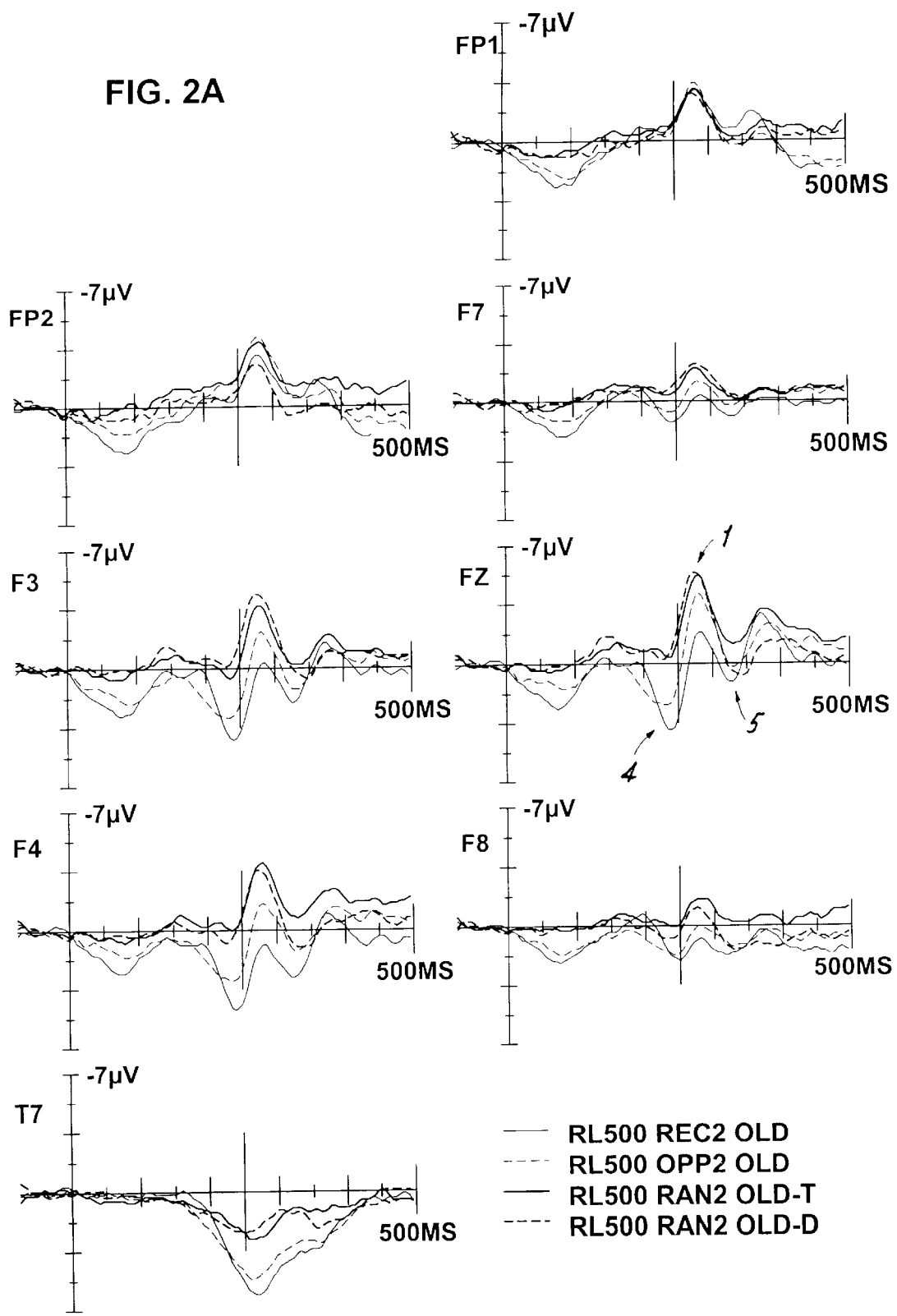
Figure 2B:
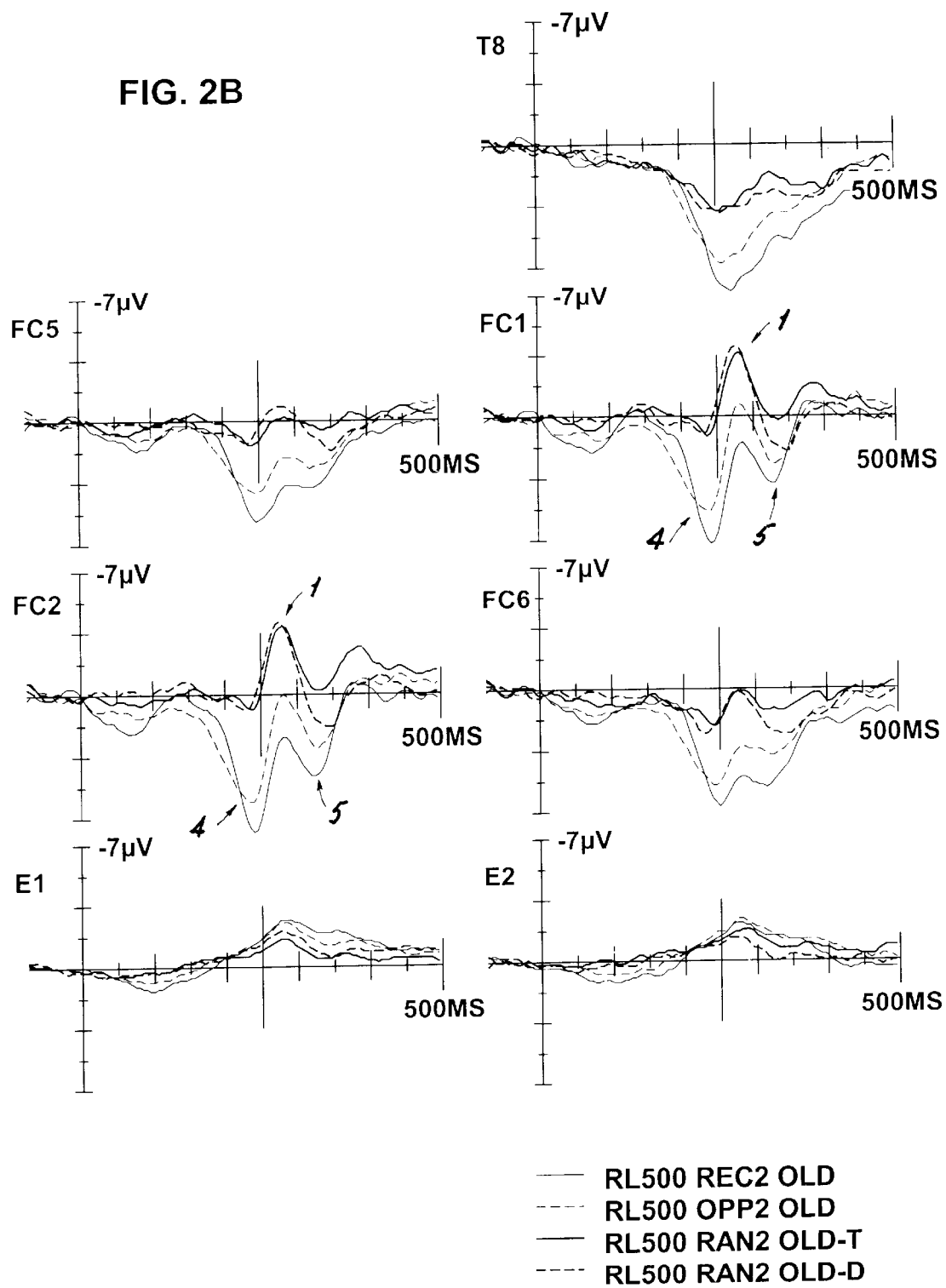
Figure 2C:
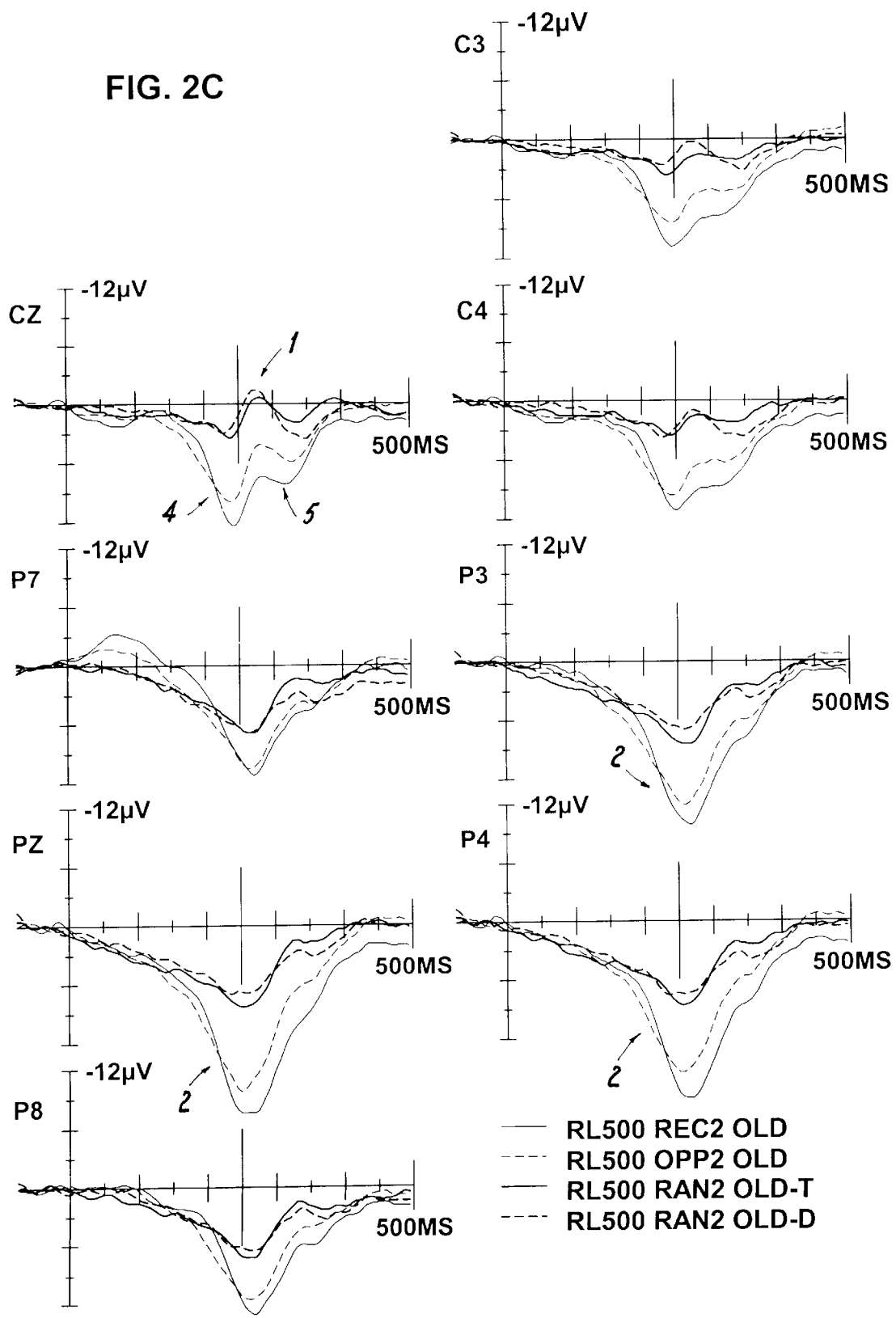
Figure 2D:
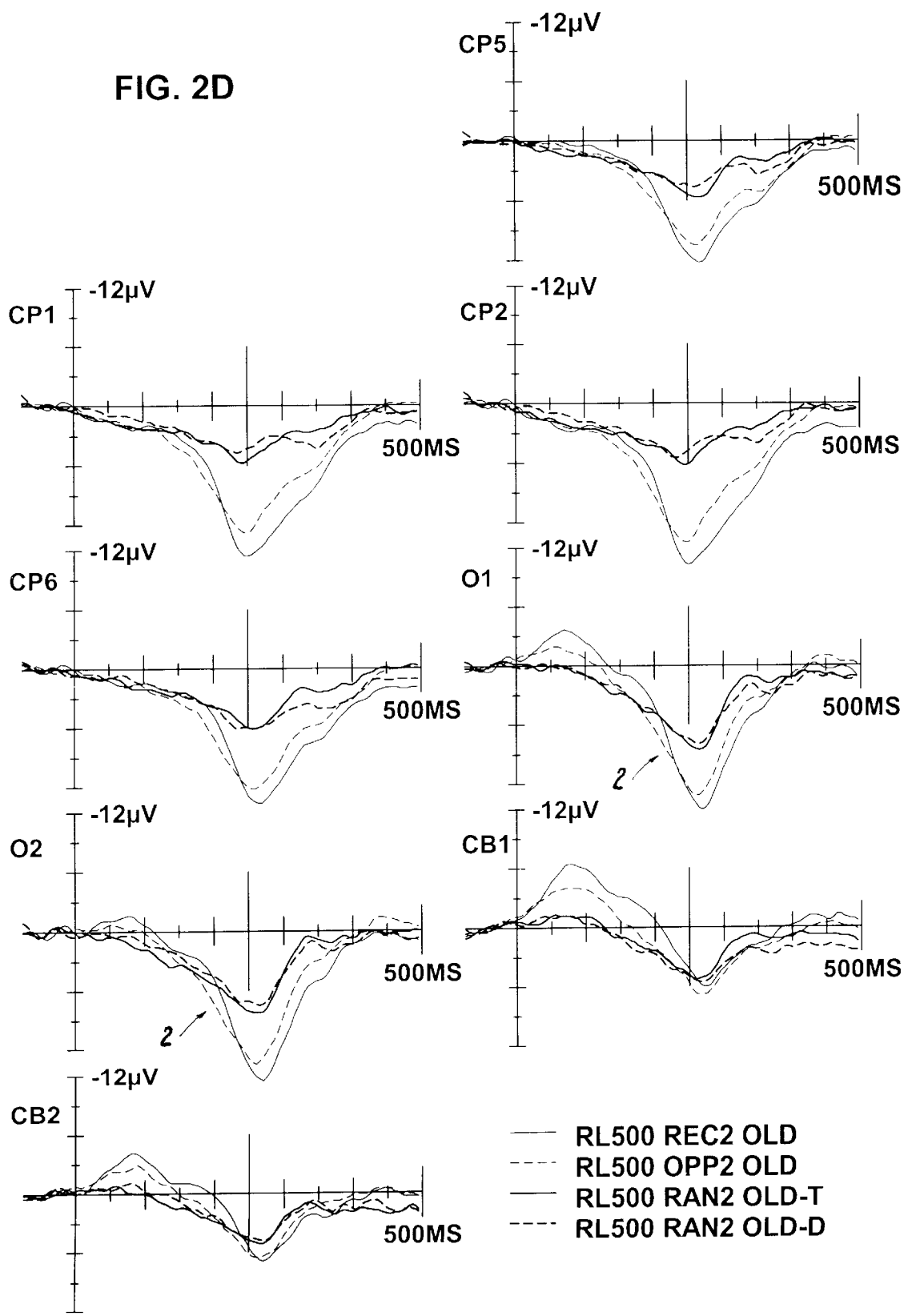
Figure 3A:
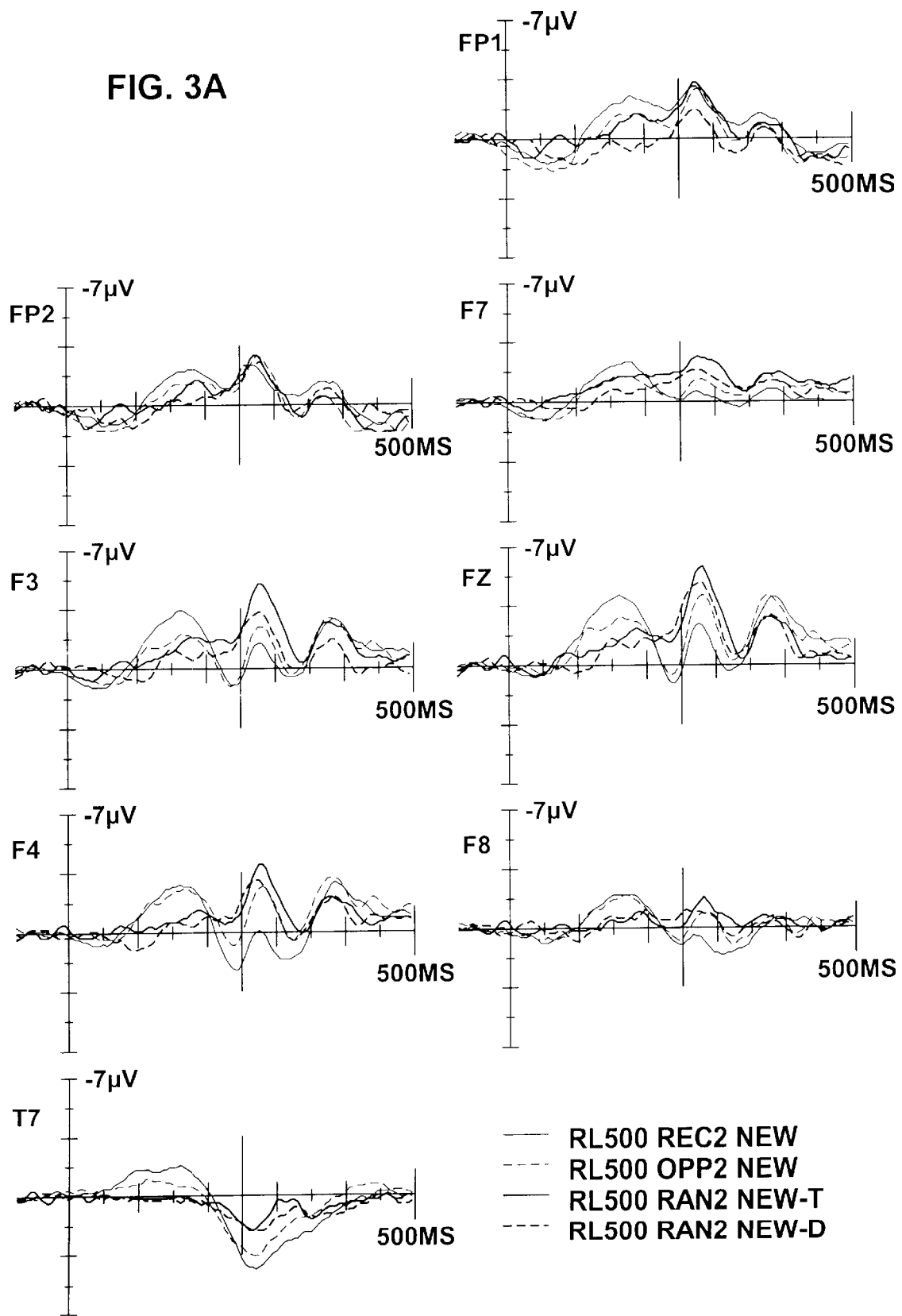
Figure 3B:
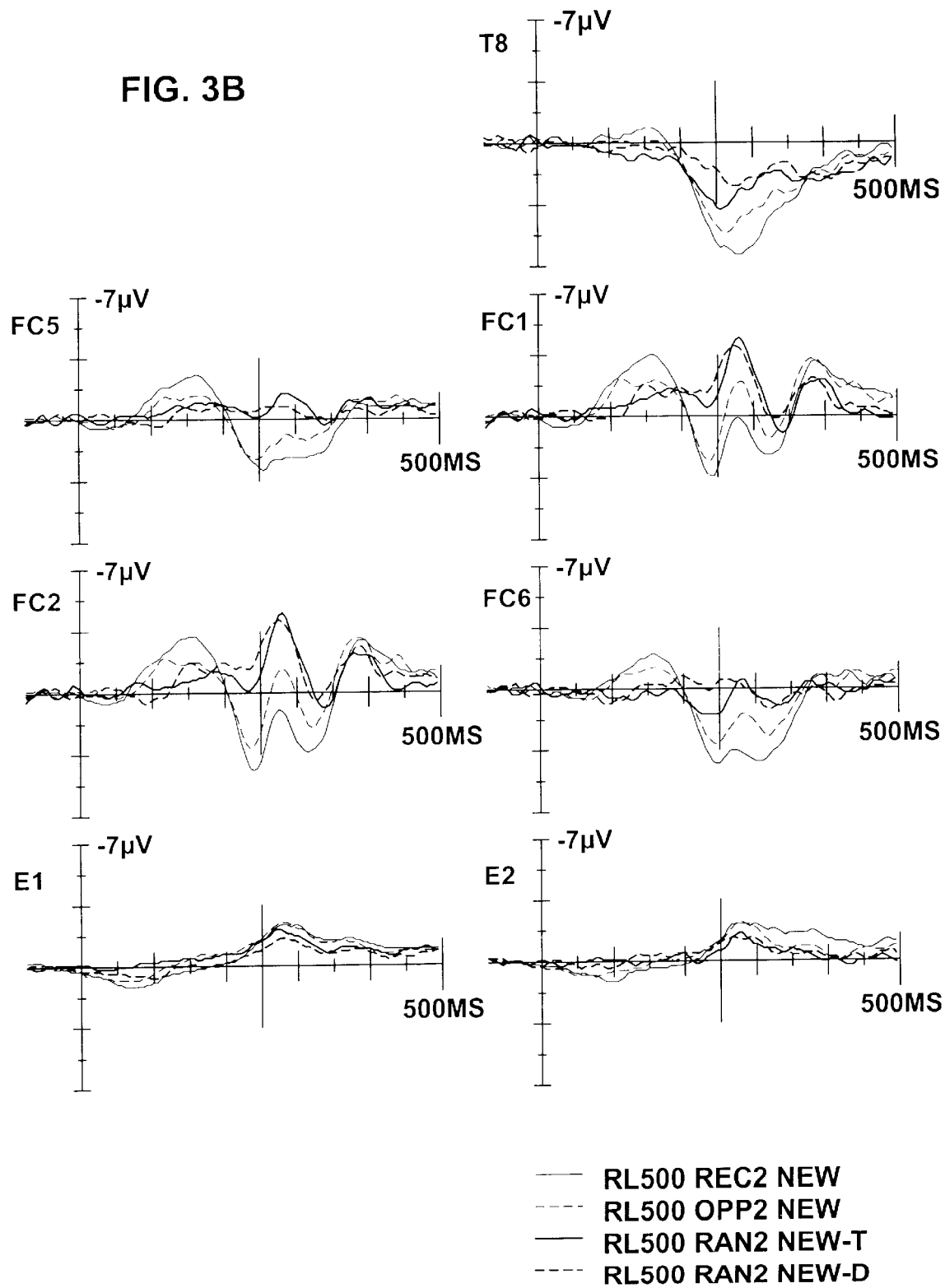
Figure 3C:
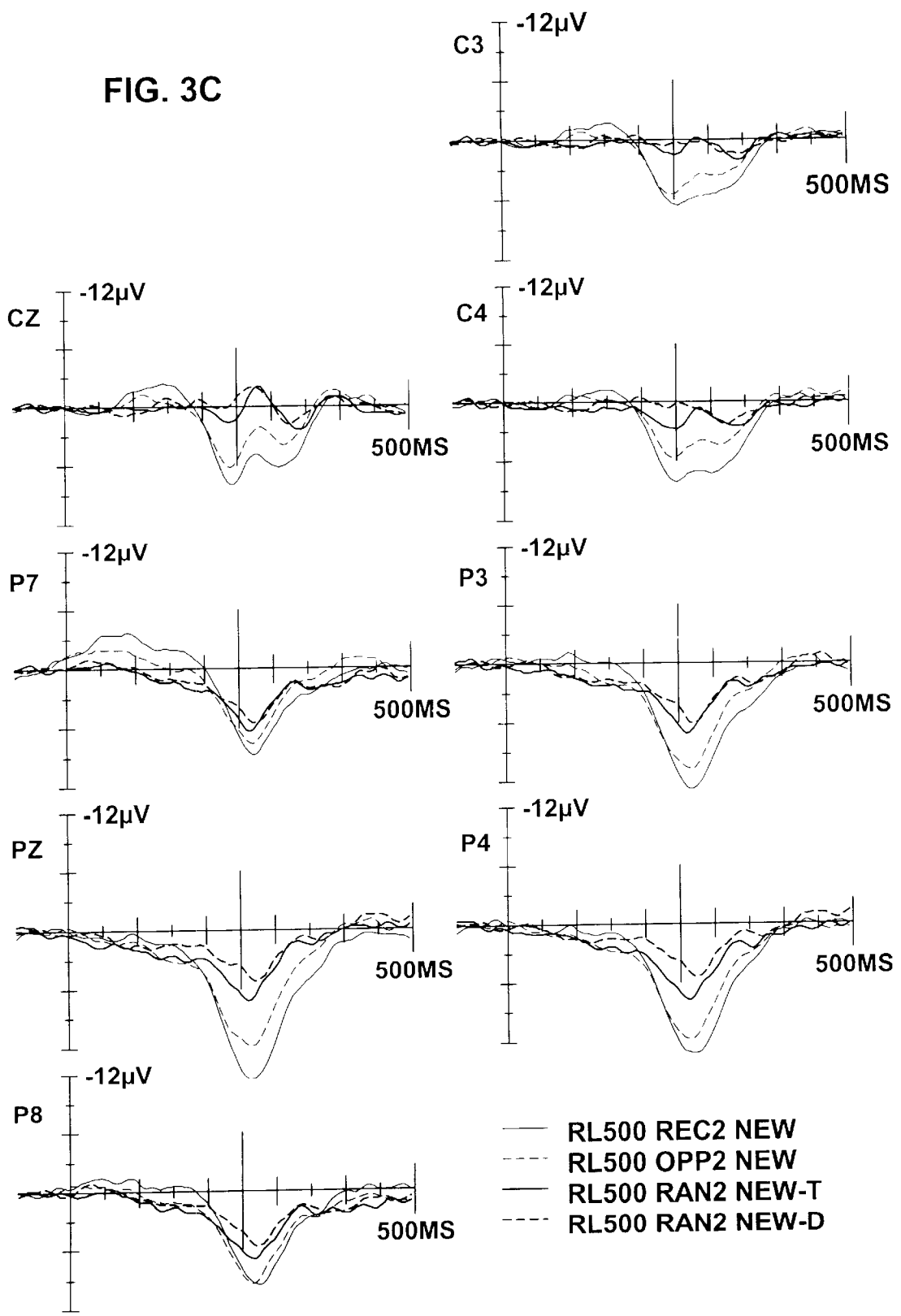
Figure 3D:
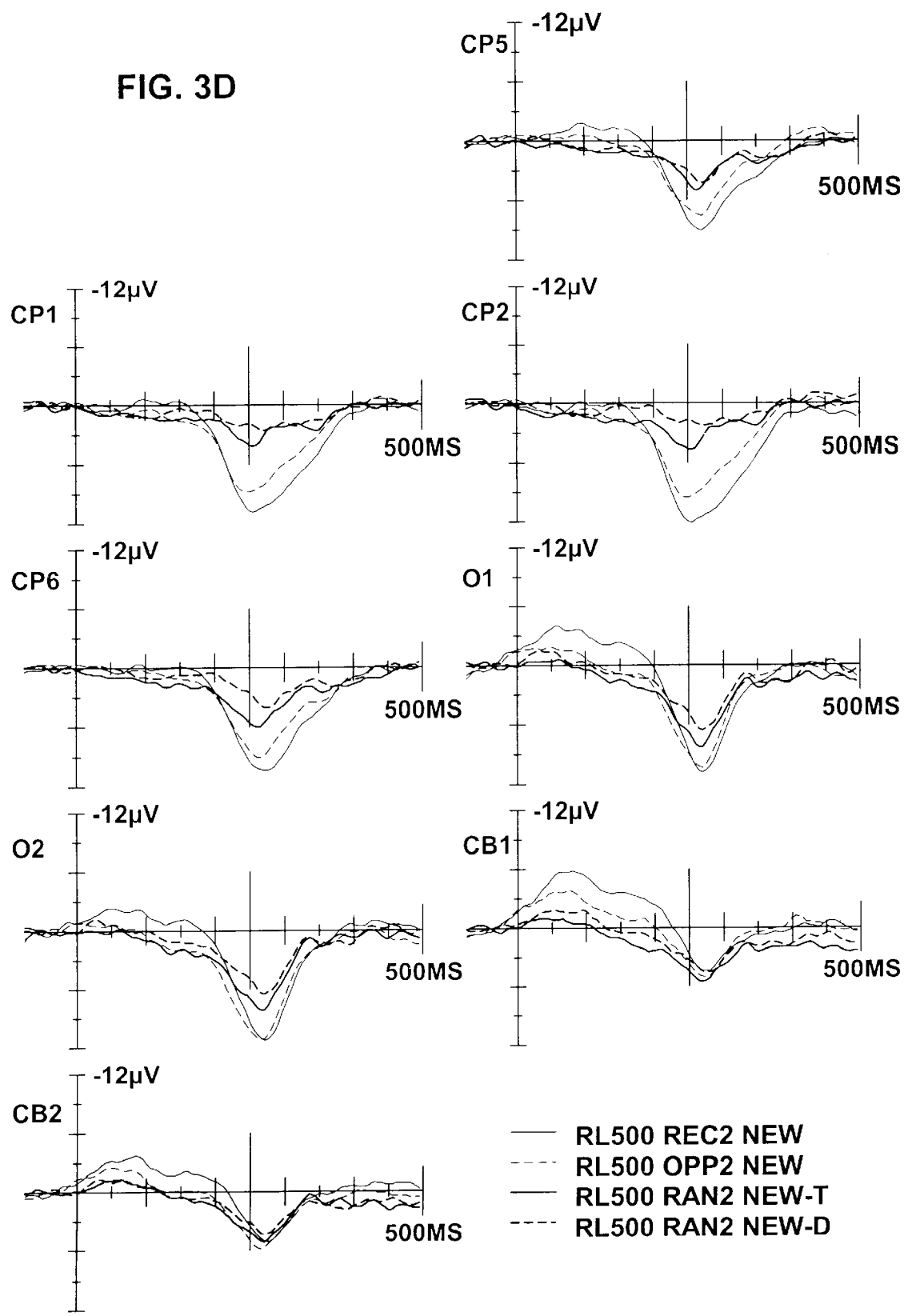
Figure 4A:
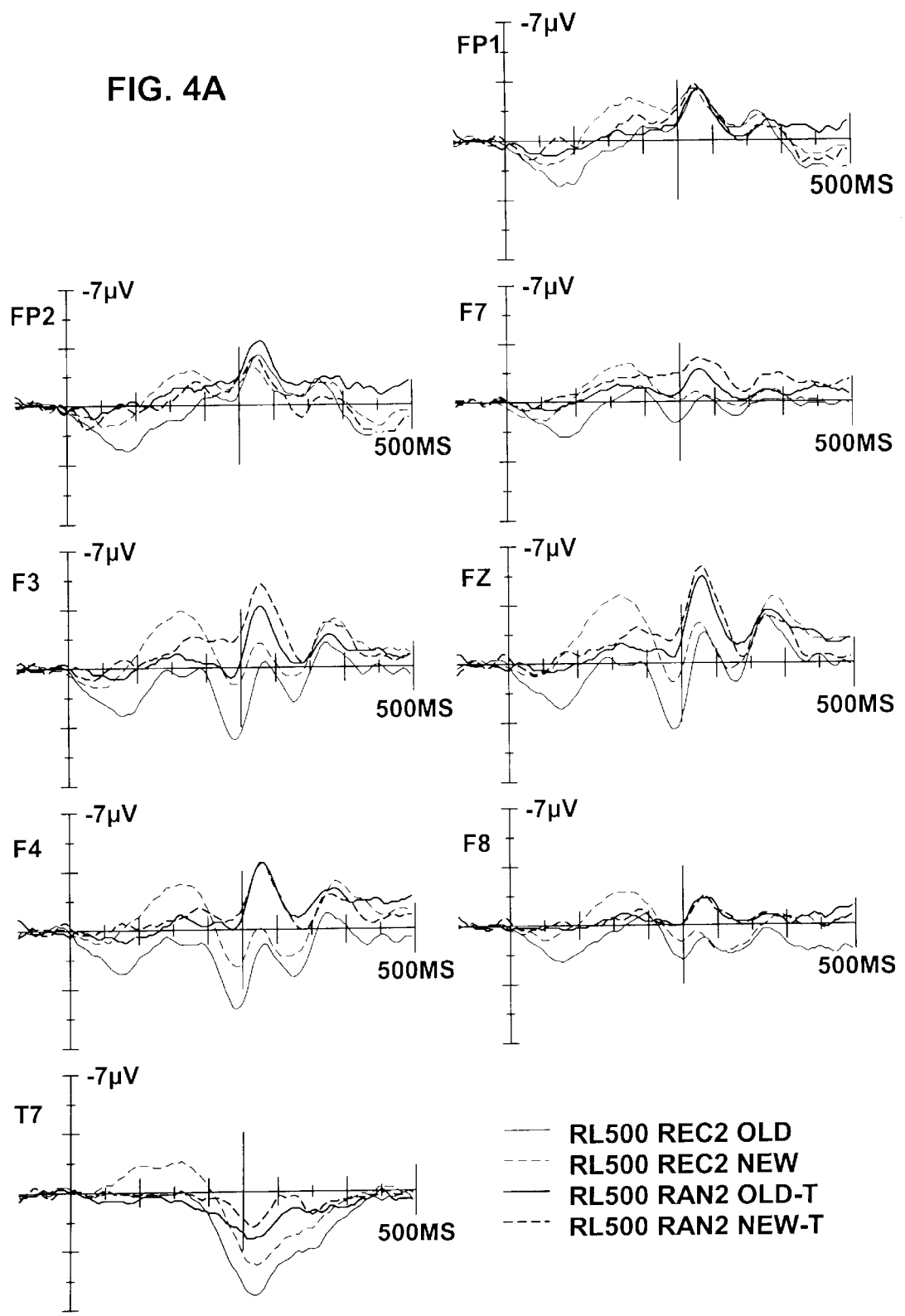
Figure 4B:
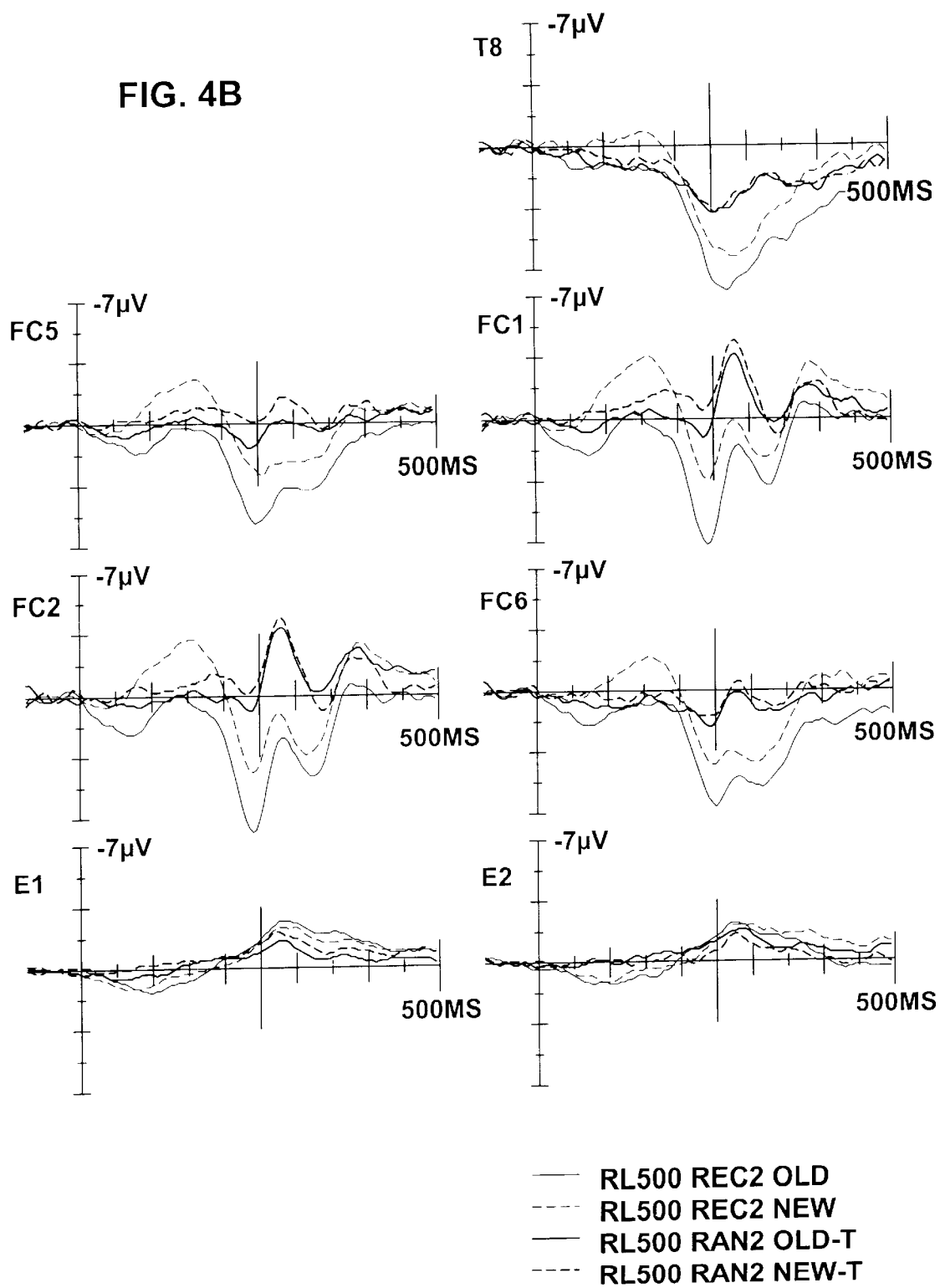
Figure 4C:
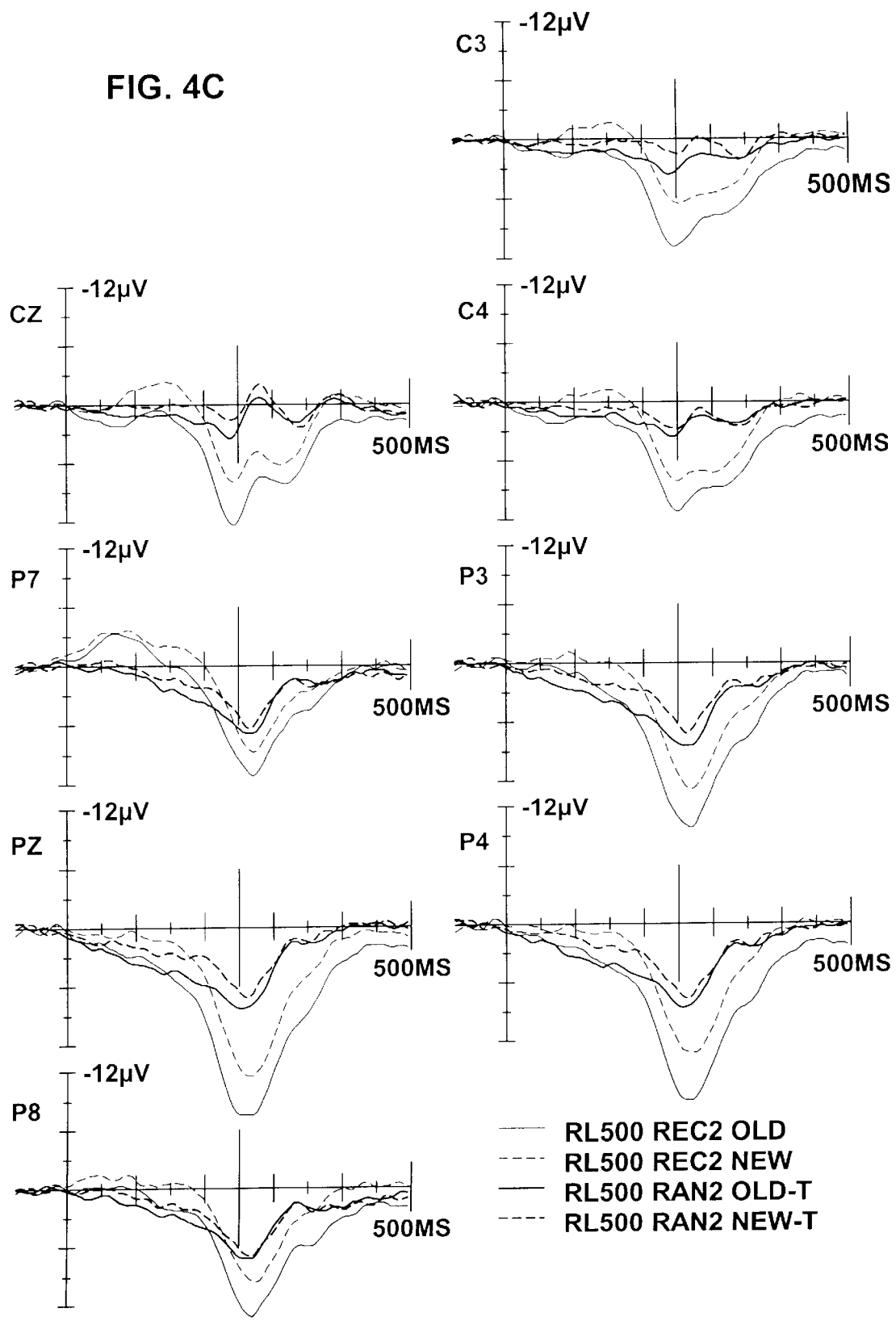
Figure 4D:
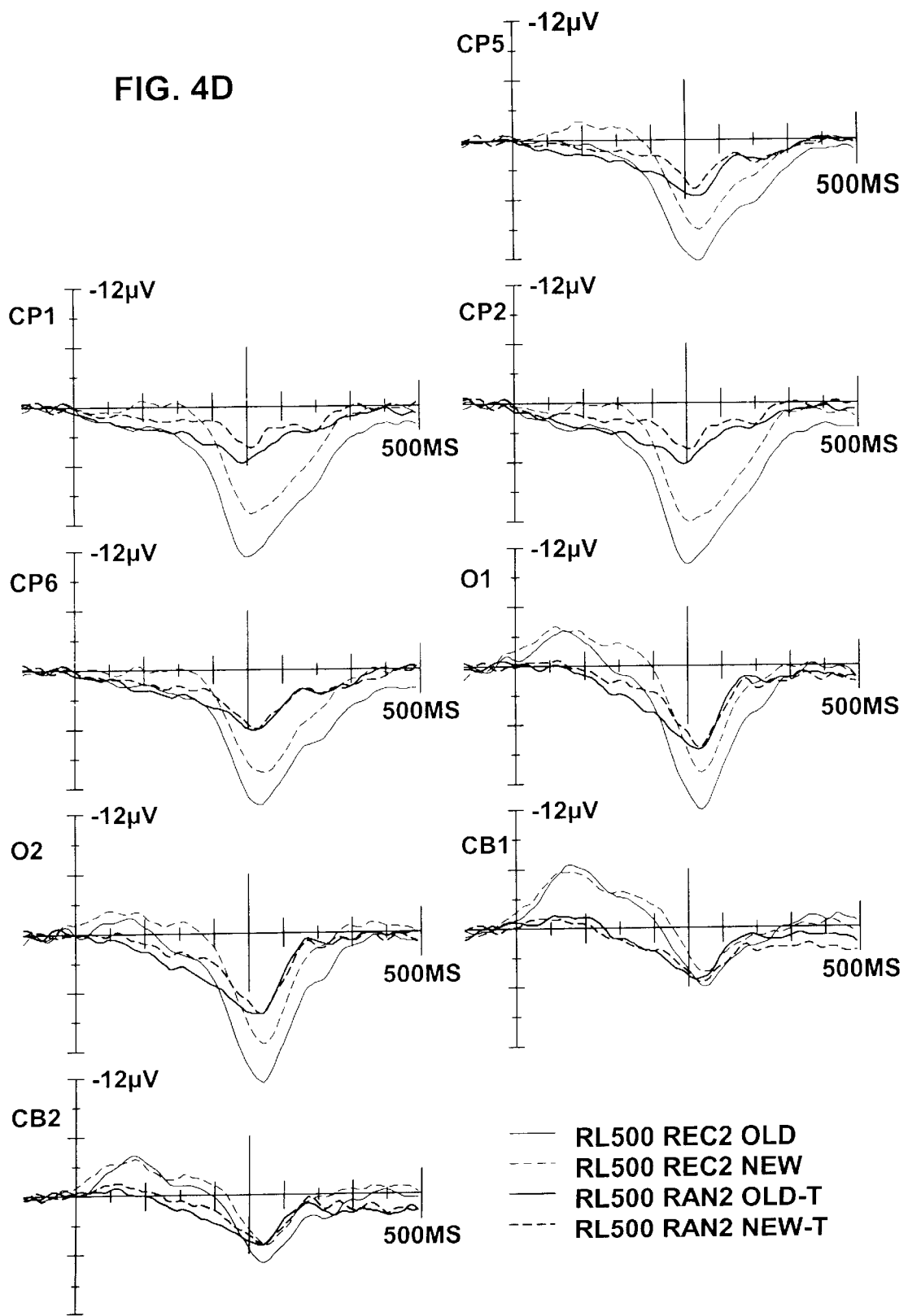
Figure 5A:
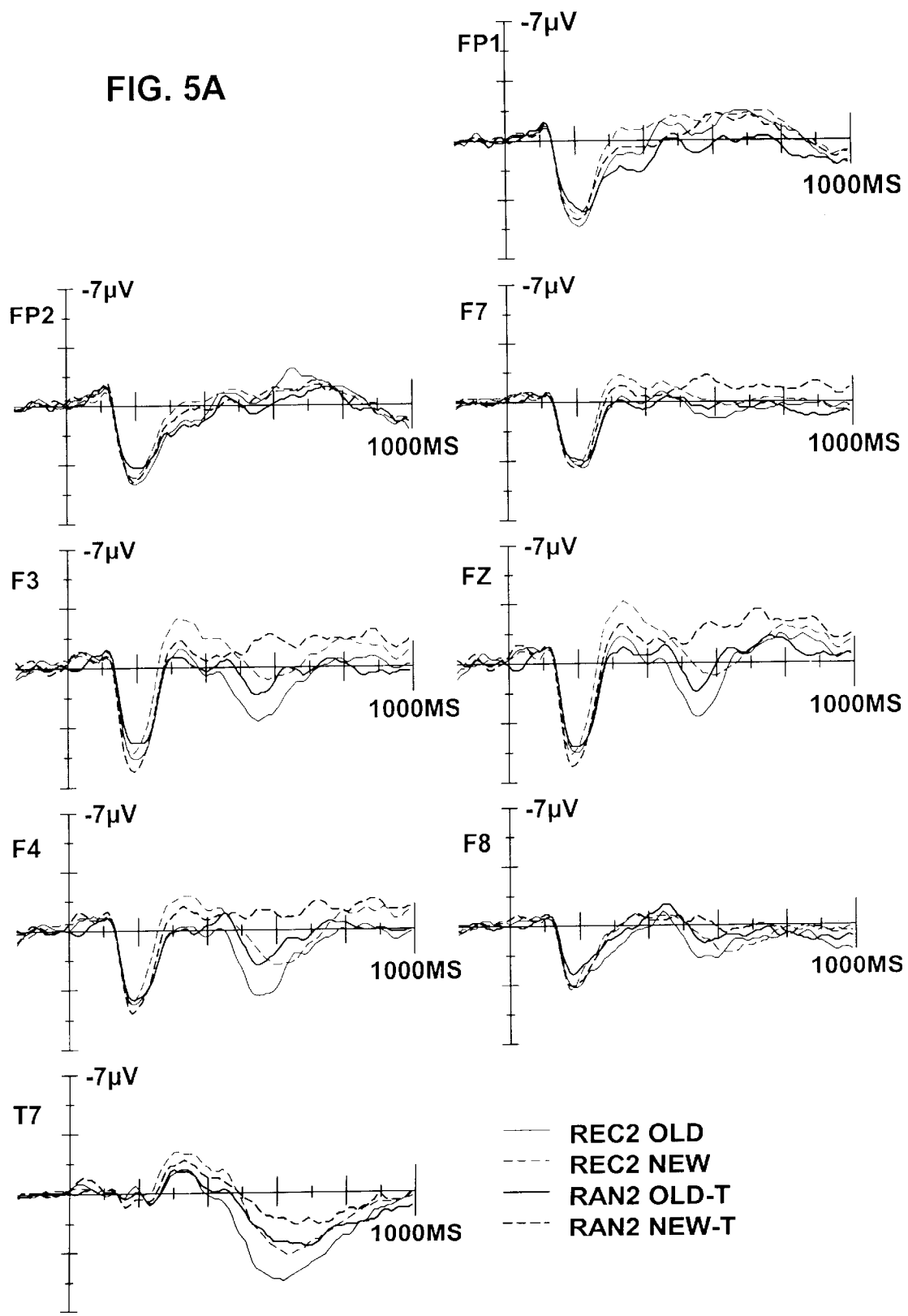
Figure 5B:
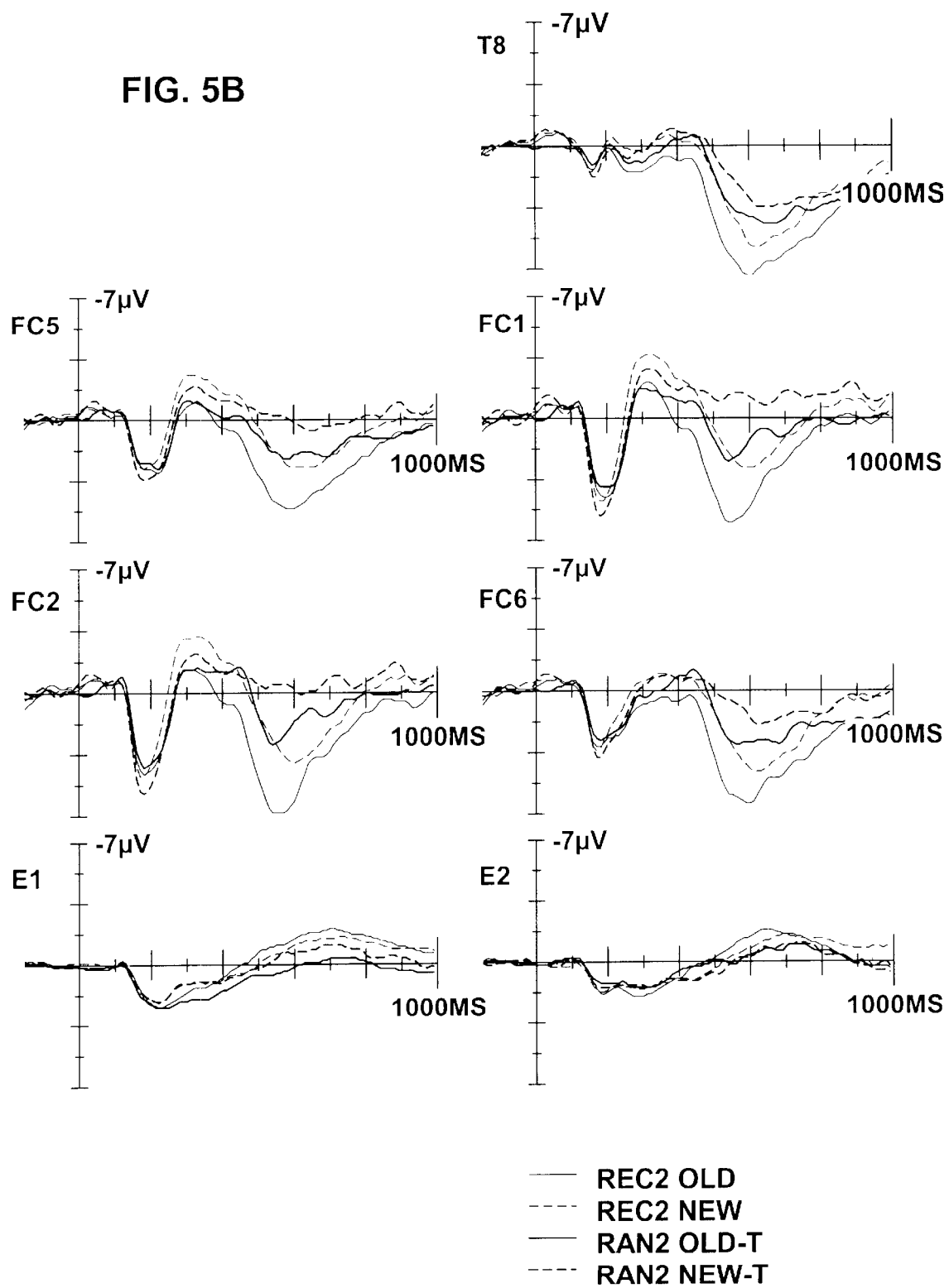
Figure 5C:
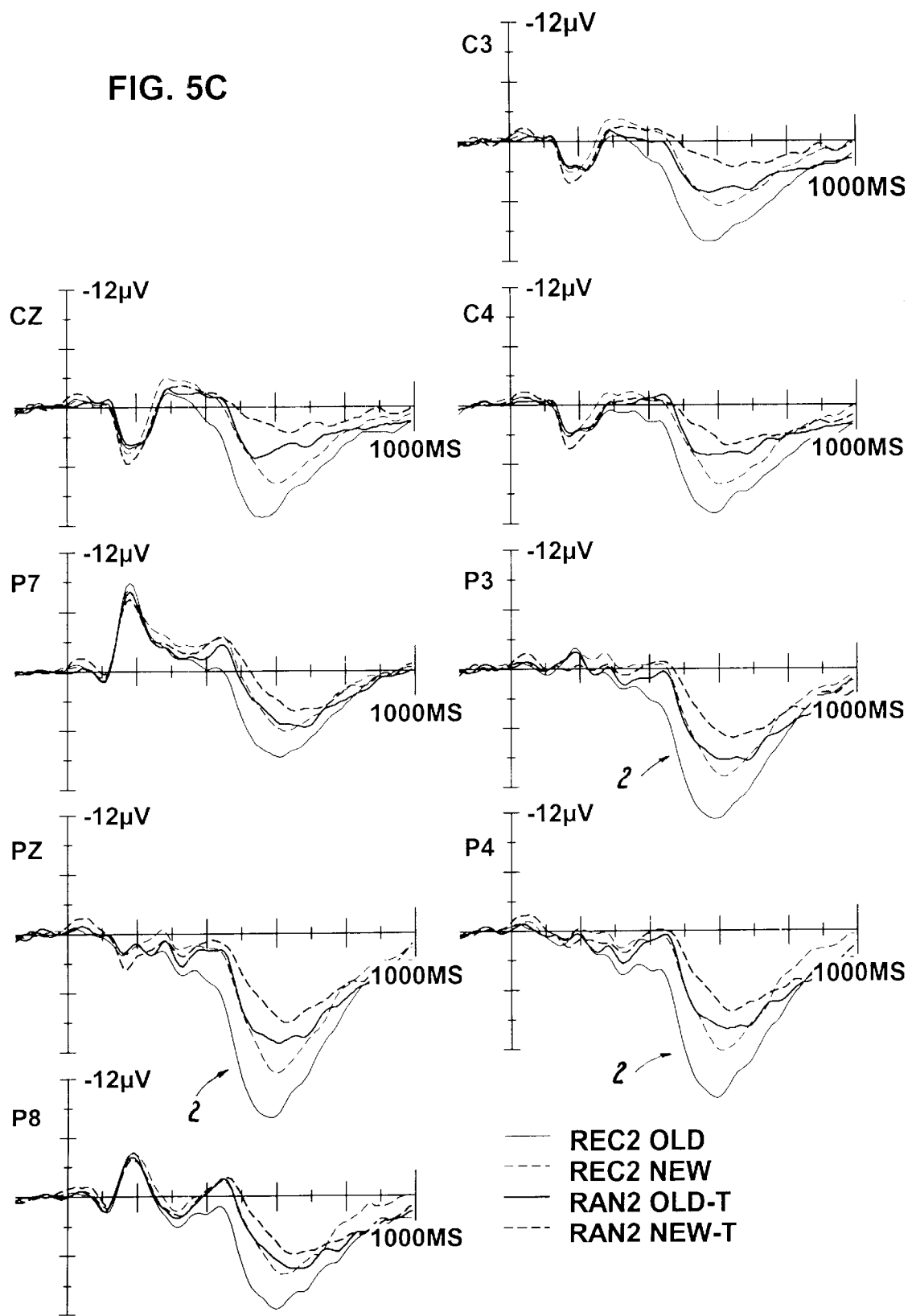
Figure 5D:
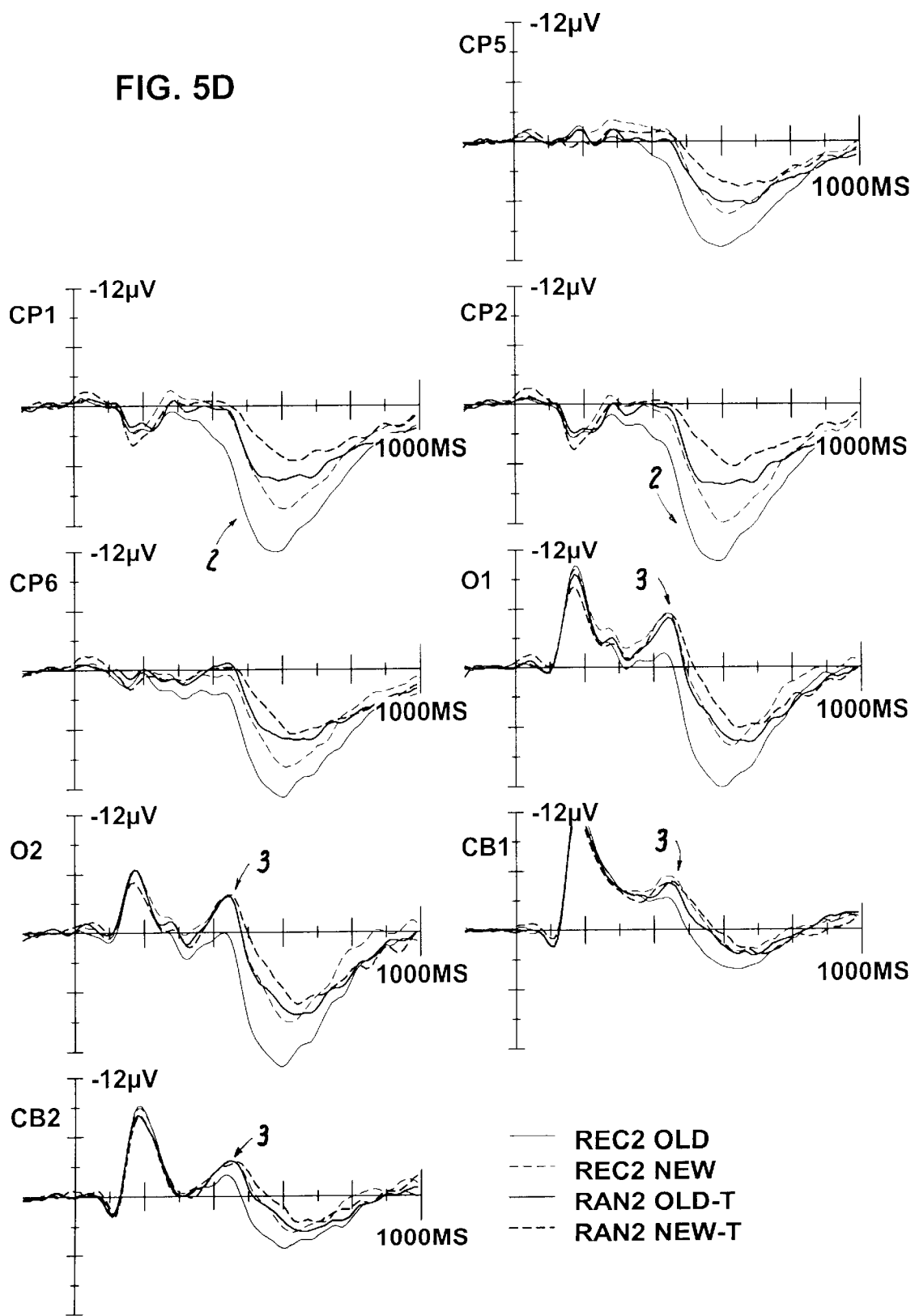
Figure 6A:
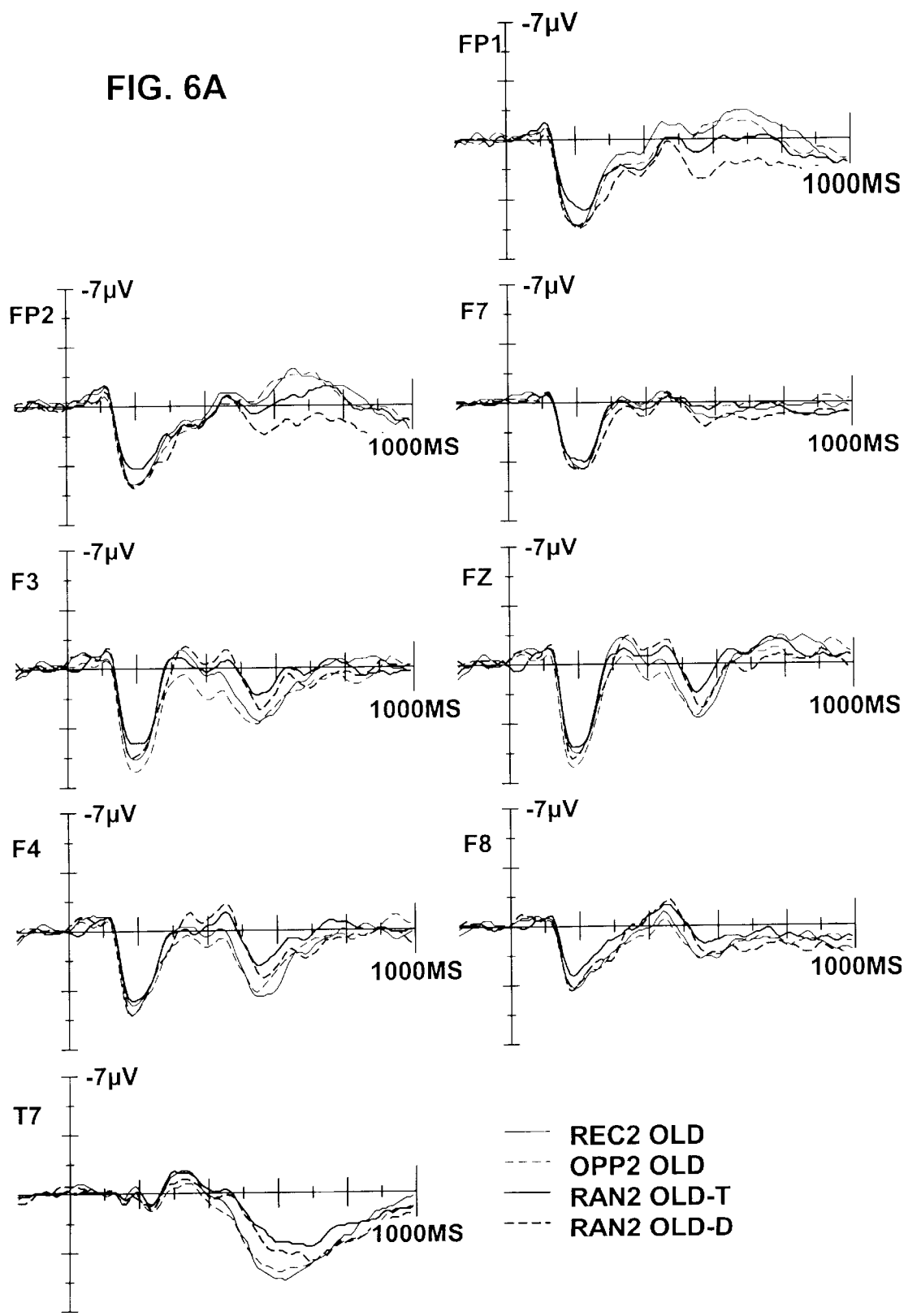
Figure 6B:
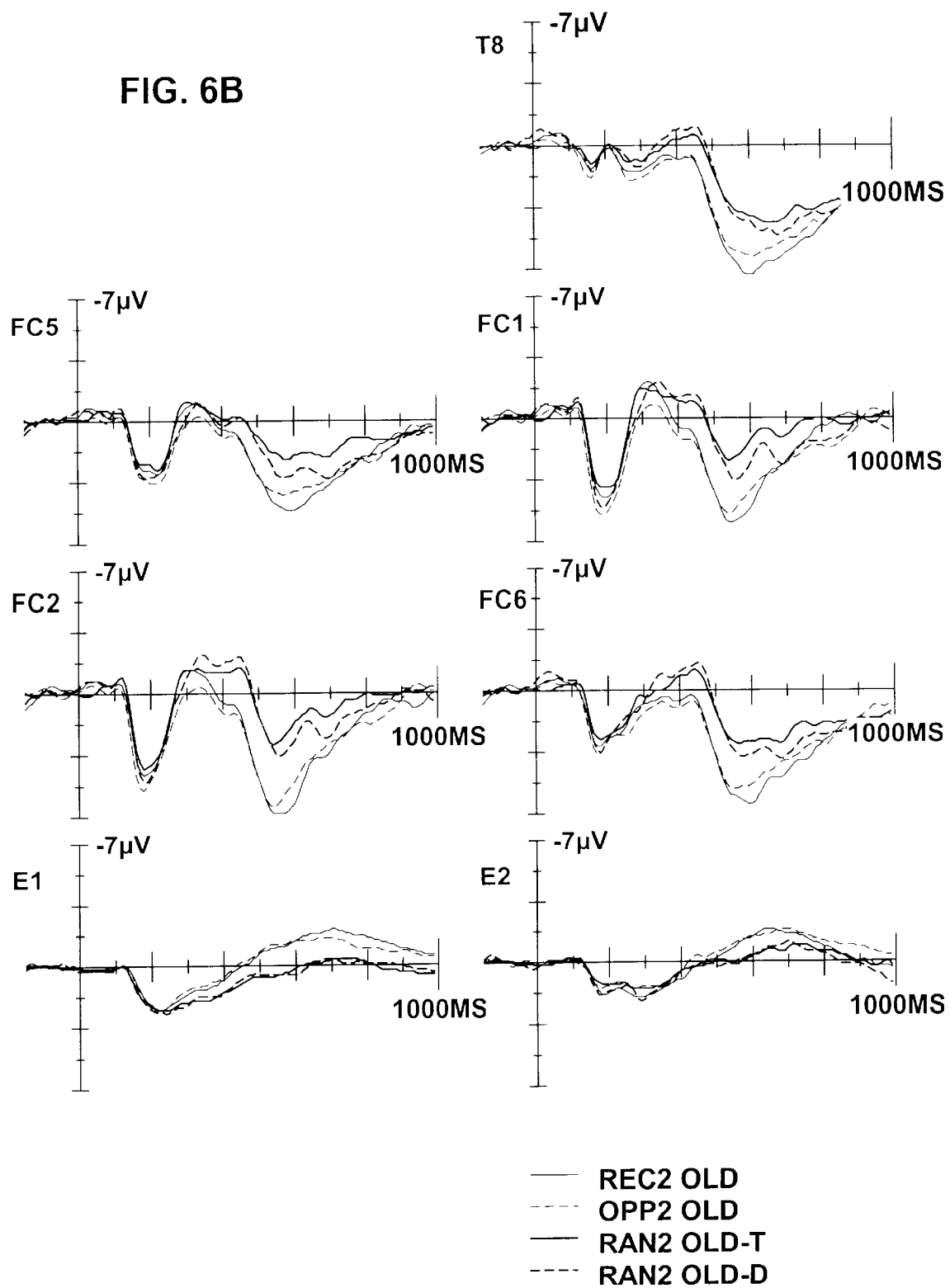
Figure 6C:
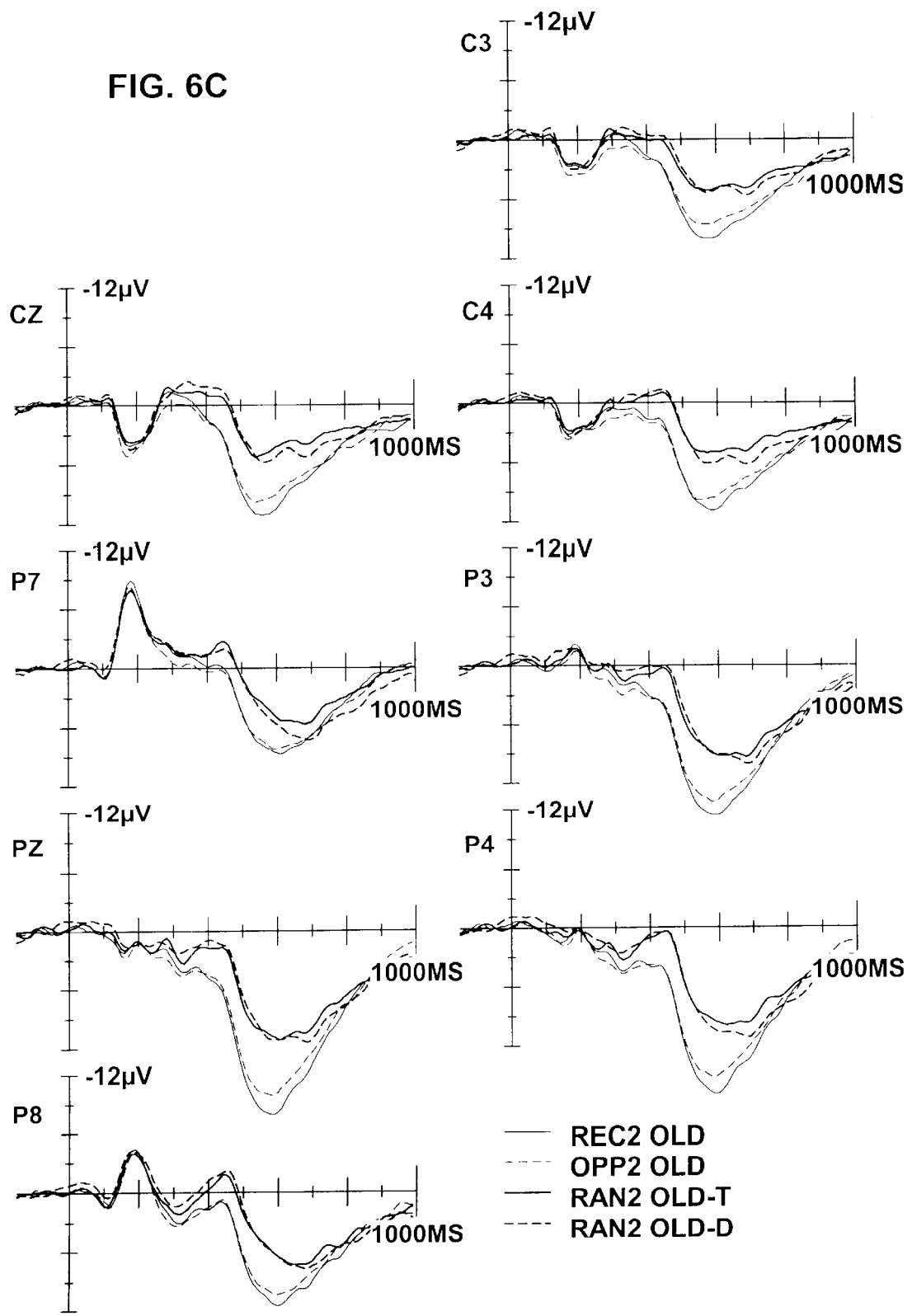
Figure 6D:
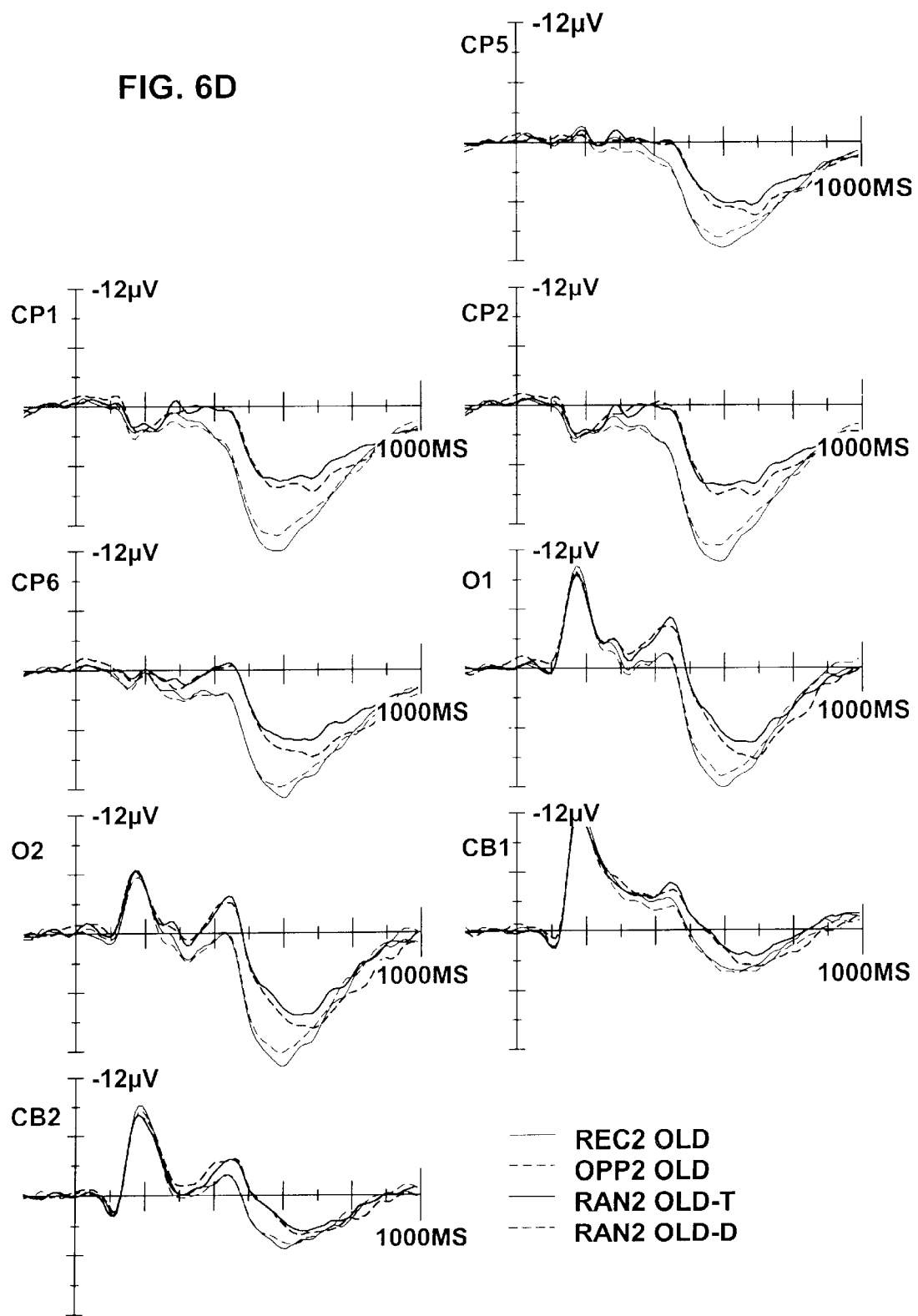

The channel numbers shown in the figure correspond to the electrodes as follows: 1, Fp1; 2, Fp2; 3, F7; 4, F3; 5, Fz; 6, F4; 7, F8; 8, T7; 9, C3; 10, Cz; 11, C4; 12, T8; 13, P7; 14, P3; 15, Pz; 16, P4; 17, P8; 18, O1; 19, O2; 20, E1; 21, E2; 22, Cb1; 23, Cb2; 24, FC5; 25, FC1; 26, FC2; 27, FC6; 28, Cp5; 29, Cp1; 30, Cp2; and 31, Cp6.

FIGS. 2–32 show ERP recordings which illustrate the various markers of deception described below. Plots of stimulus-locked averages are denoted with a S; plots of response-locked averages are denoted with a R. Plots that embody more than one deception marker have arrows pointing to the peak identifying the marker; the marker number is also indicated. Negative voltages are plotted as upward deflections.

FIGS. 2–21 show multiple plots of the recordings from 31 channels; the waveforms are arranged topographically with the front of the head at the top.

Abbreviations/definitions:

RL500=response-locked average calculated on all the individual-trial data that were shifted such that the time of the response was synchronized to the 500 ms mark. For example, before averaging, a trial with an RT of 420 ms would be shifted 80 ms to the right while a trial with an RT for 540 ms would be shifted 40 ms to the left.

RECn=Truthful recognition condition; n=1st or 2nd repetitions

OPPn=Opposite condition; n=1st or 2nd repetitions

RANn=Random condition; n=1st or 2nd repetitions

Control-Compatible=Control condition using the words "left" and "right" in which subjects responded compatibly (e.g., pressed left button for "left")

Control-Incompatible=Control condition using the words left and right in which subjects responded incompatibly (e.g., pressed right button for "left")

OLD=words in personal (episodic) memory

NEW=words not in personal (episodic) memory

OLD-T=old words in the Random condition to which subjects responded truthfully

OLD-D=old words in the Random condition to which subjects responded deceptively

NEW-T=new words in the Random condition to which subjects responded truthfully

NEW-D=new words in the Random condition to which subjects responded deceptively

CATCH=catch trials

FIG. 2. REC2 Old/OPP2 OLD/RAN2 OLD-T/RAN2 OLD-D. Marker 1, Response locked ERPs, $1^{st}$ plot. This figure shows the ERPs to old words in the three conditions (Truthful, Opposite, Random). Arrows indicate peaks corresponding to marker numbers 1, 2, 4 and 5 on recordings from electrodes Fz, Fc1, Fc2, Cz, Cp2, P4, Pz, P3, Cp1, O1, O2.

FIG. 3. REC2 NEW/OPP2 NEW/RAN2 NEW-T/RAN2 NEW-D. Marker 1 Response-Locked ERPs, 2nd plot. This figure shows the ERPs to new words in the three conditions (Truthful, Opposite, Random). Peaks are the same as indicated in FIG. 2.

FIG. 4. REC2 OLD/REC2 NEW/RAN2 OLD-T/RAN2 NEW-T. Marker 1, Response-Locked ERPs, 3rd plot. This figure shows the ERPs to old and new words in the Truthful and Random conditions. Peaks are the same as indicated in FIG. 2.

FIG. 5. REC2 OLD/REC2 NEW/RAN2 OLD-T/RAN2 NEW-T. Marker 2, Stimulus-Locked ERPs, 1st plot. This figure shows the ERPs to old and new words in the Truthful and Random conditions. Arrows indicate peaks corresponding to marker numbers 2 and 3 in recordings from electrodes Cp1, Cp2, Pz, P3, P4, O1, O2, Cb1, Cb2.

FIG. 6. REC2 Old/OPP2 OLD/RAN2 OLD-T/RAN2 OLD-D. Marker 2, Stimulus-Locked ERPs, 3rd plot. This figure shows the ERPs to old words in the three conditions (Truthful, Opposite, Random). Peaks are the same as indicated in FIG. 5.

Figure 7A:
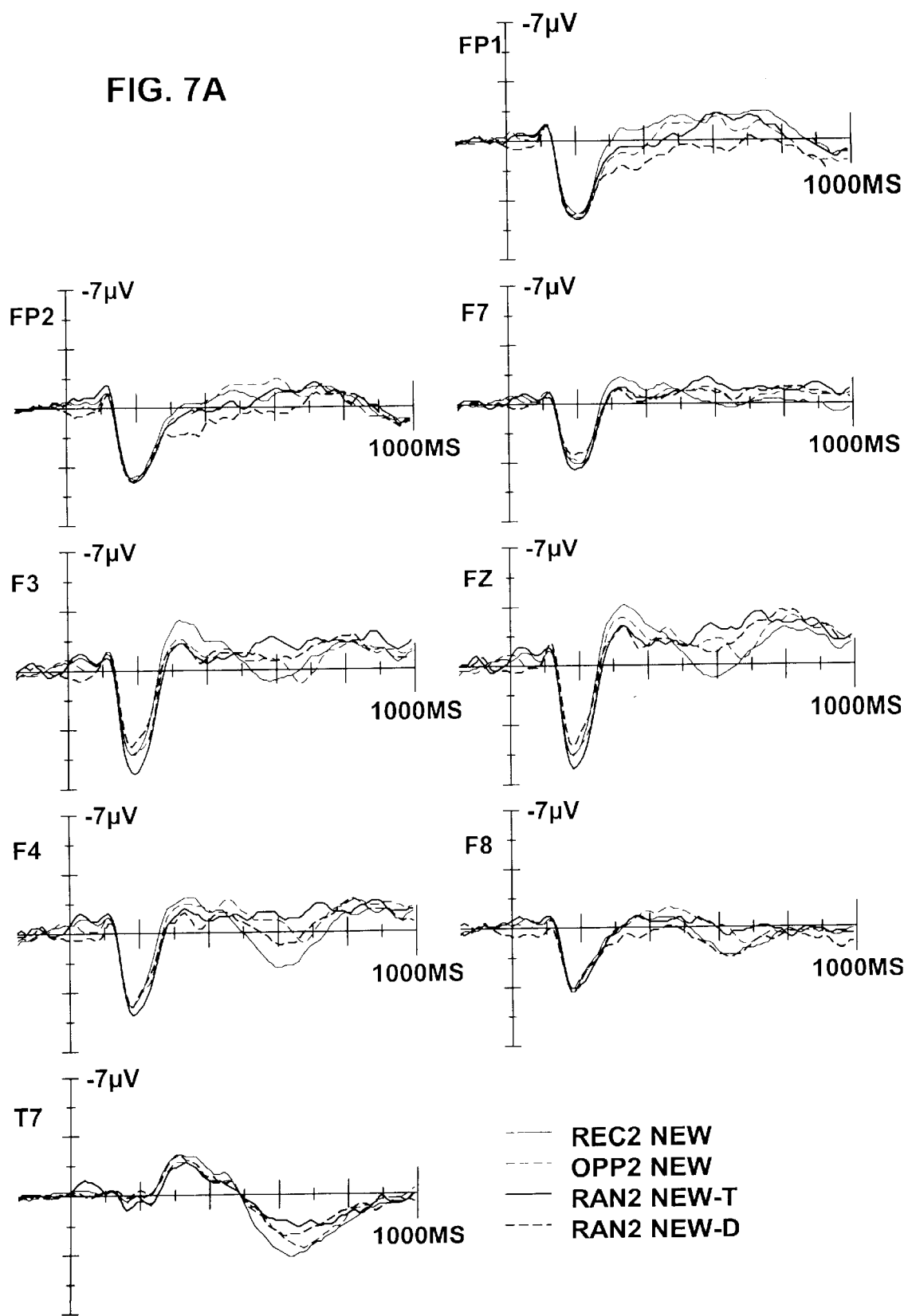
Figure 7B:
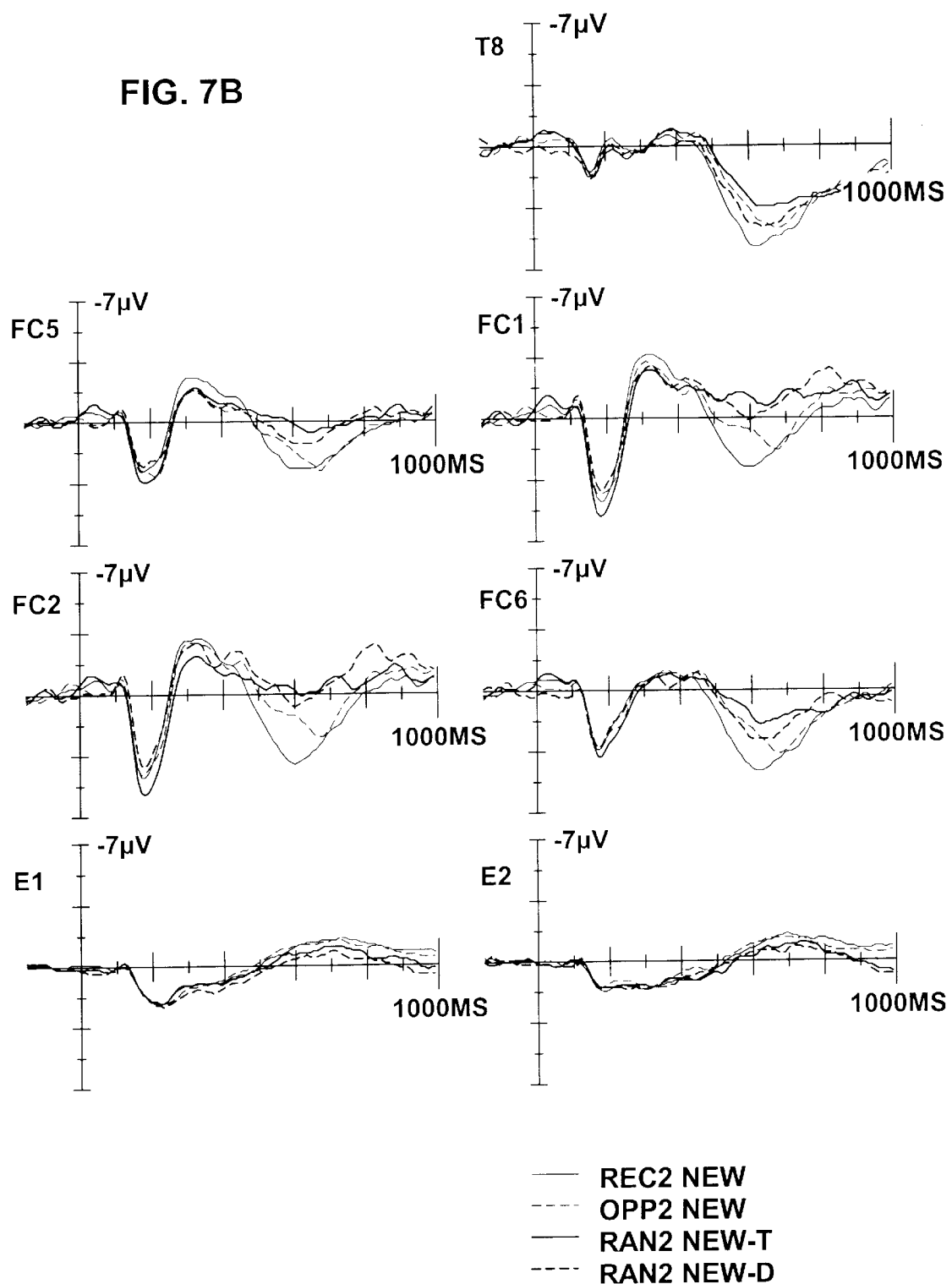
Figure 7D:
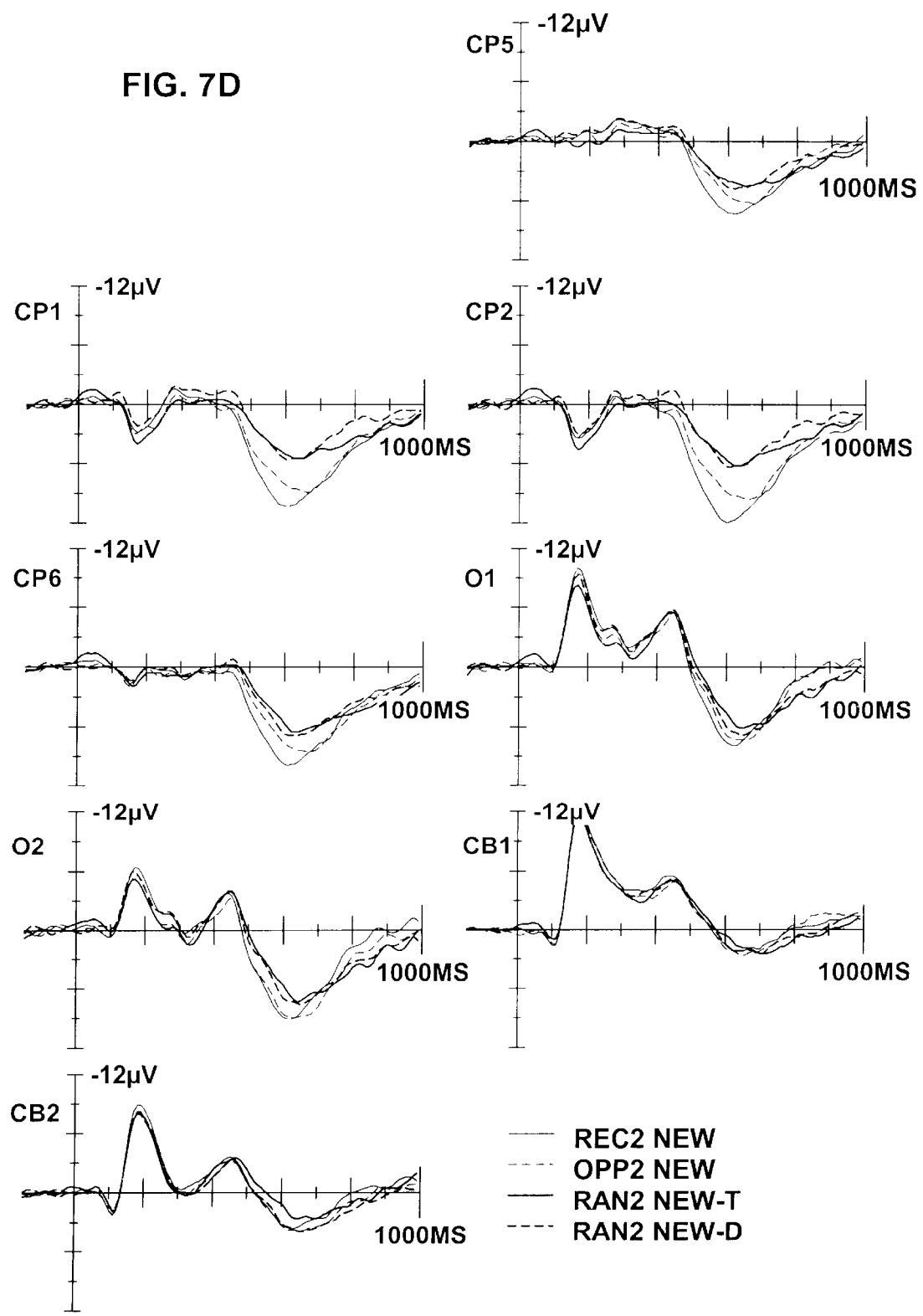
Figure 8A:
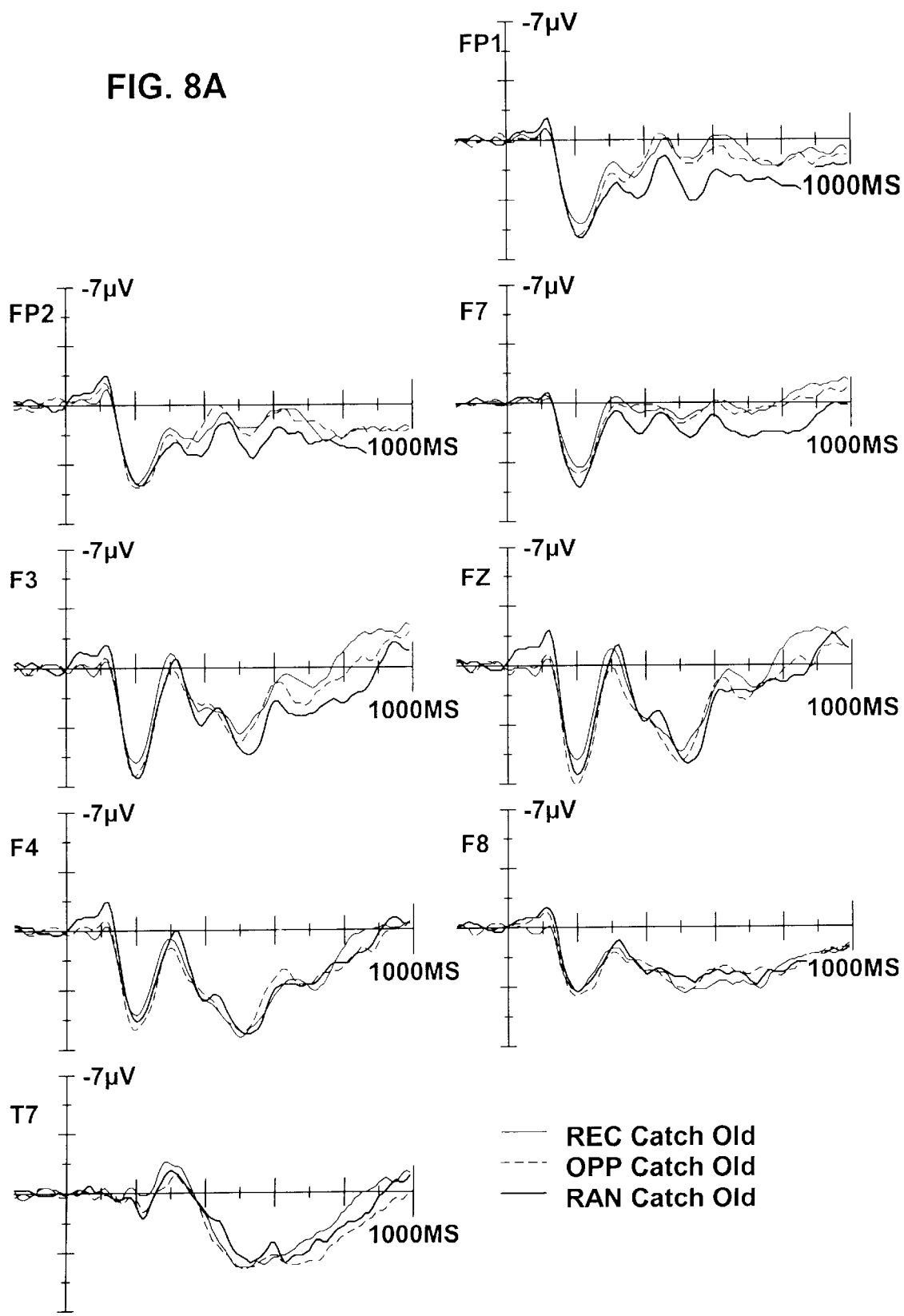
Figure 8B:
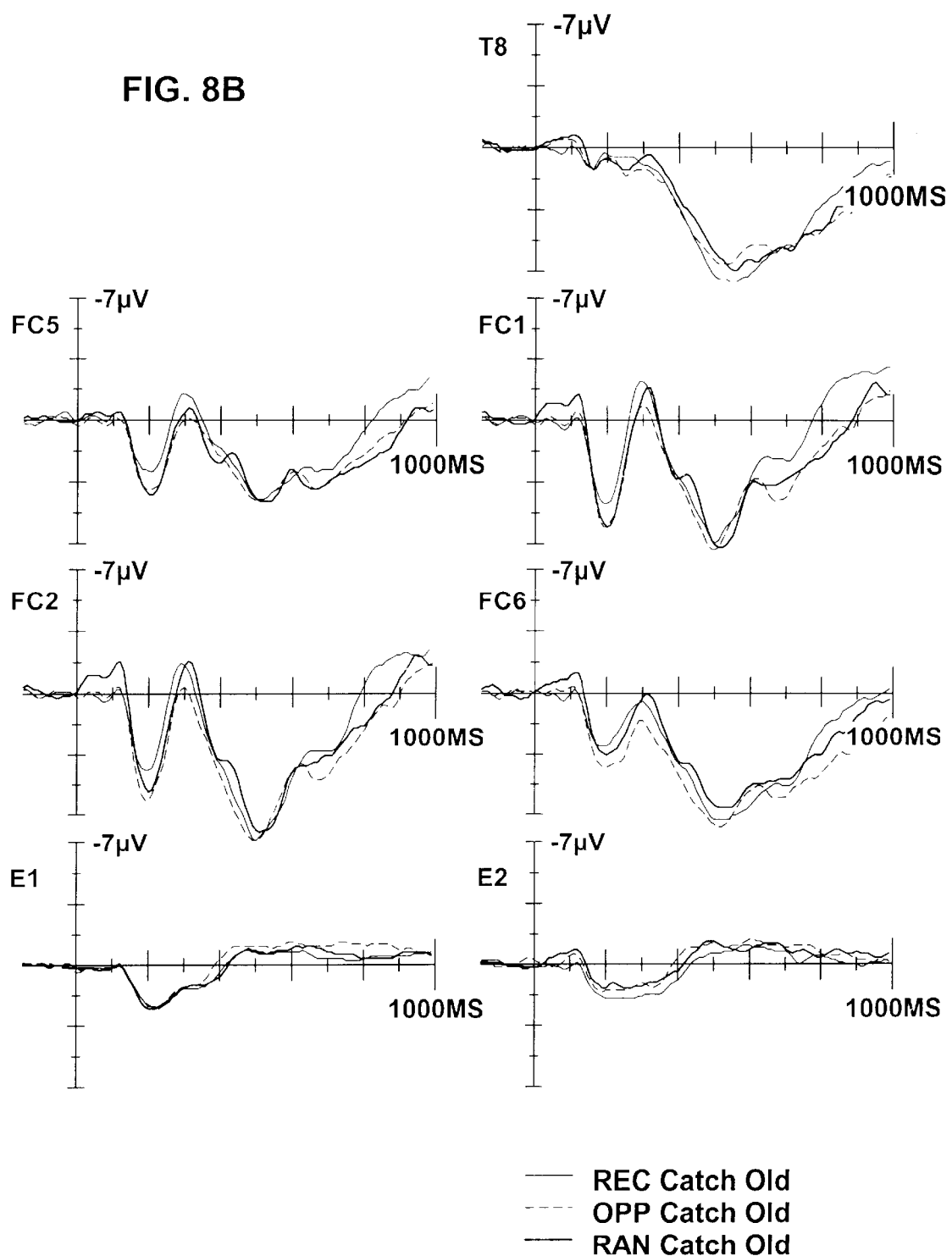
Figure 8C:
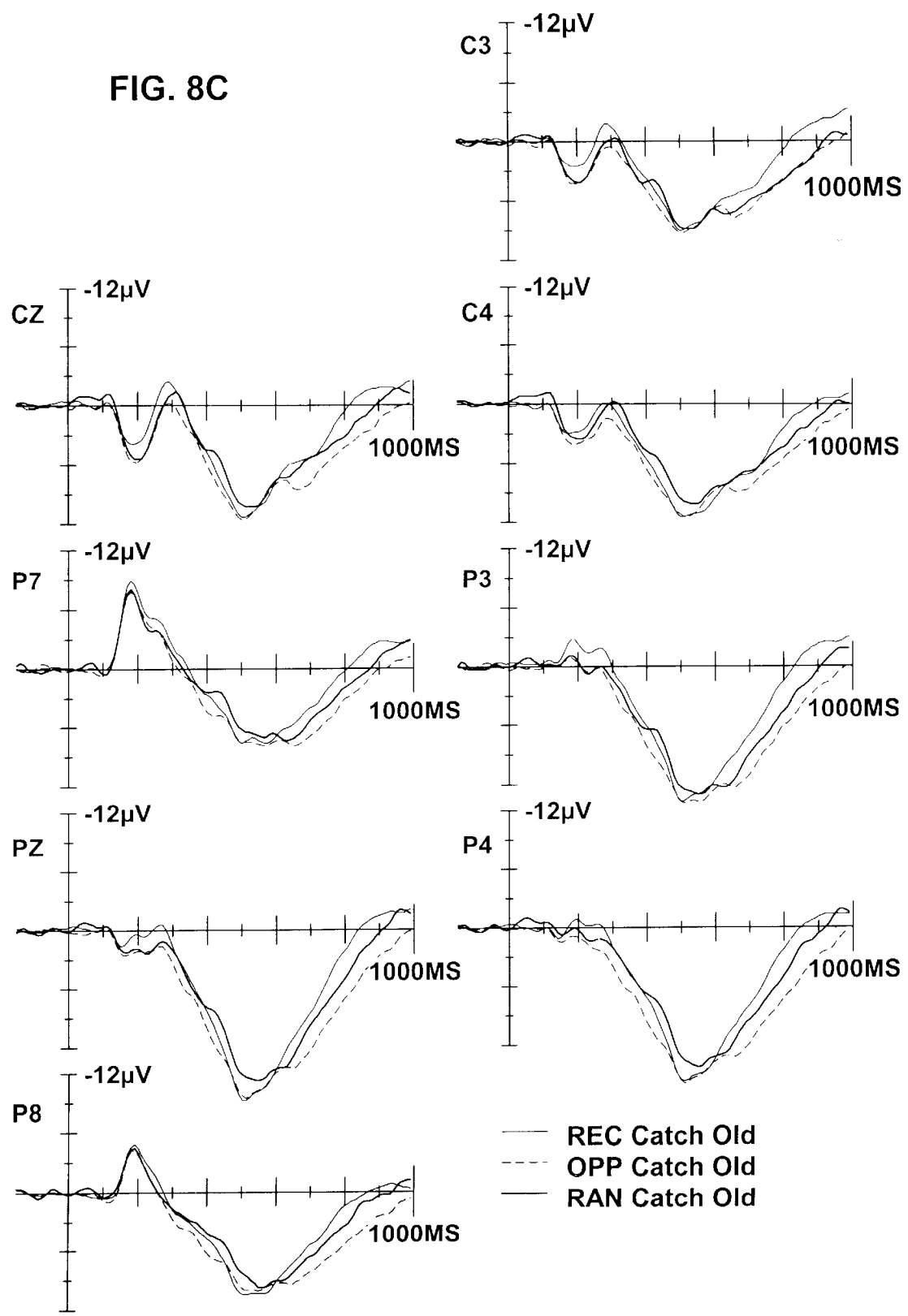
Figure 8D:
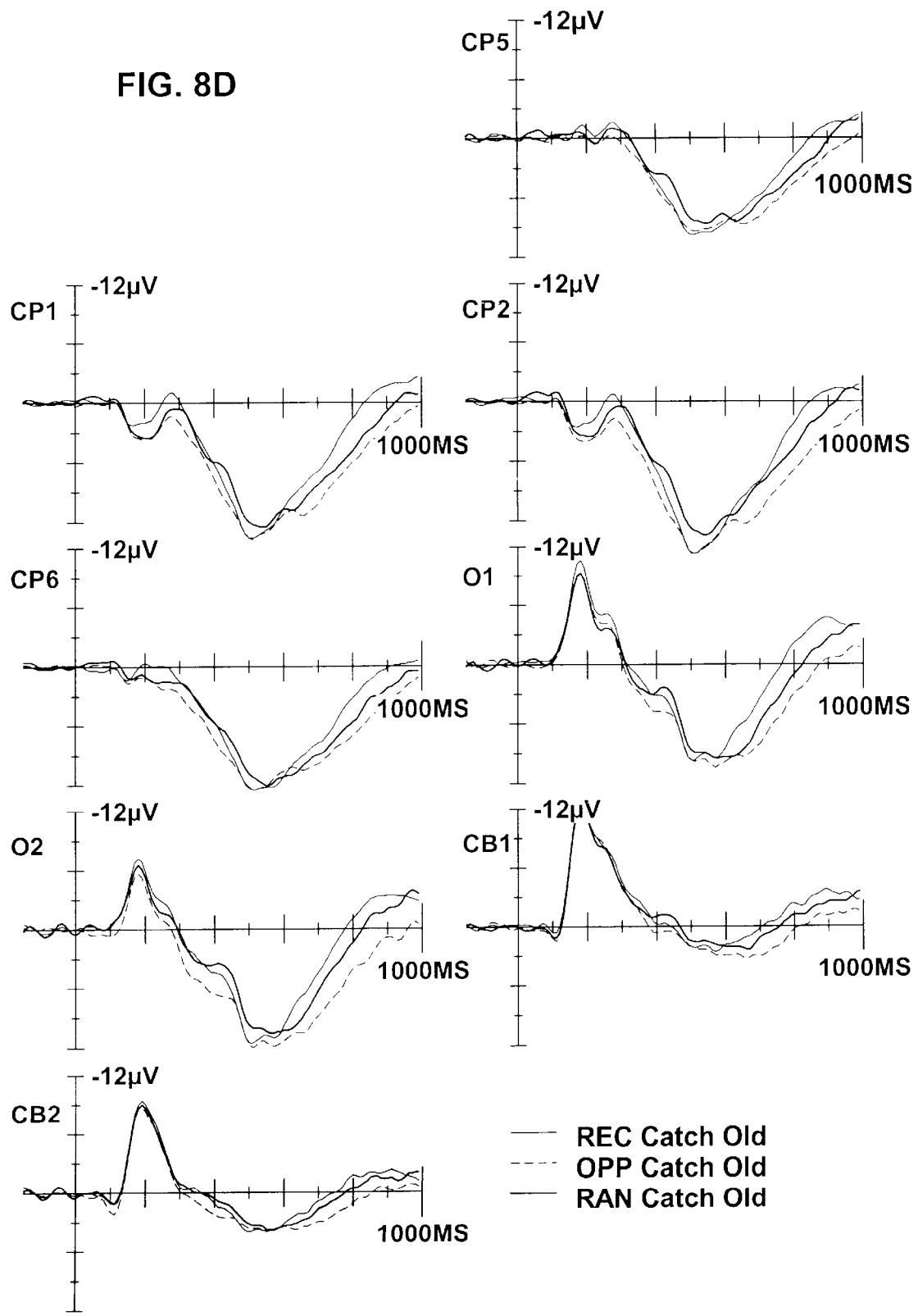
Figure 9A:
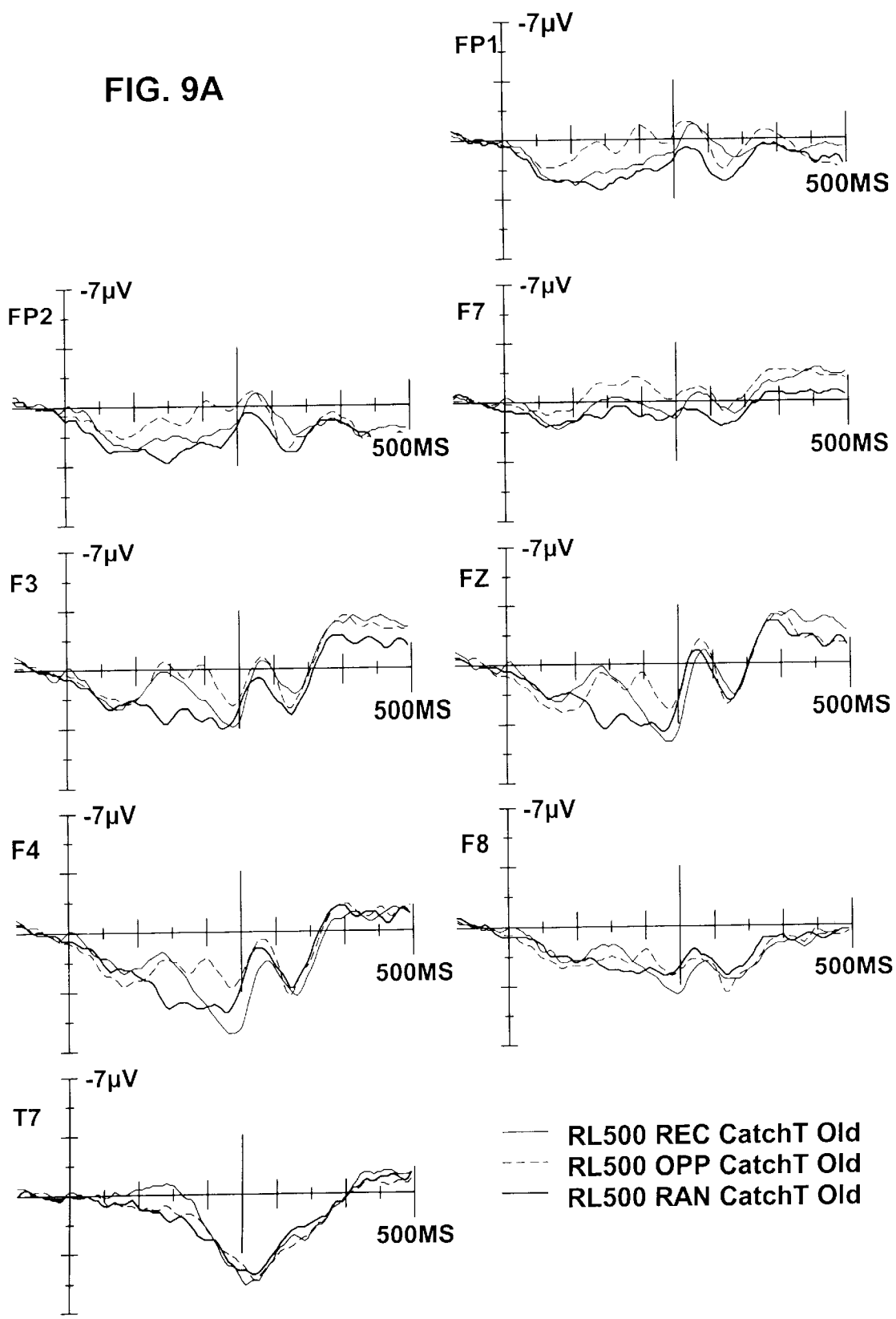
Figure 9B:
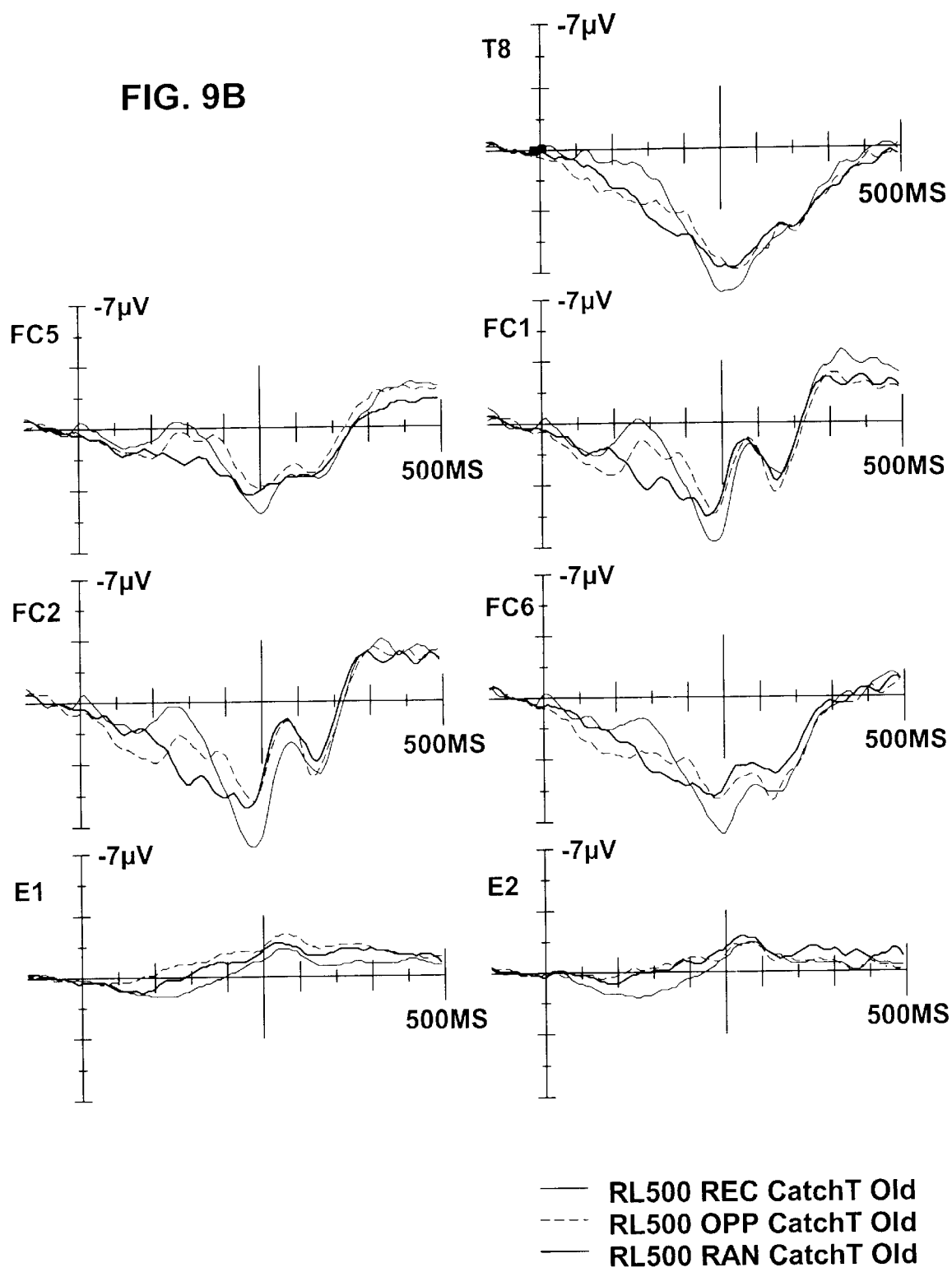
Figure 9C:
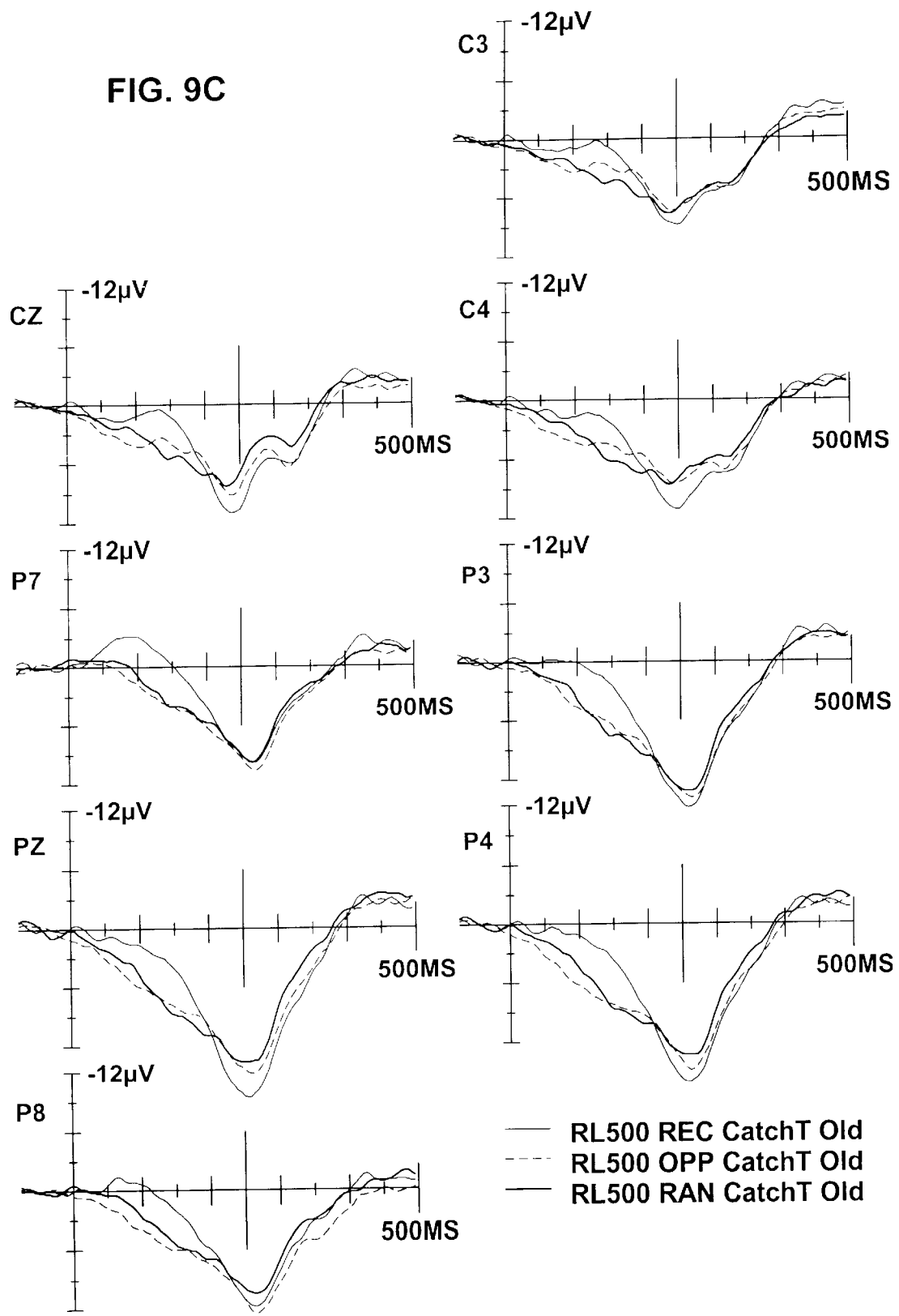
Figure 9D:
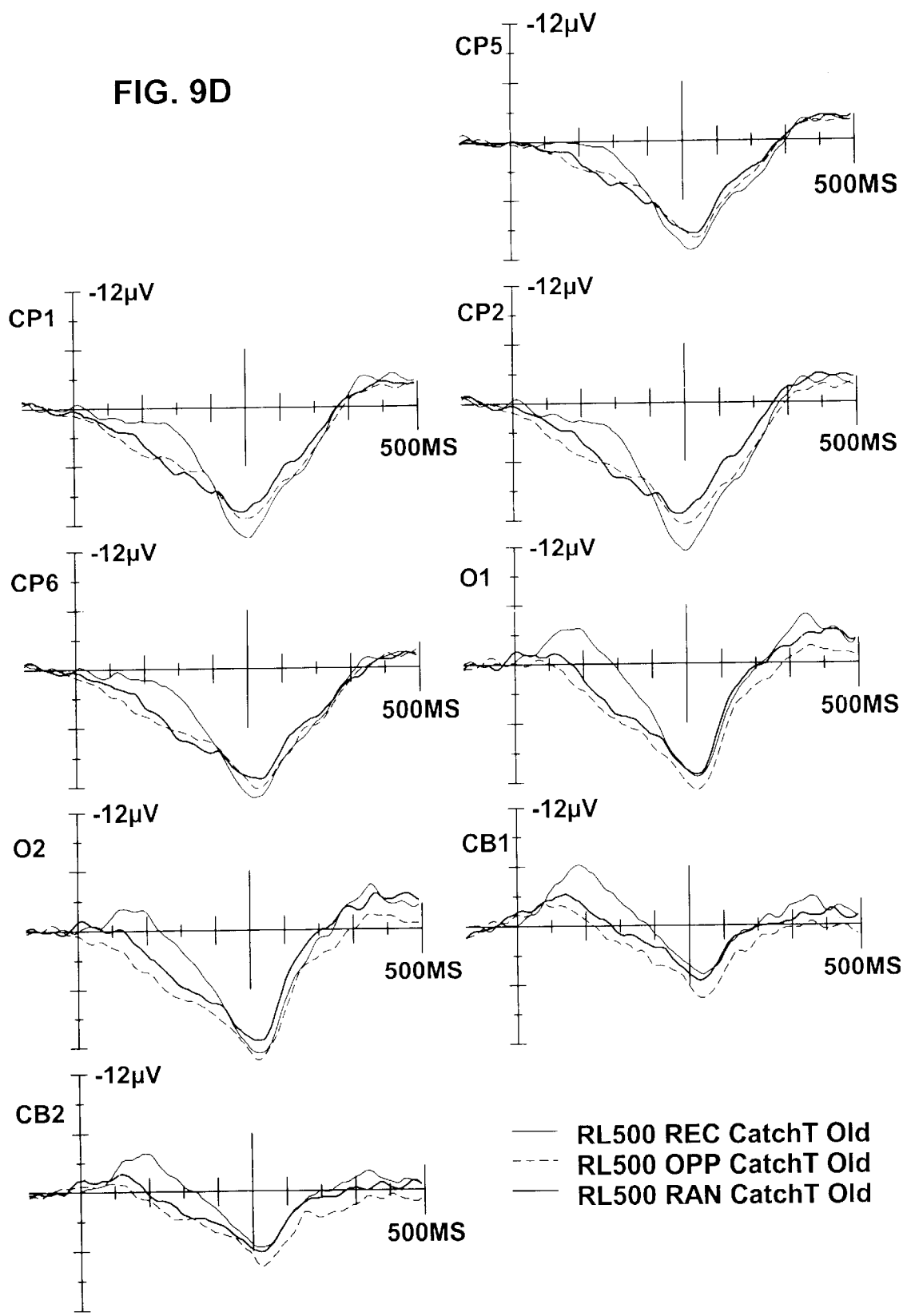
Figure 10A:
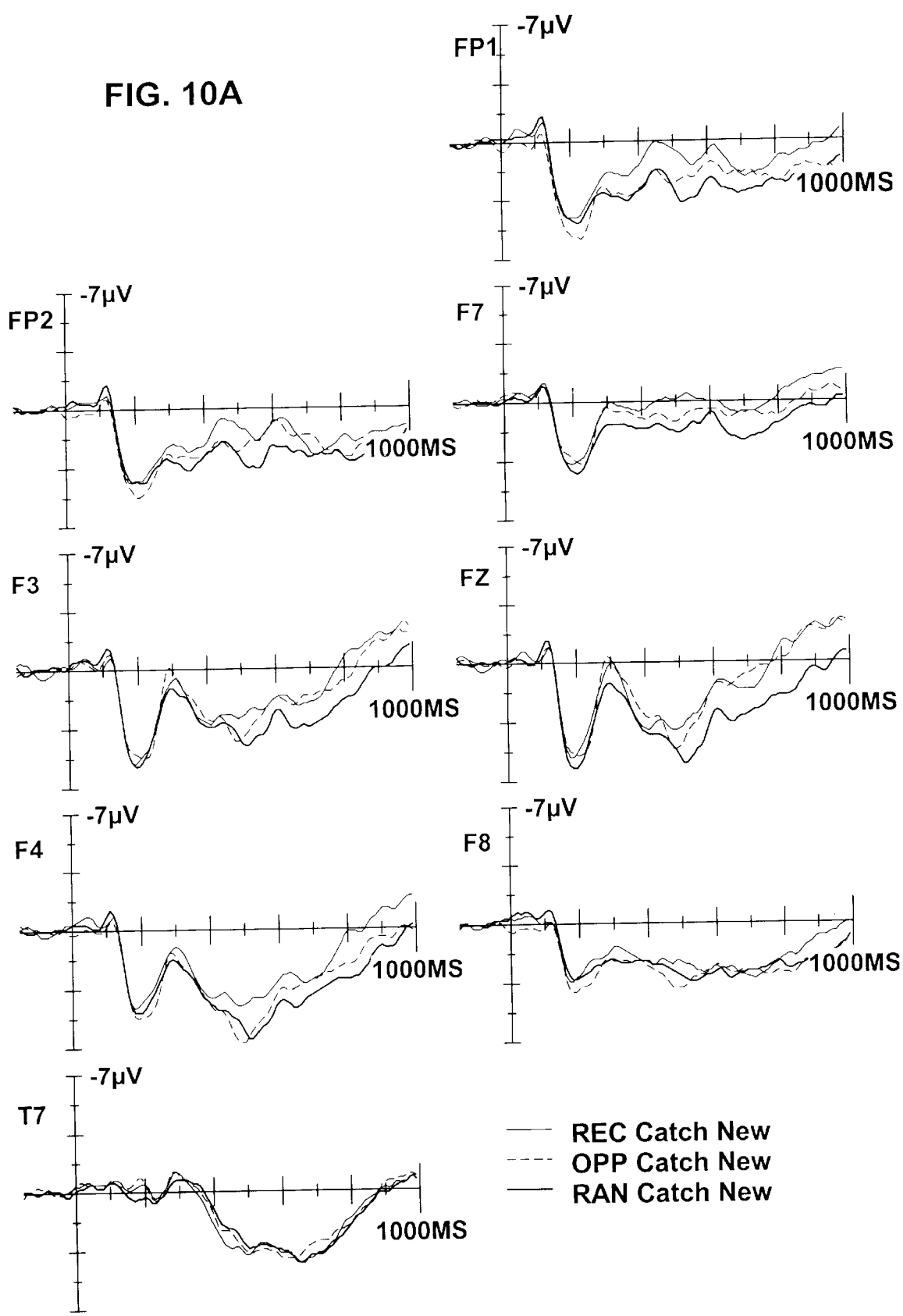
Figure 10B:
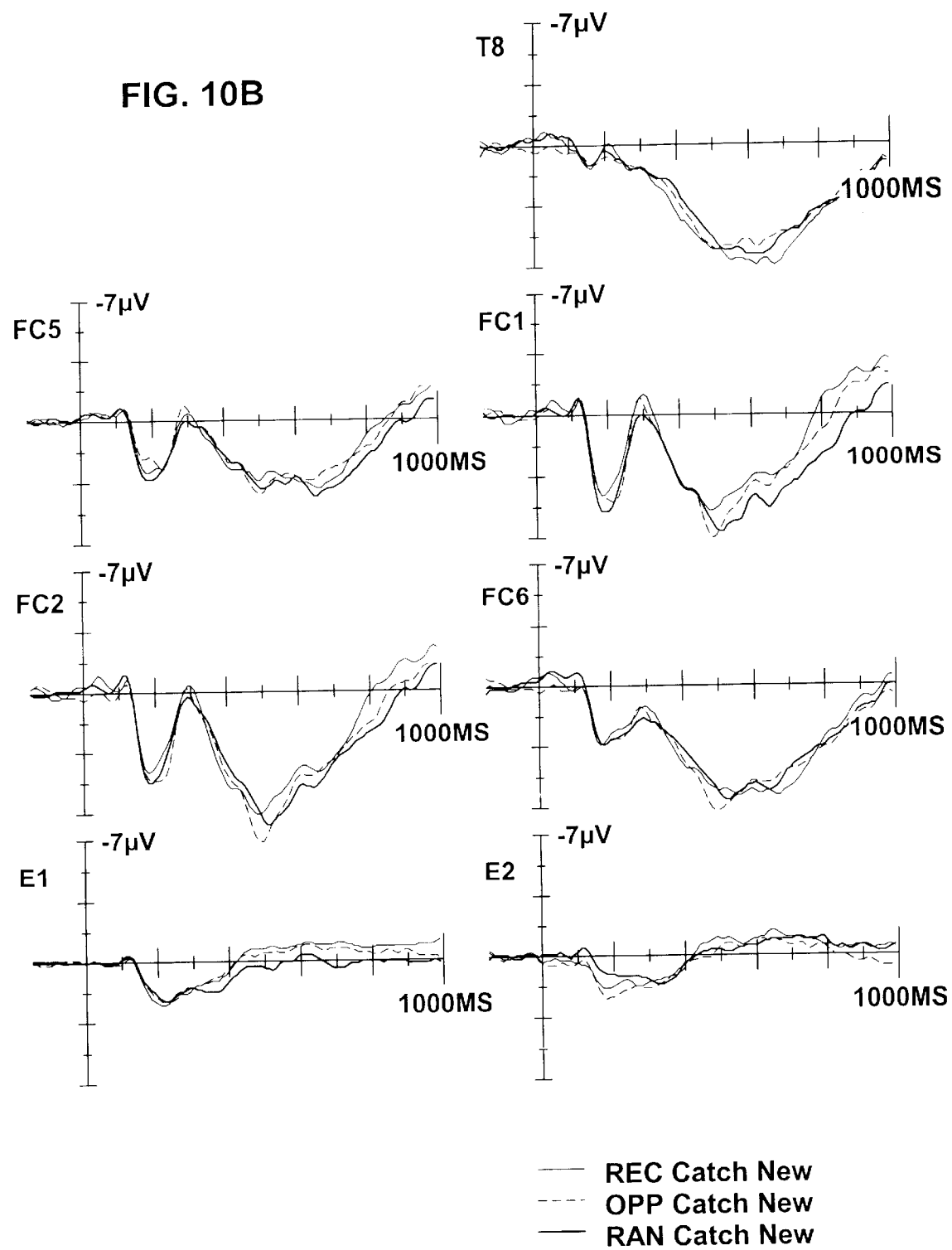
Figure 10C:
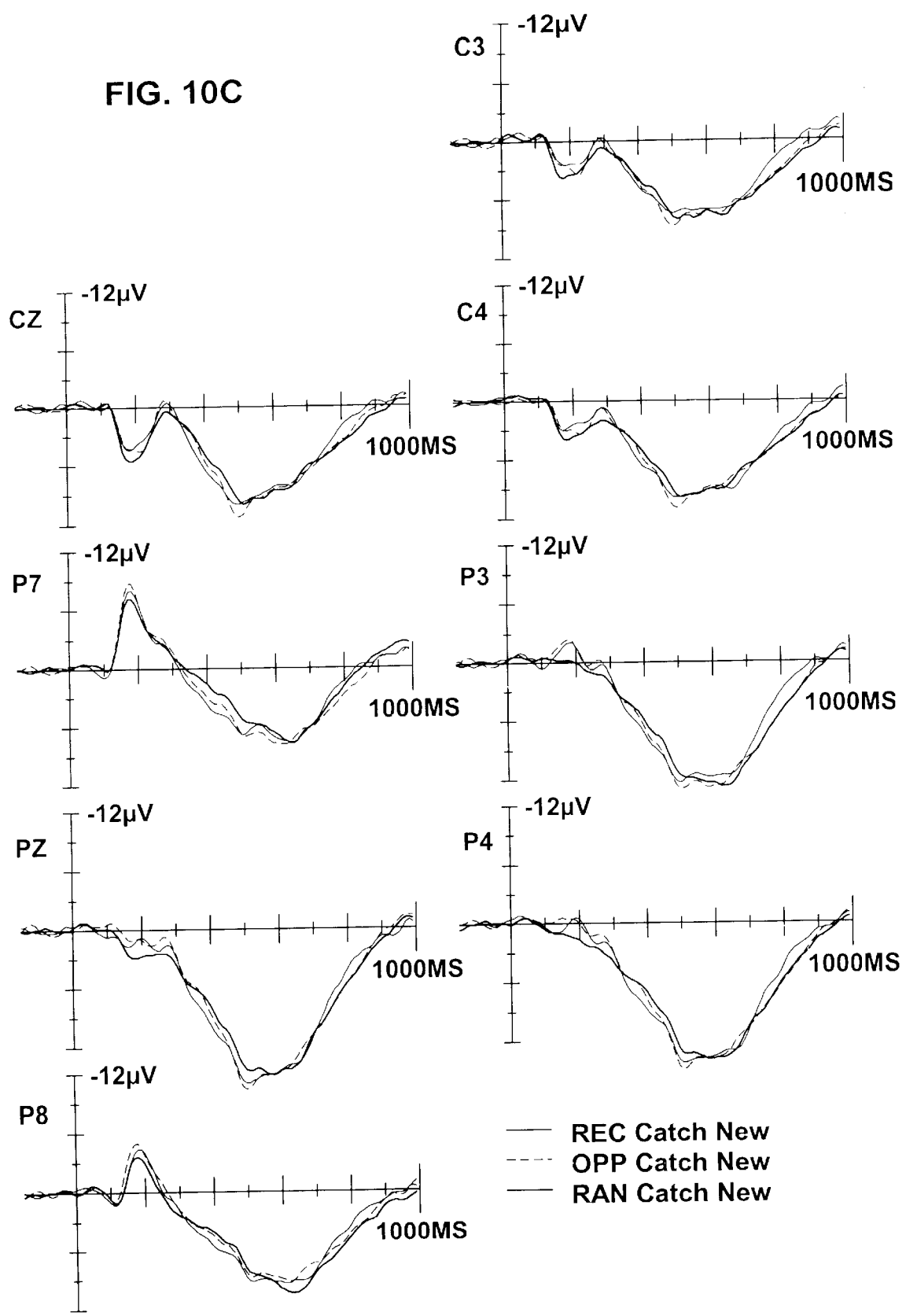
Figure 10D:
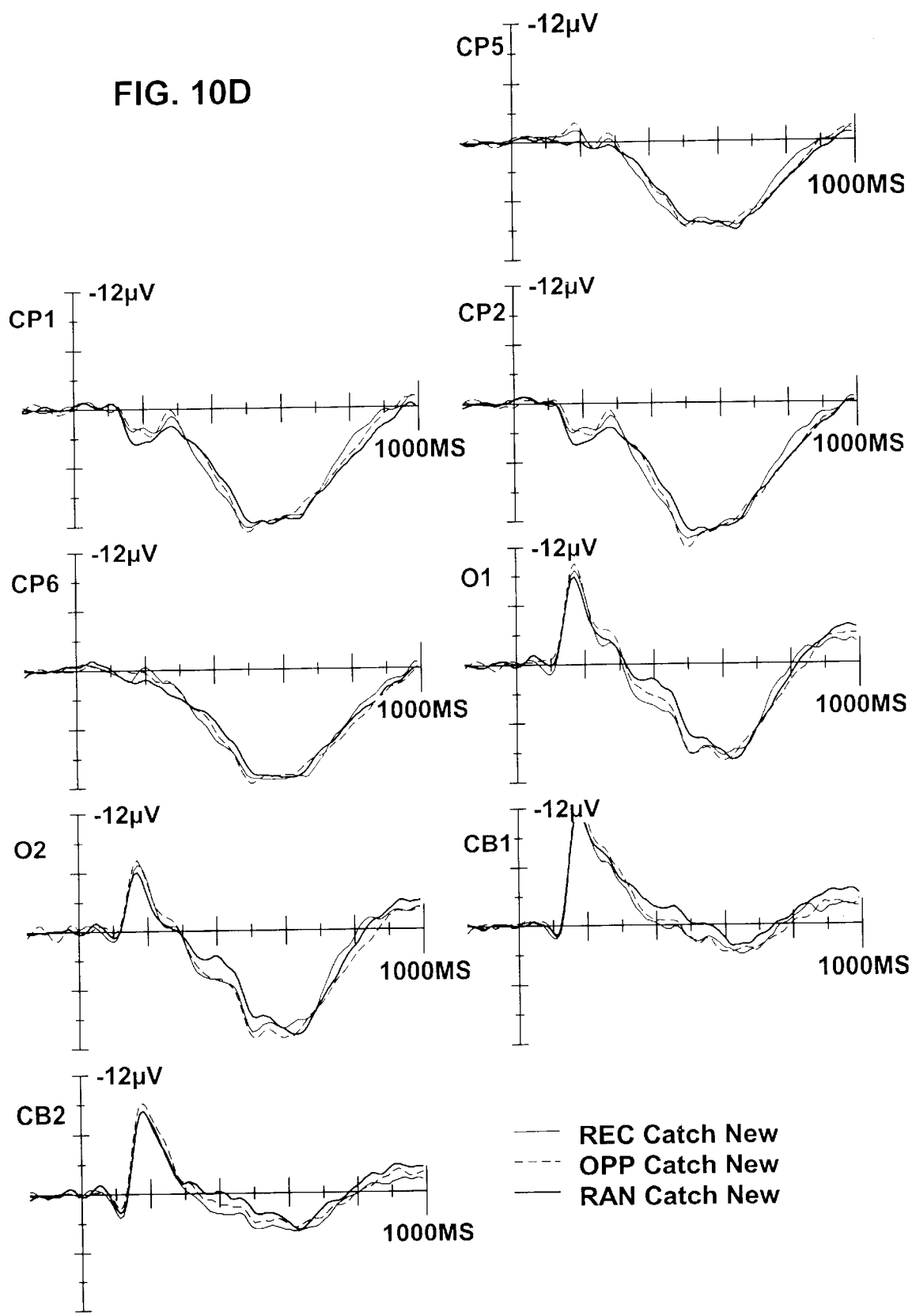
Figure 11A:
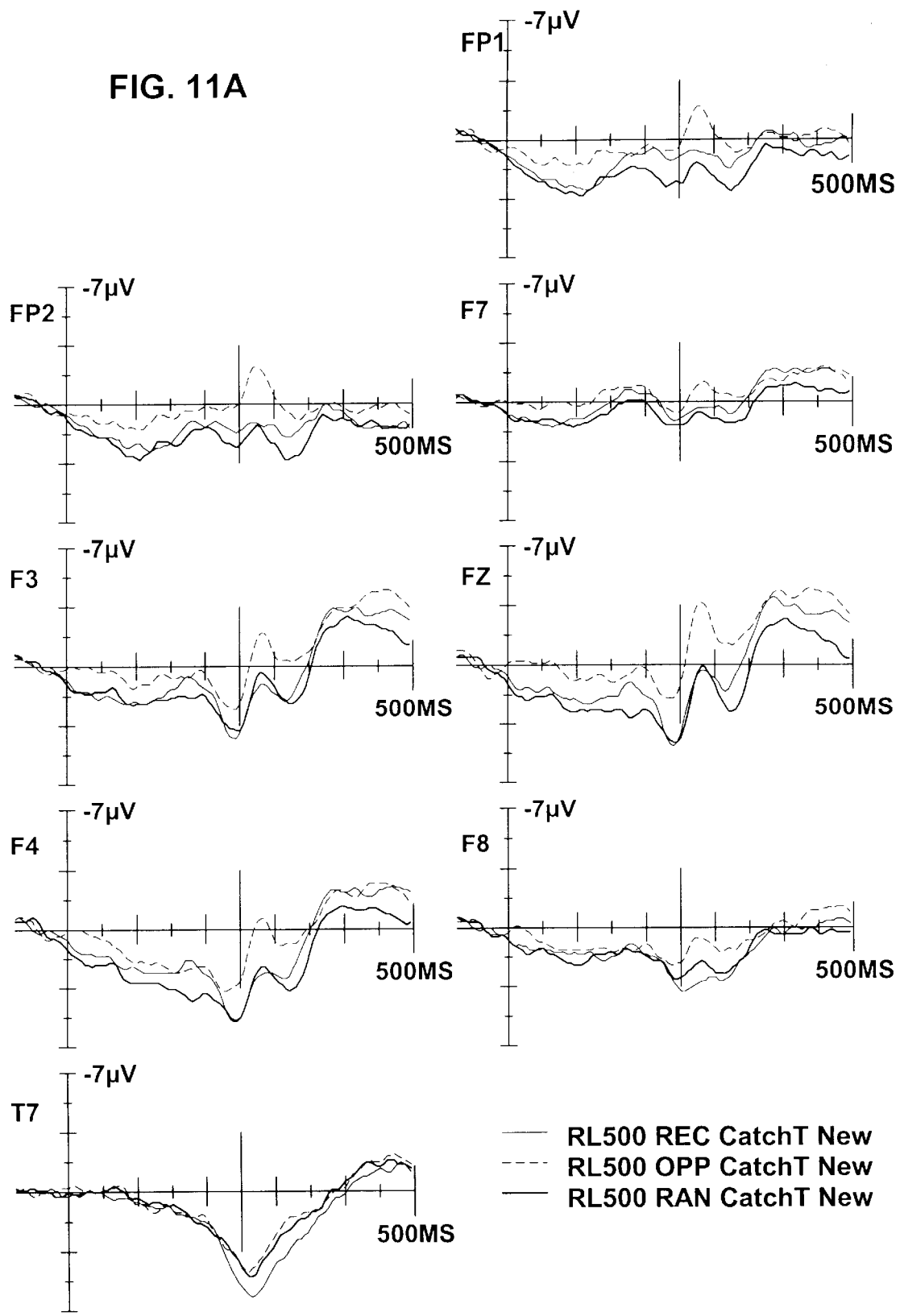
Figure 11B:
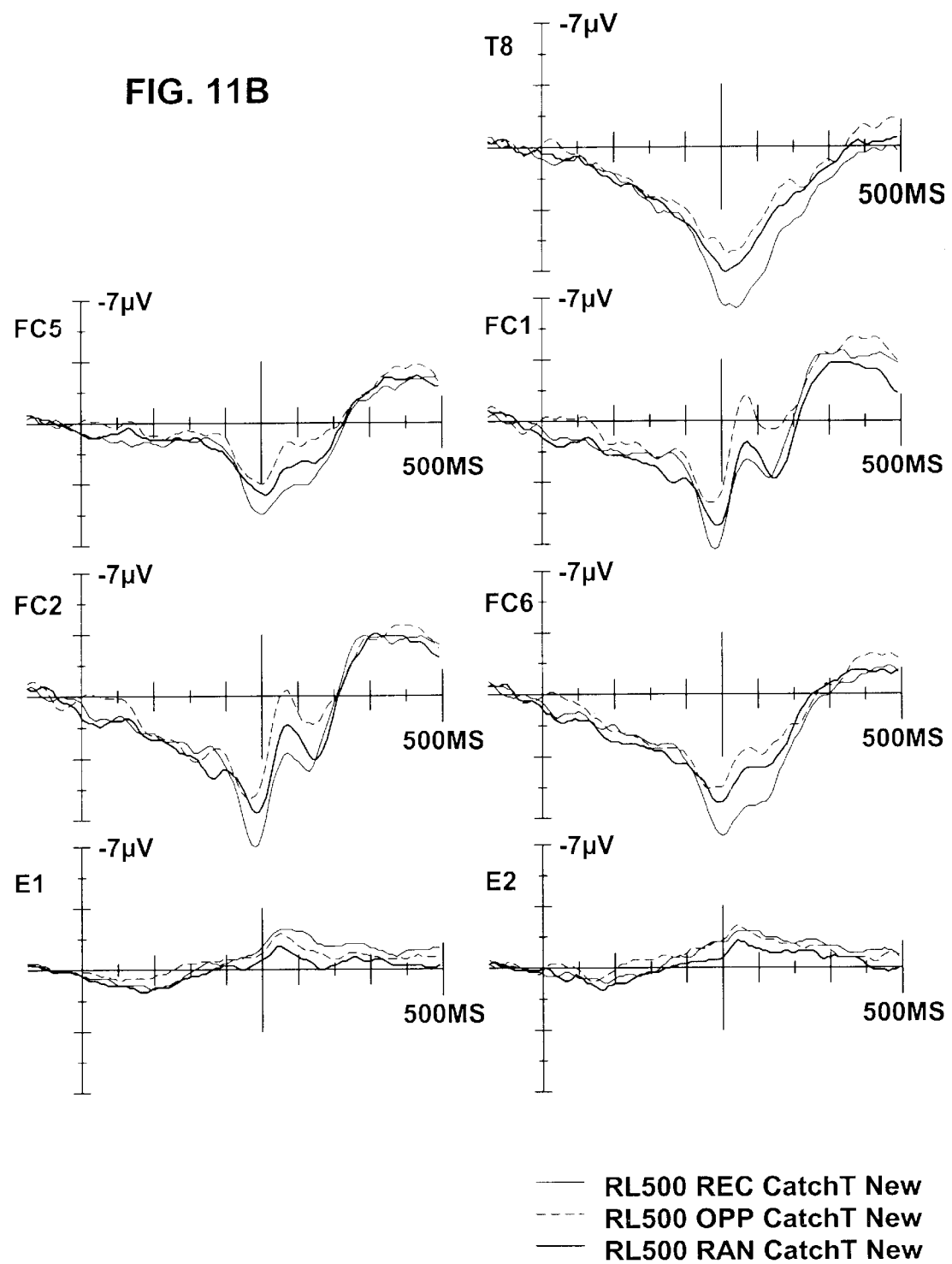
Figure 11C:
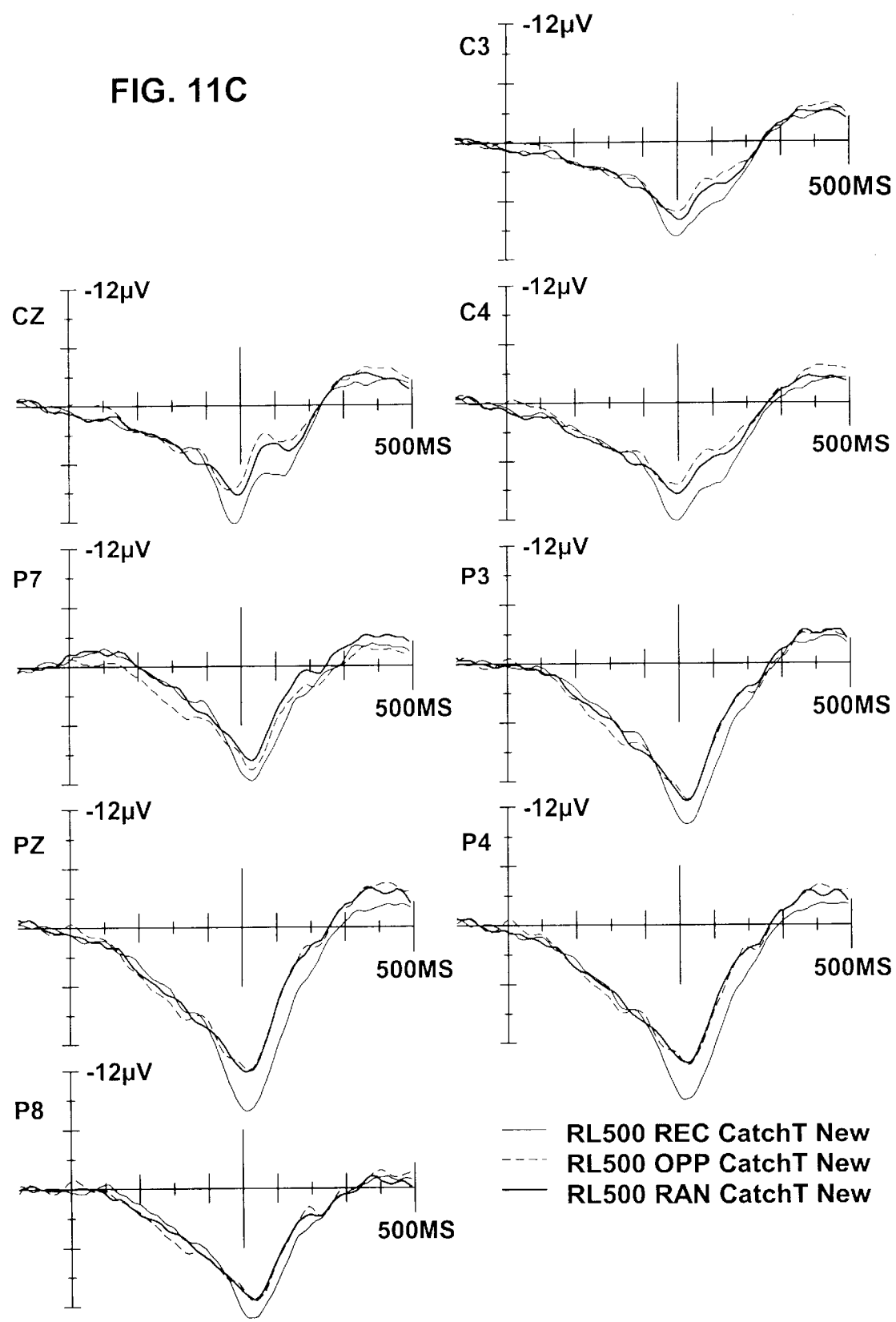
Figure 11D:
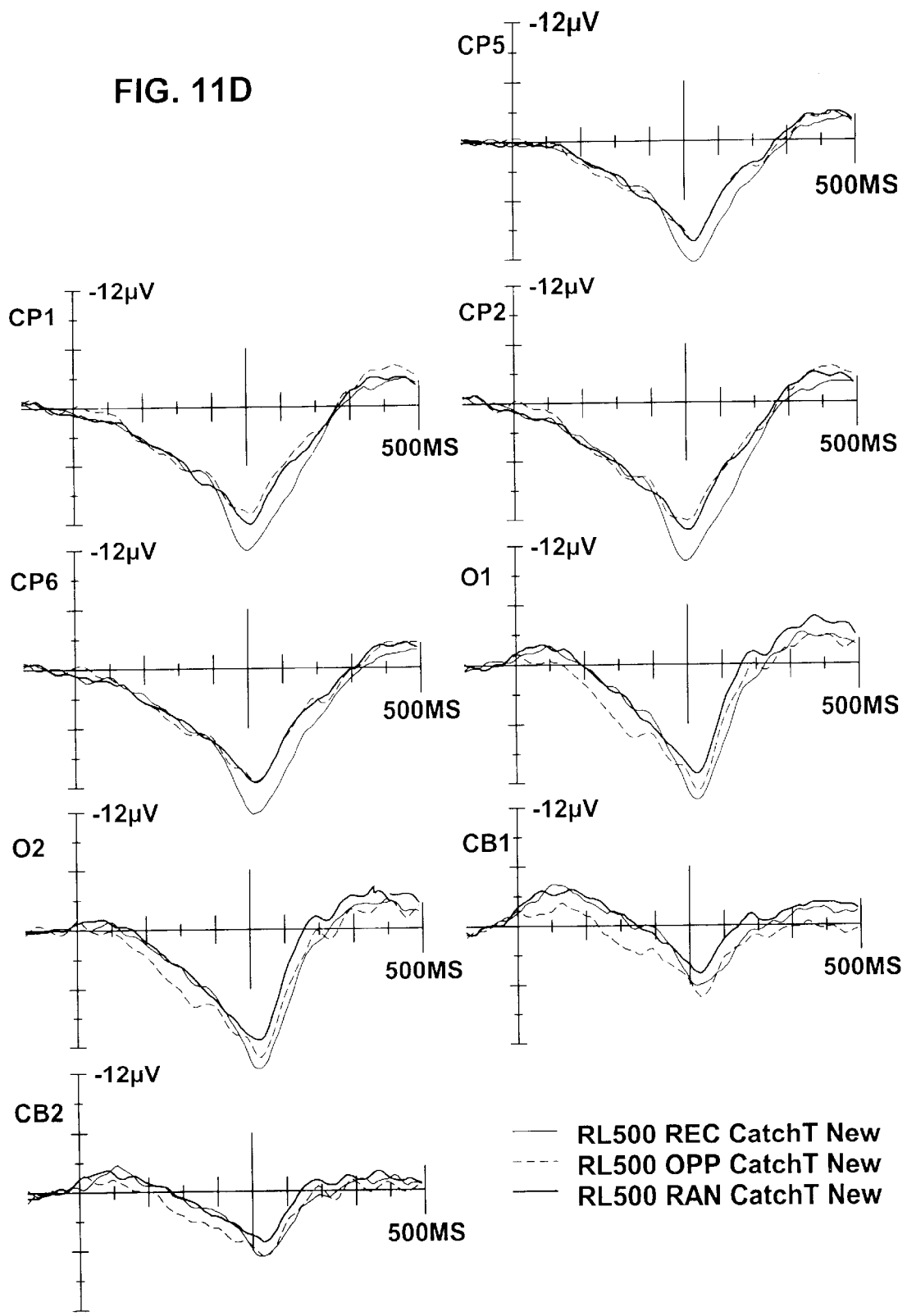
Figure 12A:
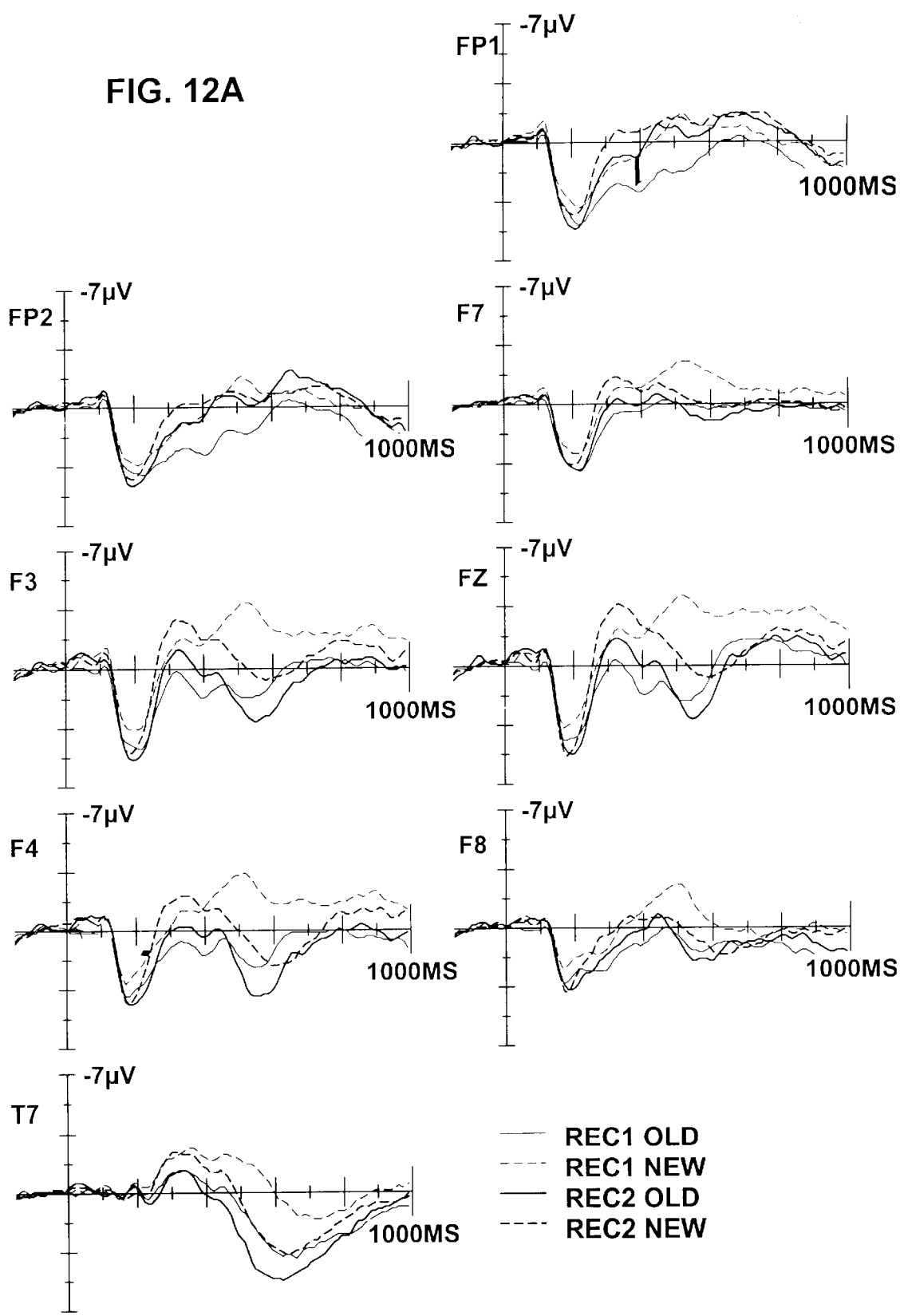
Figure 12B:
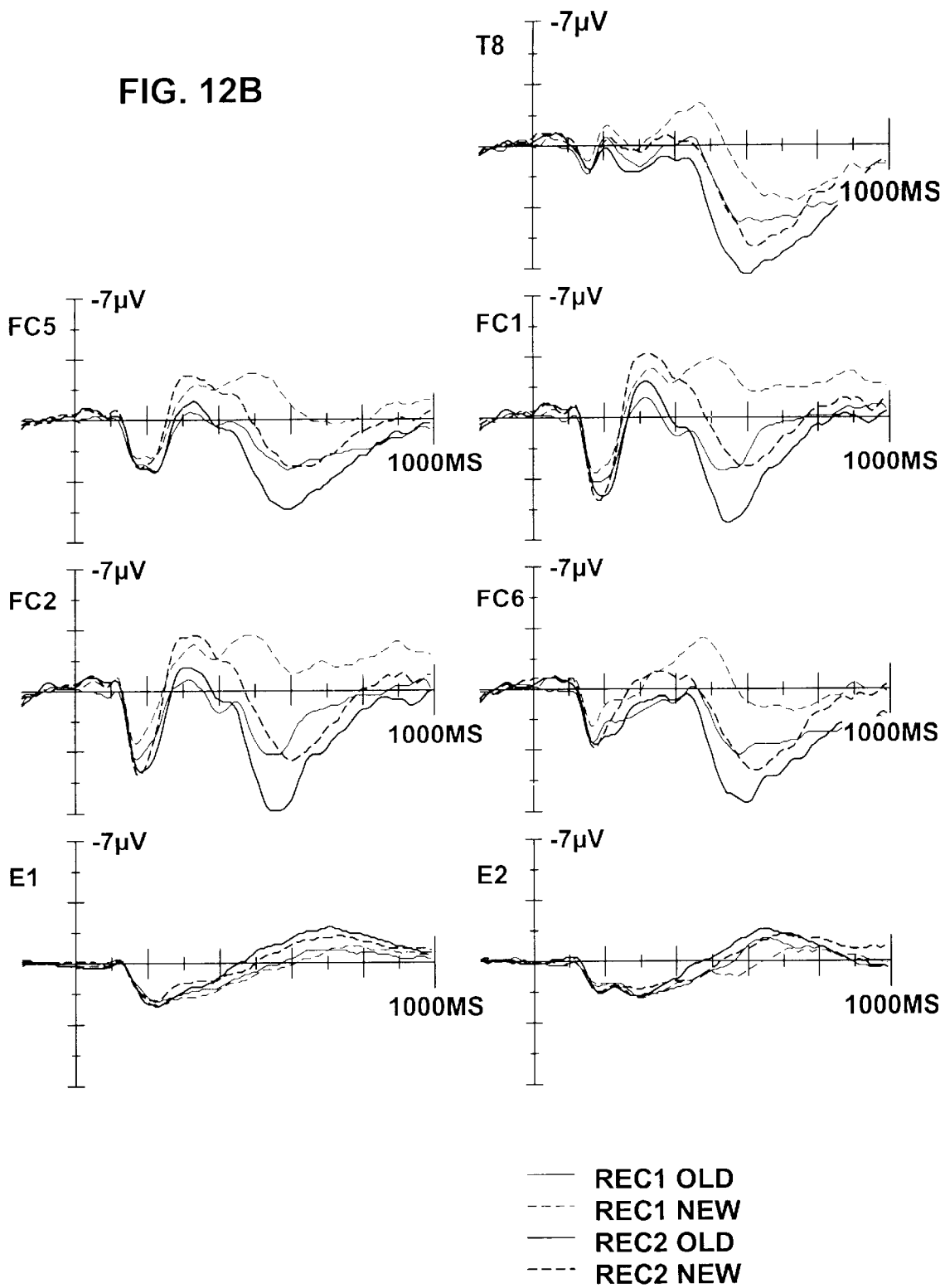
Figure 12C:
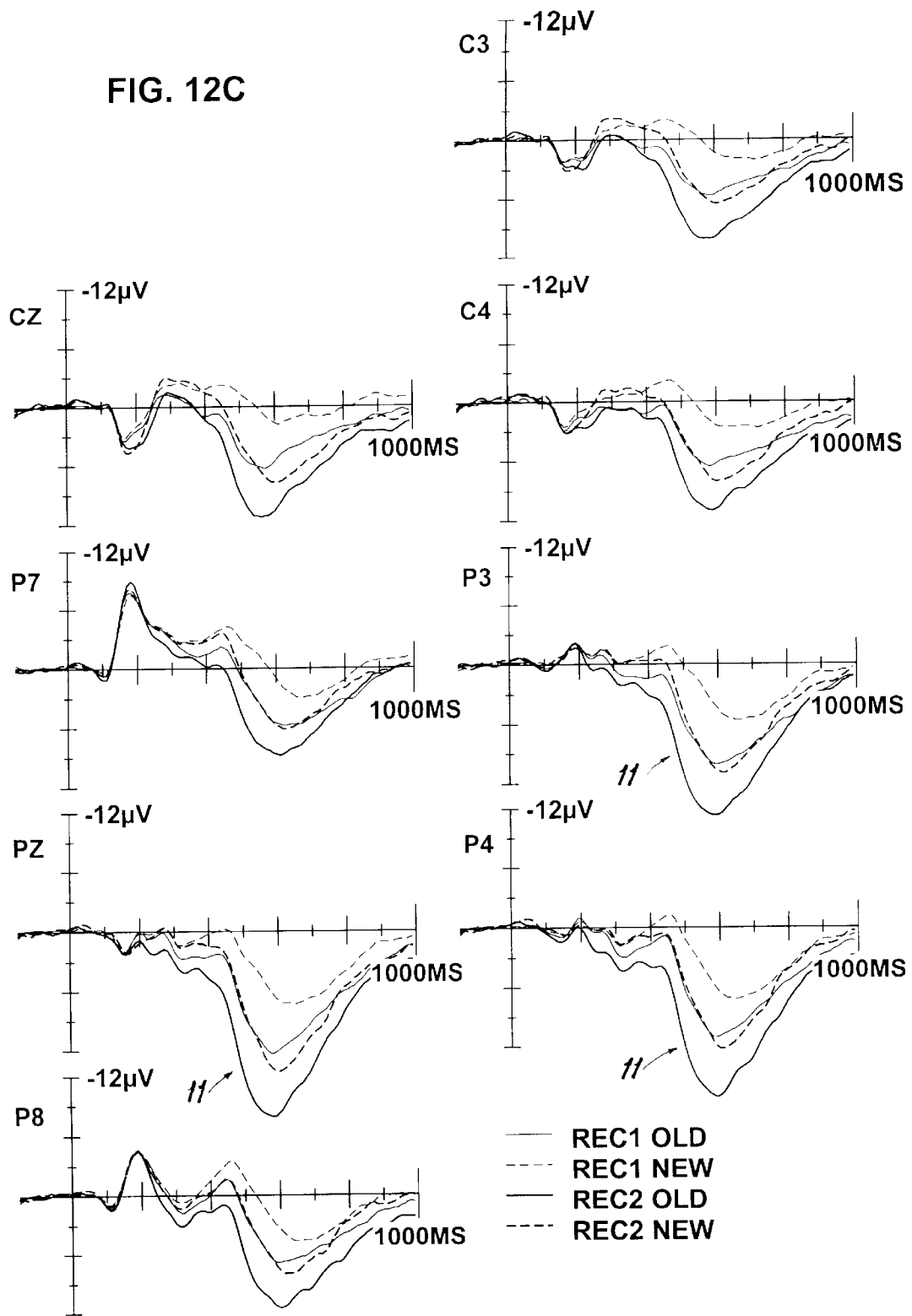
Figure 12D:
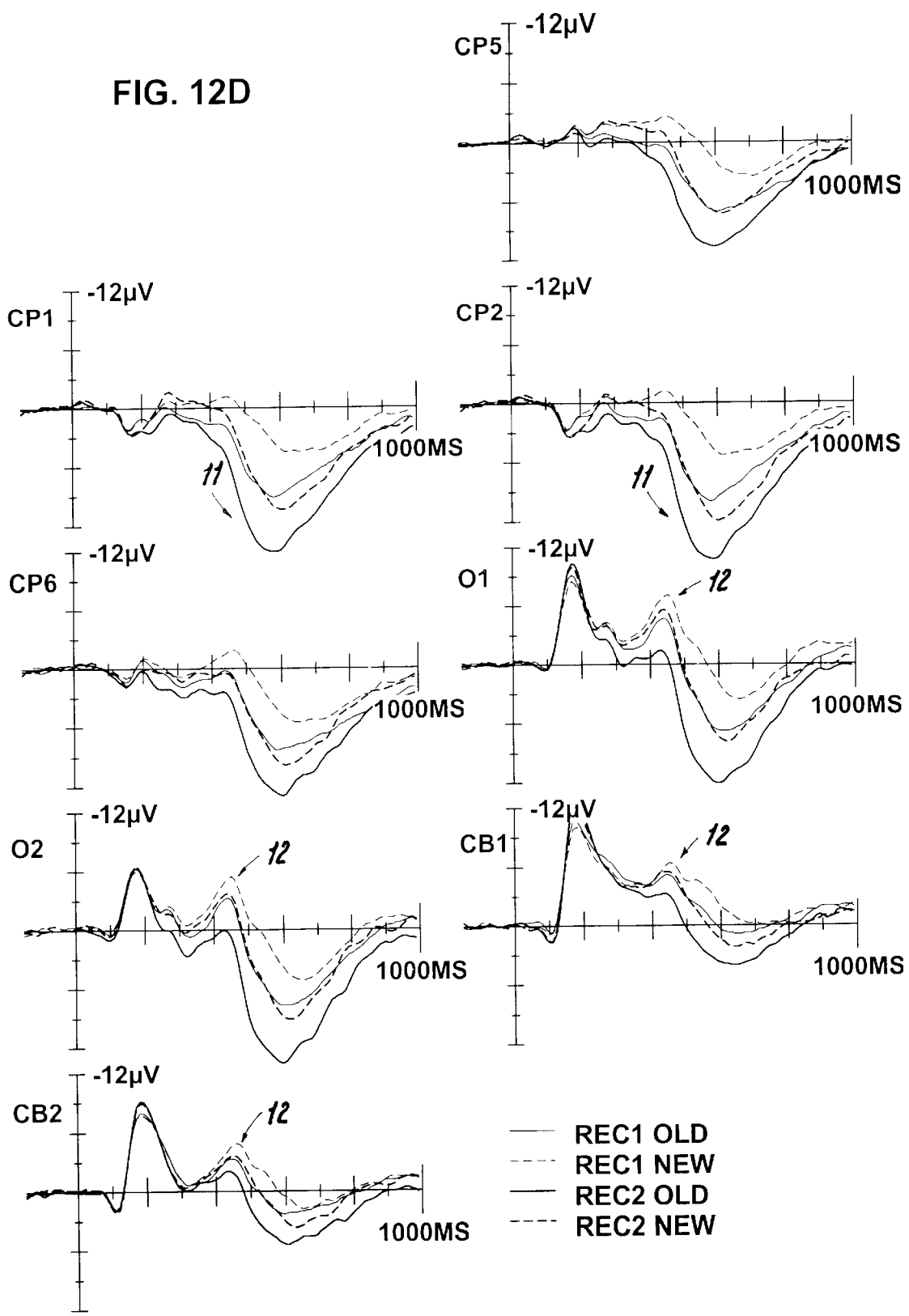
Figure 13A:
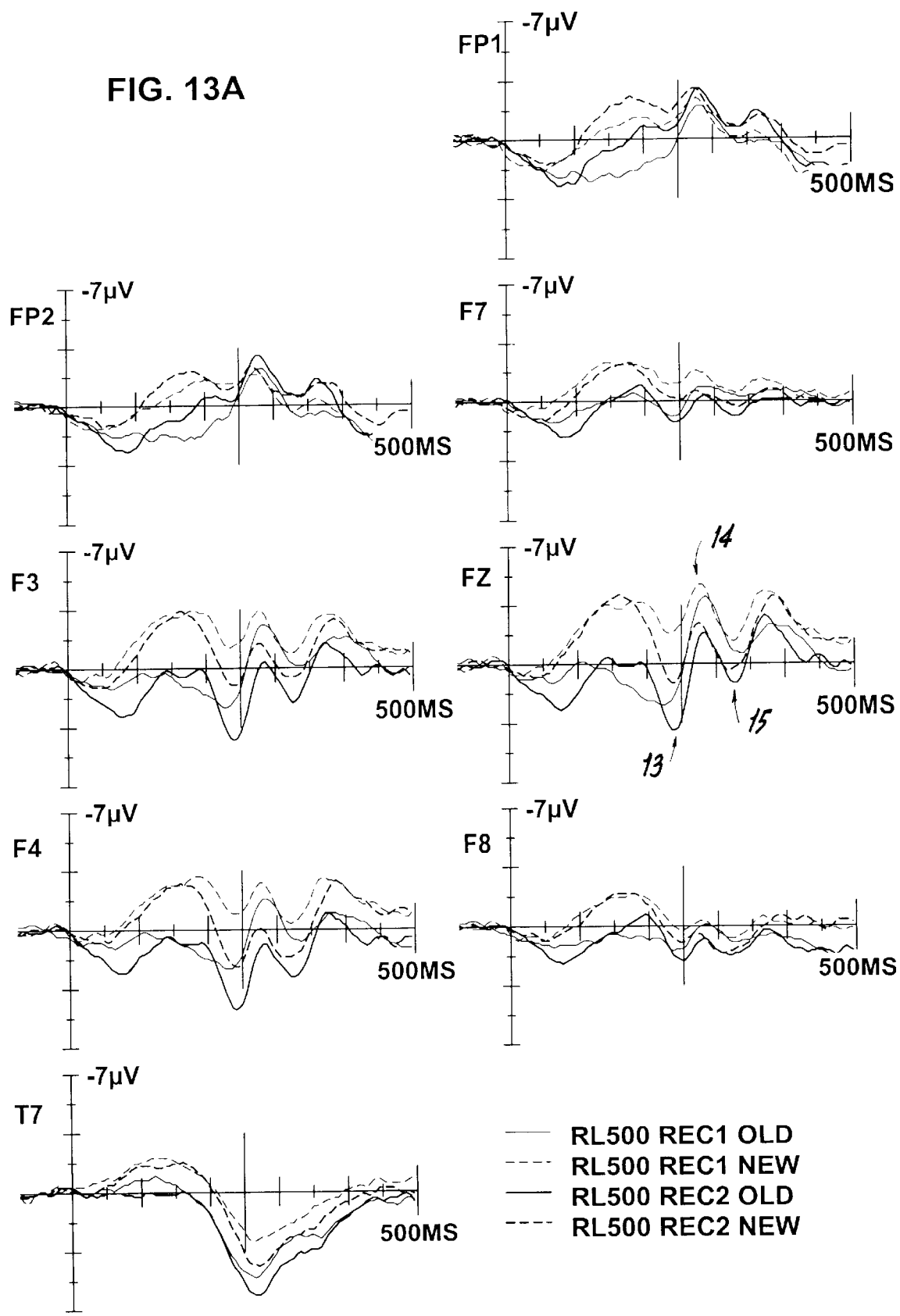
Figure 13B:
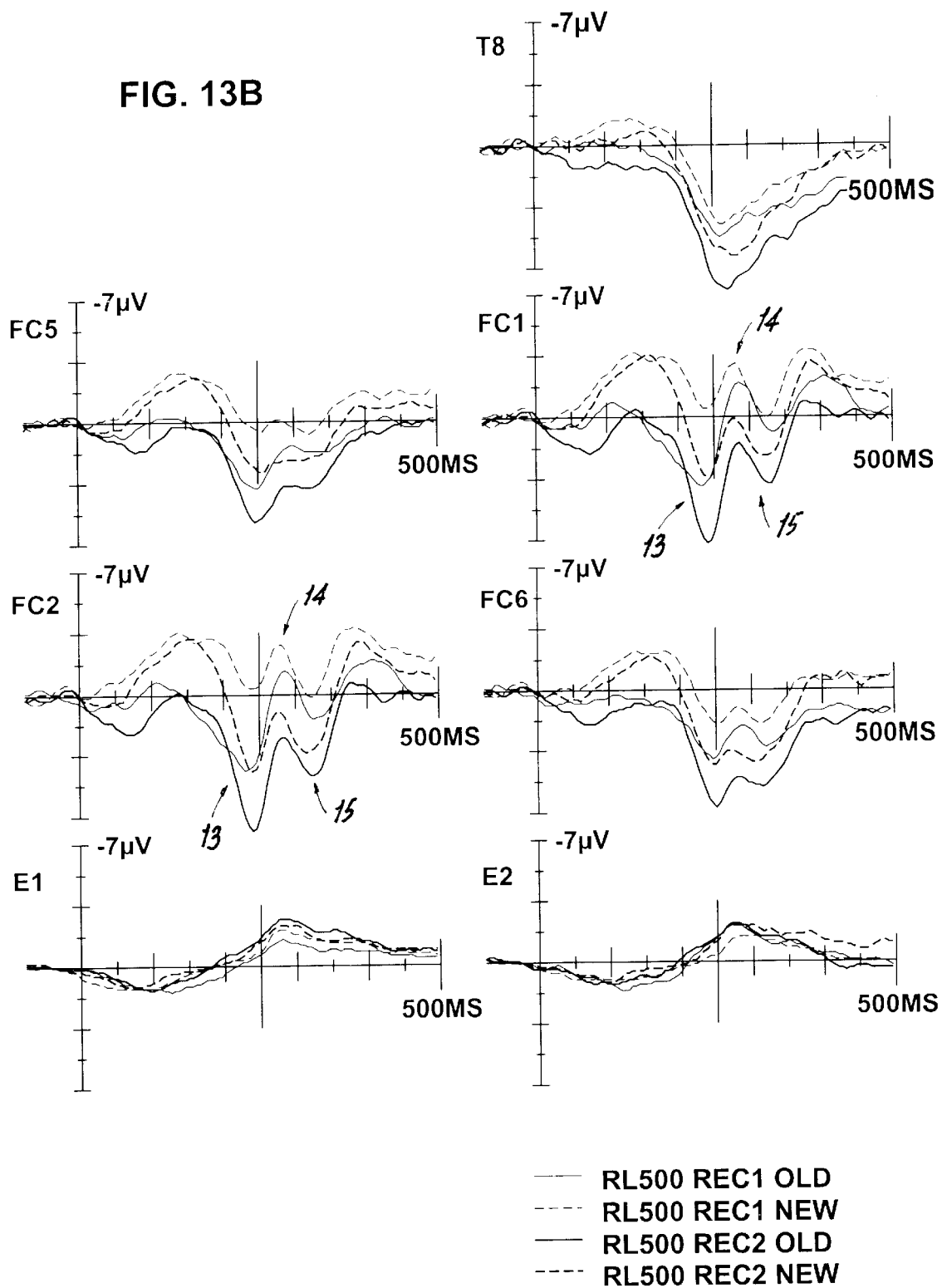
Figure 13C:
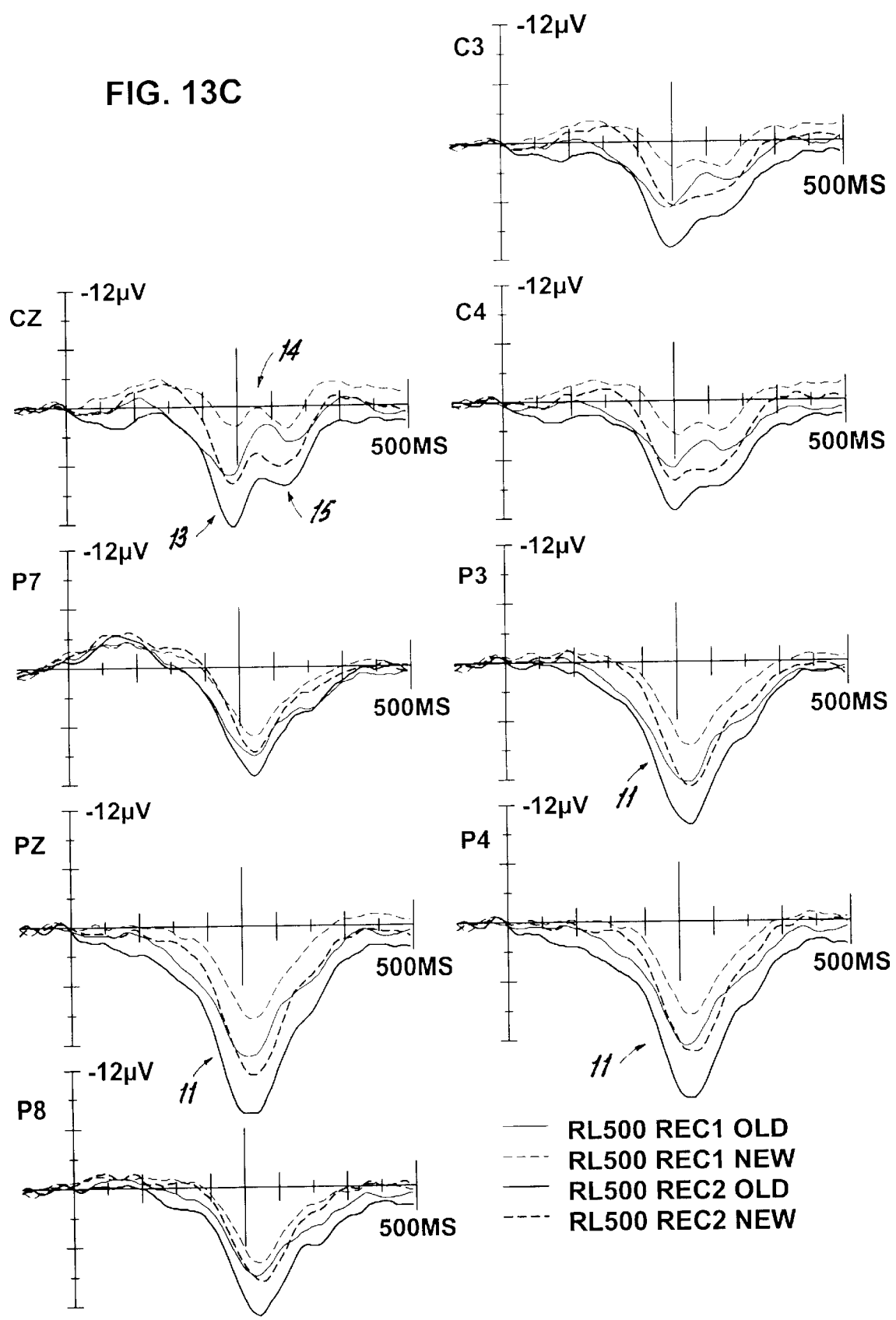
Figure 13D:
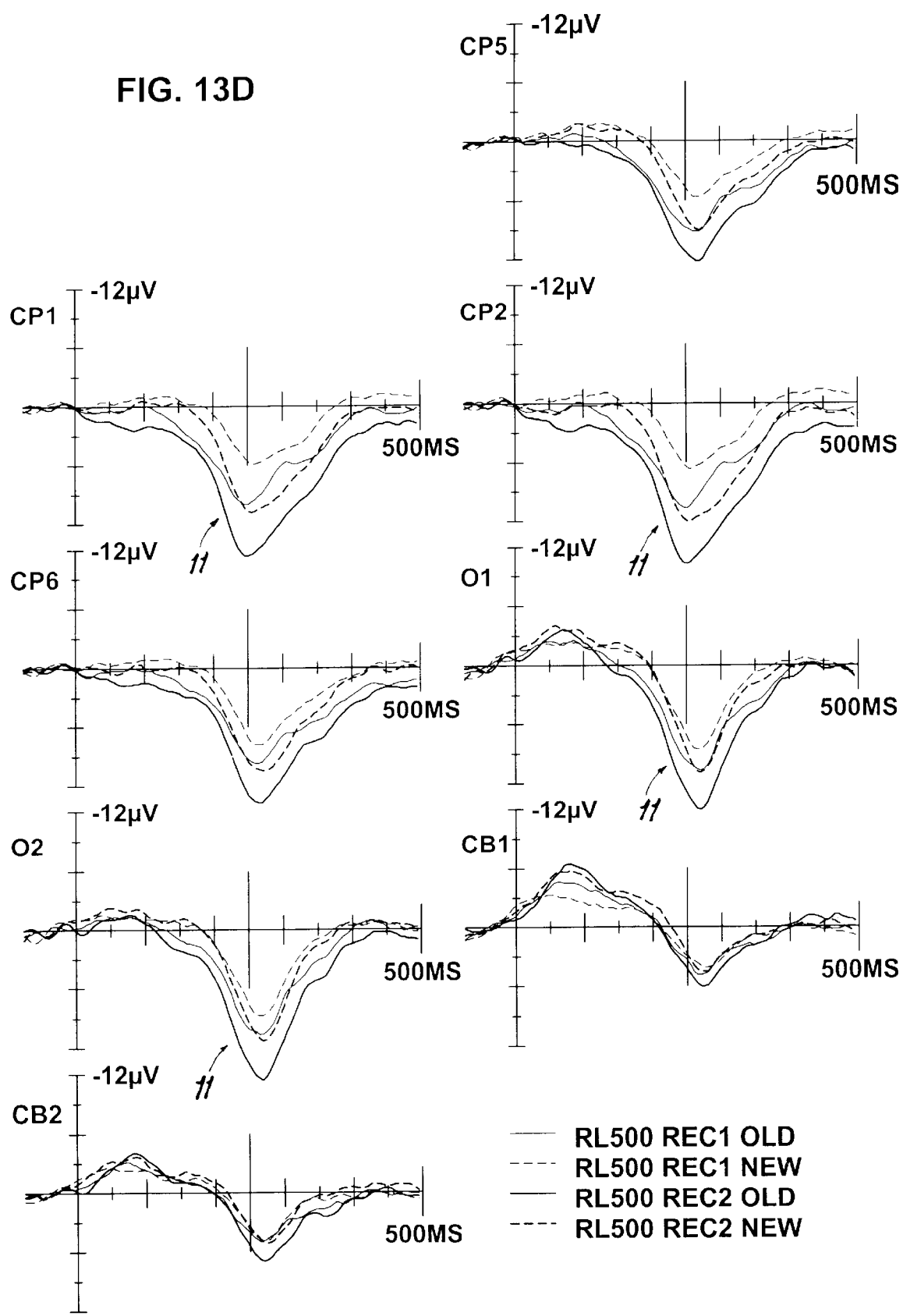
Figure 14A:
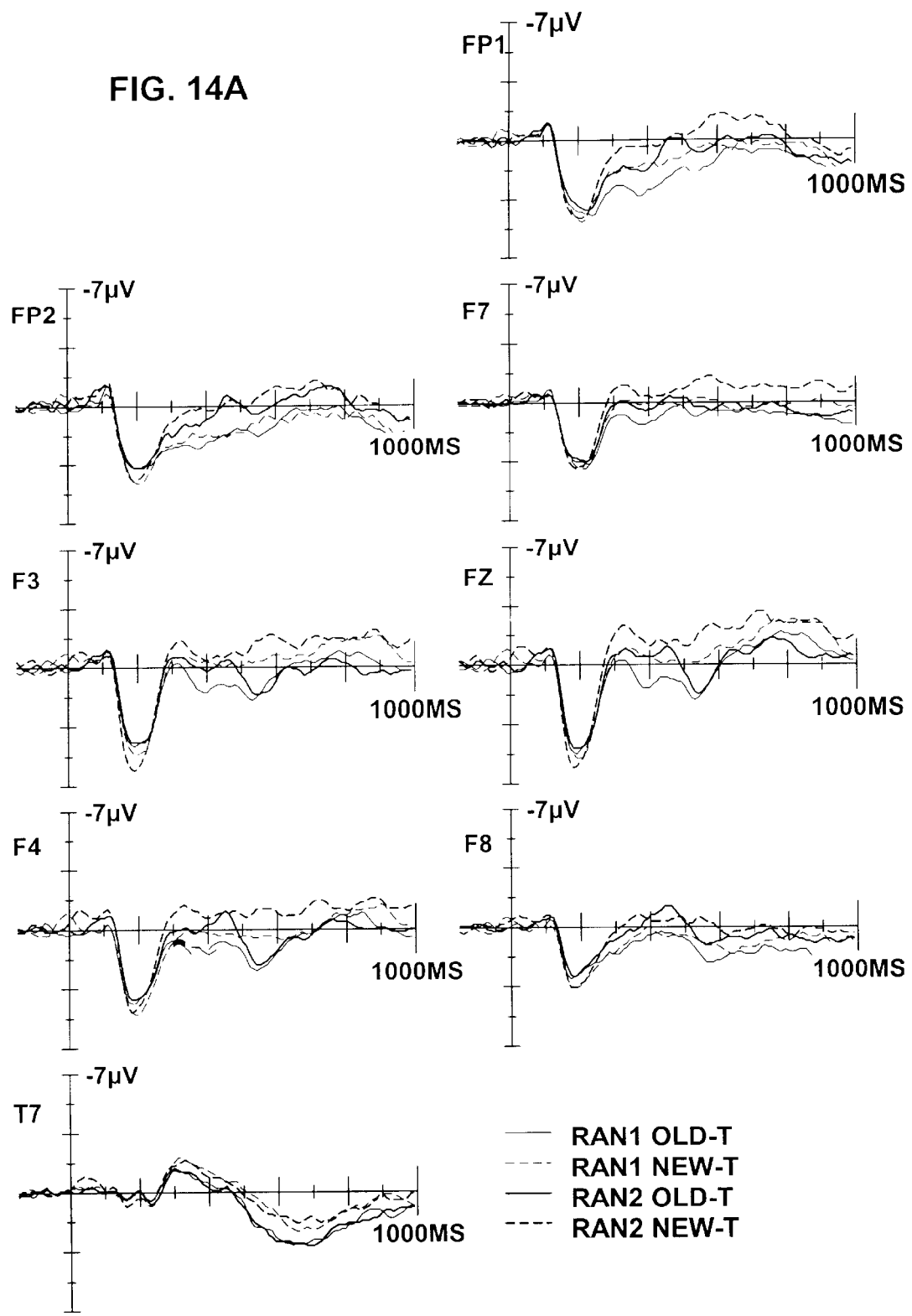
Figure 14B:
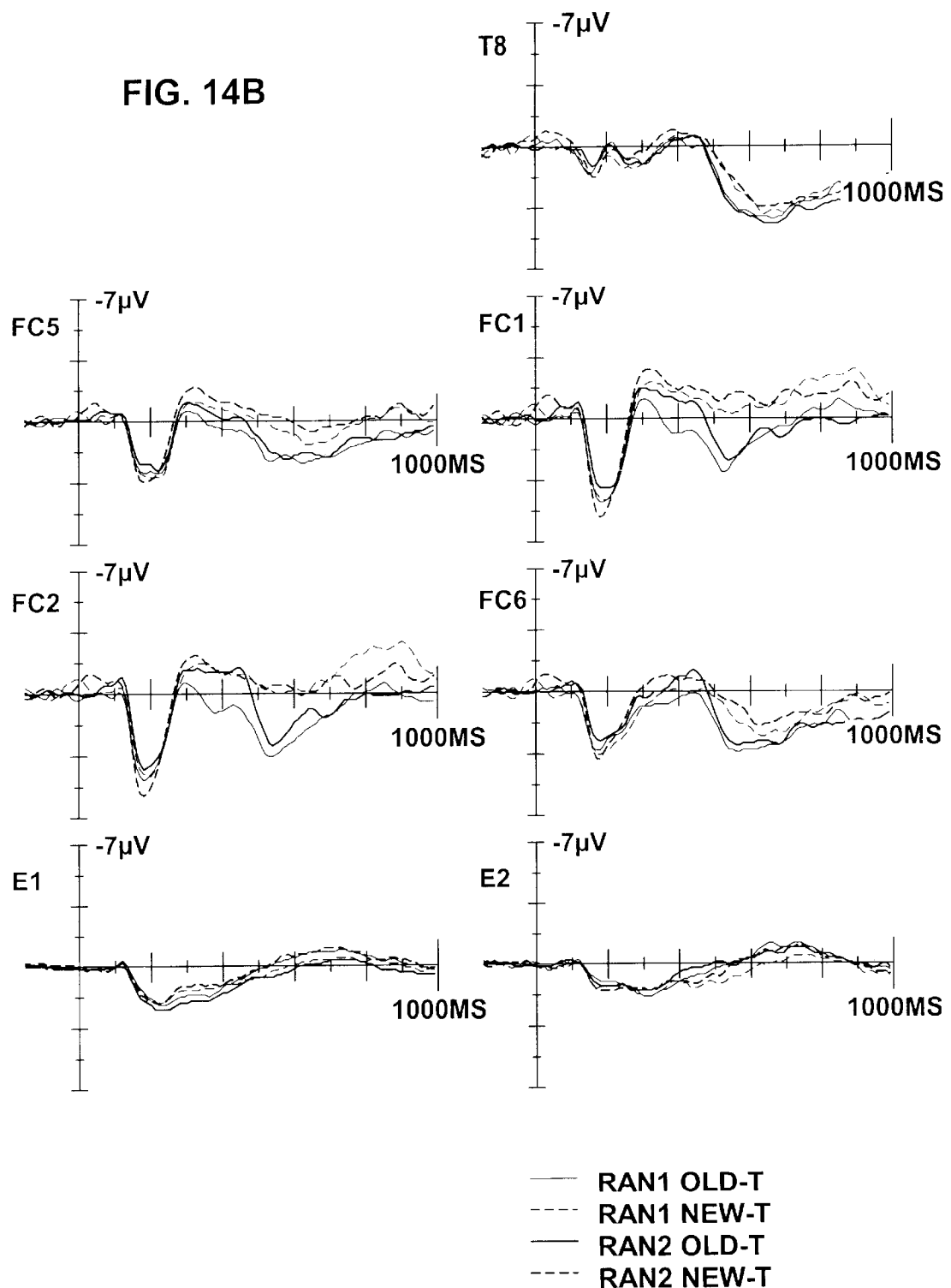
Figure 14C:
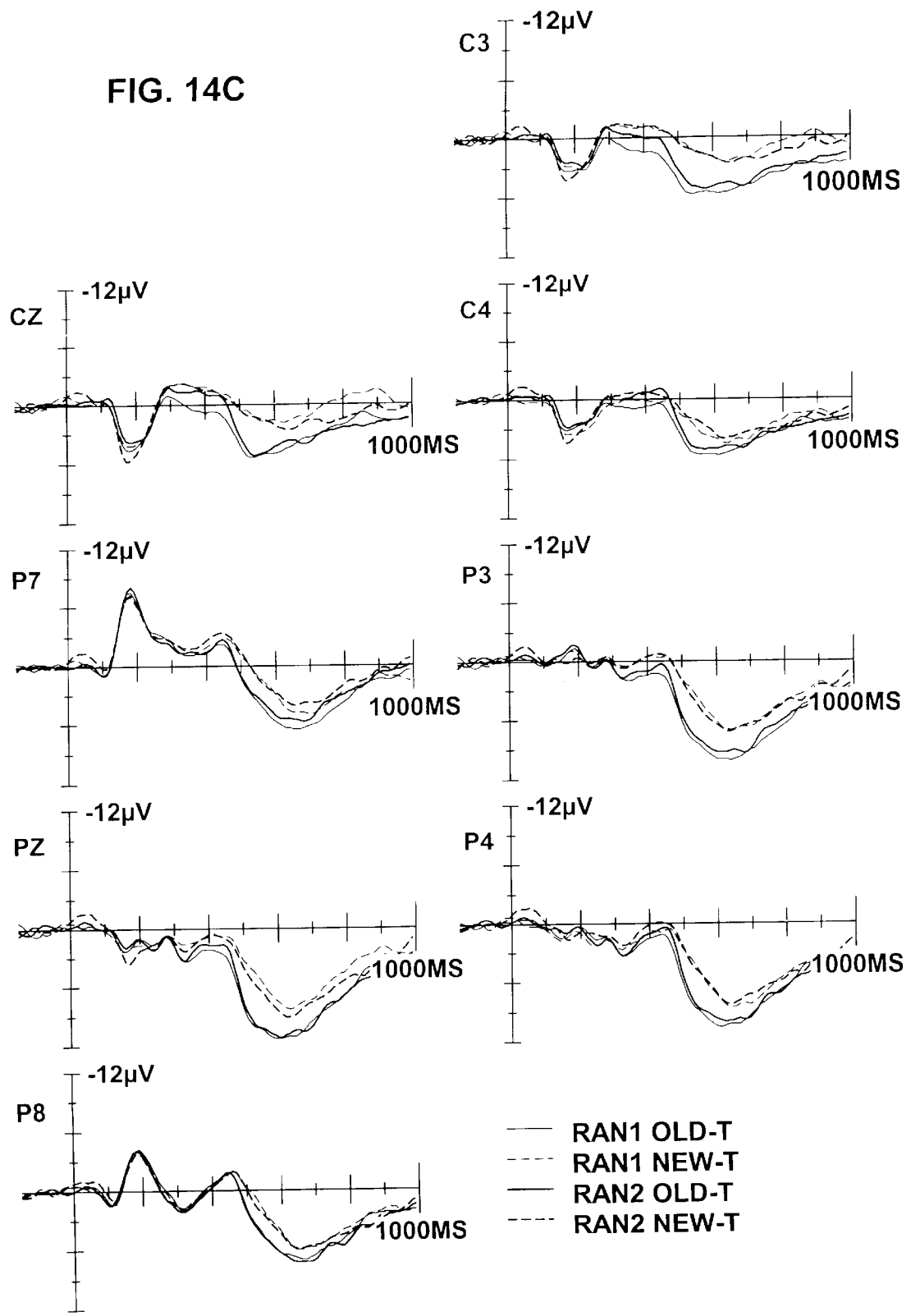
Figure 14D:
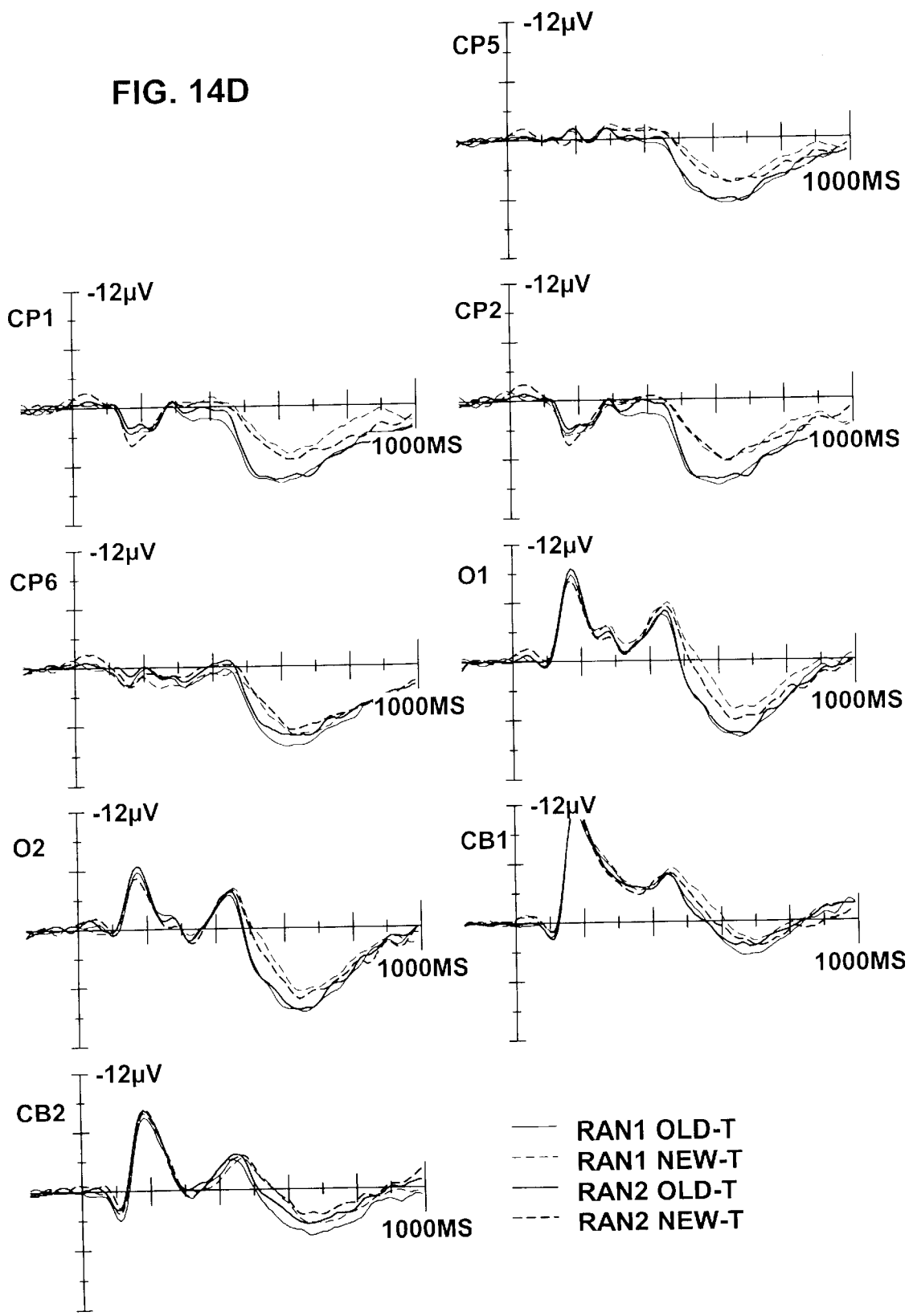

FIG. 7. REC2 NEW/OPP2 NEW/RAN2 NEW-T/RAN2 NEW-D. Marker 2, Stimulus-Locked ERP's 4th plot. This figure shows the ERPs to new words in the three conditions (Truthful, Opposite, Random). Peaks are the same as indicated in FIG. 12.

FIG. 8. REC Catch-OLD/OPP Catch-OLD/RAN Catch-OLD. Marker 9, Stimulus-Locked ERPs, 1st plot. This figure shows the ERPs to "old" catch trials in the three conditions (Truthful, Opposite, Random).

FIG. 9. REC CatchT-OLD/OPP CatchT-OLD/RAN CatchT-OLD. Marker 9, Response-Locked ERPs, 1st plot. This figure shows the ERPs to "old" catch trials in the three conditions (Truthful, Opposite, Random).

FIG. 10. REC Catch-NEW/OPP Catch-NEW/RAN Catch-NEW. Marker 9, Stimulus-Locked ERPs, 2nd plot. This figure shows the ERPs to "new" catch trials in the three conditions (Truthful, Opposite, Random).

FIG. 11. REC Catch-NEW/OPP Catch-NEW/RAN Catch-NEW. Marker 9, Response-Locked ERPs, 2nd plot. This figure shows the ERPs to "new" catch trials in the three conditions (Truthful, Opposite, Random).

FIG. 12. REC1 OLD/REC1 NEW/REC2 OLD/REC2 NEW. Marker 11, Stimulus-Locked ERPs. This figure shows the ERPs to old and new words for the two repetitions of the Truthful condition. Arrows indicate peaks for markers 11 and 12 in recordings from electrodes Cp1, Cp2, P3, Pz, P4, O1, O2, Cb1, Cb2.

FIG. 13. REC1 OLD/REC1 NEW/REC2 OLD/REC2 NEW. Marker 11, Response-Locked ERPs, 1st plot. This figure shows the ERPs to old and new words for the two repetitions of the Truthful condition. Arrows indicate peaks corresponding to marker numbers 11, 13, 14, 15, 23 and 24 in recordings from electrodes Fz, Fc1, Fc2, Cz, Cp1, Cp2, Pz, P3, P4, O1, O2.

FIG. 14. RAN1 OLD-T/RAN1 NEW-T/RAN2 OLD-T/RAN2 NEW-T. Marker 11, Stimulus-Locked ERPs, 2nd plot. This figure shows the ERPs to old and new words, truthful responses only, for the two repetitions of the Random condition. Peaks are the same as indicated in FIG. 12.

Figure 15A:
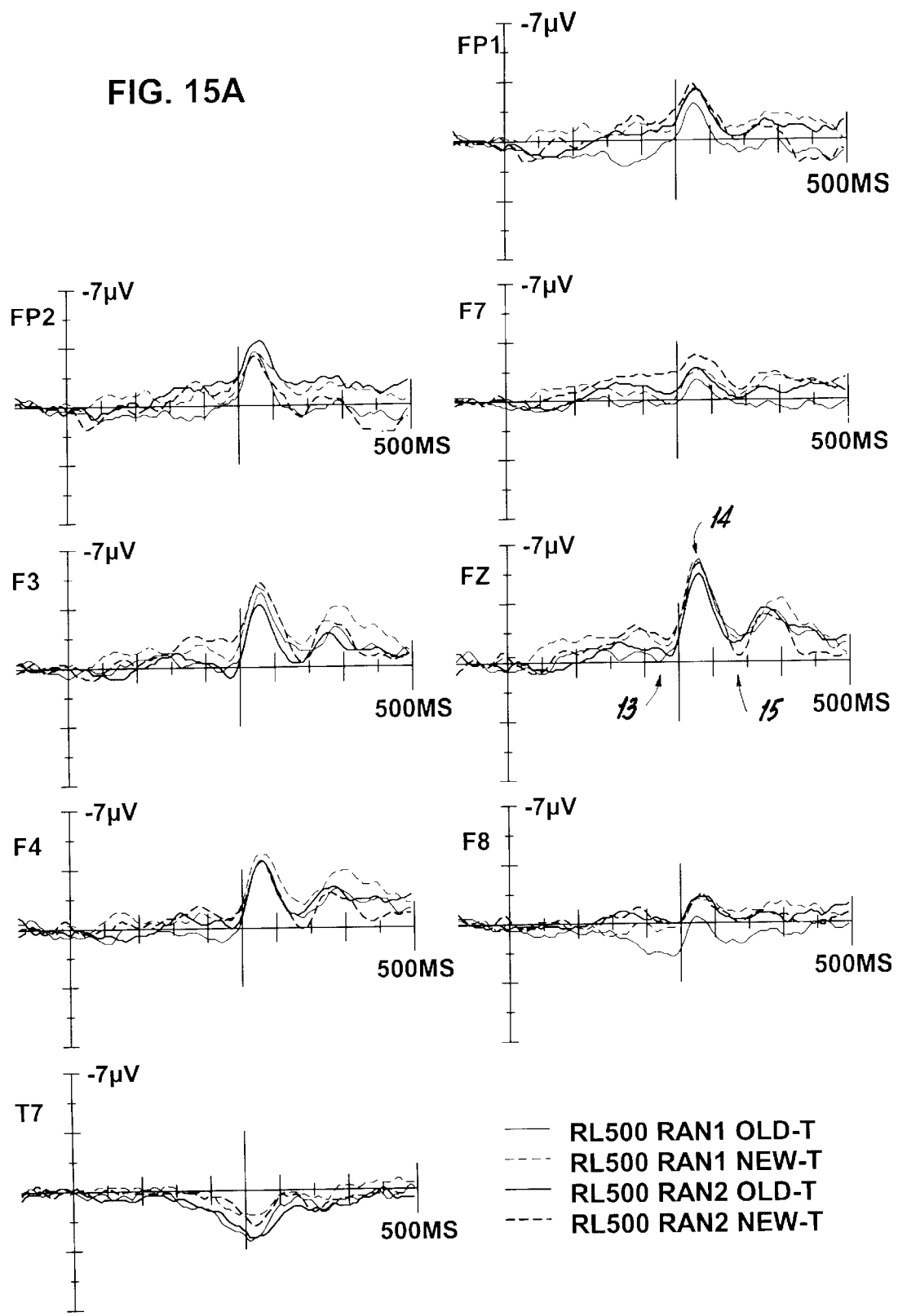
Figure 15C:
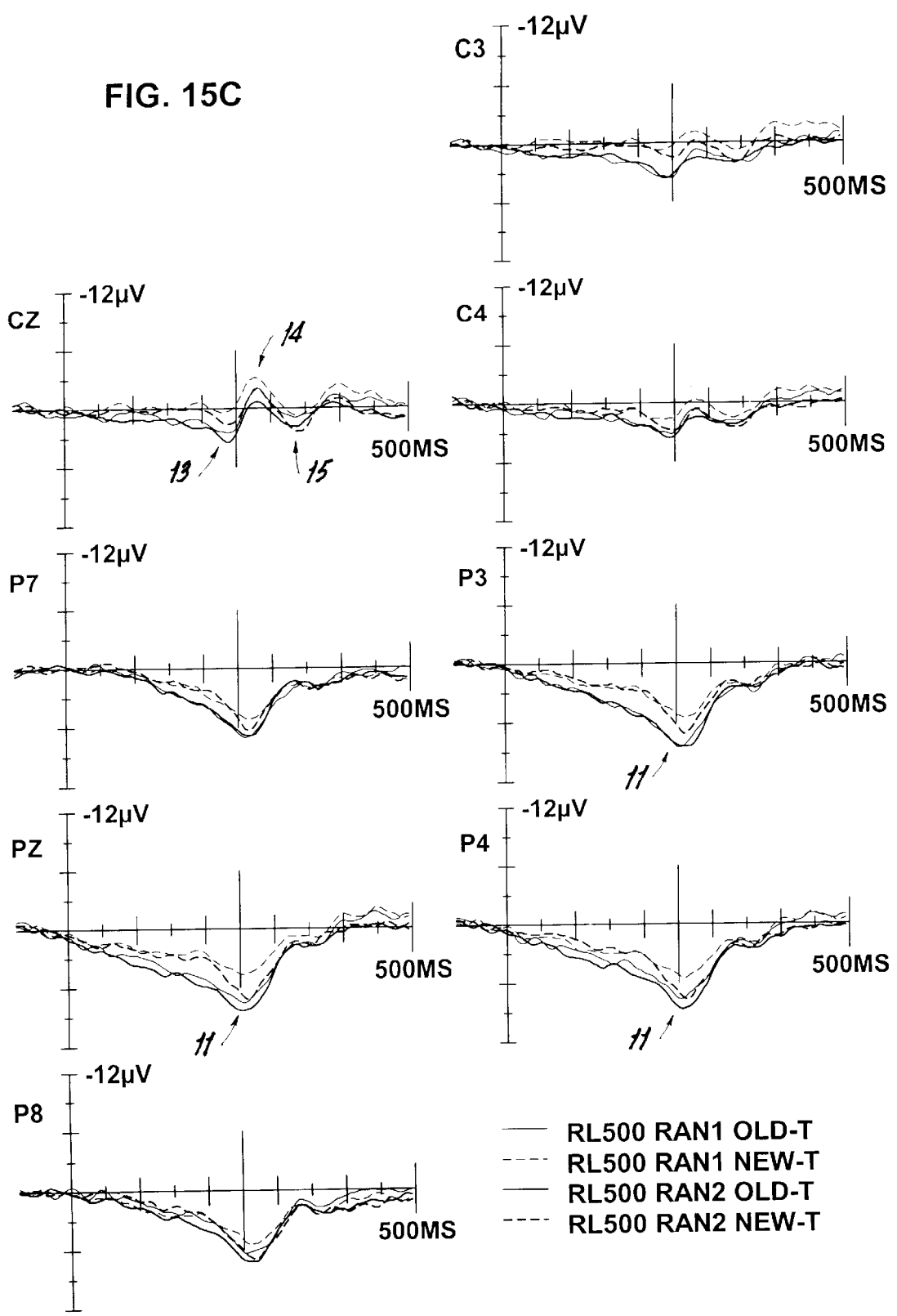
Figure 15D:
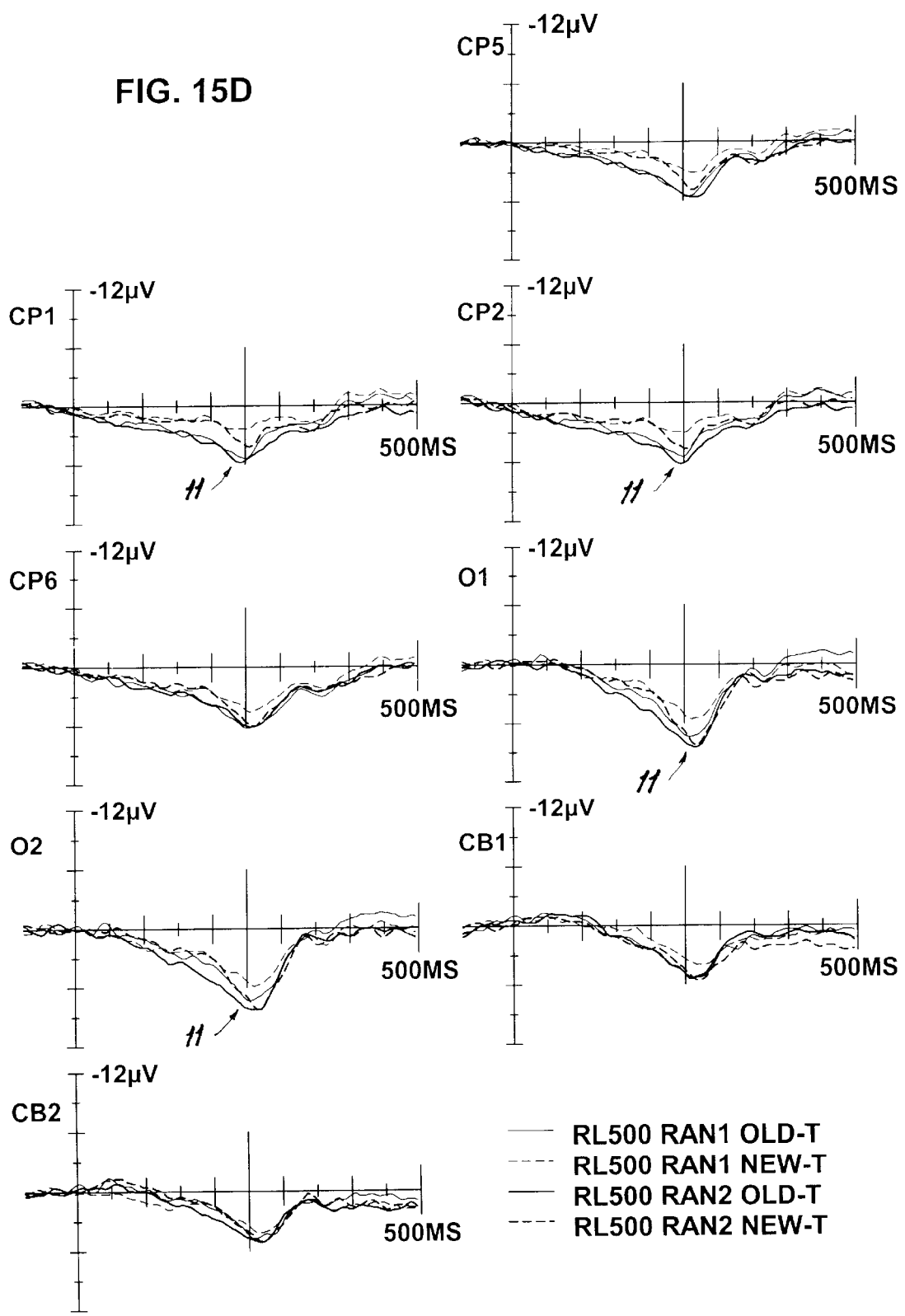

FIG. 15. RAN1 OLD-T/RAN1 NEW-T/RAN2 OLD-T/RAN2 NEW-T. Marker 11, Response-Locked ERPs, 2nd plot. This figure shows the ERPs to old and new words, truthful responses only, for the two repetitions of the Random condition. Arrows indicate peaks corresponding to marker numbers 11, 13, 14 and 15 in recordings from electrodes Fz, Fc1, Fc2, Cz, Pz, P3, P4, O1, O2.

Figure 16A:
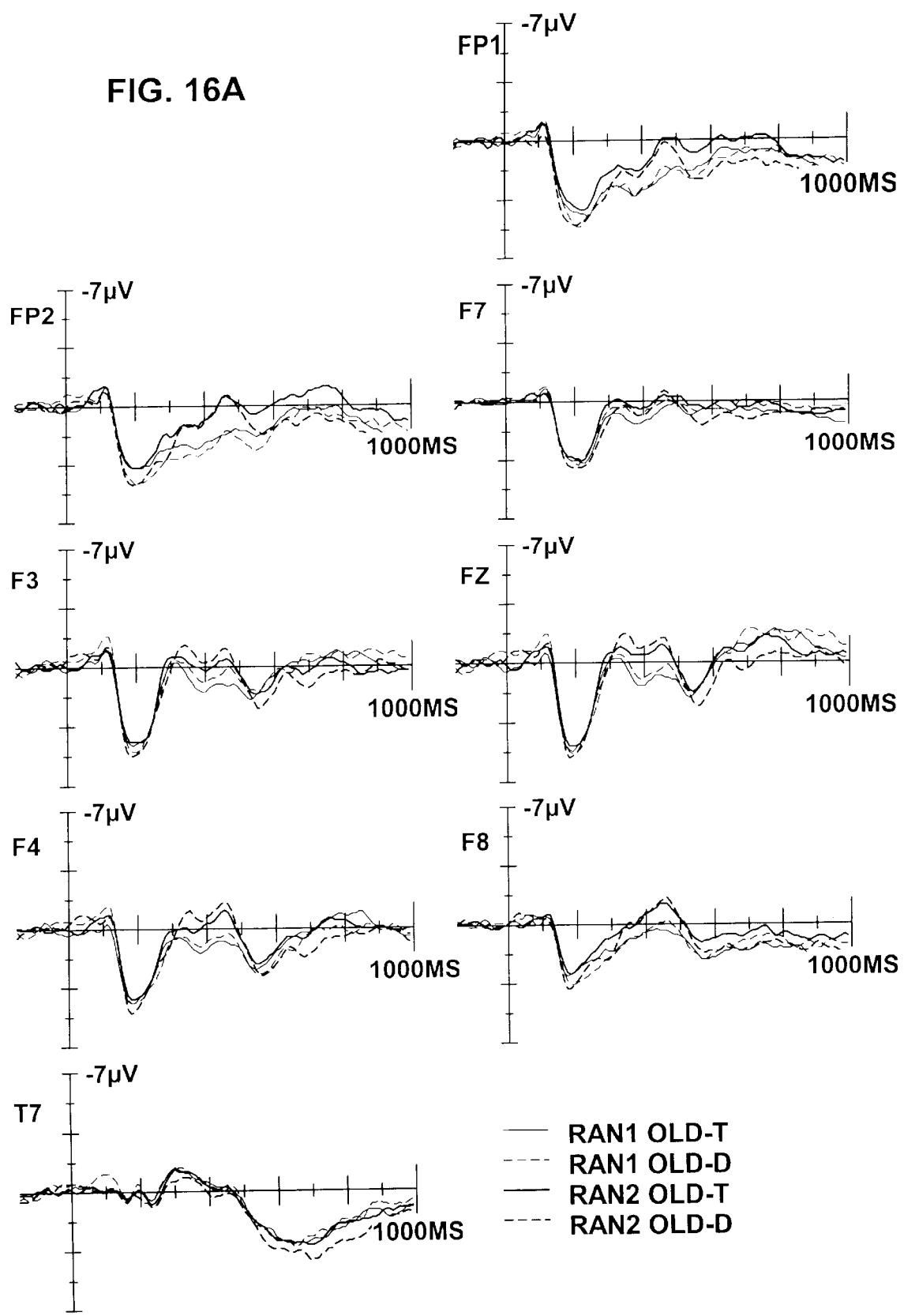
Figure 16C:
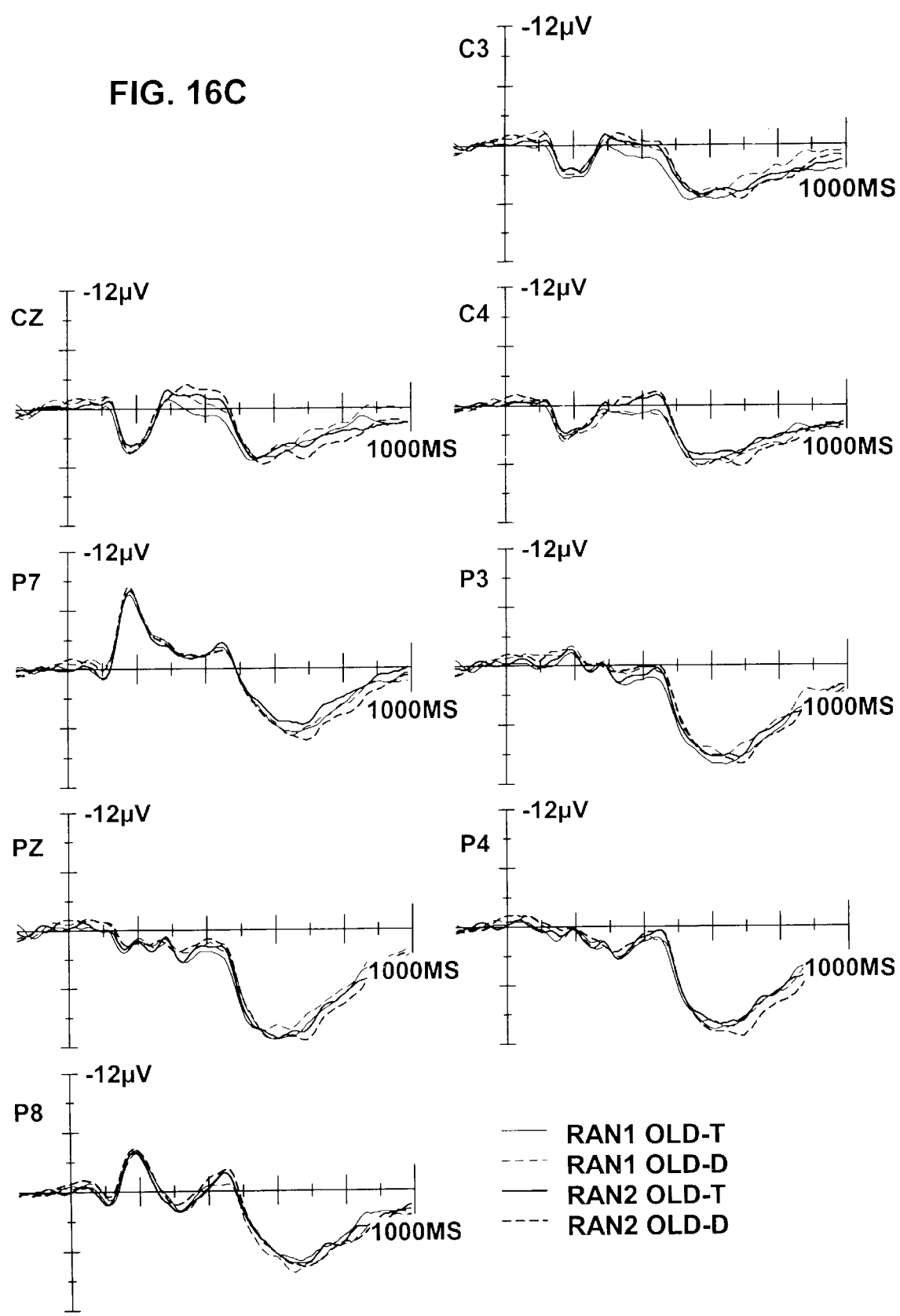
Figure 16D:
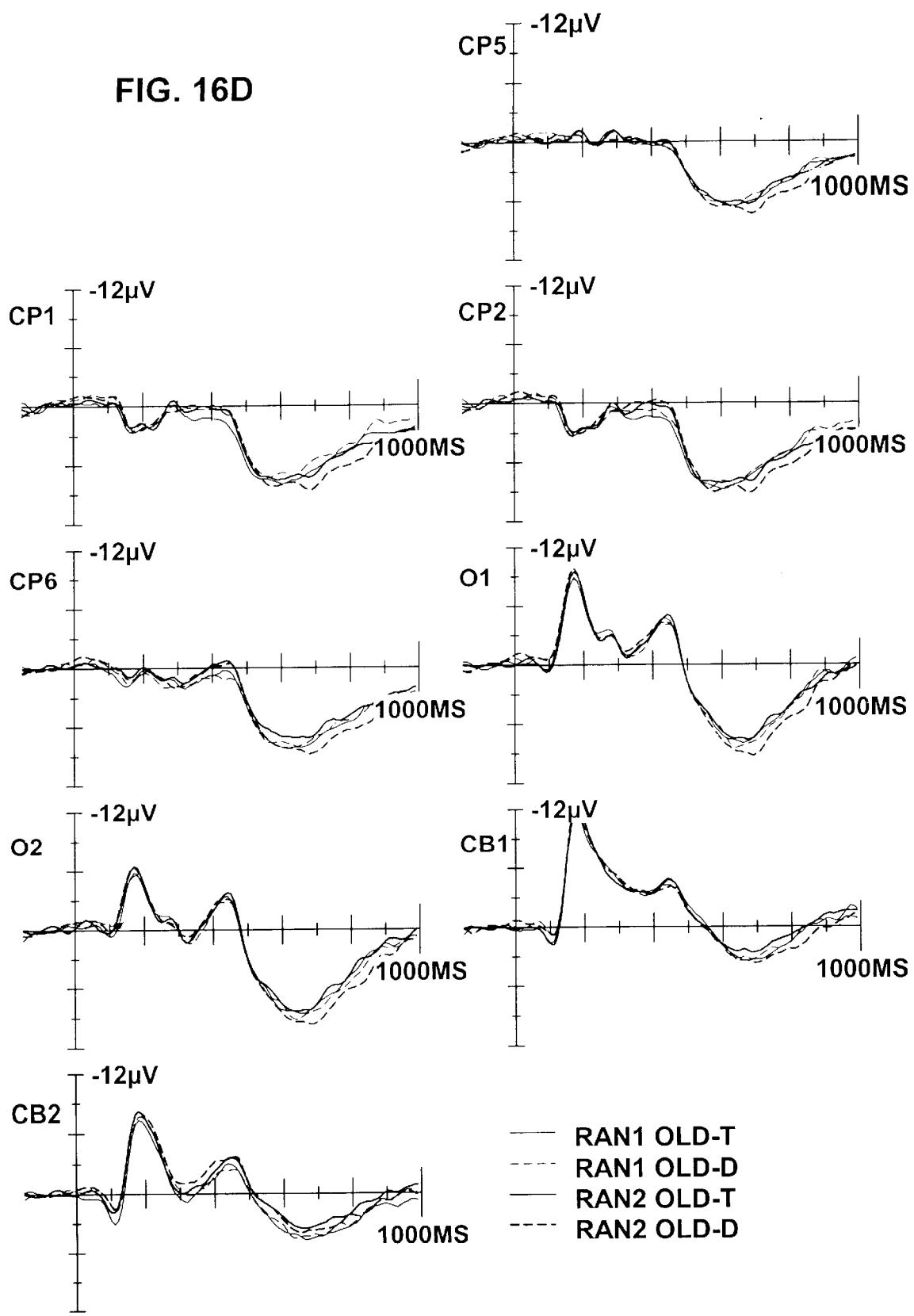
Figure 17A:
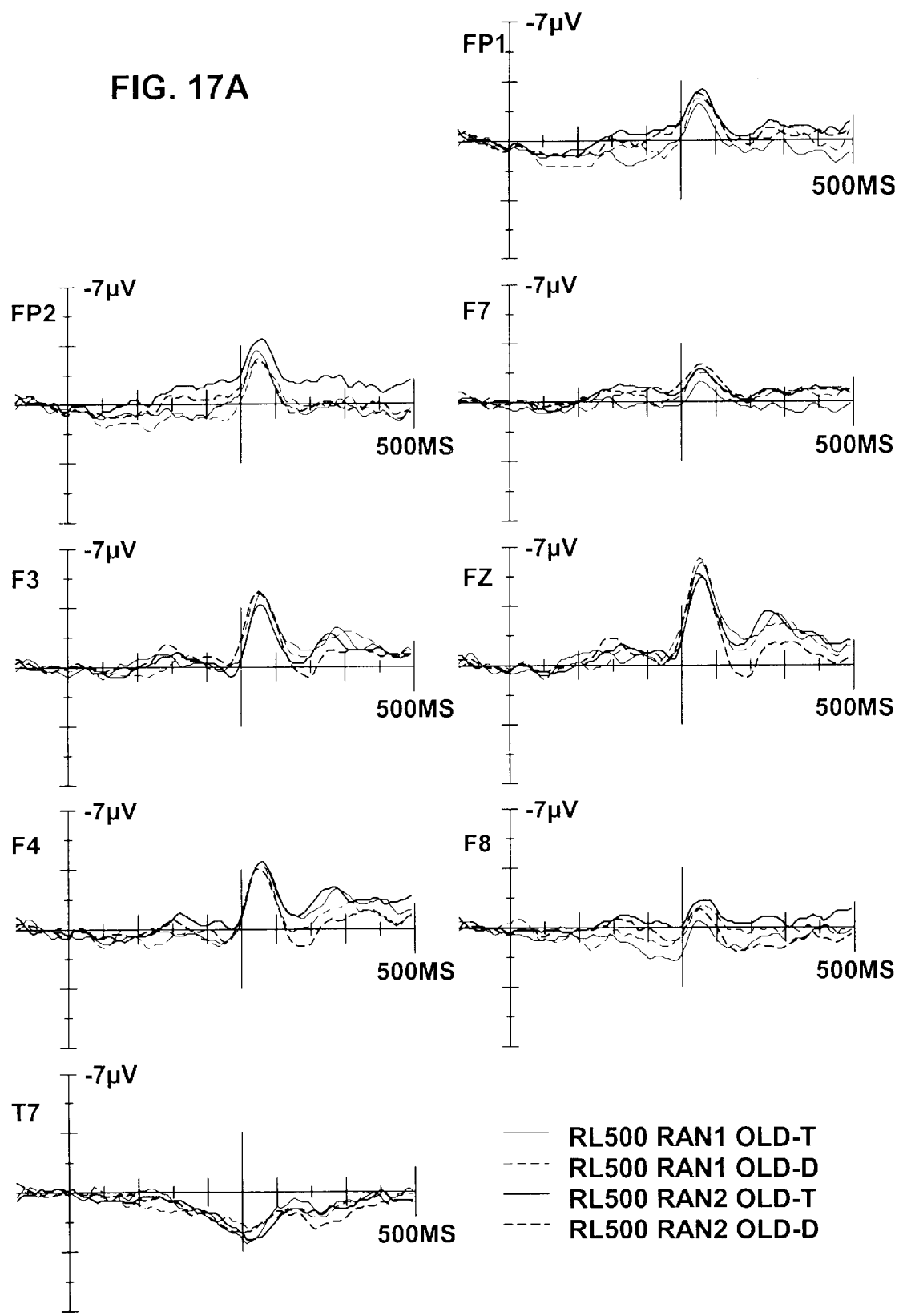
Figure 17B:
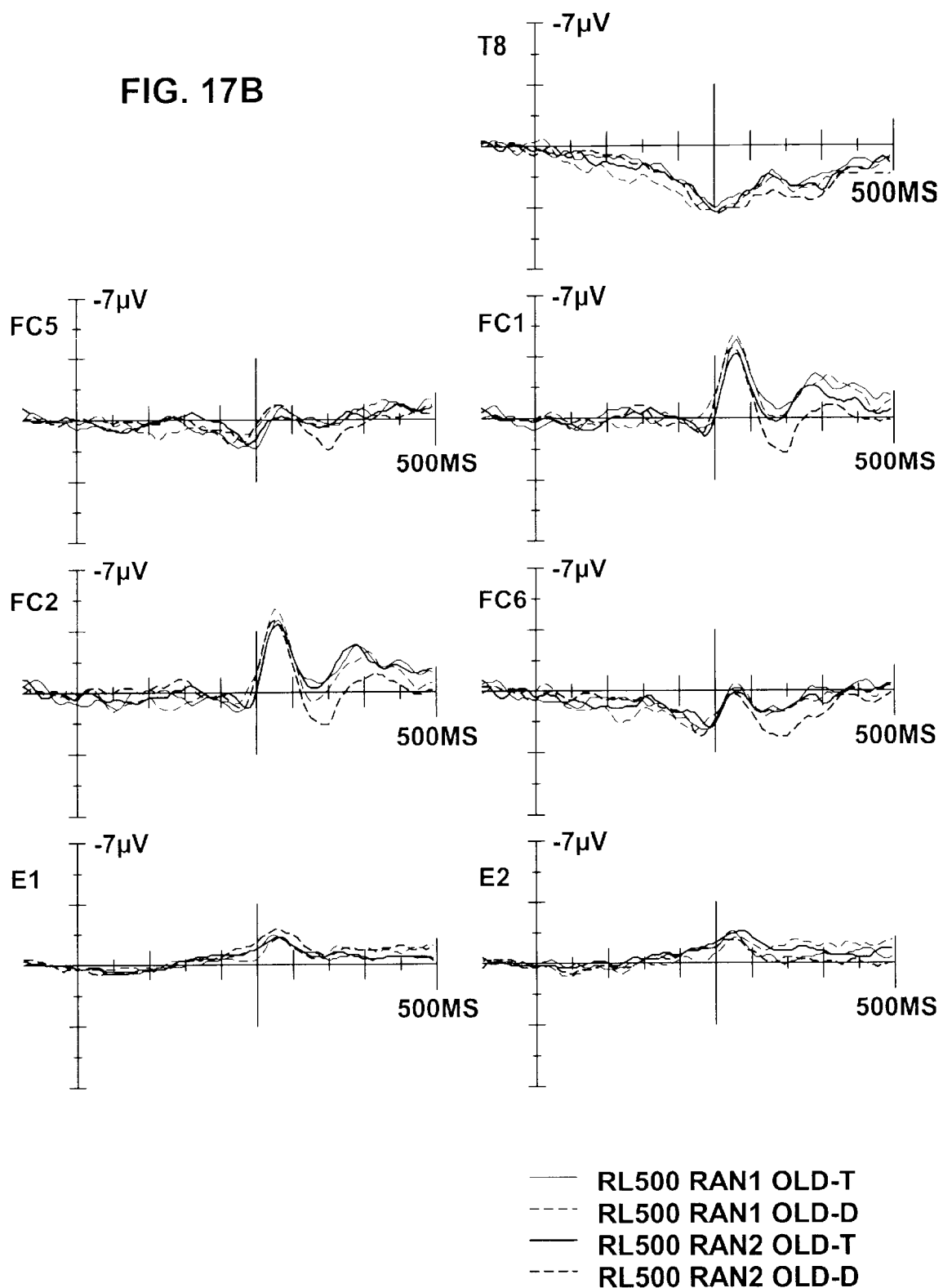
Figure 17C:
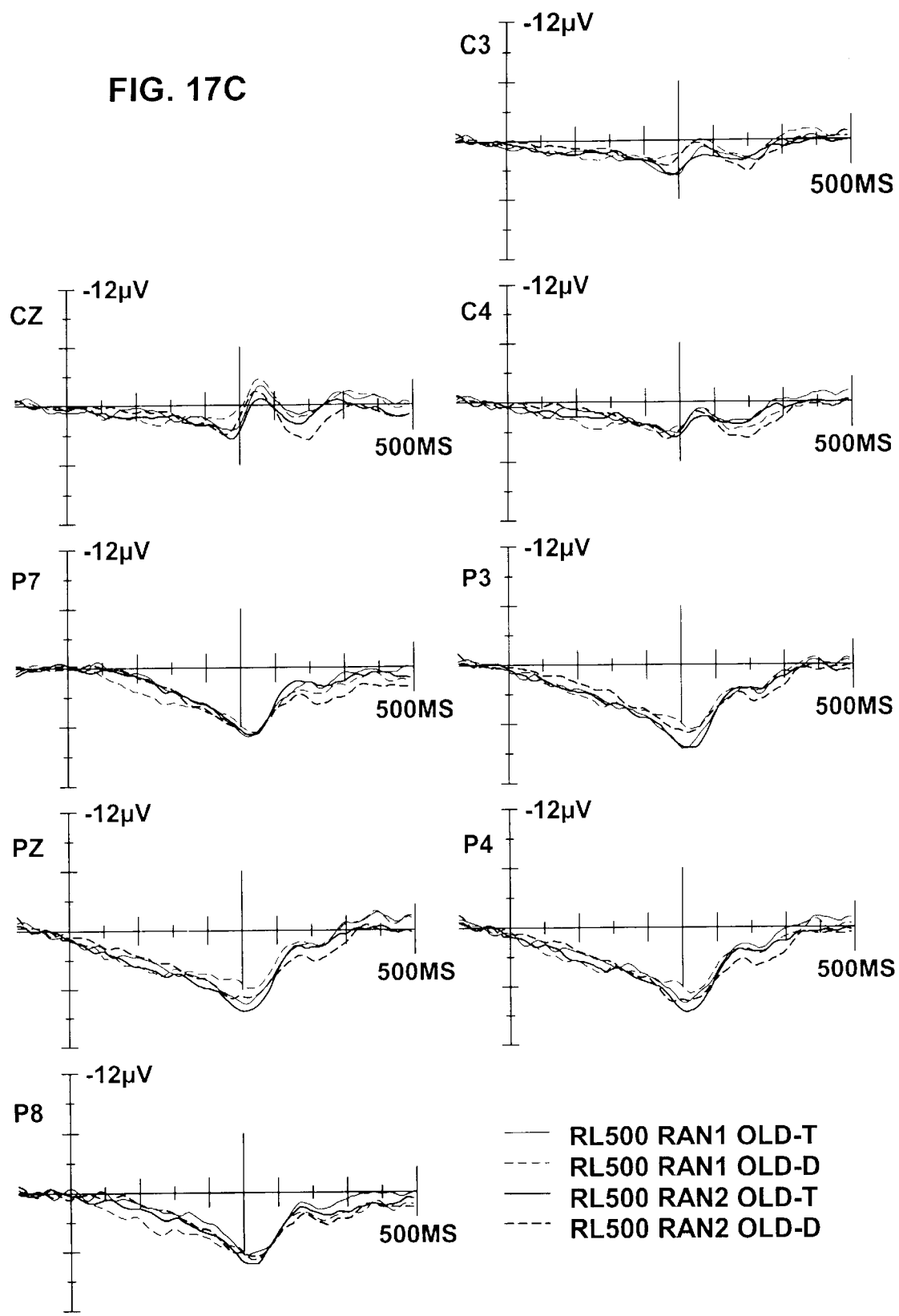
Figure 17D:
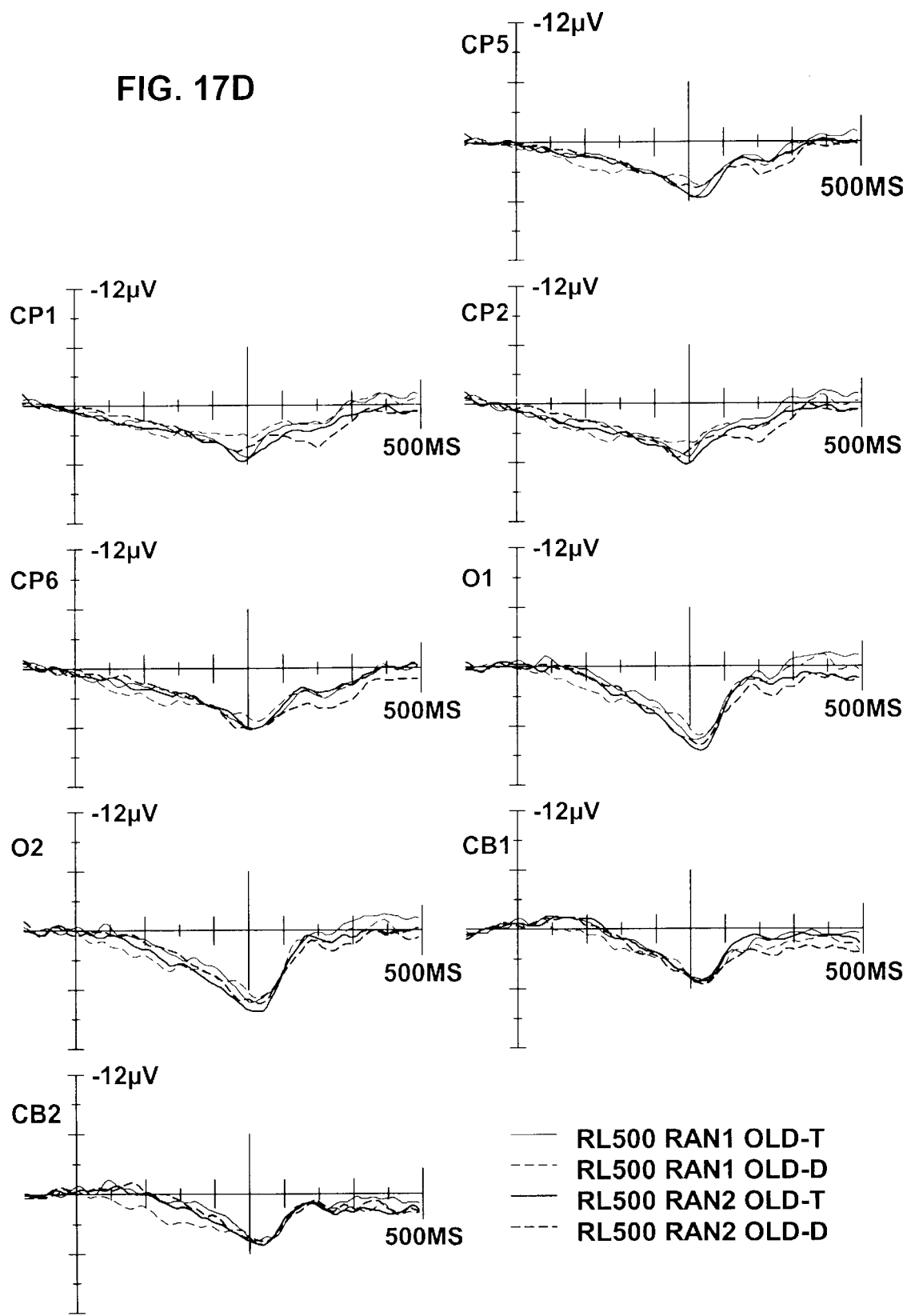
Figure 18A:
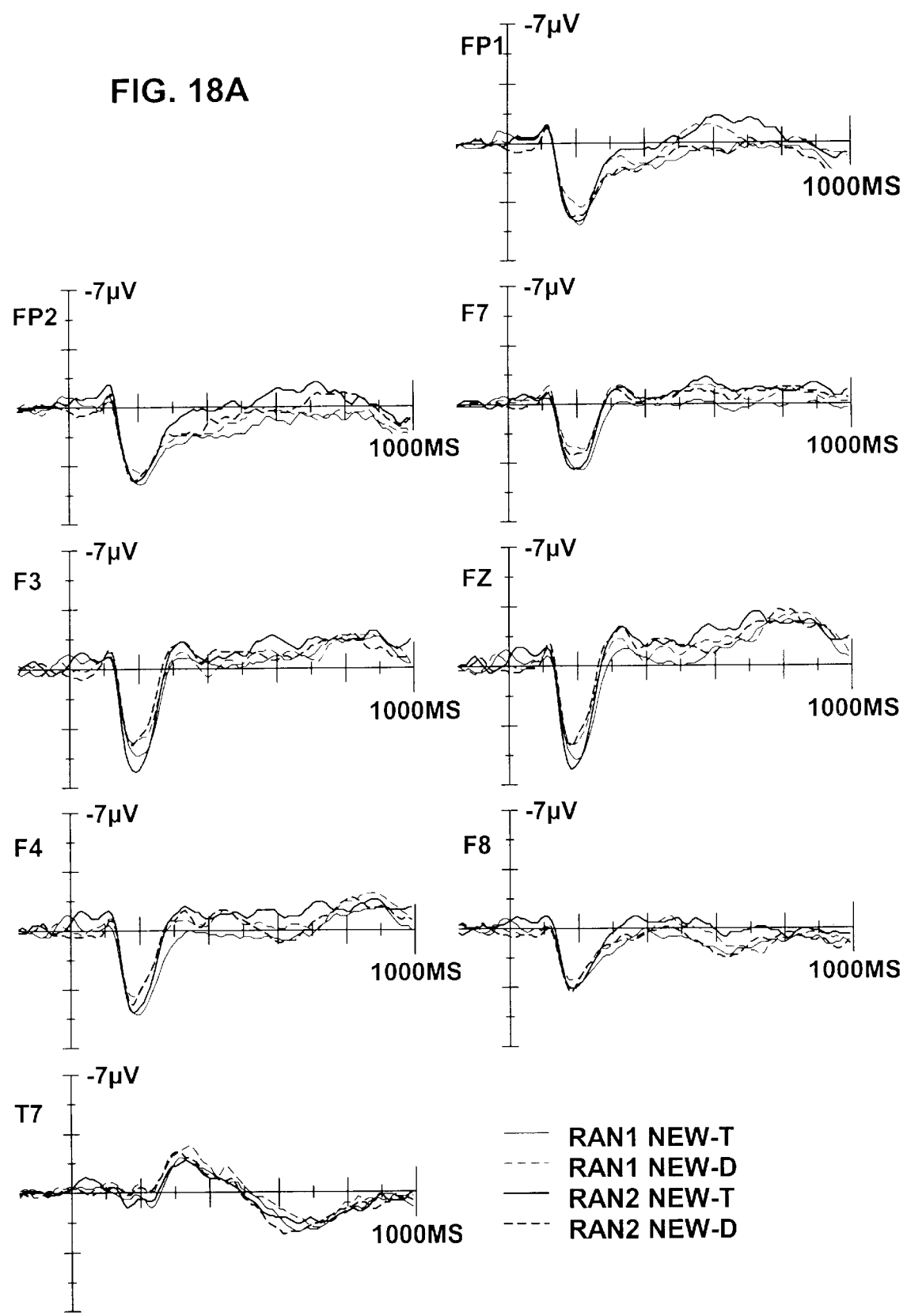
Figure 18B:
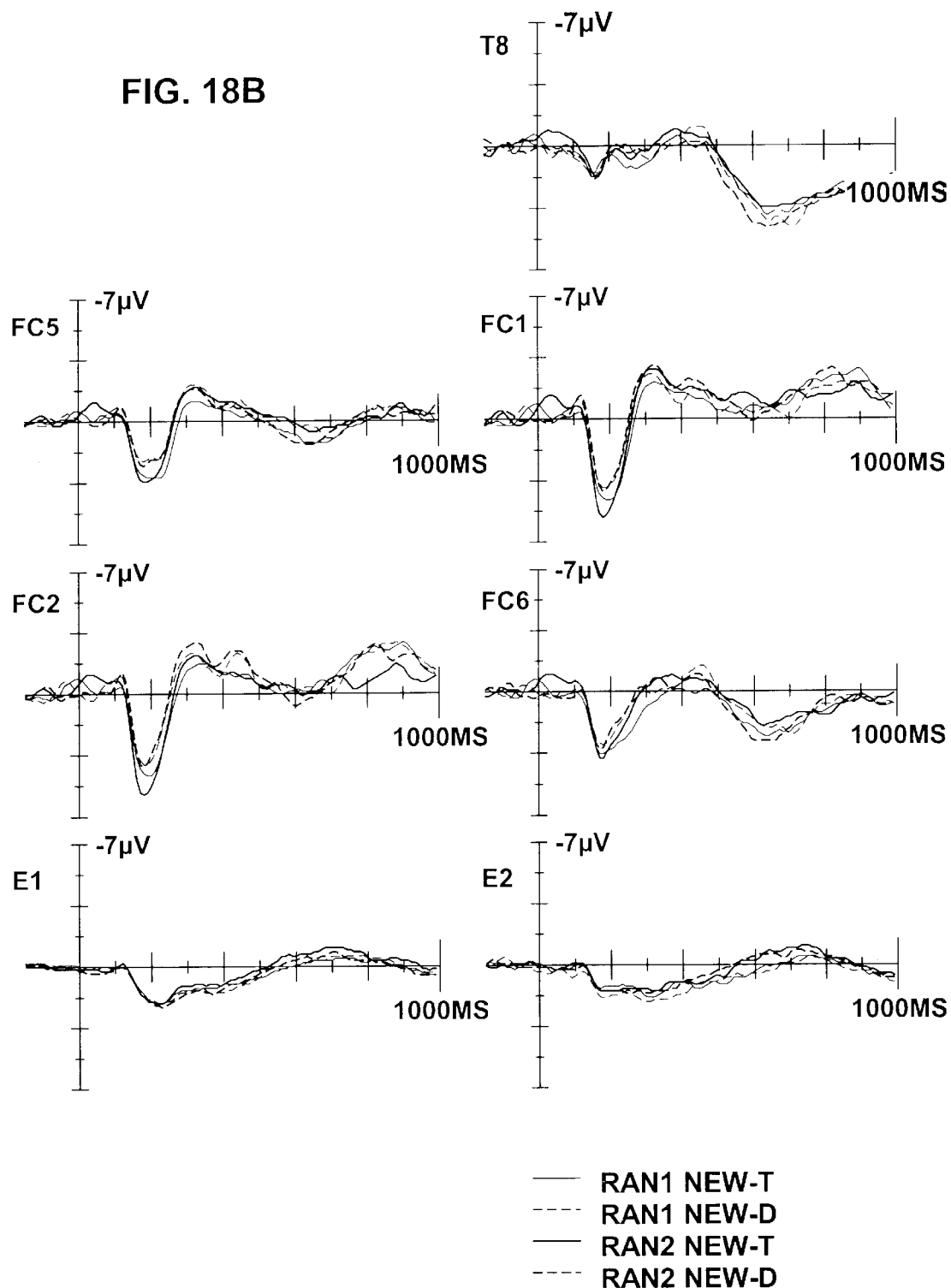
Figure 18C:
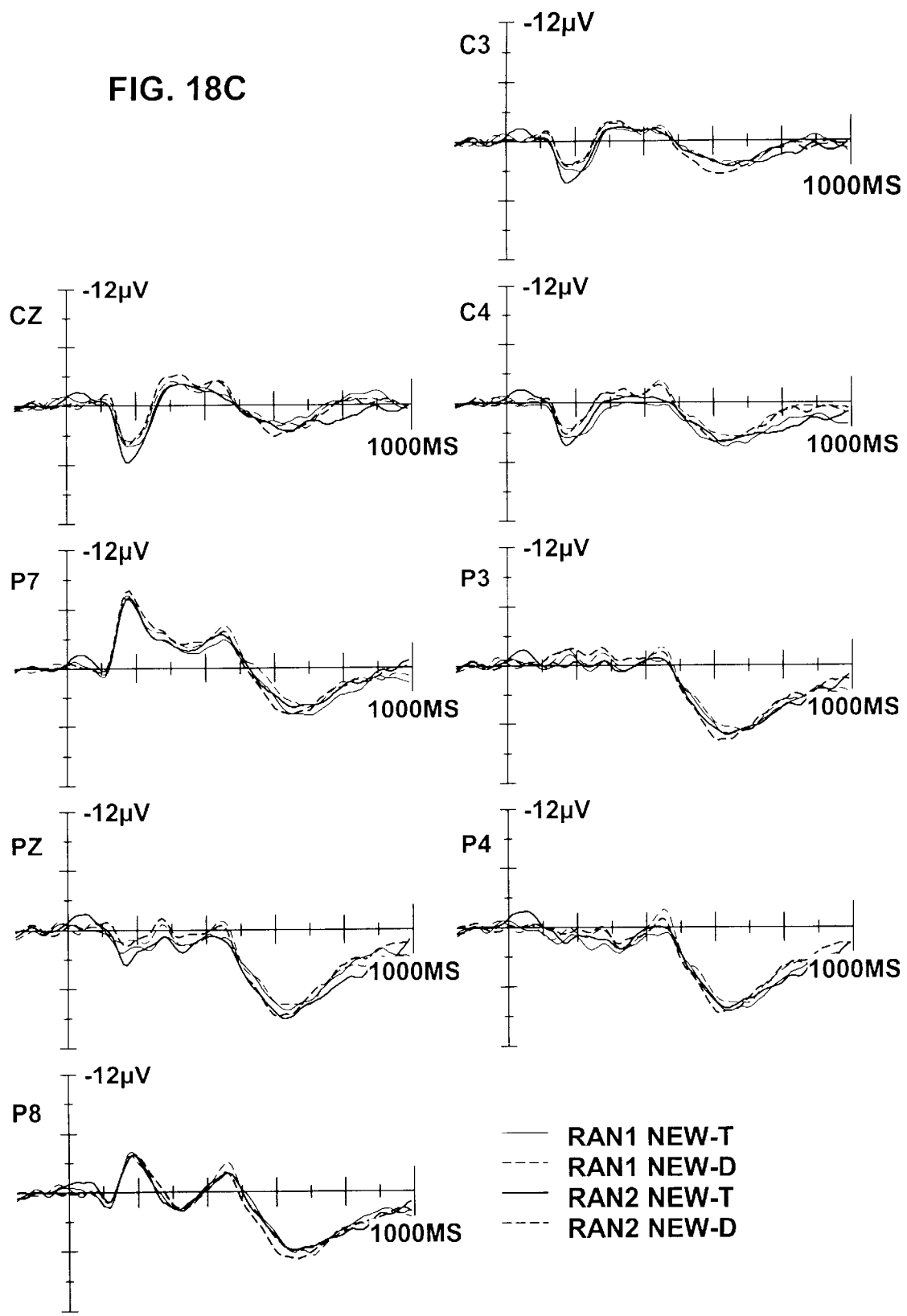
Figure 18D:
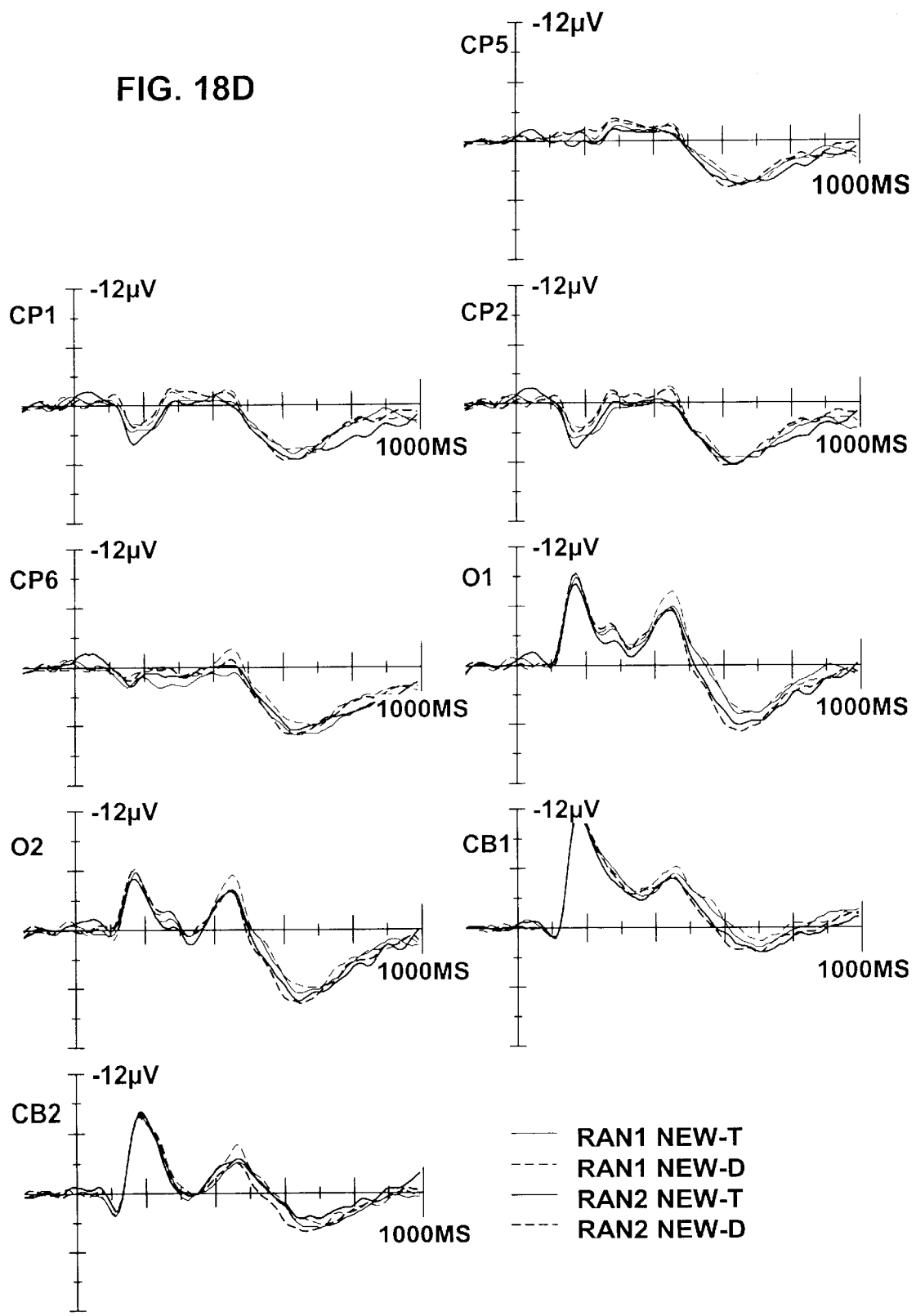

FIG. 16. RAN1 OLD-T/RAN1 OLD-D/RAN2 OLD-T/RAN2 OLD-D. Marker 11, Stimulus-Locked ERPs, 3rd plot. This figure shows the ERPs to old words for both truthful and deceptive responses for the two repetitions of the Random condition. Peaks are the same indicated in FIG. 12.

FIG. 17. RAN1 OLD-T/RAN1 OLD-D/RAN2 OLD-T/RAN2 OLD-D. Marker 11, Response-Locked ERPs, 3rd plot. This figure shows the ERPs to old words for both truthful and deceptive responses for the two repetitions of the Random condition. Peaks are the same as indicated in FIG. 13.

FIG. 18. RAN1 NEW-T/RAN1 NEW-D/RAN2 NEW-T/RAN2 NEW-D. Marker 11, Stimulus-Locked ERPs, 4th plot. This figure shows the ERPs to new words for both truthful and deceptive responses for the two repetitions of the Random condition. Peaks are the same as indicated in FIG. 12.

Figure 19A:
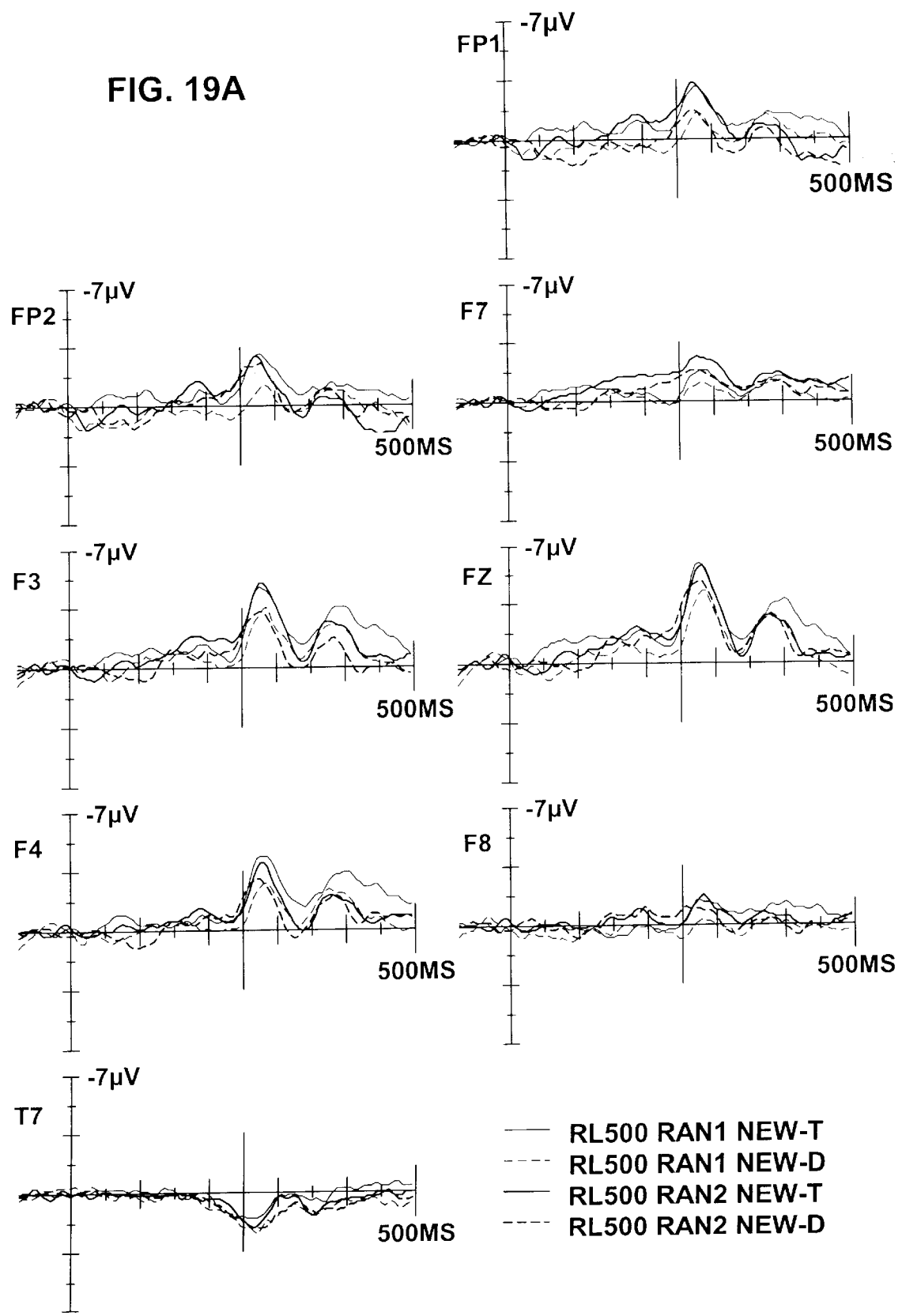
Figure 19C:
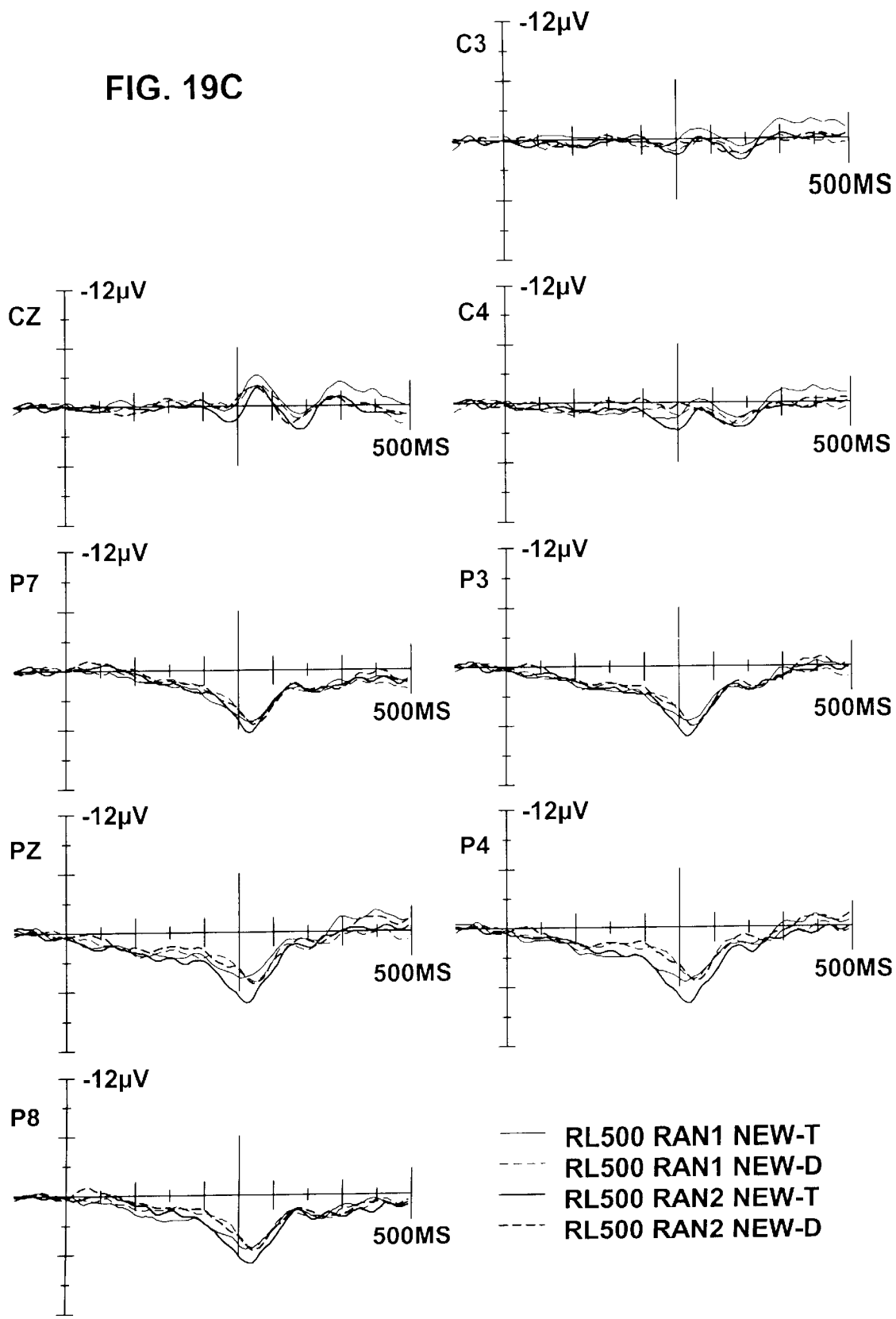
Figure 19D:
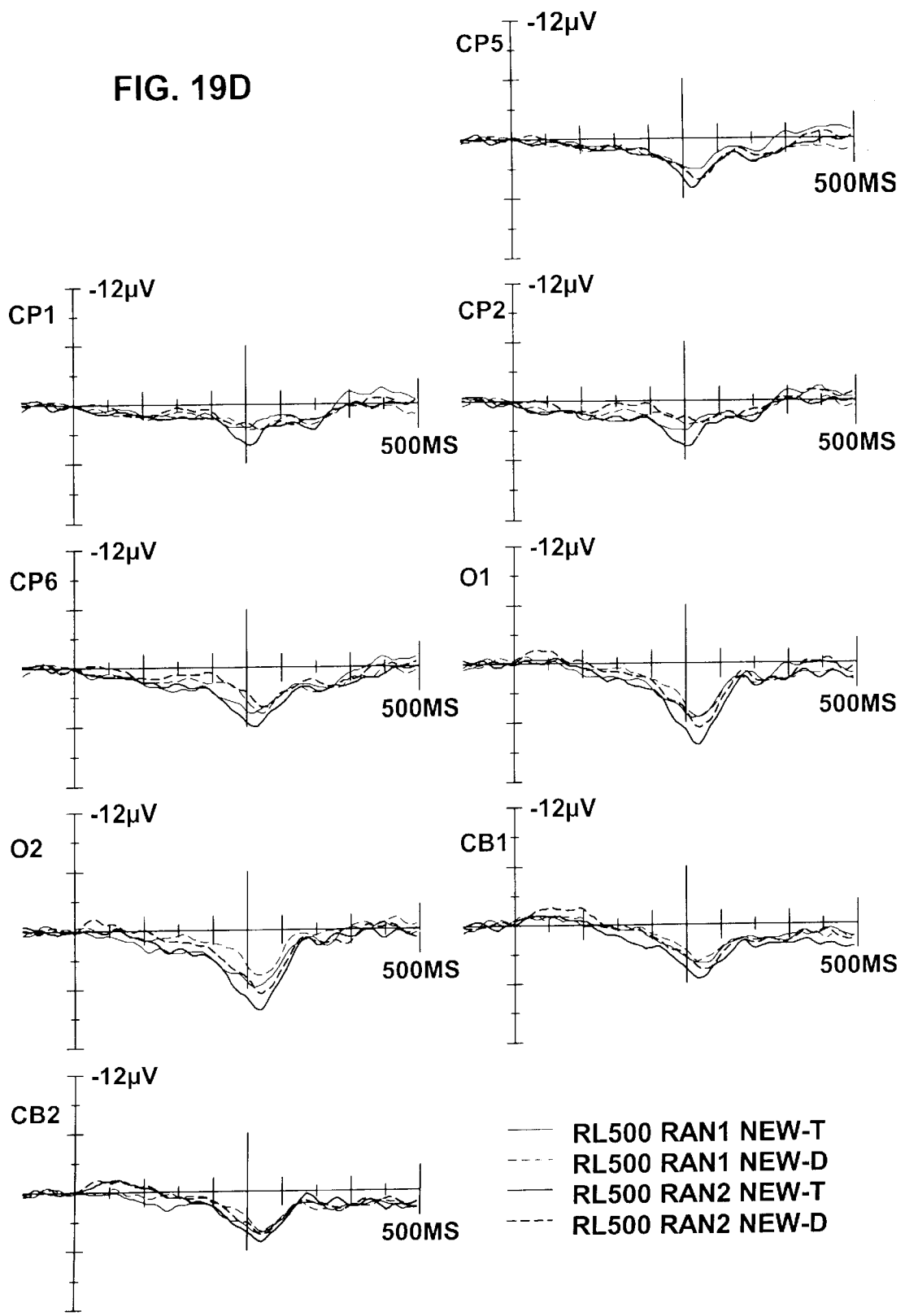
Figure 20A:
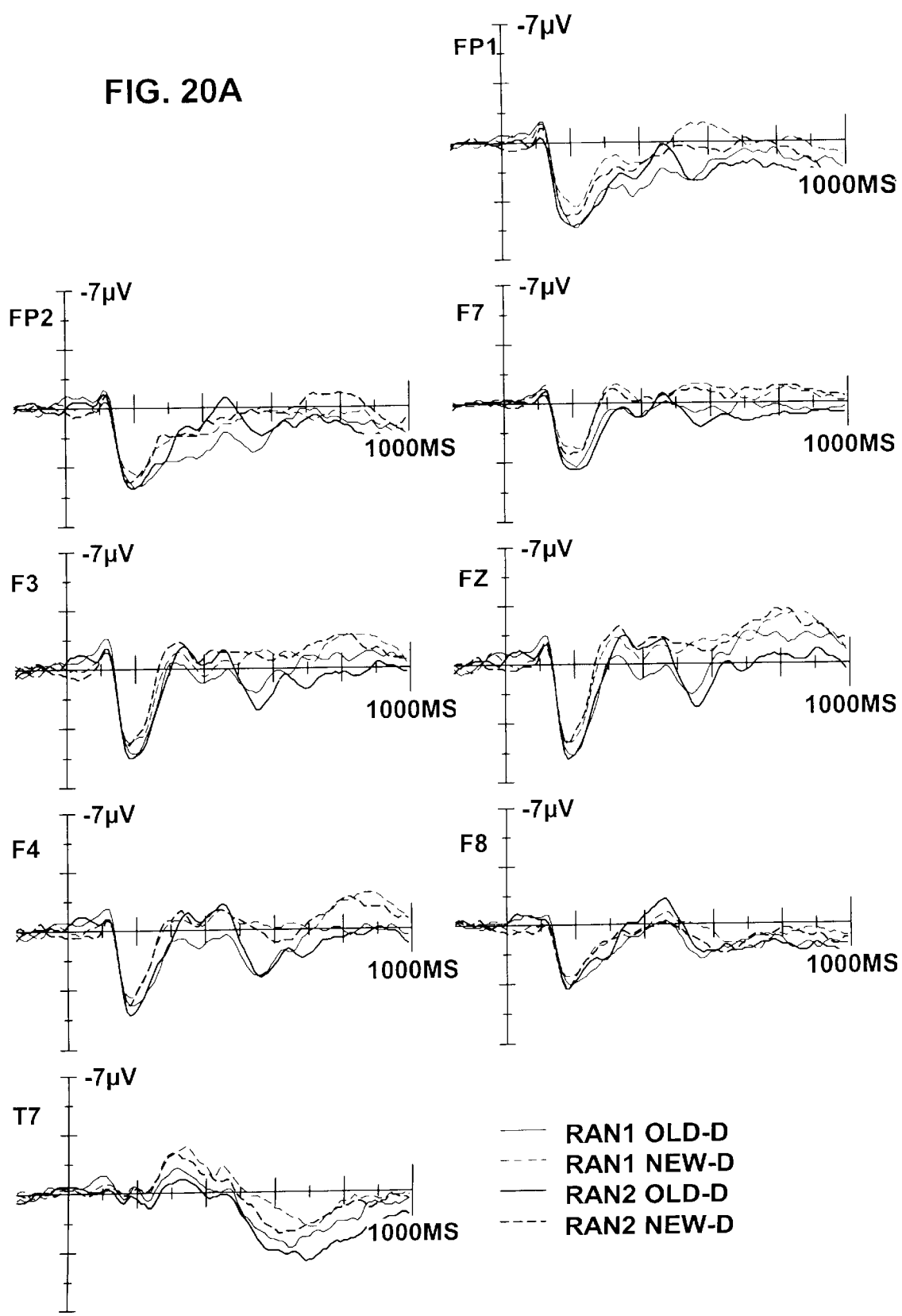
Figure 20B:
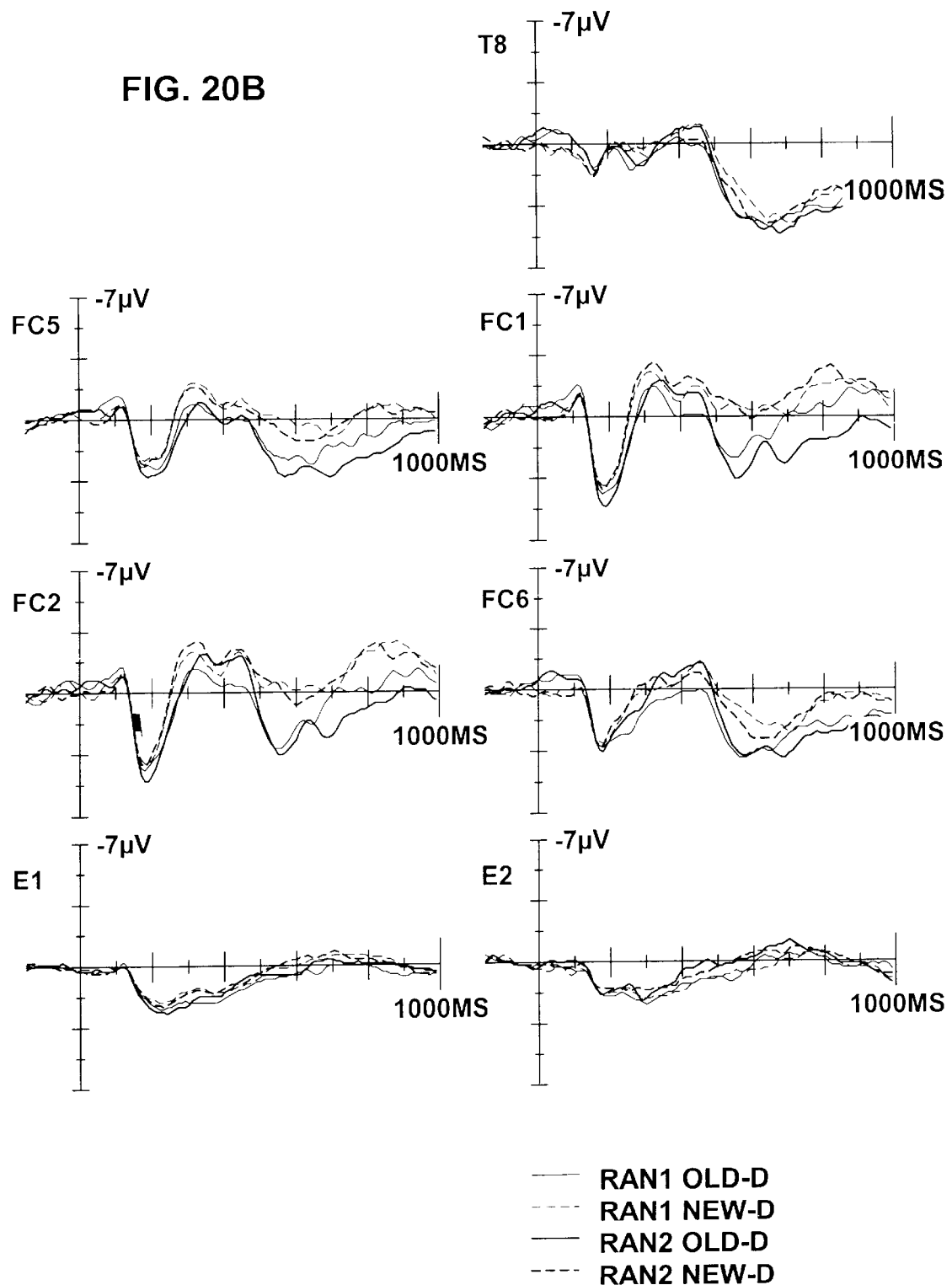
Figure 20C:
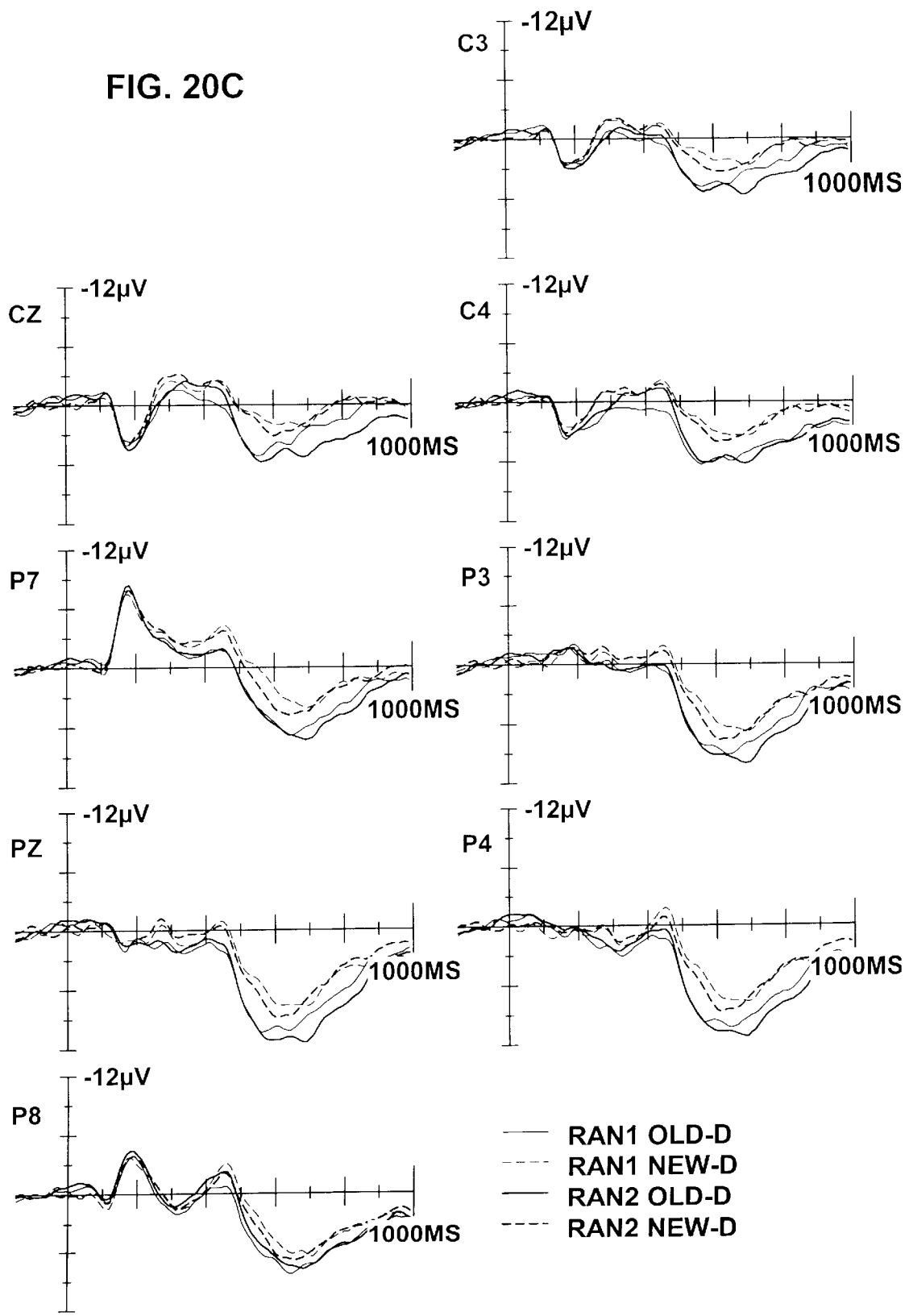
Figure 20D:
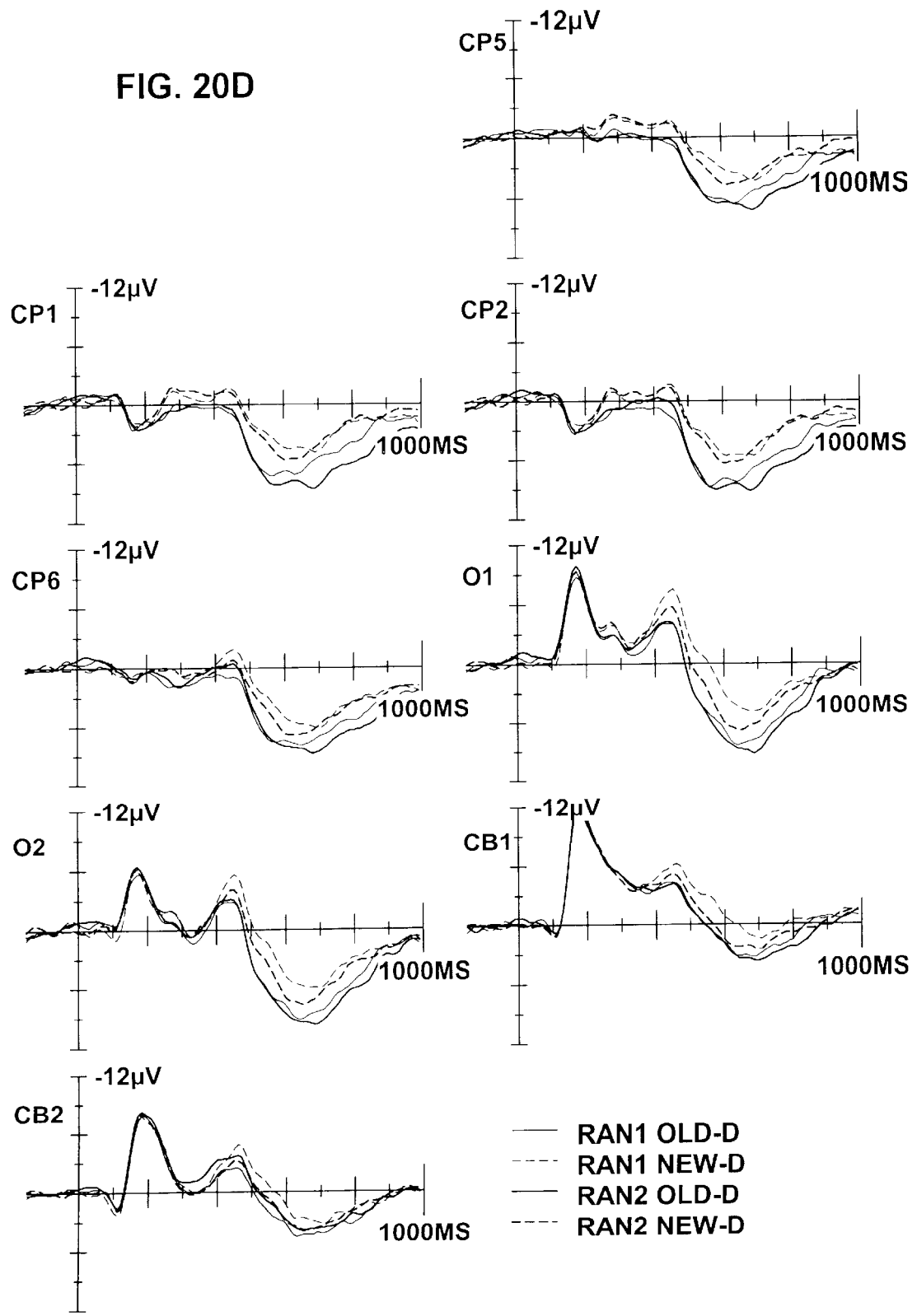

FIG. 19. RAN1 NEW-T/RAN1 NEW-D/RAN2 NEW-T/RAN2 NEW-D. CR(Truth)/FA(Lie) Marker 11, Response-Locked ERPs; 4th plot. This figure shows the ERPs to new words for both truthful and deceptive responses for the two repetitions of the Random condition. Peaks are the same as indicated in FIG. 13.

FIG. 20. RAN1 OLD-D/RAN1 NEW-D/RAN2 OLD-D/RAN2 NEW-D. Marker 11; Stimulus-Locked ERPs; 5th plot. This figure shows the ERPs to old and new words, for deceptive responses only, for the two repetitions of the Random condition. Peaks are the same as indicated in FIG. 12.

Figure 21A:
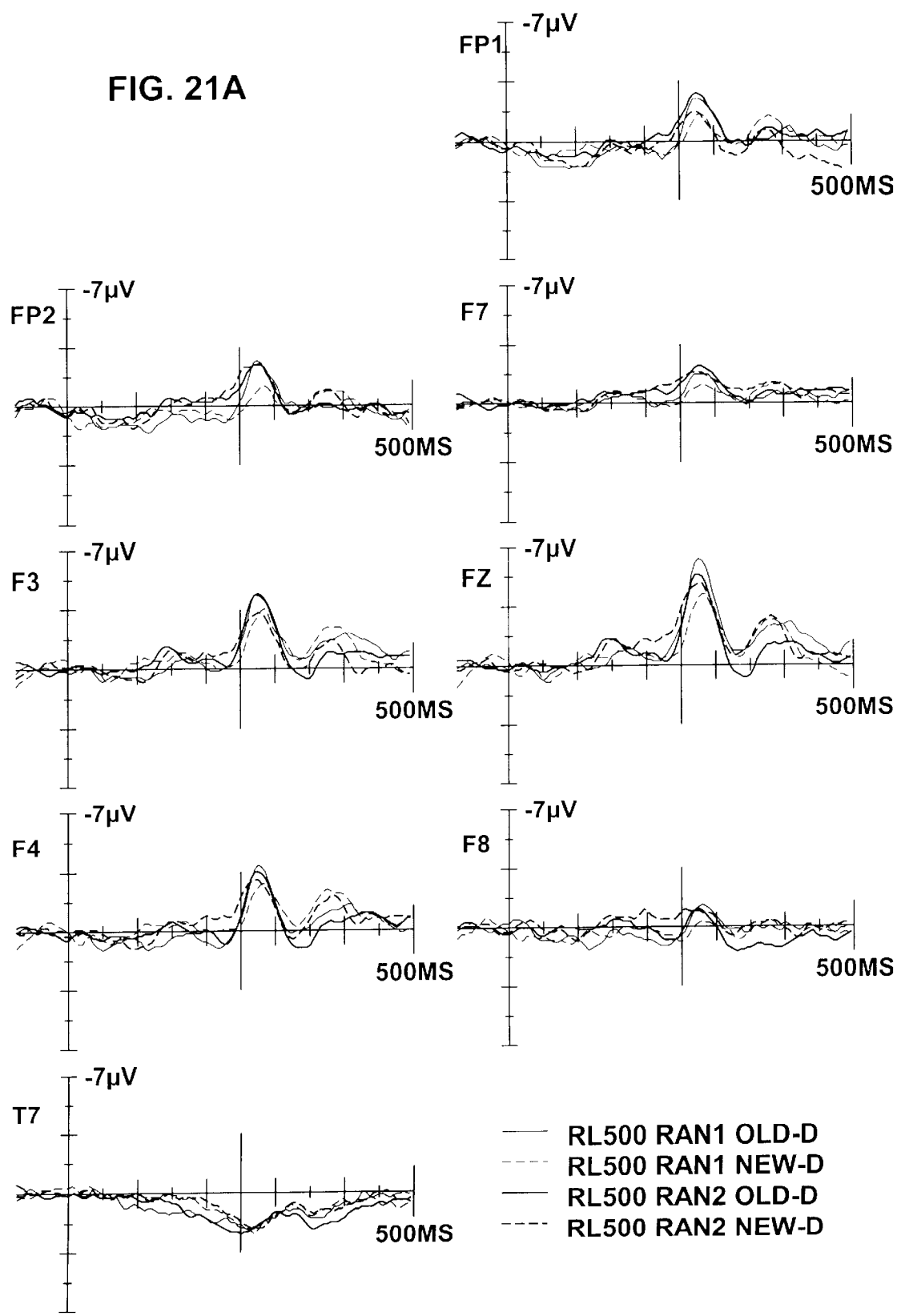
Figure 21C:
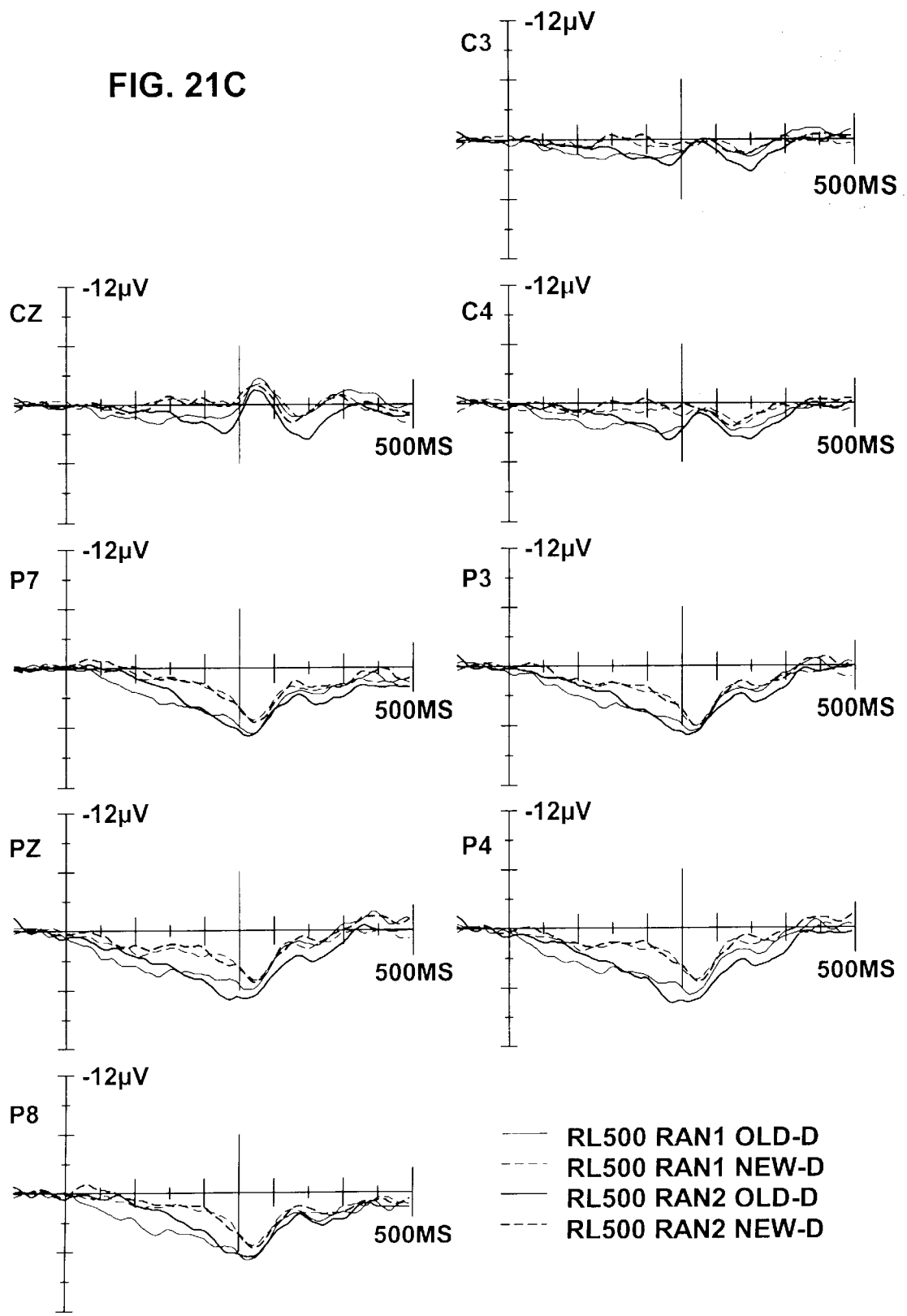
Figure 21D:
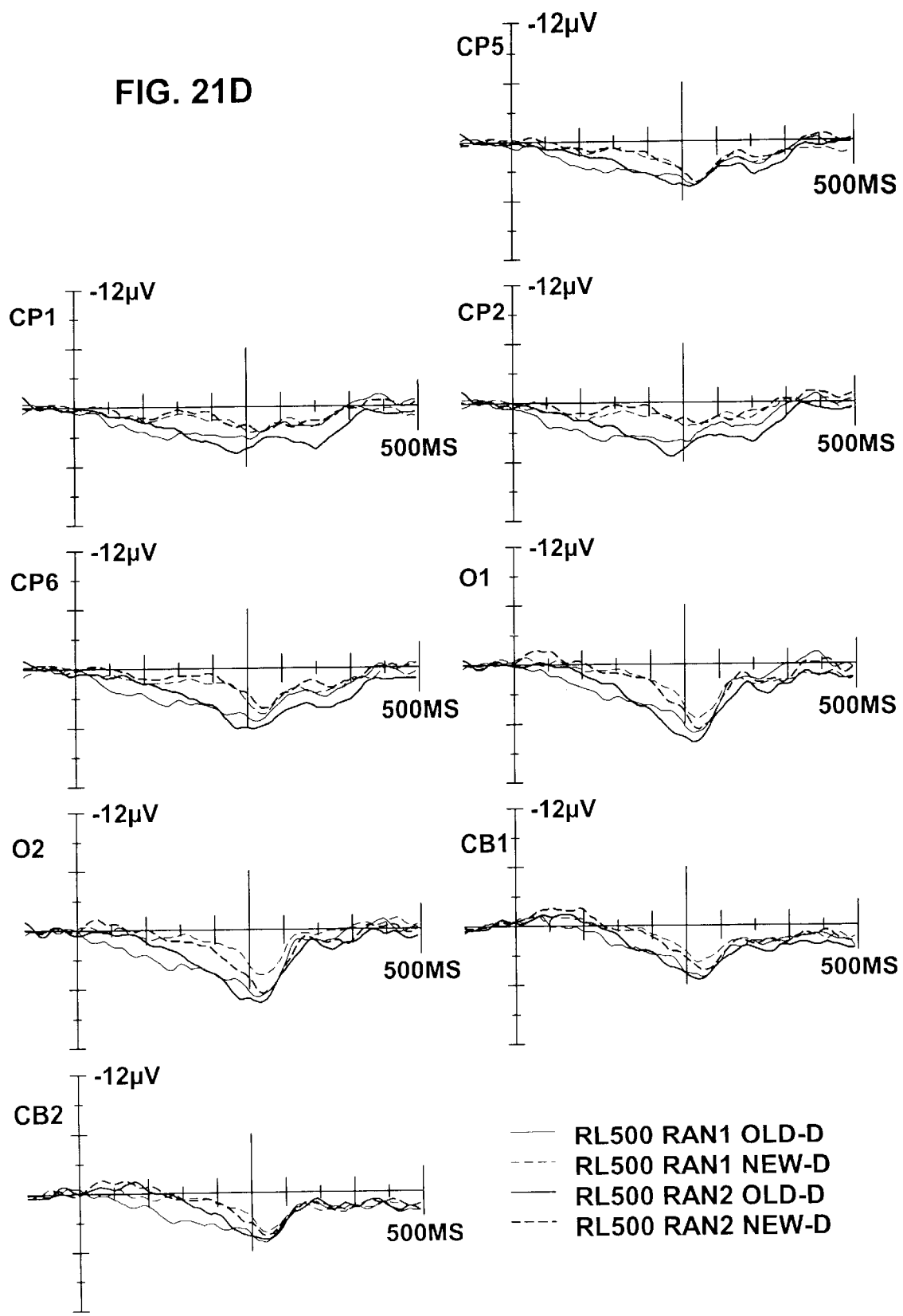

FIG. 21. RAN1 OLD-D/RAN1 NEW-D/RAN2 OLD-D/RAN2 NEW-D. Marker 11, Response-Locked ERPs; 5th plot. This figure shows the ERPs to old and new words, for deceptive responses only, for the two repetitions of the Random condition. Peaks are the same as indicated in FIG. 13.

FIGS. 22–24 are graphs of the behavioral results showing relationships between conditions.

FIG. 22. Marker 7, $1^{st}$ plot. Reaction time data from Control, Truthful, Opposite and Random conditions for 2nd repetition.

FIG. 23. Marker 8, $1^{st}$ plot. Reaction Time variability for the Control-Compatible, Control-Incompatible, Truthful-old words and Opposite-old words responses, 2nd repetition only.

FIG. 24. Marker 8, 2nd plot. Response Time variability for the old and new words for the Opposite, Random conditions, both truthful and deceptive trials, 2nd repetition only.

FIGS. 25–32 are plots of findings at the indicated electrode where the maximal differences in recordings were found.

FIG. 25. Marker 1, Response-Locked ERPs, 4th plot. Response-locked event-related potentials from the frontal-central, Fc2, site, showing the brain activity from 500 ms prior to the response to 500 ms after the response (for 2nd repetition). Negative voltages plotted as upward deflections and the vertical line labeled RT is the time when the response button was pressed. (A) Data from correct trials for Control conditions and the old word trials from the Truthful and Opposite conditions. The ERN (indicated by the arrow) is evident as a negative peak between 0 and 100 ms after the button press. (B) ERNs elicited in the Truthful and Opposite conditions trials as a function of the memory status of the words (old or new). (C) ERNs elicited on the Random-Deceptive trials compared to those elicited by the old and new words in the Opposite condition. (D) A comparison of the ERN activity elicited by the truthful and deceptive responses within the Random condition.

FIG. 26. Marker 22, $1^{st}$ plot. Potential maps (110 degree projections) showing the activity of the entire brain in the interval from 40–100 ms after the subject's response with the front of the head at the top (for 2nd repetition). These potential maps show the distribution of negative (shaded/reds) and positive (unshaded/blues) voltages, calculated on the basis of the across-subject averages. The top and bottom rows show the brain activity when subjects made compatible and incompatible responses, respectively. The first column shows the data from the Control-Compatible (top row) and Control-Incompatible (bottom row) conditions. The second column shows the data for the old words in the Truthful (top row) and Opposite (bottom row) conditions. The third and fourth columns show, respectively, the data for the old and new words from the Random-Truthful (top row) and Random-Deceptive (bottom row) trials.

FIG. 27. Marker 24, Stimulus-Locked ERPs, $1^{st}$ plot. This figure shows the ERPs to old and new words elicited at the parietal, P3, electrode site in the Truthful, Opposite and Random conditions, for the 2nd repetition. The difference between the old (solid lines) and new (dashed lines) word ERPs in the 400–800 ms interval is the parietal old/new difference (also known as the left posterior old/new effect).

FIG. 28. Marker 23, Stimulus-Locked ERPs, 2nd plot. This figure shows the ERPs to old and new words elicited at the frontal, F3, electrode site in the Truthful, Opposite and Random conditions, for the 2nd repetition. The difference between the old (solid lines) and new (dashed lines) in the 300–500 ms interval is the frontal old/new difference (also known as the left frontal old/new effect).

Figure 29B:
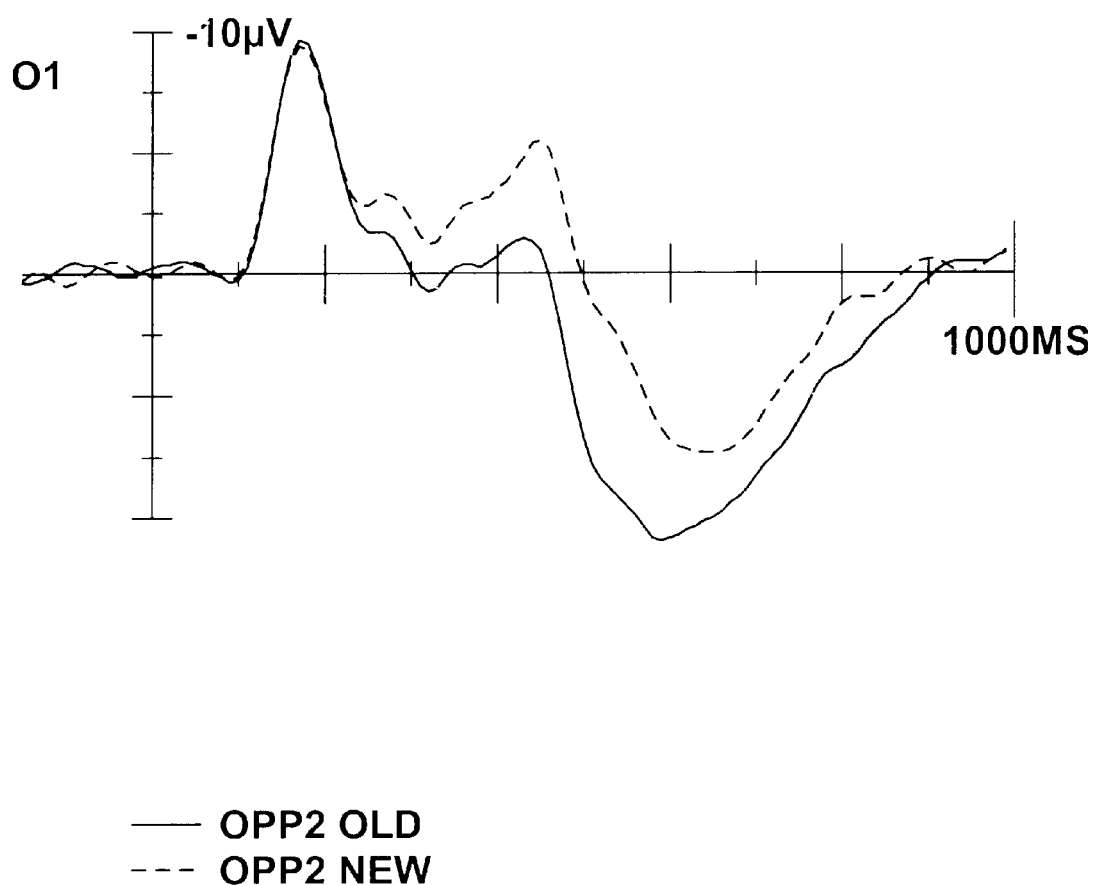
Figure 29C:
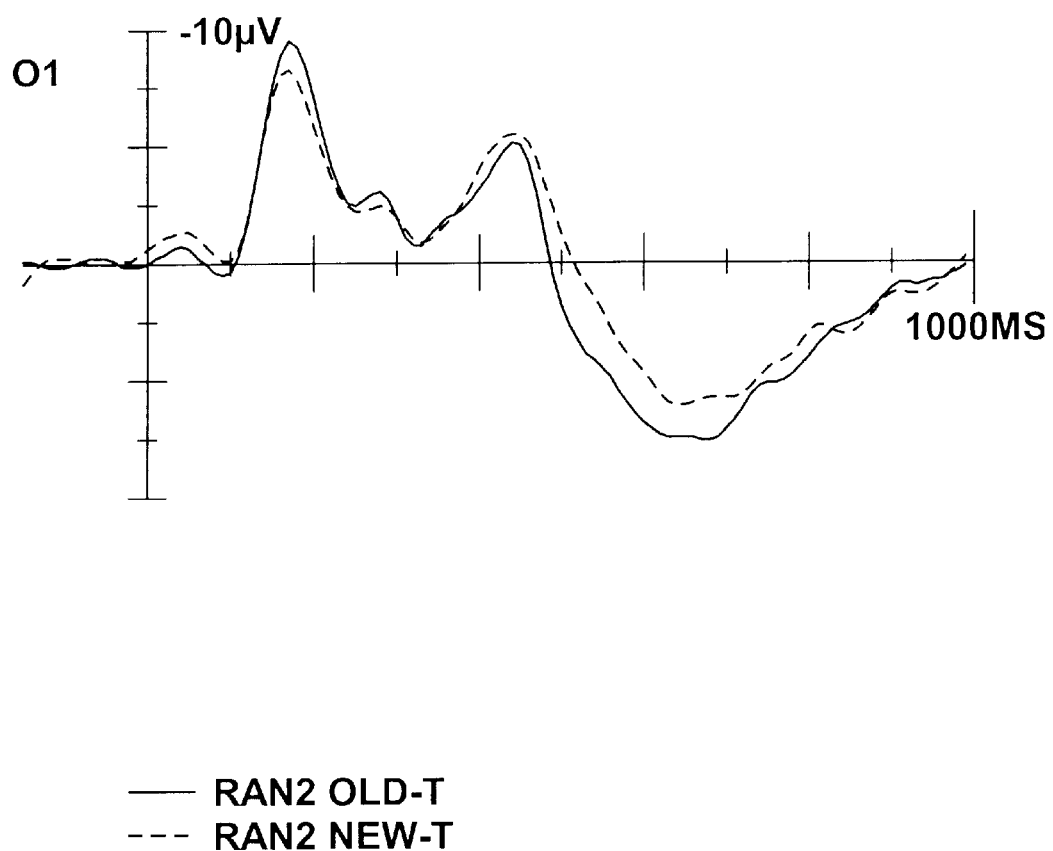
Figure 29D:
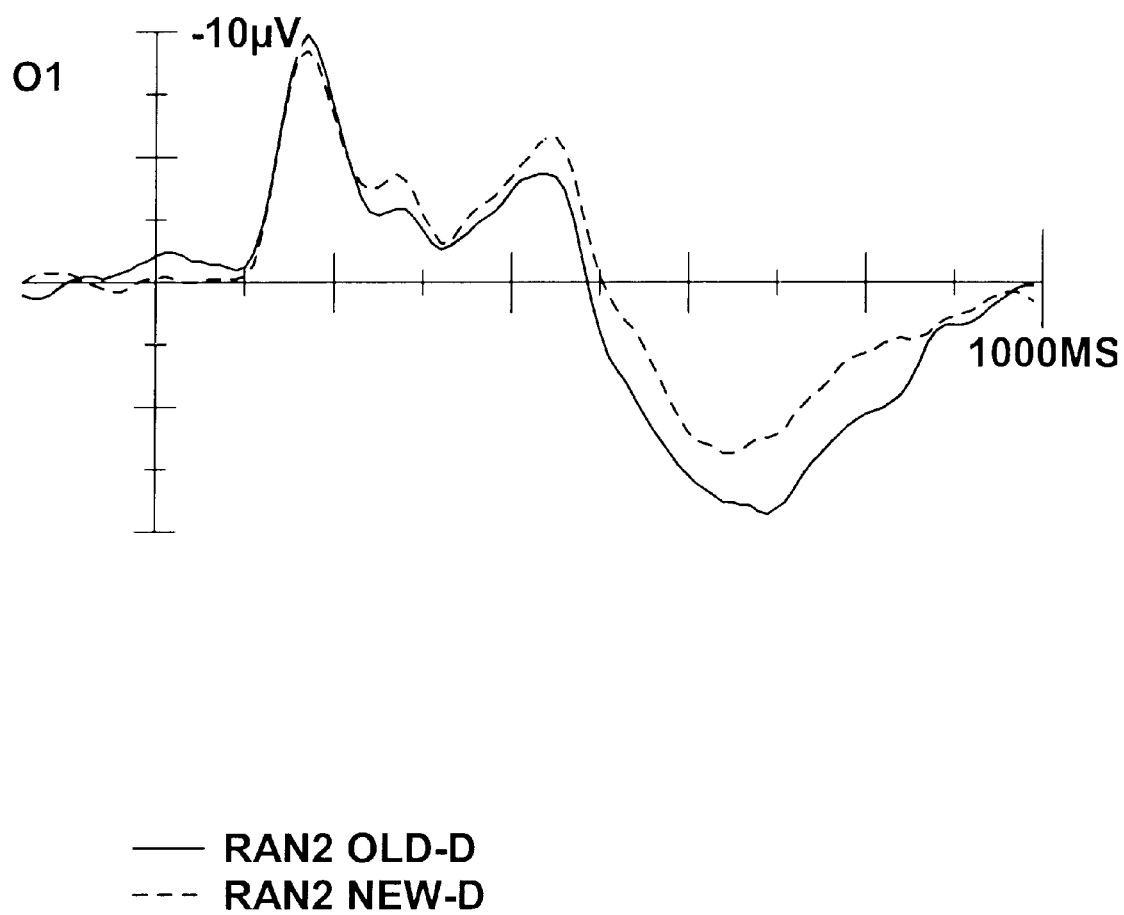

FIG. 29. Markers 3 and 25, Stimulus-Locked ERPs, 1st plot. This figure shows the ERPs to old and new words elicited at the occipital, O1, electrode site in the Truthful, Opposite and Random conditions, for the 2nd repetition. The difference between the old (solid lines) and new (dashed lines) in the 300–500 ms interval is the occipital old/new difference.

Figure 30A:
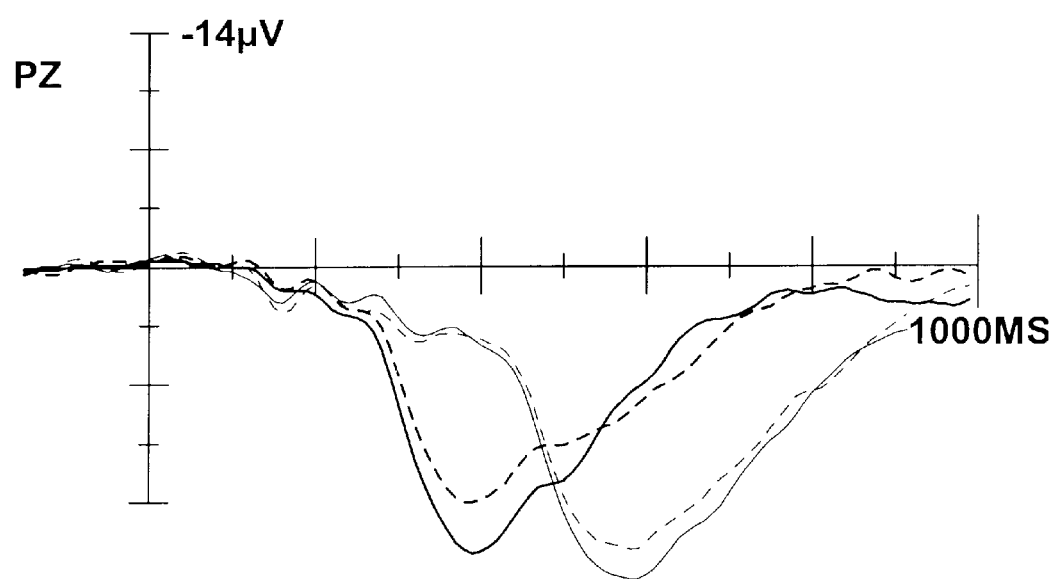
Figure 30B:
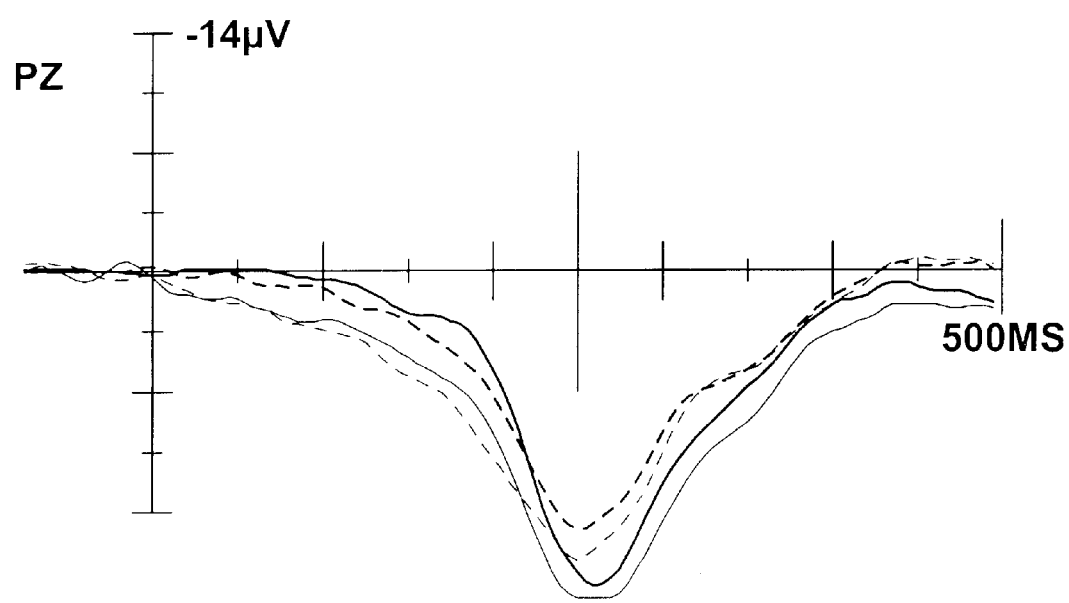

FIG. 30. Marker 2A, Stimulus-Locked and Response-Locked ERPs, 5th plot. This figure shows the ERPs elicited by the stimuli in the two control conditions (Control-Compatible (thin solid line) and Control-Incompatible (thin dashed line)) and by the old words in the Truthful and Opposite recognition conditions at the parietal, Pz, electrode site. The difference between the Truthful (thick solid lines) and Opposite (thick dashed lines) ERPs in the 400–800 ms interval shows the reduced P300s elicited by deceptive responses.

Figure 31A:
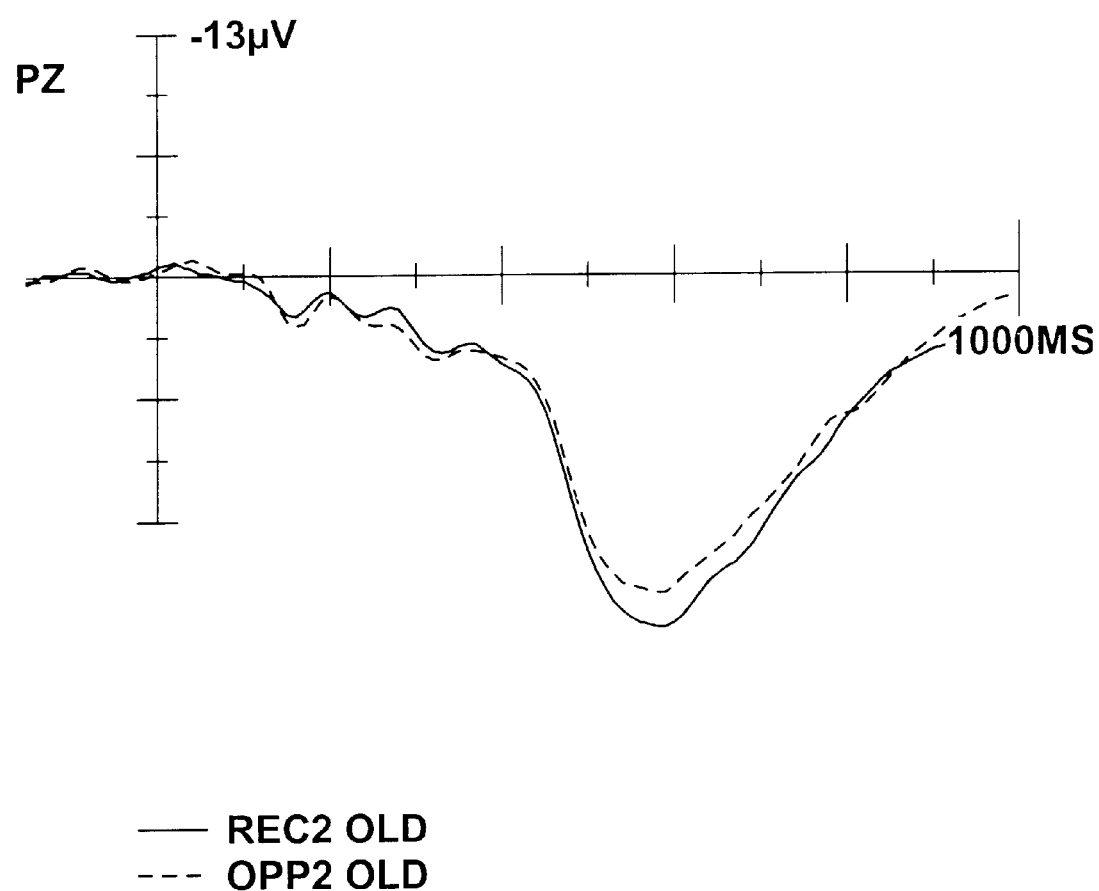
Figure 31B:
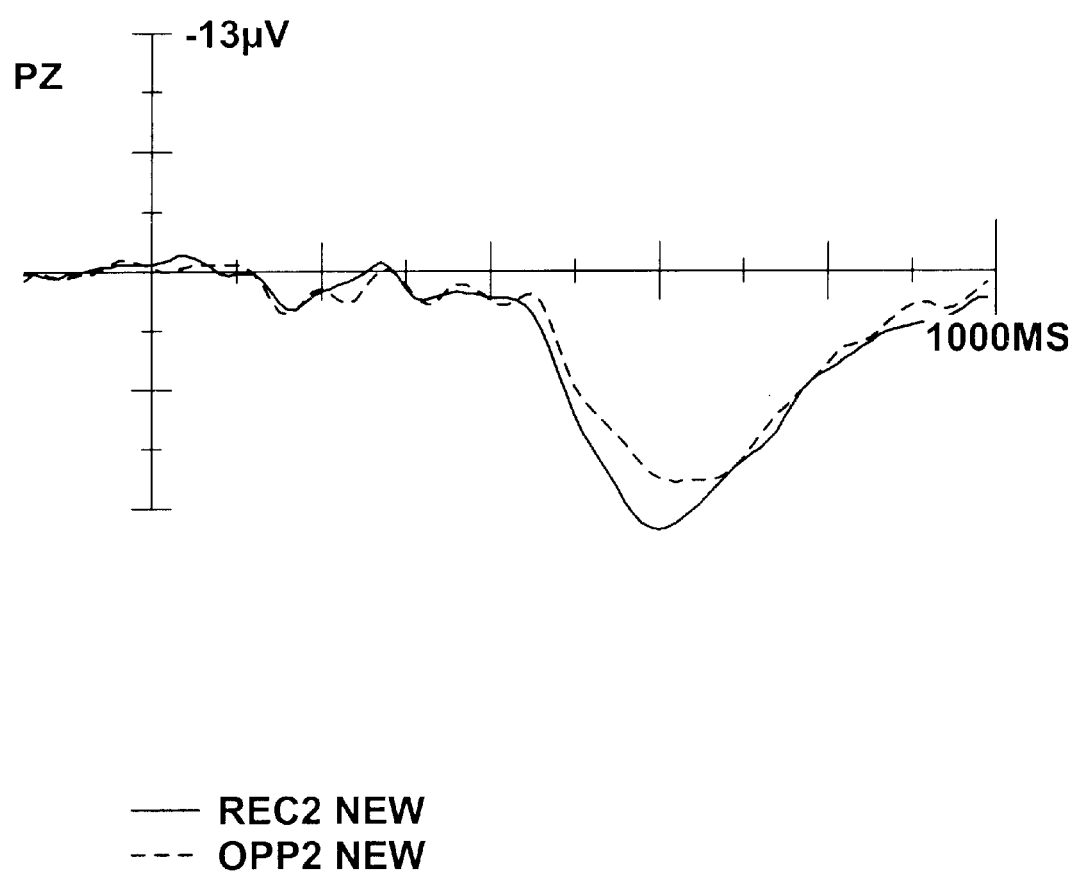

FIG. 31. Marker 2A, Stimulus-Locked ERPs, 6th plot. This figure shows the ERPs elicited by the old and new words in the Truthful and Opposite recognition conditions at the parietal, Pz, electrode site. The difference between the Truthful (solid lines) and Opposite (dashed lines) ERPs in the 400–800 ms interval shows the reduced P300s elicited by deceptive responses.

Figure 32A:
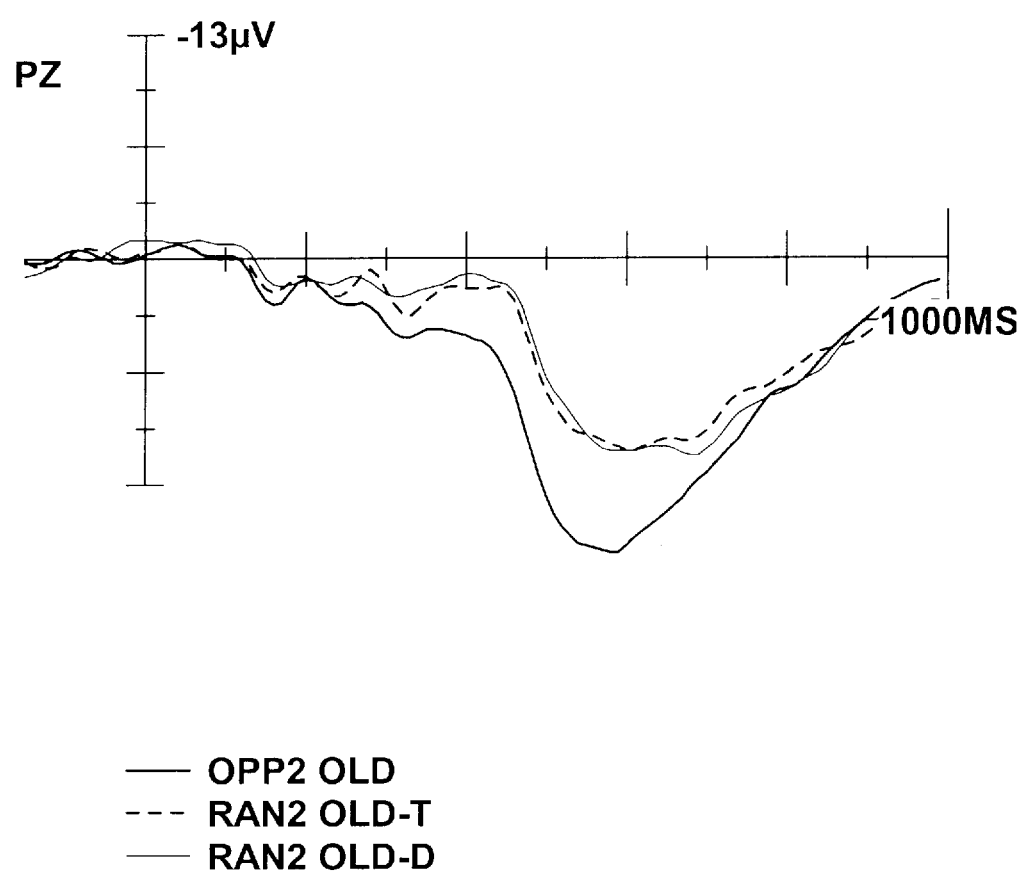
Figure 32B:
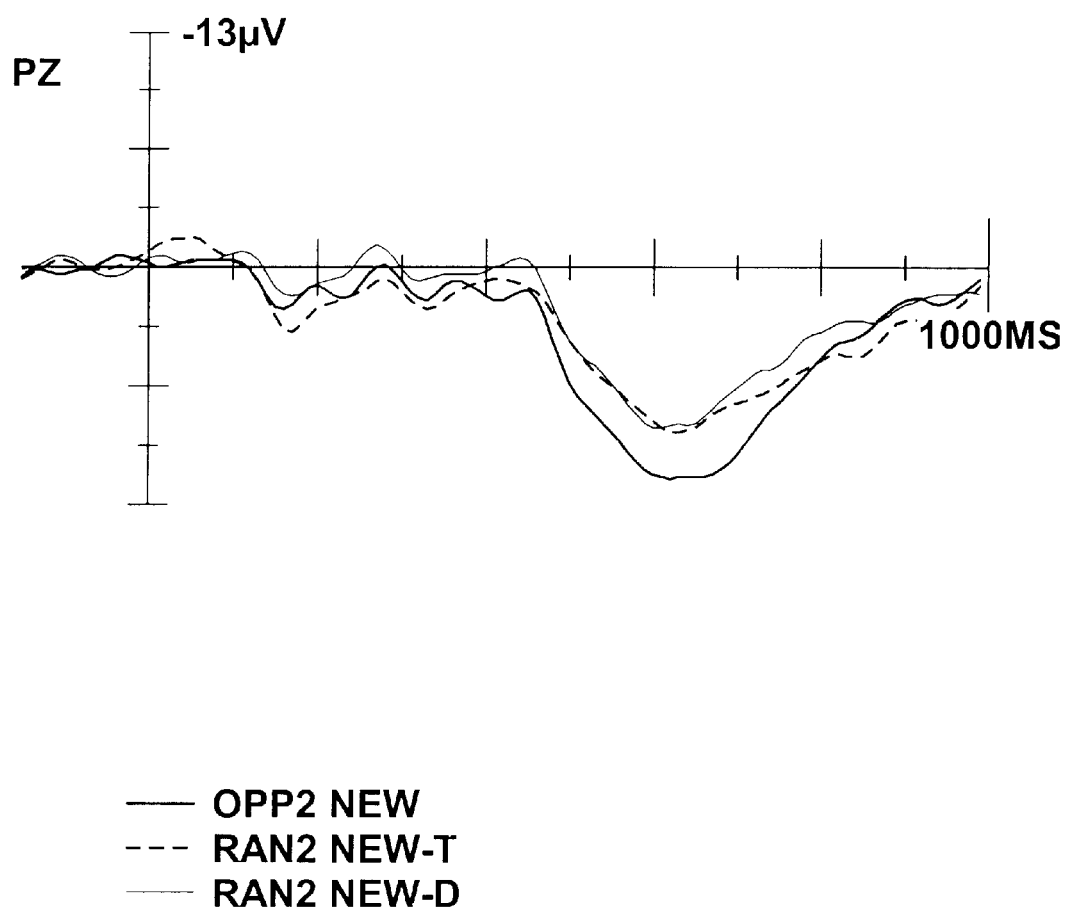

FIG. 32. Marker 2A, Stimulus-Locked ERPs, 7th plot. This figure shows the ERPs elicited by the old and new words in the Opposite and Random recognition conditions at the parietal, Pz, electrode site. The difference between the Opposite (heavy solid lines) and Random (thin solid lines, dashed lines) ERPs in the 400–800 ms interval shows that, when subjects monitor the pattern of their deceptive responses (i.e., unpracticed responses), P300 amplitudes are reduced significantly more than when subjects make a practiced deceptive response.

DETAILED DESCRIPTION OF THE INVENTION

Deception occurs when a subject makes a response related to a memory that is incompatible with the content of that memory. When a subject responds that they did not do or say something that they actually did or said, their response is conceptually incompatible with their experience; this type of conflict is referred to as a conceptually-driven response conflict. Incompatible responses may require the subject to overcome the moral imperative to make the compatible, or truthful, response. Maintaining a deception may also require the subject to monitor their responses in a "strategic" manner to ensure that the pattern and identity of the responses are consistent throughout an inquisition. Ensuring consistency, in turn, may require increased mental effort and controlled processing resources overt that required for being non-deceptive. Finally, deception may involve additional components such as the subject's intent to deceive and emotional reactions.

Definitions

"Subject" is the person being tested.

"Experience" is an item in a subject's memory. Experience includes past actions and events involving the subject alone or with others, thoughts including thoughts about past or future plans, actions, attitudes, beliefs, and views. Items in a subject's experience include any physical or mental activity that leads to the formation of a memory.

An item "not in experience" is an item that may or may not be in the subject's memory such as those related to a fabrication, e.g., a confabulation.

A "test item", also referred to herein as "stimulus," are the items a subject is tested about, e.g., does the subject have the item in memory?; is the subject planning or intending to perform an act? Test items may comprise a wide variety of material including word, sentence and/or fact verification, questions about beliefs, plans or past experiences or exposure to people, places, information, etc.

All the test items presented to a subject in a test are a "Test Series", comprising all the relevant and irrelevant stimuli to be tested.

A "relevant item" is an item that a subject is tested about and is an item or stimulus that may have been learned at or before the testing session, and includes items in experience and not in experience.

"Irrelevant" is an item used to generate control responses for comparison to responses to relevant items. An irrelevant item is not in the subject's memory (experience). In any test scenario, the irrelevant items are designed to elicit a response representative of items not in memory ("new" items in memory tests). Irrelevant items are similar to the relevant items in that they are associated with the general subject matter of relevant items ("match" ), however differ in one or more specific aspects that are not part of the subject's experience (e.g., if the relevant items are about the theft of money, the irrelevant items may be about the theft of other types of items).

"Old" items are relevant items.

"New" items are irrelevant items.

A "known" item is an item in a subject's experience. An "unknown" item is an item not in a subject's experience.

"Compatible" responses are those that are not in conflict with the stimuli.

"Incompatible" responses are responses that are in conflict with the stimuli.

"Negative shift" means that the ERP waveform elicited during a deceptive response is more negative in the defined time interval than an ERP elicited by a truthful response.

"Accuracy" is a performance measure that equals the number of trials having a correct response divided by the total number of trials.

"Significant" means statistically significant at the 0.05 level or better, i.e., there is less than a 5% chance that the observed difference is due to chance.

"Deception" means a response related to an experience that is incompatible with the truth or the content of the memory for that experience. Deception may also involve an intentional response about something not in experience, e.g., a fabrication, such as a false alibi. Certain types of deception inherently include intent, such as confabulation.

"Perceptually-driven-response conflict" is a situation induced when one aspect of a stimulus suggests one particular response while another aspect of the same stimulus suggests a different, competing response.

"Conceptually-driven response conflict" is a situation in which the subject makes a response that is incompatible with the subject's experience.

The terms frontal, parietal, temporal and occipital all refer to standard terminology for the different lobes of the brain. When commonly used in descriptions of ERP activity, these terms refer to the area of the scalp overlying the different brain lobes. Central refers to the center of the top of the head.

The term "component" means a "source of controlled, observable variability (Donchin, E. et al., "Cognitive Psychophysiology: the endogenous components of the ERP." In Calloway, E. et al. (Eds), Event-Related Brain Potentials in Man. New York, Academic Press, pp 349–441, 1978) in the ERP that takes the form of a positive or negative peak or shift. The ERP components constitute the ERP markers.

"Stimulus-locked ERPs" are averaged ERP data that use the time of stimulus onset as the reference point for aligning the single-trial ERP waveforms.

"Response-locked ERPs" are averaged ERP data that use the time of the subject's response on each trial as the reference point for aligning the single-trial ERP waveforms, usually to some arbitrary time point.

"Amplitude" is the magnitude or amount of brain activity represented by an ERP component or shift. Baseline-to-peak and area are two ways, among others, that can be used to quantify a component's amplitude. Baseline-to-peak amplitude is measured by finding the largest or smallest voltage in a specified time range and subtracting the average voltage obtained from a pre-stimulus baseline interval. A component's area is measured by summing all ERP activity within a specified time window range and subtracting the average voltage obtained from a pre-stimulus baseline interval. While either method results in essentially the same information, the area method may be less susceptible to residual noise and latency jitter in the averaged ERP.

"Latency" refers to the timing of an ERP component. One measure of latency, peak latency, is the time at which the peak, i.e., the point of highest voltage, occurs relative to a reference time, usually stimulus onset. Other measures, such as the beginning (onset) or end (offset) of a peak or shift can also be used as latency measures.

"Scalp distribution" is the pattern of voltage variations obtained when an ERP component is measured at multiple locations on the scalp during a given time span. The scalp distribution can be defined in terms of both the specific location(s) of maximum peak amplitude (positive or negative) and the spatial characteristics of the voltages surrounding the peak. Scalp distribution is analyzed by comparing the amplitudes obtained for two different sets of data, (e.g., the data obtained from Truthful versus Deceptive responses) at a particular group of electrodes that includes locations where the component is at or near its maximum and sites located away from the maximum. For example, if the component is maximal at Pz, activity at Cz and Fz might be included in the comparison. For methods of quantifying a component's scalp distribution and interpretation of activity, see, e.g., Johnson (1993).

The present invention provides a method for identifying the neural-behavioral signature of deception by recording brain activity when subjects respond deceptively. Brain activity is measured by extracting ERPs from an electroencephalogram (EEG) using standard stimulus presentation and signal analysis methods (Picton, T. W. et al., above).

The method of the invention is based on the identification and characterization of ERP and behavioral markers of deception that occur when a subjects responds deceptively to a stimulus. The deception may be about items both either in a subject's experience (when a subject asserts that they do not know something that they do know; when a subject asserts that they have not done something that they have done) or not in a subject's experience (when a subject states they know something that they do not know; when a subject states that they have done something that they have not done). The markers, described below, may be used singly or in combination or in addition to other markers to detect deception or the presence of guilty knowledge. Generally any one or combination of the measures described herein may be present in any paradigm that is used to detect deception, e.g., presentation of stimuli regarding past events (sentence verification, fact verification) or regarding intent or future plans or guilty knowledge. These markers provide a more reliable and sensitive method of detecting deception and guilty knowledge than prior methods. An advantage of the method is that the number of markers permits creation of ranges of scores for probable deception, probable truth and indeterminate. The ranges may be calculated in different ways: e.g., 1) a simple sum of the number of markers indicating deception, 2) a division of the markers into categories (individual ERP, individual behavioral, repetition ERP, repetition behavioral, etc) with a score for each that, combined in some way, leads to a score on which a determination of deception can be based).

The method of detecting deception and/or guilty knowledge is based on one or more of the following measures, or "markers" of deception.

| MARKERS |  |
|---|---|
| Individual Series-Derived Measures of Deception | |
| ERP Markers | |
| 1 Significantly larger maximal amplitude in ERN between 0 and 100 ms after the response over the central-frontal scalp in response-locked ERP averages. | The ERN is a negative ERP component with a latency between 0 and 100 ms after the response. The ERN/Nc exhibits a maximal amplitude over the central-frontal scalp region that is significantly larger, i.e., more negative, in response-locked ERP averages when a subject is deceptive (see FIGS. 2, 3, 4 and 25). |
| 2 Smaller maximal amplitude in P300 between 400–800 ms after the stimulus over the parietal-central scalp region in stimulus-locked averages./Smaller maximal amplitude between −100 before the response and +300 ms after the response in response-locked averages. | The P300 is a positive ERP component with a latency between about 400 and 800 ms after a stimulus. The P300 exhibits a maximal amplitude over the parietal-central scalp region that is significantly smaller, i.e., less positive in stimulus-locked ERP averages, when a subject is deceptive (see FIGS. 5, 6, 7, 25, 26). This marker is also apparent as a smaller maximal amplitude between −100 before the response and +300 ms after the response in the response-locked ERP averages (see FIGS. 2, 3 and 4). |
| 3 Larger negativity maximal over occipital and inferior temporal scalp between 300 and 500 ms after the stimulus in stimulus-locked ERP averages. | A significantly larger negativity in the stimulus-locked ERPs, maximal over occipital and inferior temporal scalp appears between 300 and 500 ms after the stimulus when a subject is deceptive (see FIGS. 5, 6 and 29). This enhanced ERP activity appears when a subject classifies an item as irrelevant when the subject knows that the item is relevant, i.e., lies (see FIGS. 6 and 29). This factor also indexes "guilty knowledge" because it occurs when a subject is deceptive about an item that is in memory. |
| 4 Smaller medial frontal-central scalp maximal positivity between −100 and 0 ms before the response in response-locked ERP averages. | A medial frontal-central maximal positivity in the response-locked ERPs, present in the −100 and 0 ms interval before the response, is significantly smaller, i.e., less positive, when a subject is deceptive (see FIGS. 2, 3, 4 and 25). |
| 5 Smaller medial frontal-central scalp maximal positivity between 100 and 200 ms after response in response-locked ERP averages. | A medial frontal-central maximal positivity in the response-locked ERPs, present between 100 and 200 ms after the response, is significantly smaller, i.e., less positive, when a subject is deceptive (see FIGS. 2, 3, 4 and 25). |
| 6 Larger negative shift between −100 before response and +200 ms after response maximal over medial central-frontal scalp in response-locked ERP averages. | When a subject is deceptive, there is a significantly larger negative shift in the ERP between −100 before and +200 ms after the response in response-locked averages that is maximal over medial central-frontal scalp (see FIGS. 2, 3, 4, 25). <br><br> This marker may be characterized either as a difference between −100 and +200 due to the activity of each of the three markers 1/4/5 or to a superimposed negative shift described here. |
| Behavioral Markers | |
| 7 Slower speed of response | Speed of response (RT) is significantly slower when a subject is deceptive (see FIG. 22 & Table 3). |

-continued

| | MARKERS | |
|---|---|---|
| 8 | Larger variability of speed of response. | The variability of the RTs (e.g., standard deviation, SD) is significantly greater when a subject is deceptive (see Table 2). |
| 9 | Slower speed of response in catch trials. | RT is significantly slower for catch trials when a subject is deceptive (see Table 5). |
| 10 | Larger variability of speed of response in catch trials. | The variability (e.g., standard deviation, SD) of the RTs for catch trials is significantly greater when a subject is deceptive (see Table 5). |

Repetition Series-Derived Measures of Deception

ERP Markers

| 11 | Smaller P300 amplitude increase over parietal scalp between 400 and 800 ms after stimulus in stimulus-locked ERP averages./ Smaller P300 amplitude increase over parietal scalp between −100 before to +300 ms after response in response-locked ERP averages. | There is little, if any, P300 amplitude increase in a deceptive subject with repeated testing, i.e., a significantly smaller increase (see FIGS. 12, 14, 16 and 18). This effect is evident over parietal scalp in stimulus-locked averages between 400 and 800 ms after stimulus and in the response-locked ERP averages between −100 before to +300 ms after the response (see FIGS. 13, 15, 17 and 19). This is in contrast to studies wherein repeated testing of relevant items in a truthful subject's personal memory showed significant increases in P300 amplitude for both relevant and irrelevant stimuli. (Johnson R, Jr. 1995B; Johnson R Jr. et al. 1998; Johnson R Jr. et al, 1985). |
| 12 | Maximal negativity over occipital-inferior temporal scalp between 300 and 500 ms after stimulus in stimulus-locked ERP averages. | A stimulus-locked occipital-inferior temporal maximal negativity between 300 and 500 ms. There is no decrease or a minimal decrease in amplitude, i.e., a significantly smaller decrease, when a subject is deceptive. This component normally decreases in amplitude, i.e., becomes more positive, over repetitions when subjects are truthful (see FIGS. 12, 14, 16 and 18). |
| 13 | Smaller increase in positivity over medial frontal-central scalp between −100 and 0 ms before response in response-locked ERP averages. | There is a minimal or no increase in amplitude when a subject is deceptive in response-locked medial frontal-central positivity, i.e., a significantly smaller increase, between −100 and 0 ms before the response (see FIGS. 13, 15, 17 and 19). This component normally increases in amplitude, i.e., becomes more positive, over repetitions when a subject is truthful. |
| 14 | Smaller decrease in ERN over medial central-frontal scalp between 0 and 100 ms after response in response-locked ERP averages. | There is a minimal or no decrease , i.e., a significantly smaller decrease, in amplitude when a subject is deceptive in response-locked medial central-frontal ERN between 0 and 100 ms after the response (see FIGS. 13, 15, 17 and 19). In contrast, this component decreases in amplitude, i.e., becomes less negative, over repetitions when a subject is truthful. |
| 15 | Smaller increase in positivity over medial central-frontal scalp between 100 and 200 ms after response in response-lockd ERP averages. | There is a minimal or no increase in amplitude when a subject is deceptive in response-locked medial central-frontal positivity, i.e., a significantly smaller increase, between 100 and 200 ms after the response (see FIGS. 13, 15, 17 and 19). This component normally increases in amplitude, i.e., becomes more positive, over repetitions when subjects are truthful. |
| 16 | Smaller positive shift, maximal over medial central-frontal scalp between −100 before and +200 ms after the response in response-locked ERP averages. | When a subject is deceptive, the positive shift, maximal over medial central-frontal scalp, that occurs with test repetition between −100 before and +200 ms after the response in the response-locked averages is significantly smaller or absent (see FIGS. 13, 15, 17 and 19). The marker may be characterized either as a difference between −100 and +200 due to the activity of each of the three markers 13/14/15 or to a superimposed negative shift described here. |

Behavioral Markers

| 17 | Smaller decrease in speed of response. | A deceptive subject does not show a significant decrease in speed of response RT with repetition (see Table 2). This is in contrast to repeated testing of items in a truthful subject's personal memory has been shown to be associated with significant decreases in RT to old and new words (Johnson R, Jr. 1995B; Johnson R Jr. et al. 1998; Johnson R Jr et al. 1985). |
| 18 | Smaller decrease in variablity in speed of response. | A deceptive subject does not show a significant decrease in RT variability with repetition (see Table 3). This is in contrast to results obtained from repeated testing of items in a truthful subject's personal memory which is associated with significant decreases in RT variability to old and new words. |

Other Markers

| 19 | Increased P300 latency. | P300 latency is significantly increased when subjects are deceptive. (see Table 4). |
| 20 | Lower response accuracy. | Response accuracy is significantly less when subjects are deceptive (see Table 1). |
| 21 | Smaller response accuracy in catch trials. | Response accuracy is significantly less in catch trials when subjects are deceptive (see Table 5). |
| 22 | ERN scalp distribution. | The scalp distribution of the ERN (markers 1 and 6) is significantly different, as determined by standard distribution analyses procedures described herein, when a subject is deceptive compared to when they are truthful (see FIG. 26). This distribution can be determined by comparing the distributions of the ERNs obtained in the control and test series. |

Guilty Knowledge (GK) Markers

| 23 | A smaller negativity maximal over left central-frontal scalp between 300 and 500 ms after stimulus in stimulus-locked ERP averages. | A smaller negativity maximal over left central-frontal scalp between 300 and 500 ms in the stimulus-locked averages for relevant than irrelevant stimuli (see FIG. 28) appears when a subject possesses guilty knowledge. |
| 24 | A larger positivity maximal over left-parietal occipital scalp between 500 and 800 ms after stimulus in stimulus-locked ERP averages. | A larger positivity maximal over left-parietal occipital scalp between 500 and 800 ms after stimulus in the stimulus-locked averages for relevant than irrelevant stimuli (see FIGS. 4, 5, 12, 13, 14 and 27) appears when a subject possesses guilty knowledge. |
| 25 | Same or smaller negativity maximal over occipital and inferior temporal scalp between 300 and 500 ms after stimulus in stimulus-locked ERP averages. | The same or smaller negativity maximal over occipital and inferior temporal scalp between 300 and 500 ms after stimulus in the stimulus-locked averages for relevant than irrelevant stimuli (see FIGS. 5, 6 and 29) appears when a subject possesses guilty knowledge. |

All markers typically appear in both in relevant and irrelevant trials except for marker 3, which typically appears in relevant trials. The markers described above, except for the guilty knowledge measure, index when a subject has responded deceptively. Some of these markers (e.g., P300, ERN) also index the "state" of being deceptive, that is, they indicate when a subject engages in strategic monitoring (maintains a deception over time or during a series of tests)

regardless of how the subject responded, truthfully or deceptively, to individual terms in a series.

Deception Testing Procedures

Stimuli In addition to words, other types of stimuli (e.g., pictures, voices, sounds, smells or sentences) known in the field of ERP studies may be used in the method of the invention.

Test Series and Control Series—A Test series comprises relevant items (stimuli) that the examiner is trying to query the subject about (e.g., past actions/experiences, attitudes, future plans) randomly mixed with irrelevant items. They may consist of a smaller number of items (e.g., 5–10) that may or may not be repeated, or a larger number (e.g., 10–60) of unrepeated items. The ERP activity and behavioral markers obtained for responses in a Test Series are compared to the ERP activity measured in response to randomly mixed relevant and irrelevant stimuli/questions in a Control series. The Control series determines the nature of each subject's neural and behavioral response patterns when they respond truthfully to a series of stimuli pertaining to items in memory and items not in memory. The degree of match between the stimuli used in the Control and Test series is not critical to the practice of the method of the invention. After each stimulus is presented, the subject categorizes the stimulus as either known/unknown in memory based tests, or true/false in fact/sentence/attitude/plan/thought verification tests.

The number of relevant and irrelevant items presented in the Test and Control Series may vary or may be presented with equal frequency; in the method that tests for guilty knowledge, relevant and irrelevant items are presented with equal frequency.

Individual Series and Repetition Series

An Individual Series compares one Test Series against one Control Series. A test series and its Control Series is known as a "set". Markers 1–10 are evident when comparing one Test Series and the corresponding Control Series.

In a Repetition Series, an Individual Series (i.e., a "set" comprising a Test Series and a Control series) is repeated one or more times and the responses from one set are compared to another set in that repeated series. In Repetitions, the relevant items may be presented twice or more in the additional sets of Test and Control series, using different lists of comparable irrelevant items for each repetition. Repeated series ensure reliability due to the increase in the number of responses that are analyzed and provides additional markers. Markers 11–18 are evident when comparing responses from one set , e.g., the first repetition, and another set, e.g., the second repetition.

Catch Trials—Two types of "catch" trials, one each for the relevant (old) and irrelevant (new) stimulus categories, are presented in a certain percentage (e.g., 5–40%) of the total number of trials. For the relevant and irrelevant catch trials, the subject is instructed to maintain the stimulus-response pairings assigned by the tester for the other relevant and irrelevant trials. For example in a catch trial that comprises as stimuli the words "RELEVANT" and "IRRELEVANT" or "OLD" and "NEW", the subject is instructed to respond by making the assigned response for that stimulus category ("RELEVANT", "IRRELEVANT", "OLD", "NEW", respectively) as quickly as possible. Catch trials may comprise stimuli presented in a manner analogous, e.g., via word, picture or voice, to the method used to present the Test and Control stimuli.

Response—The subject's primary task in each test/condition is to make a speeded discriminative response to the relevant and/or irrelevant stimuli by designating each item as relevant or irrelevant as quickly as possible. The information regarding category selection, i.e. the response, is typically relayed by pressing a button, e.g., a button for known items and another button for unknown items. Alternate means of response may be used including switches, lights, sensors or any means that sense movement or sound. The information regarding which category is selected, the speed of response (RT), and brain activity is collected or monitored following each stimulus.

Deception may be induced during memory-retrieval experiments in two ways: 1) by creating a simple conflict in which subjects respond overtly in a way that is in direct opposition to the truth (e.g., if the answer is "yes", respond "no") and, 2) by creating a more complex conflict situation in which subjects are required to respond randomly to the stimuli with the caveat that they are to make equal numbers of truthful and deceptive responses. This second method is a model of the situation in which a subject "keeps track of their story." A truthful recognition experiment in which the subject responds correctly to all stimuli is also included for comparison, as are response compatible and incompatible control series. Finally, to assess the effects of test repetition on brain activity, the truthful and both deceptive conditions are repeated one or more times ("repetitions"). In all three conditions, subjects perform a recognition test in which they see a random series of "old" words (the words they are given to memorize) intermixed with and equal number of "new" words (words that were similar but not on their list). The subject's task is to press one button with one finger as quickly as possible for old words and to press a different button with another finger for new words. On about 20% of the trials, either the word "OLD" or the word "NEW" appears on the screen. In these "catch" trials, the subject's task is to press the button corresponding to the word category as quickly as possible. The use of catch trials serves as an important control for the deception experiments. The truthful and random conditions are also run without catch trials. Comparisons with the same series that had catch trials revealed that there were no significant differences in the ERP or behavioral measures.

Guilty Knowledge Guilty knowledge may be used to distinguish truthful from deceptive responses. In the GK test, responses are elicited by asking a equal number of irrelevant and relevant along with control items.

Monitoring

ERP Measures

ERPs are recorded from electrodes affixed to the subject's scalp in a similar manner and in similar locations as used to obtain an EEG (American Electroencephalographic Society, 1991; Picton T. W. et al. In: F. Boller and J. Grafman (Eds.), Handbook of Neuropsychology, Volume 10. Amsterdam: Elsevier, pp 3–74, 1995). Typical sites on the scalp include Pz, Cz, Fz, Fp1, Fp2, F7, F3, F4, F8, T7, C3, C4, T8, P7, P3, P4, P8, O1, O2, Fc5, Fc1, Fc2, Fc6, Cp5, Cp1, Cp2, Cp6, Cb1, Cb2, left canthus, right canthus, right mastoid, left mastoid, using any one of these locations, or another suitable location, as a reference electrode (FIG. 1). A wide variety of recording sites and parameters (e.g., bandpass, sampling rate and epoch), other than those used to obtain the present results, can be used to obtain the same or similar results.

The ERP waveform consists of a series of positive and negative voltage deflections, known as "peaks" or components, that mark the passage of information through the nervous system. Each peak/component has its own characteristic latency and scalp distribution. The markers described above are the differences in a subject's ERP activity obtained by comparing the ERPs elicited in the Control and Test series. An increase in amplitude may also be described as a shift in the same polarity; a decrease in amplitude my be described as a shift in the opposite polarity. Thus marker 2 may be characterized either as a difference due to an enhanced positivity or a superimposed negative shift in both stimulus-locked averages and response-locked averages; marker 3 may be characterized either as a difference due to an enhanced positivity or a superimposed negative shift; marker 11 may be characterized as a difference due to an enhanced positivity or a superimposed negative shift; and marker 12 may be characterized as a difference due to an enhanced positivity or a superimposed negative shift.

The ERPs elicited by the stimuli are extracted from the EEG recorded at each electrode site, separately for the Control and Test series, separately for the relevant and irrelevant categories of stimuli and separately for each repetition, resulting in a total of four types of averages for each repetition for each electrode site. An analog-to-digital conversion of the EEG in a specific time interval (i.e., epochs) around a particular event is performed. For example, the stimulus onset time and the timing of the subject's response on each trial may be used as reference points to compare ERP activities. Stimulus-locked ERPs (SL ERPs) are calculated using an epoch that is linked to the time of the onset of the stimulus, e.g., from a short time before (baseline) to 1–2sec after the stimulus. The response-locked ERPs (RL ERPs) are calculated by shifting the single-trial EEG epoch to align the response time (RT) obtained on each trial to some arbitrarily chosen time point (e.g., 500 ms after stimulus onset), which becomes time zero. In RL ERPs, ERP activity with latencies less than 0 reflects brain activity present before the response; ERP activity with latencies greater than 0 reflects brain activity occurring after the response.

The digitized EEG epochs (both SL ERPs and RL ERPs) for each trial are averaged by summing the activity at each point and dividing by the number of trials included in the average. Averaging is a signal processing technique that extracts the ERP from the EEG. The ERP is a non-random process that is embedded in the EEG, a random process. Thus, averaging over trials cancels out the random EEG, leaving the ERP. The amplitudes were quantified by subtracting the averaged activity in the pre-stimulus baseline from that obtained in the specified time windows in the SL and RL ERPs. The resulting SL and RL ERPs form an identifiable pattern of positive and negative voltages that reveal the brain responses to the test and control responses, from which deception can be detected.

In a preferred embodiment, the results of the analysis are obtained using the baseline-to-peak measurement technique, however, other standard methods of quantifying the averaged ERP waveform, or the single trials used to create that waveform, may be used. These methods include those described in Picton et al. (1995), including Principal Components Analysis (PCA); source analysis; peak-to-peak measures using other peaks that are in the ERP waveform, temporally adjacent or otherwise; "single-trial analysis techniques" such as Step-wise Discriminant Analysis; analysis on transformed EEG and ERP activity such as Laplacian/Current Source Density derivations, or any other EEG/ERP analysis technique.

There are a number of standard analytic approaches that may be used to analyze the individual-subject data to determine if there are significant differences for the behavioral and electrophysiological measures between the obtained irrelevant and relevant responses and whether each particular behavioral or electrophysiological measure was significantly greater or less than the control truthful pattern of responses. These approaches include analysis of both the single-trial ERP waveforms, after suitable digital filtering, and averaged ERP waveforms. One method that may be utilized to determine if the behavioral and ERP markers produce different relevant and irrelevant responses is the bootstrap method (Wassermann & Bockenholt, 1989) which has been previously utilized in ERP research (Farwell & Donchin, 1991; Honts & Devitt, 1992; Johnson & Rosenfeld, 1992; Rosenfeld et al., 1996, 1999). In the bootstrap method, multiple independent samples (simulating what would be obtained from different subjects) are created from the original set of trials by taking random samples, with replacement, of a portion of the entire set of trials. In this way, many independent samples can be created and then analyzed using standard statistical procedures (e.g., ANOVA). Other methods used to quantify individual-subject electrophysiological data include Bayesian statistical methods and factor-analytic approaches (Allen, in press 2001; Allen et al., 1992). Before using either of these methods, standard digital filtering techniques may also be applied to reduce levels of noise in the waveforms prior to quantification (Picton et al., 1995).

Analyses of Component Scalp Typographies—The presence of possible topographic differences between conditions, signifying that different patterns of neural generator activity are present, is revealed by significant interactions between the experimental effects and electrode factor in an analysis of variance (ANOVA) (Johnson, 1993; Ruchkin et al., 1999). However, since significance in these interactions can be due to amplitude differences between conditions, between sites, or both, it is necessary to scale the data to remove any amplitude differences due to condition effects. Thus, the amplitude data in each topographic profile comparison are first scaled so that the root-mean-square (RMS) of the across-subject average amplitudes from the different conditions are the same (vector normalization procedure: McCarthy and Wood, 1985; and see Johnson, 1993). If topographic differences remain in the RMS-scaled, vector-length normalized, data, there should be a significant interaction between the two factors (e.g., electrode and task) in an ANOVA. Other amplitude normalization procedures, such as described by McCarthy and Wood, 1985, may be used.

Vector-Length Normalization Procedures—To normalize each pair of Irrelevant and Relevant averages, 1) the amplitudes for each electrode site used in the comparison are squared; 2) the square root of the sum of the squared values for the included electrodes is calculated; 3) the amplitude for each electrode site is divided by the result from step 2 above for each group or condition; 4) a standard ANOVA is calculated on the normalized amplitude data. A significant electrode by condition interaction indicates that there are different scalp distributions between the responses to the Relevant and Irrelevant ERP responses.

For Individual series, the results obtained in the Control series are compared to and/or subtracted from the results obtained in the Test series; for Repetition Series, one set of Test and Control stimuli is compared to another set of Test and Control stimuli and the resulting differences for the Test and Control series are compared; for Guilty Knowledge, individual pairs of test and control relevant and irrelevant stimuli within a set of stimuli are compared. If the result of the subtraction is zero or near zero, that marker indicates that the response is not deceptive; if the subtraction is significantly greater than zero, the marker indicates that the response is deceptive. For example, the ERN type of ERP activity may be isolated by subtracting the RL ERPs elicited by items in the Control series from the ERN in the RL ERPs elicited by the Test items. This difference will be significantly greater than 0 if the subject is responding deceptively. Alternatively, the quantified ERP and behavioral indices from the Control and Test Series can be compared directly for differences using standard statistical procedures. The final determination of deceptive/non-deceptive activity/behavior is based on the detection of changes in one or more of the ERP and/or behavioral measures described above.

ERP averages are calculated for the relevant and irrelevant stimulus categories based on how the tester has categorized each stimulus, irrespective of the manner in which a subject categorized the stimulus.

The method described herein advantageously provides a number of behavioral and central nervous system markers of deception, alterations in ERP activity that occur when subjects are deceptive about information in their memory, that can be used singly or in any combination as part of any procedure to determine if a subject is being truthful or deceptive during an examination. The method of the invention detects deceptive responses by quantifying behavioral performance and the pattern of one or more ERP markers from activity elicited when subjects are presented with stimuli to which they must respond. Some of the markers described herein detect deception per se since their patterns of altered brain activity are essentially the same when a subject denies that an item is in memory when it is and when the subject responds that an item is in memory when it isn't. The guilty knowledge marker can distinguish an item from experience from an item not in experience, i.e., the ability to detect guilty knowledge. The combination of the ERP markers and the guilty knowledge marker permits the tester to determine when the subject is being deceptive by confabulation. The guilty knowledge marker provides a direct measure of the presence of personal information in memory ("experience") and is highly insensitive to countermeasures. New items classified as old and old items that are not in memory both generate an ERP that is identical to that elicited by new, inexperienced items.

An attempt to consciously manipulate any of the ERP markers may enhance the identified alteration in that ERP. Although not meaning to be bound by any theory, it is believed that the changes (decreased amplitude) observed in the P300 ERP component may be due to the superposition of the secondary deception task on the primary recognition memory task. Since an attempt to consciously manipulate any CNS measure has the practical effect of taking resources away from the primary task, it may produce an even greater decrease in the P300 component. By the same reasoning, the alterations in RT and RT variability described above may also increase if countermeasures are attempted.

A further advantage of the method of the invention is that the data may be obtained from using as few as 3 electrodes placed on the head. Thus, the method of detecting deception described herein is relatively simple and non-invasive.

The following examples illustrate various aspects of the invention and are not intended to be limiting thereof.

EXAMPLE

This example describes the determination of whether there is behavioral and/or brain activity that is specific to deceptive responses and whether individuals can disguise a neural signature produced by an item when it is retrieved from long-term memory.

Methods and Materials

Subjects Twenty-five subjects (right-handed, native English speakers, 15 females, mean age=21.9, S.D.=3.2) were paid $10.00 per hour for their participation. Subjects were thoroughly briefed about the nature of the experiment and signed informed consent was obtained from each in accord with Queens College Institutional Review Board procedures.

Stimuli One week before the experiment, subjects were given a list of 60 unrelated words to memorize ("old" words). After electrode placement, subjects were seated in a dimly-lit room. In each series, the 60 old words were randomly presented along with 60 new words on a computer terminal for 300 ms in all uppercase letters, using white letters on a black background (2750 ms average trial duration). Different lists of new words were used for each test, picked from a pool of 15 lists that were constructed by randomly selecting words from a master list, with all lists balanced for word frequency. Each series also contained 25 "catch trials" on which either the word "OLD" or the word "NEW" was presented. Catch trials were included to prevent subjects from altering the assigned stimulus-response mapping.

Test Conditions

Recognition—Subjects performed a standard old/new recognition test under three instructional conditions (Truthful, Opposite and Random). Behavioral performance and brain electrical activity were recorded while subjects responded truthfully and deceptively about previously memorized information.

1) Truthful—This condition provided a baseline indication of the behavioral and electrophysiological activity for truthful (i.e., compatible) responses about items in memory. The experimental design of the Truthful condition was similar to that of the Control-Compatible condition with both having a minimum of conflicting response information, except that the subjects had to search their memory to categorize the stimuli.

2) Opposite—Subjects were instructed to respond in direct opposition to the truth about whether particular items were stored in their memory. The experimental design of the Opposite condition was similar to that of the Control-Incompatible condition, except that the conflicting response information could only be provided by access to personal memory, i.e., a conceptual conflict. Since the subjects responded deceptively to every single item, there was no requirement to think about the meaning of the response (i.e., if the answer is "no," say "yes"; if the answer is "yes," say "no"). Therefore, this condition is similar to what might occur in a "practiced" deception, when the answer is given automatically.

3) Random—The Random condition studied monitoring of deceptive responses by a subject. Subjects were instructed to respond in a manner that met two goals. First, they were to respond as randomly as possible with the goal of making equal numbers of truthful and deceptive responses for both old and new words. Second, they were instructed to monitor both the number and pattern of their responses at each point in the series in order to determine if this goal was being met and which future responses needed to be made to bring their responses into compliance with the goal. The effects of the long-term monitoring task could be isolated from the effects of response conflict by comparing the markers obtained on the Random-Deceptive trials with those from the Opposite condition. Since the subjects were instructed to decide whether to respond deceptively to each item separately, this condition is similar to what might occur in a "unpracticed" deception, when thought is given to what the answer should be given (i.e., a non-automatic, controlled response).

OLD/NEW Recognition Test Old words were randomly mixed with an equal number of new words (words that are similar but not on the list to be memorized). Subjects were shown the words one at a time. In 20% of the trials, catch trials, consisting of the words "old" or "new" also appeared. Subjects were instructed to press one button for old words and for the catch word "OLD", and another button for new words and the catch word "NEW" (e.g., left button for "old", right button for "new"). The recognition test was conducted under three instructional conditions:

1) Truthful Memory condition—Subjects were instructed to answer truthfully, that is, subjects pressed the button designated "old" when they saw an old word or the word "OLD" and the button designated "new" when they saw a new word or the word "NEW." Thus, in the Truthful memory condition, virtually all responses were compatible with the truth.

2) Opposite Memory condition—Subjects were instructed initially to make the same responses as in the Truthful Memory condition, and then were told "to lie or try to hide what you know by pressing opposite of my instructions" (e.g., press the "old" button for new words). Thus, in the Opposite memory condition, virtually all their responses were incompatible with the truth.

3) Random Memory condition—Subjects were instructed to respond in a manner that met two goals. First, they were to respond as randomly as possible with the goal of making equal numbers of truthful and deceptive responses for both old and new words. Second, they were instructed to monitor closely both the number and pattern of their responses at each point in the series in order to determine if this goal was being met and which future responses needed to be made to meet the goal. Thus, in the Random memory condition, one-half of their responses were compatible with the truth and one-half were incompatible with the truth.

Control Conditions Subjects were also tested in two control series in which the words "LEFT" and "RIGHT" appeared randomly and equiprobably. The purpose of the compatible and incompatible control conditions was to create situations in which the neural-behavioral signature of a perceptually-driven response conflict could be isolated, and provided a baseline for comparing perceptually-driven and conceptually-driven response conflicts.

Control-Compatible—In this condition, subjects pressed the button on the side indicated by the stimulus (e.g., left button for "LEFT", right button for "RIGHT"). Thus, in this condition, the subject's responses were compatible with the stimulus.

Control-Incompatible—In this condition, subjects were instructed to press the opposite button of that indicated by the stimulus (e.g., right button for "LEFT", left button for "RIGHT"). Thus, in this condition, the subject's responses were incompatible with the stimulus.

In both the control and memory conditions, subjects were instructed to respond as quickly as possible and, in the memory conditions, to be especially careful to be quick and accurate in their responses to the catch trials.

Since the quality of a subject's deceptive responses depended on their memory for the word list they had been given, it was necessary to screen out subjects who were not sufficiently familiar with the list. Thus, every subject first performed a Truthful condition and the 6 subjects who did not meet the recognition criterion (84% correct) were dropped. To ensure that subjects adequately performed the long-term monitoring task in the Random condition (i.e., produced equal numbers of trials in all four response categories), the number of trials in each category for the remaining 19 subjects were tested with a Chi-square. Three subjects showed a significantly different number of corrects and incorrects in either old, new, or both and thus were excluded from further analyses. All analyses presented here are based on remaining 16 subjects who met both performance criteria.

Over the session, subjects performed the Truthful, Opposite and Random memory conditions twice and the control conditions once. Other than the first (Truthful) series, the order of all the other series was randomized over subjects, with half the subjects performing the Opposite condition before the Random condition and vice versa. Only the data from the second repetitions of the memory conditions are presented and discussed herein. The pairing of responding hand with the response buttons was counterbalanced across subjects. Since there were no stimulus-related differences in the Control conditions in the behavioral or ERP measures, that data for the "LEFT" and "RIGHT" trials were collapsed.

ERP Recordings and Quantification All ERP markers were identified in the interval from 0 to 1000 ms in the SL ERP averages and in the interval from −500 to +500 ms in the RL ERP averages. ERP activity was recorded from 32 scalp sites using tin electrodes embedded in an elasticized cap (FIG. 1). The reference electrode was placed at the left canthus (FIG. 1, location 33). Eye movements (EOG) were recorded from above (FIG. 1, location 1) and 2 cm below the outer canthus of the left eye (FIG. 1, location 20 ) and trials contaminated with EOG artifacts (signals greater than 50 $\mu$V during any 6 sampling points) were excluded from the averages. Subjects were grounded with a forehead electrode. During averaging, all scalp-recorded activity was digitally re-referenced to an average of the FIG. 1, location 33 and FIG. 1, location 32 sites. The EEG was amplified 20,000 times with a bandpass of 0.03–35 Hz (−3 dB/octave) and sampled at 100 Hz for 2150 ms, beginning 150 ms prior to stimulus onset. Response-synchronized averages were calculated by shifting each single-trial waveform such that the RT for that trial was aligned with an arbitrarily selected time (500 ms). The resulting ERP waveform epoch spans 2000 ms, beginning 500 ms prior to the RT and continuing until 500 ms after the RT.

Component areas were quantified by summing the activity in the intervals listed above for each marker, after subtracting the activity in the 150-ms baseline. P300 latency was quantified by finding the largest positive peak within a time range (300–600 ms for the Control conditions and 500 to 800 ms for the memory conditions). The data for each marker were analyzed with separate repeated-measures ANOVAs. In all cases, ANOVA results were corrected using the Greenhouse-Geisser epsilon correction procedure and only the epsilon-corrected degrees of freedom, rounded down to the nearest whole number, are presented.

Results

The Role of Response-Conflict in Deception

Response-Locked Averages

To determine the extent to which the processes used to monitor perceptually-driven and conceptually-driven conflicts were similar, the data from the Truthful and Opposite memory conditions were compared with those from the Control-Compatible and Control-Incompatible conditions to identify when subjects made compatible (Control-Compatible, Truthful-old) and incompatible responses (Control-Incompatible, Opposite-old) to stimuli. In this comparison, for the memory conditions, only the data for the old words were used; thus, incompatible responses were made only on the basis of conceptual information (information contained only in their memory). To evaluate the behavioral data, separate ANOVAs were done on the response accuracy, response speed and response variability data using the factors Response (Compatible, Incompatible) and Condition (Control, Memory-old words).

While subjects' responses were very accurate overall in the Control, Truthful and Opposite conditions, performance (response) accuracy decreased in both tasks when subjects made perceptually- and conceptually-incompatible responses (Table 1).

TABLE 1

Response Accuracy (% Correct) for both Repetitions as a Function of Condition
Mean and Standard Deviation (in parentheses)
(N = 16)

|  | Control | | | | Recognition | | |
|---|---|---|---|---|---|---|---|
|  | Compatible | Incompatible |  | Truthful | Opposite | Random-Truthful | Random-Deceptive |
| First Repetition | | | | | | | |
| Left/Right | 98.2 (2.1) | 95.3 (3.4) | Old | 92.0 (4.3) | 94.2 (4.8) | 27.2 (3.1) | 22.8 (3.0) |
|  |  |  | New | 93.0 (4.6) | 94.6 (3.2) | 27.4 (3.0) | 22.6 (3.0) |
| Second Repetition | | | | | | | |
|  |  |  | Old | 96.5 (3.2) | 92.7 (4.6) | 25.5 (4.0) | 24.7 (4.0) |
|  |  |  | New | 96.2 (2.7) | 97.7 (2.8) | 25.1 (2.8) | 24.7 (2.9) |

The ANOVA revealed that a small (3.4%) but significant performance decrement was associated with the requirement to make an incompatible response [$F(1,15)=34.8$, $p<0.0001$], as was the finding that accuracy was 2.2% lower overall in the memory conditions compared to the control conditions [$F(1,15)=6.6$, $p<0.05$]. RTs also varied as a function of condition and response type (see Table 2, FIG. 22).

cessing (e.g., the requirement to search personal memory), there was no difference in the extent to which response conflict slowed RT in the two tasks (Response×Condition: $F<1$). According to the logic of the Additive Factors Method (Sternberg, 1969), variables that affect mental processes that occur independently and/or in separate processing stages produce significant main effects in an ANOVA, but no significant interaction. The results revealed that the effects of task and response compatibility on response accuracy and speed were independent and additive and that the effect of making an incompatible response did not differ between perceptually-driven and conceptually-driven response conflicts.

The third behavioral measure, RT variability, quantified as the standard deviation, also varied across these four conditions. As shown in FIG. 23, the RT distributions for the two conditions when subjects made incompatible responses were broader and less peaked compared to the conditions with

TABLE 2

Reaction Time (in ms) for both Test Repetitions as a Function of Condition
(N = 16)

|  | Control | | | | Recognition | | |
|---|---|---|---|---|---|---|---|
|  | Compatible | Incompatible |  | Truthful | Opposite | Random-Truthful | Random-Deceptive |
| First Repetition | | | | | | | |
| Left/Right | 399 | 459 | Old | 643 | 673 | 800 | 809 |
|  |  |  | New | 693 | 719 | 827 | 835 |
| Second Repetition | | | | | | | |
|  |  |  | Old | 599 | 648 | 766 | 773 |
|  |  |  | New | 625 | 687 | 787 | 829 |

These data reveal that slowed significantly, by an average of 54 ms, on incompatible trials compared to compatible trials [$F(1,15)=17.7$, $p<0.001$] and RTs in the Memory conditions were an average of 196 ms slower than in the Control tasks [$F(1,15)=335.9$, $p<0.00001$]. However, despite the fact that the memory tasks required more extensive stimulus processing (e.g., every stimulus was now different) and task procompatible responses. An ANOVA on the SDs of the RTs (see Table 3) revealed that RT variability was significantly increased by both stimulus-response incompatibility [82 vs 106 ms for compatible and incompatible responses, respectively: $F(1,15)=20.5$, $p<0.0005$] and by condition [78 and 110 ms for the Control and Memory trials, respectively: $F(1,15)=31.6$, $p<0.0001$]. Consistent with the appearance of the distributions in FIG. 23, the Response×Condition interaction was not significant (p=0.27) indicating that the increased response variability associated with having to make an incompatible response was not affected by the different processing requirements of these two tasks.

Figure 25A:
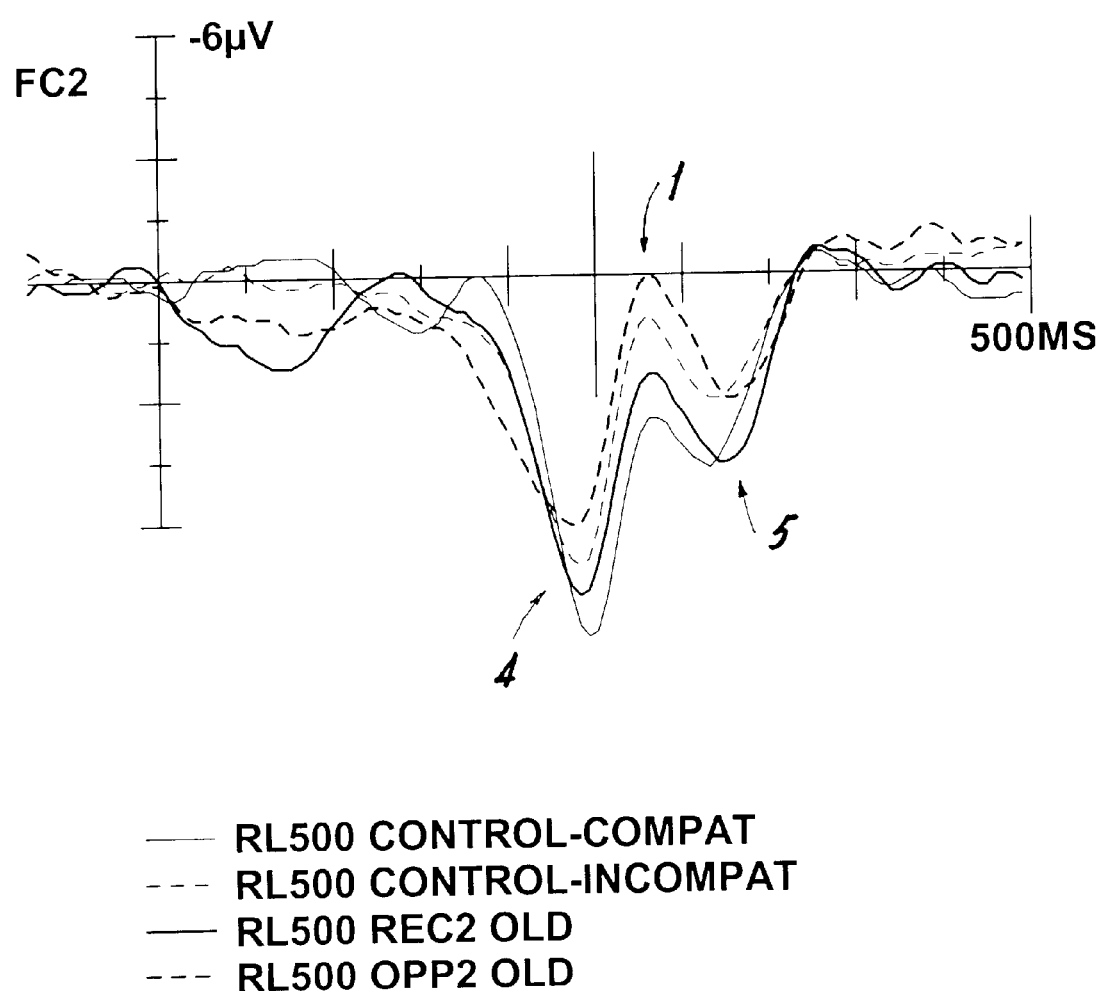

FIG. 25A shows that the ERN, evident as the negative peak maximal at 70 ms after the response, varied in amplitude across conditions (also see FIGS. 2, 3, 4). Larger ERNs were elicited regardless of whether the conflicting response information was contained in the stimulus (perceptually-driven) or in the subject's memory (conceptually-driven). An ANOVA on ERN amplitude using the factors Condition (Control, Memory) and Response (Compatible, Incompatible) and Electrode (F3, Fz, F4, FC1, FC2, Cz) (FIG. 1, locations 4, 5, 6, 25, 26, 10) revealed that significantly larger ERNs were elicited whenever subjects made incompatible responses, both in the Control-Incompatible and Opposite conditions [$F(1,15)=15.6$, $p<0.002$], although there was no effect of Condition on ERN amplitude ($p=0.15$). Consistent with the behavioral results, the absence of a significant Response×Condition interaction ($p=0.14$) indicated that these two variables operated independently in affecting ERN amplitude.

Topographic maps of the brain activity at the time of the ERN (FIG. 26) revealed the presence of a large positivity over posterior scalp (i.e., P300) and a smaller and more diffuse negativity over frontal scalp (i.e., ERN). This negativity was larger over fronto-central scalp in the Control (left column) and Memory ($2^{nd}$ column; Truthful on top, Opposite on bottom) conditions when subjects made incompatible responses (bottom row), which is seen as a "dip" in the contour lines there. After normalization of the amplitudes, an ANOVA showed that significant Electrode by Response interactions were found for both the Control [$F(1,27)=4.9$, $p<0.05$] and Memory conditions [$F(1,26)=6.5$, $p<0.02$] which confirmed that the ERNs elicited on incompatible trials (in both the Control-Incompatible and Opposite conditions) was due to a different pattern of brain activity than was responsible for the ERNs elicited on compatible trials.

To determine if memory status (i.e., whether the word is old or new) affected the behavioral and ERN measures, the data from these two recognition conditions were tested in a series of ANOVAs using the factors Stimulus (Old, New) and Condition (Truthful (compatible), Opposite (incompatible). As shown in FIG. 22, deceptive responses were, on average, 57 ms slower than truthful responses [$F(1,15)=20.1$, $p<0.0005$] and RTs for new words were an average of 33 ms slower than for old words [658 ms vs 625 ms for new and old words, respectively: $F(1,15)=29.1$, $p<0.0001$]. The lack of a Response×Stimulus interaction [$F(1,15)=1.2$, $p=0.28$] indicated that the effect of making a deceptive response on RT was independent of the memory status of the words. RT variability (see Table 3) was also significantly greater for deceptive compared to truthful responses (136 vs 97 ms, respectively) [$F(1,15)=19.0$, $p<0.001$] and for new words (121 ms) compared to old words (112 ms) [$F(1,15)=7.1$, $p<0.02$]. Consistent with the RT results, the Response×Stimulus interaction was not significant [$F(1,15)=2.75$, $p=0.12$]. Using the Additive Factors logic (Sternberg, 1969), the lack of significant Stimulus×Condition interactions for RT and RT variability indicated that the effect of conflict on RT was independent of whether subjects were deceptive by falsely denying knowing words they did know or falsely claiming to know words that they didn't know.

Figure 25B:
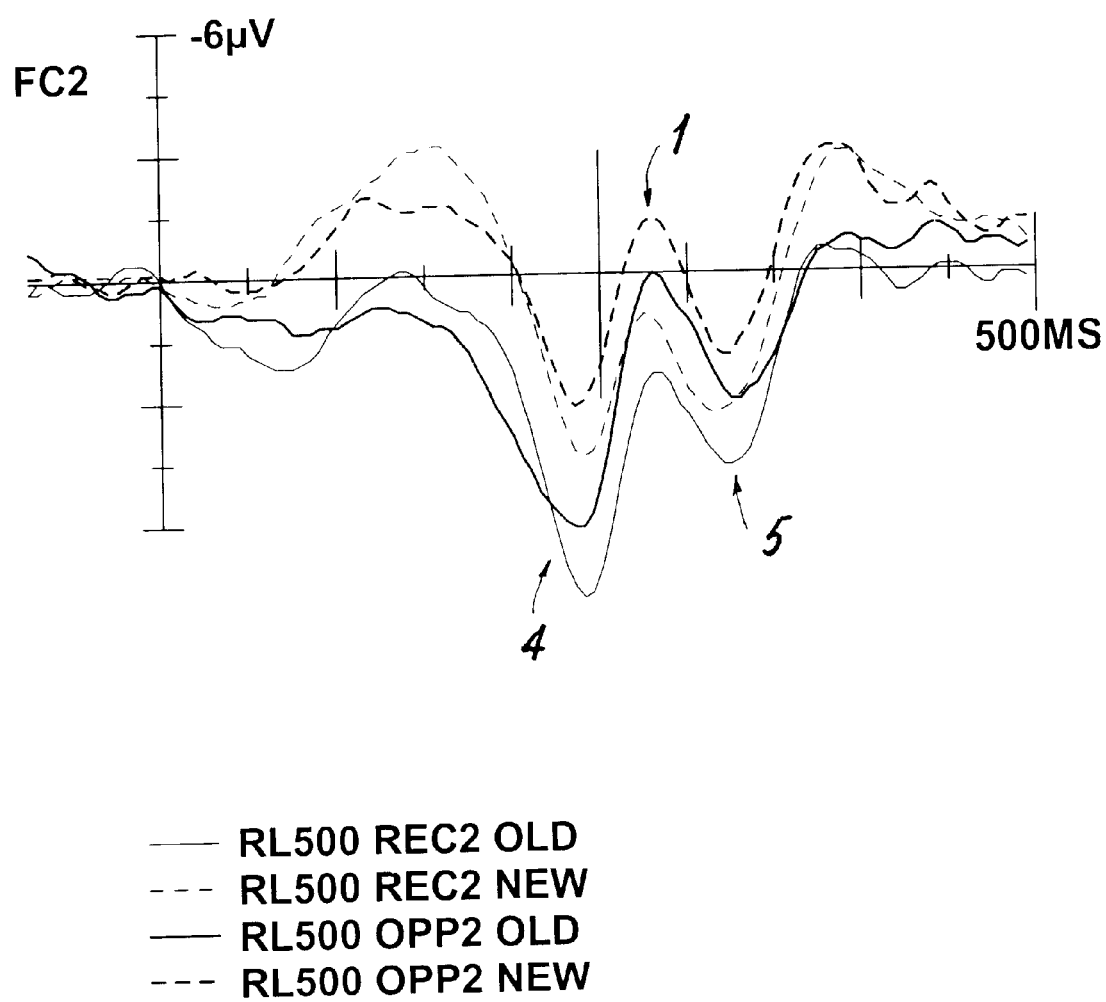

ERN amplitude was also affected by the memory status of the words, independently of the effects of response compatibility (see FIG. 25B). Words not in memory elicited larger ERNs than the old words, but in both cases larger ERNs were elicited in the Opposite condition. An ANOVA confirmed that new words elicited larger ERNs than old words [$F(1,15)=7.4$, $p<0.02$] and that there were no differences in the magnitude of the response incompatibility effects as a function of memory status [Stimulus×Condition: $p=0.59$]. The data from the Control, Truthful and Opposite conditions indicated that the stimulus and task variables all had additive effects on RT slowing and ERN amplitude; thus both measures were directly related to overall task difficulty. In contrast, the effect of conflict was due to a different pattern of brain activity that remained constant and unaffected by these stimulus and task variables.

Role of Long-Term Monitoring in Deception

The Random condition permitted isolation of the effects of the long-term monitoring task, over and above the effects of response conflict (i.e., Random-Deceptive vs Opposite) and comparisons of truthful and deceptive responses that were randomly intermixed (i.e., Random-Truthful vs Random-Deceptive).

The effects of the monitoring task on the behavioral measures were tested in a series of 2-way ANOVAs using the factors Condition (Opposite, Random-Deceptive) and Stimulus (old, new). Response accuracy in the Random condition could not be compared with any other condition since the subjects were instructed to make equal numbers of correct and incorrect responses. However, the imposition of the monitoring task did result in RTs that increased by more than 100 ms compared to those in the Opposite condition, despite the fact that subjects made deceptive responses in both [$F(1,15)=16.1$, $p<0.002$] (See Table 2 and FIG. 22).

TABLE 3

Response Time Variability (Standard Deviation, in ms) for both Test Repetitions as a Function of Condition (N = 16)

| | Control | | Recognition | | | |
| --- | --- | --- | --- | --- | --- | --- |
| | Compatible | Incompatible | | Truthful | Opposite | Random-Truthful | Random-Deceptive |
| First Repetition | | | | | | | |
| Left/Right | 69 | 87 | Old | 122 | 132 | 193 | 201 |
| | | | New | 108 | 149 | 196 | 206 |
| Second Repetition | | | | | | | |
| | | | Old | 96 | 125 | 178 | 175 |
| | | | New | 98 | 144 | 186 | 201 |

New words produced slower RTs than old words in both conditions [F(1,15)=15.0, p<0.002], although the amount of response slowing due to making a deceptive response did not differ across conditions or stimuli (Condition×Stimulus: F<1). As evident from Table 3 and FIG. 24, the subjects' responses were significantly more variable when subjects had to monitor their deceptive responses. Because there were four stimulus categories in the Random condition but only two in the Opposite condition, the Random data in FIG. 24 were normalized (i.e., roughly doubled) so that direct comparisons could be made across conditions. The SD of the RT increased to 188 ms on the Random-Deceptive trials from 134 ms in the Opposite condition [F(1,15)=20.9, p<0.0005]. The SD of the RT for new words (172 ms) was also significantly greater than the SD for old words (150 ms) [F(1,15)=6.8, p<0.02].

Figure 25C:
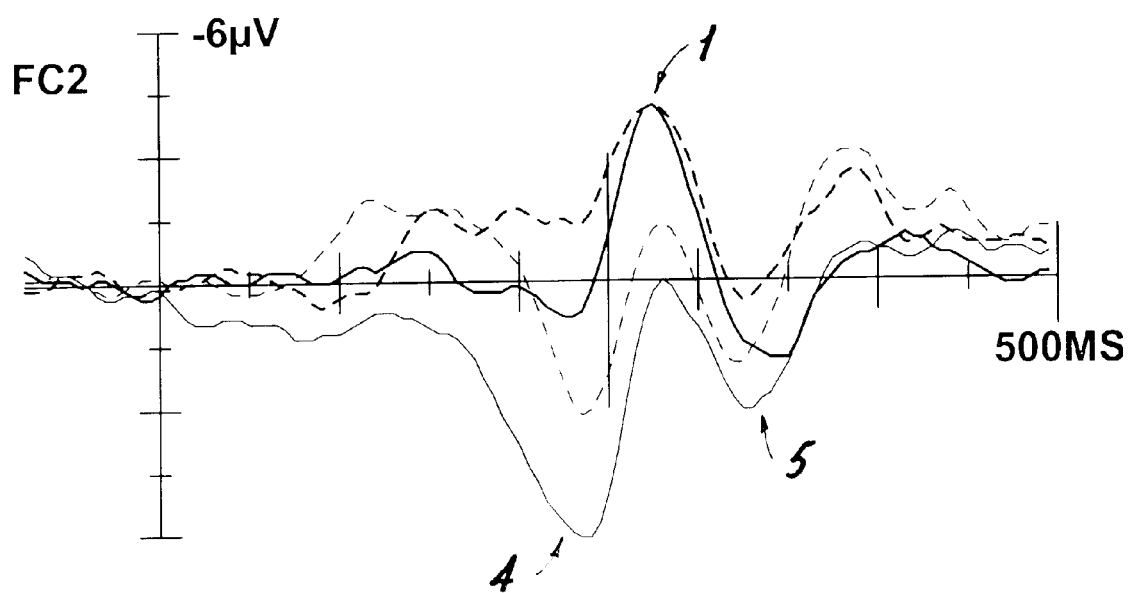

The waveforms in FIG. 25C show that ERNs were significantly larger in the Random condition compared to the Opposite condition [F(1,15)=14.9, p<0.002] (also see FIGS. 2, 3, 4), again in the absence of a Condition×Stimulus interaction (p=0.14). ERN activity was greatly enhanced when subjects engaged in the long-term monitoring task to meet specified goals, although there were no longer any amplitude differences as a function of the memory status of the words as was the case in the Truthful and Opposite conditions. Topographic maps of ERN activity in the Random condition (FIG. 26, two right columns; Random-Truthful on top, Random-Deceptive on bottom) showed that, in contrast to the Truthful and Opposite conditions, there was a clear negative focus centered over medial frontal scalp. An ANOVA on normalized ERN amplitudes confirmed that the Random-Deceptive ERNs were generated by a different pattern of brain activity than that for ERNs elicited in the Opposite condition [F(2,35)=22.5, p<0.00001]. This result indicated that tactical and strategic monitoring processes depended on different patterns of brain activity.

To assess the relative effects of response conflict and strategic monitoring, the data from the truthful and deceptive trials within the Random condition were compared. In contrast to the Control and Opposite conditions, making incompatible responses within the Random condition produced fewer effects. The effects of the monitoring task on the behavioral measures were assessed in 2-way ANOVAs using the factors Response (Truthful, Deceptive) and Stimulus (old, new). As can be seen from Table 2 and FIG. 22, Random-Deceptive RTs were, on average, 25 ms longer than Random-Truthful RTs [F(1,15)=6.8, p<0.02] and new word RTs were, on average, 38 ms longer than the responses to the old words [F(1,15)=10.3, p<0.01], although the amount of response slowing due to making a deceptive response did not differ across stimuli (Condition×Stimulus: [F(1,15)=1.5, p=0.23]. As evident from the data in Table 3 and FIG. 24, all the distributions of the subjects responses in the Random condition were considerably broader and flatter than those for the Opposite condition. Because there were four stimulus categories in the Random condition but only two in the Opposite condition, the Random data in FIG. 24 were normalized (i.e., roughly doubled) so that direct comparisons could be made across conditions. As evident from the data in FIG. 24, the response and stimulus variables had a minimal effect when subjects were monitoring their performance. Thus, unlike previous comparisons, the SD of the RT for the truthful and deceptive trials was nearly the same, at 182 ms and 188 ms, respectively (F<1). Similarly, the SDs for the old and new words only differed by a non-significant 18 ms [F(1,15)=2.3, p=0.15] and there was no Response× Stimulus interaction [F(1,15)=1.1, p=0.32].

Figure 25D:
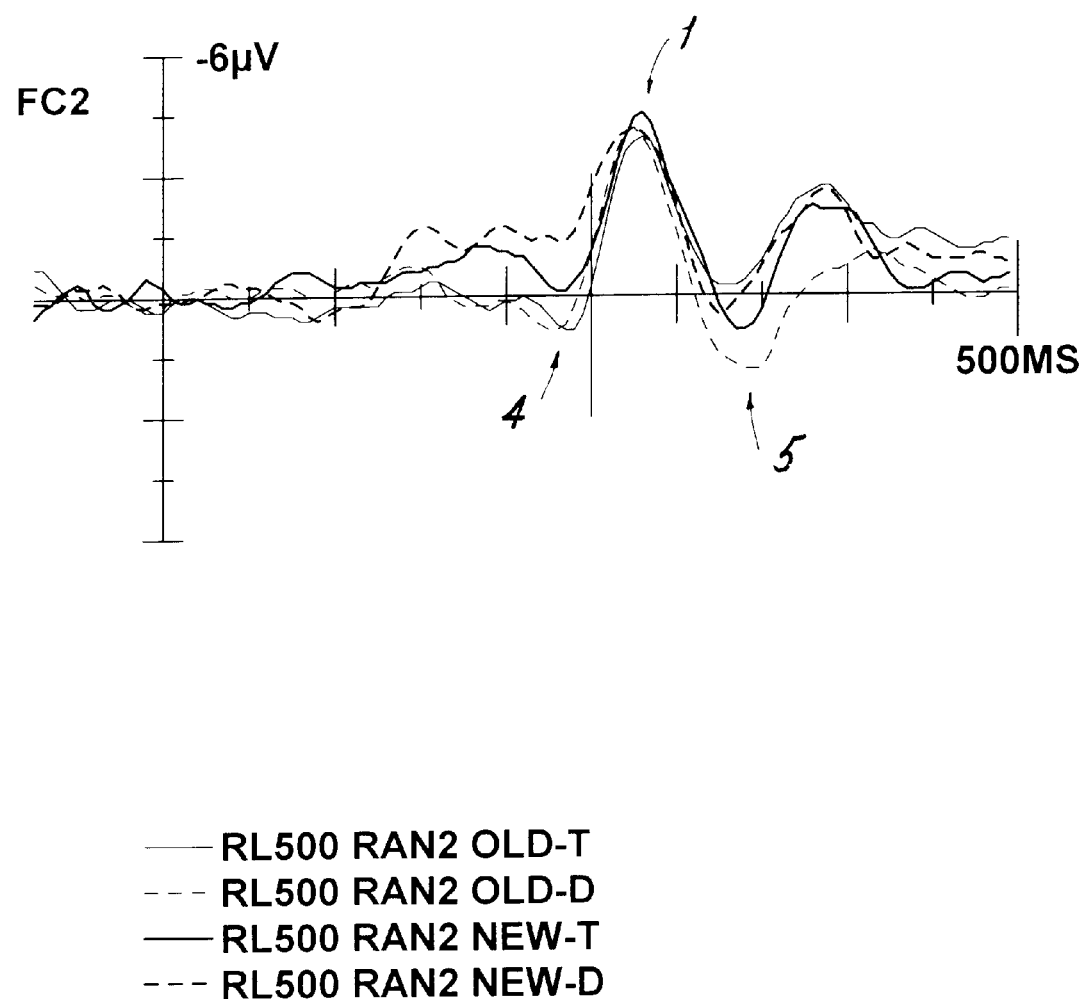
Figure 27A:
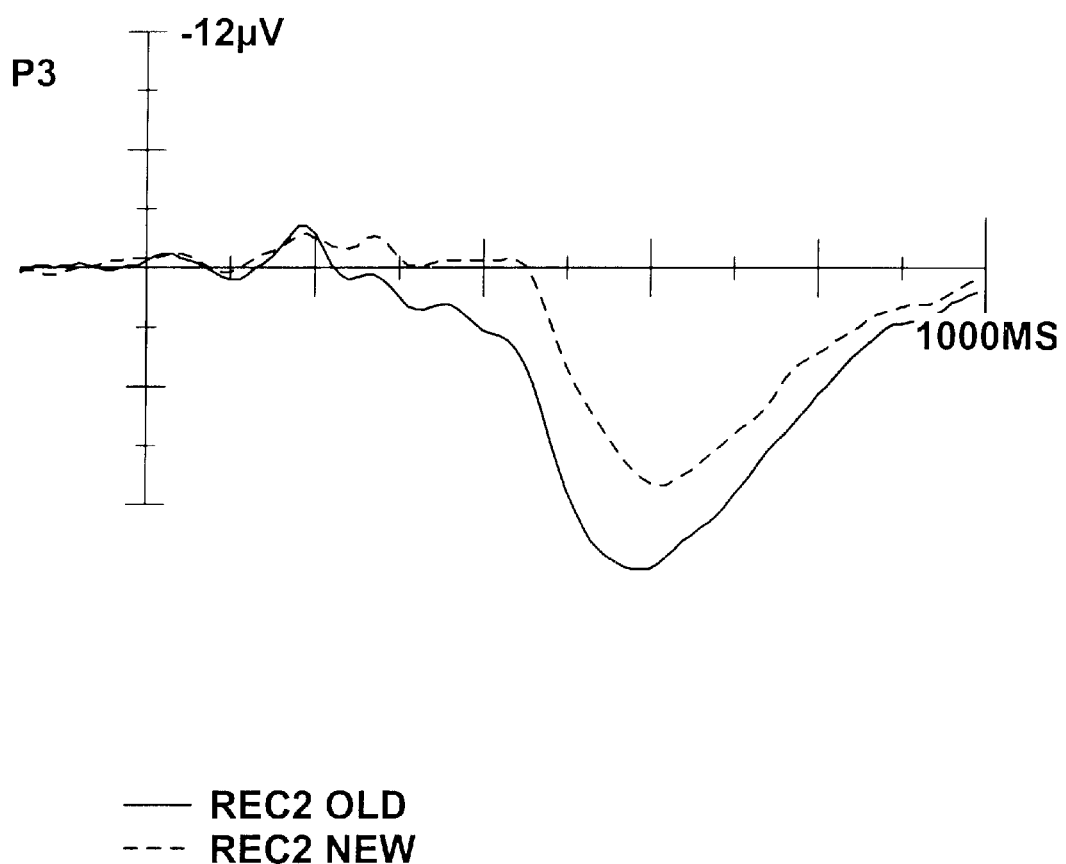
Figure 27B:
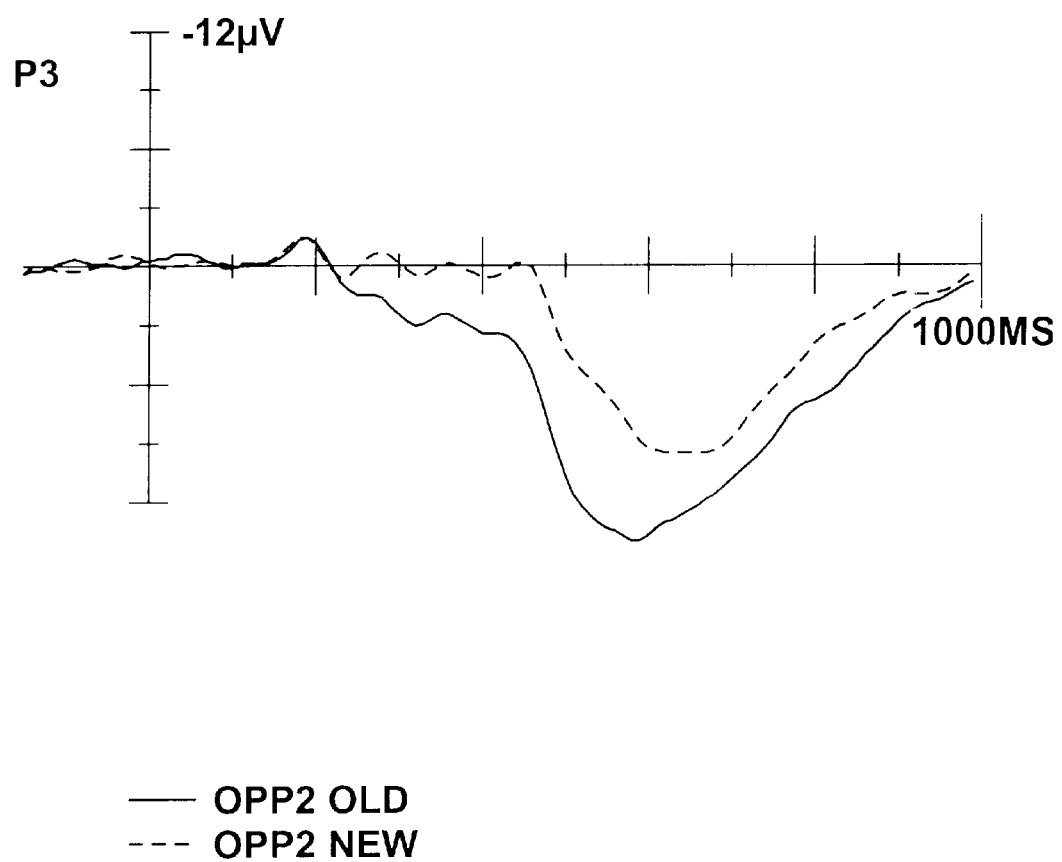
Figure 27C:
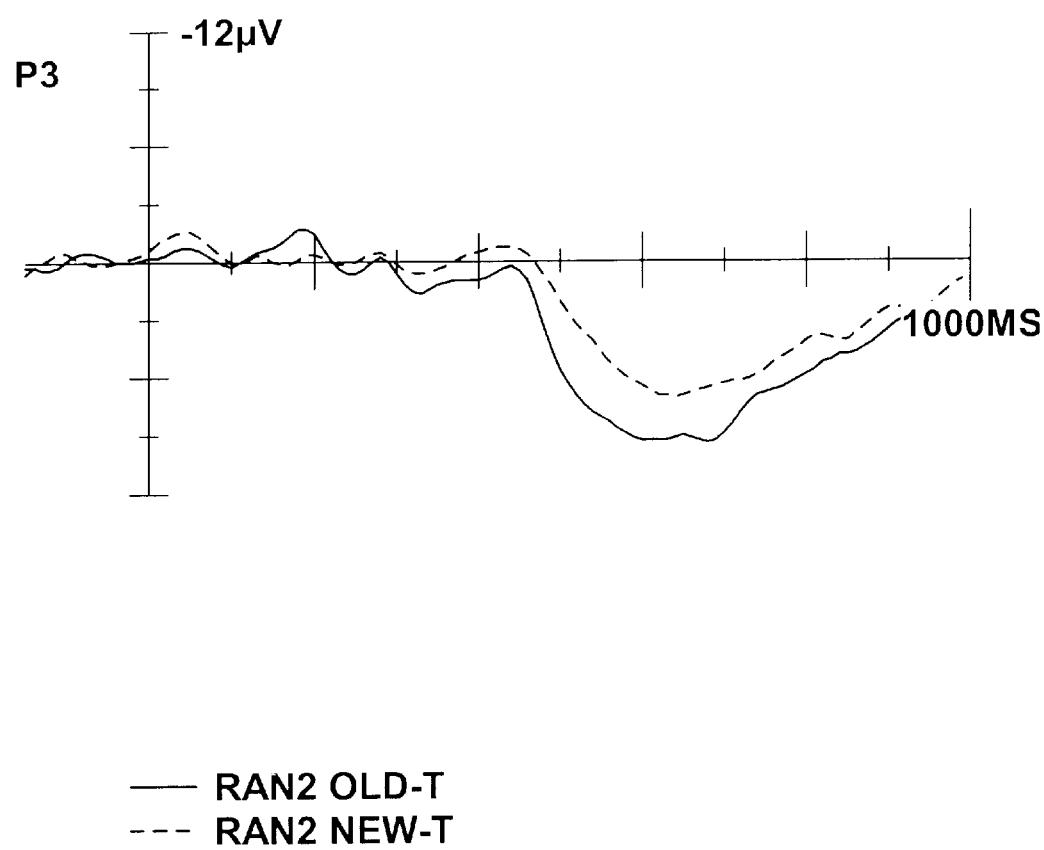
Figure 27D:
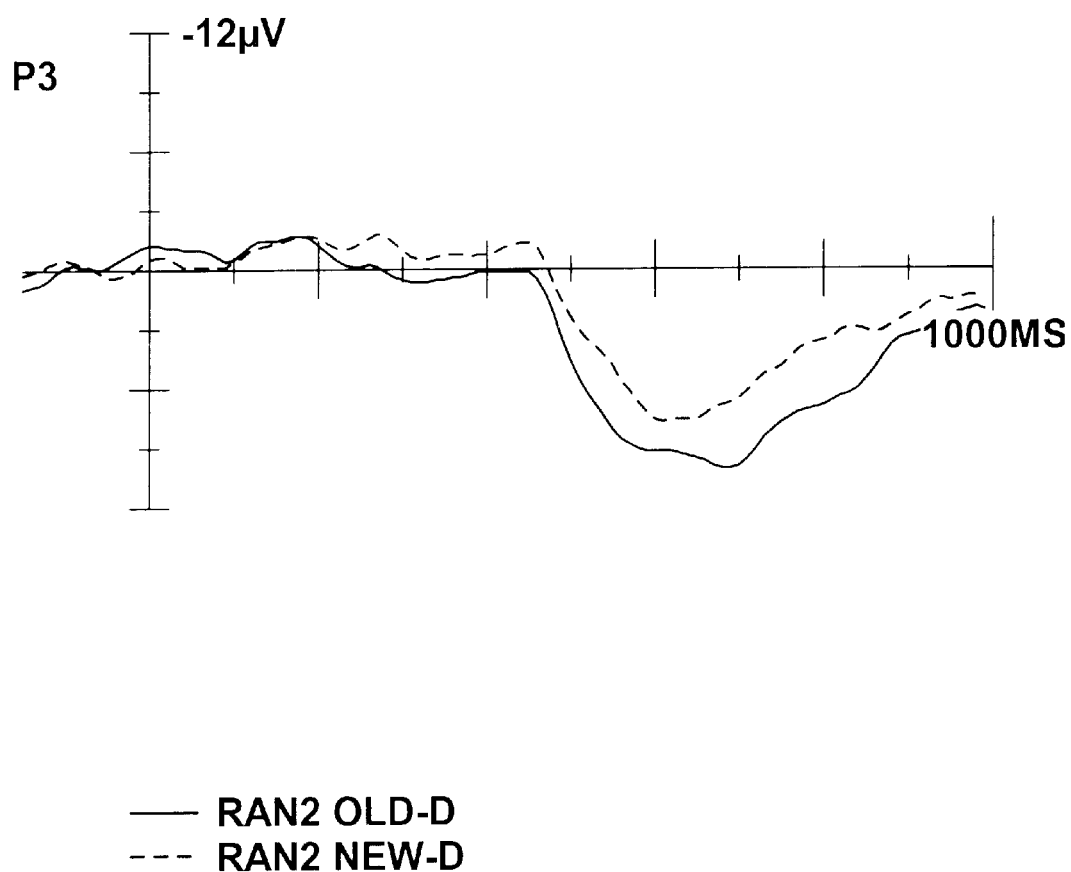
Figure 28A:
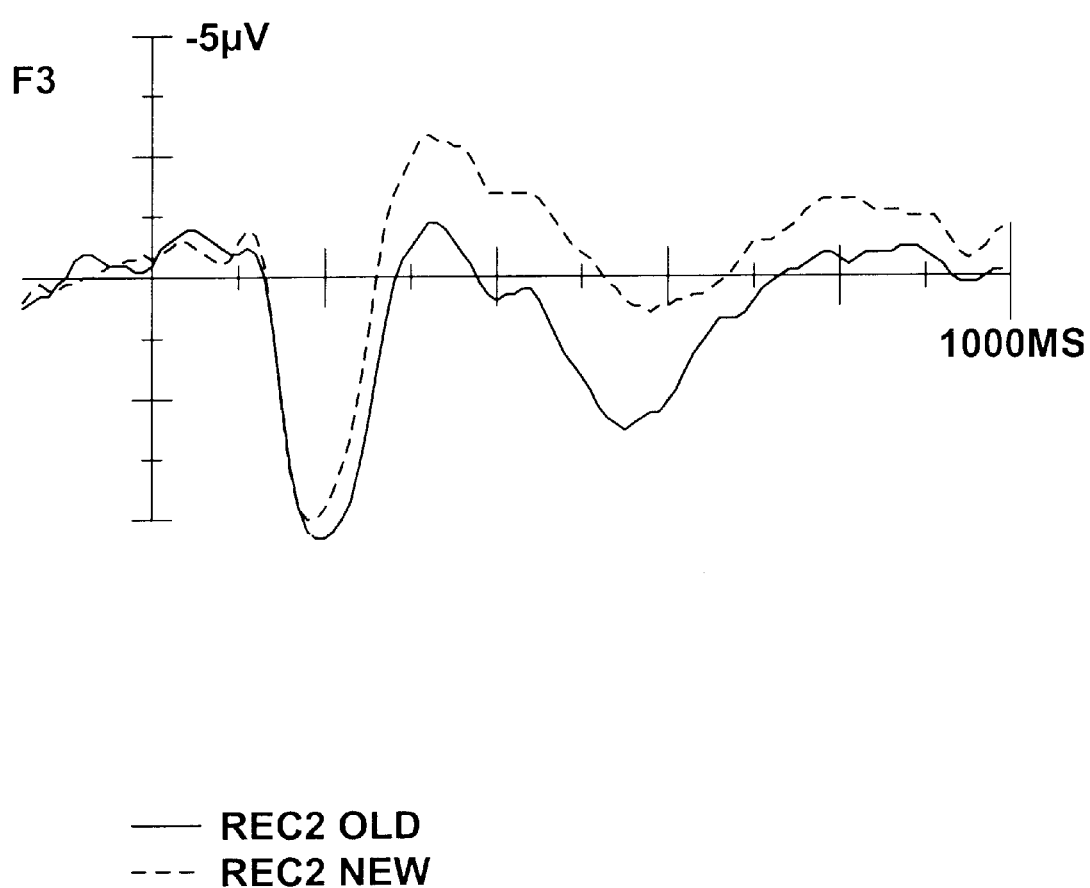
Figure 28B:
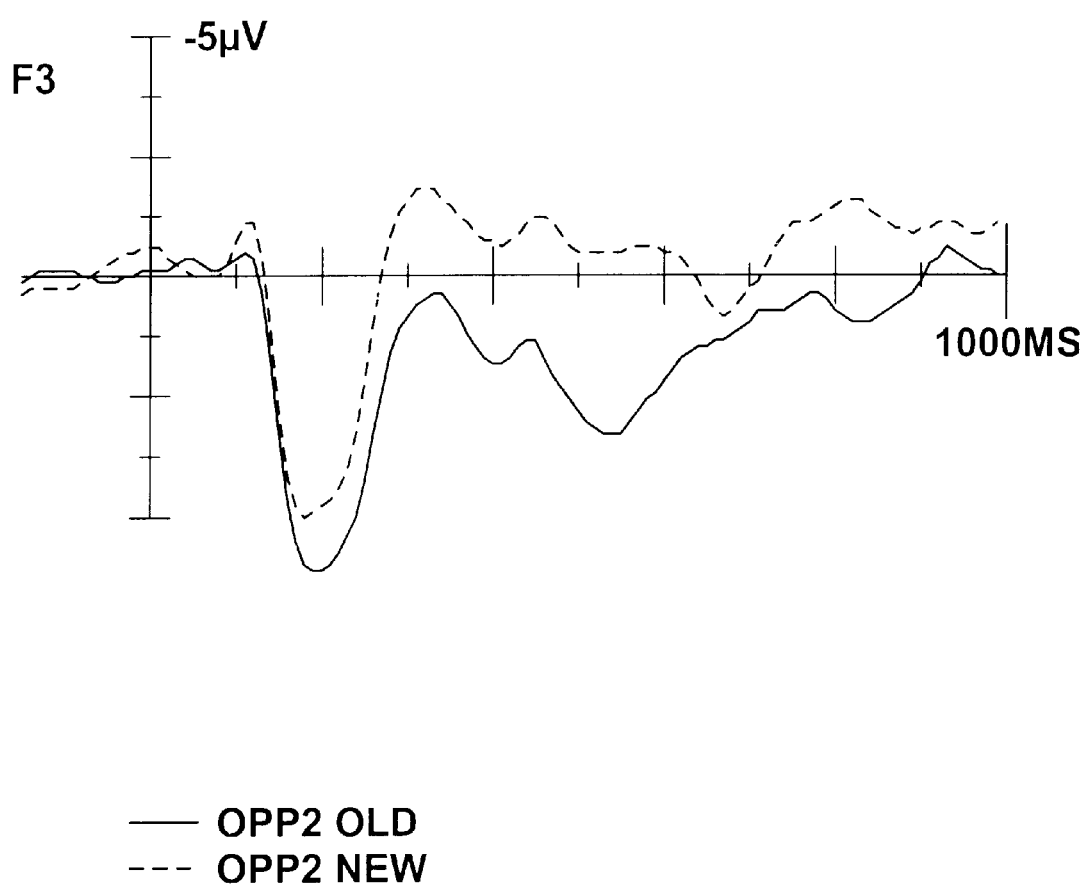
Figure 28C:
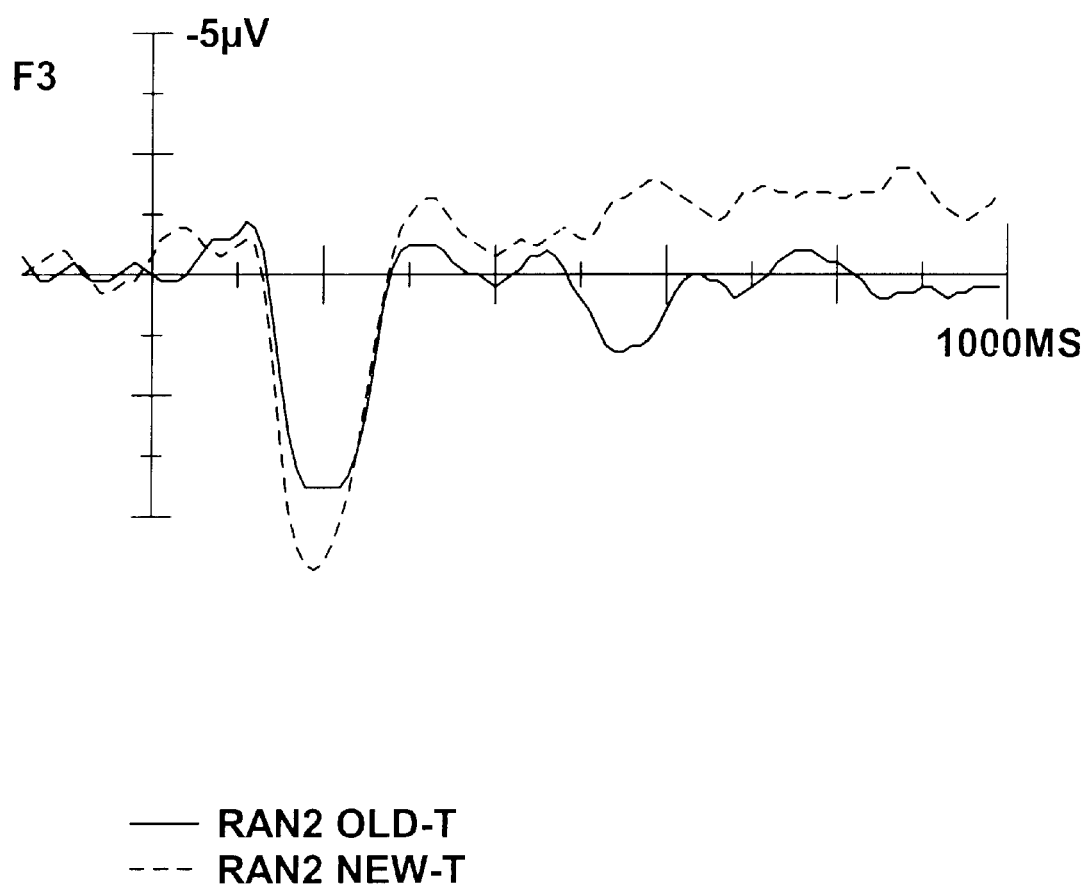
Figure 28D:
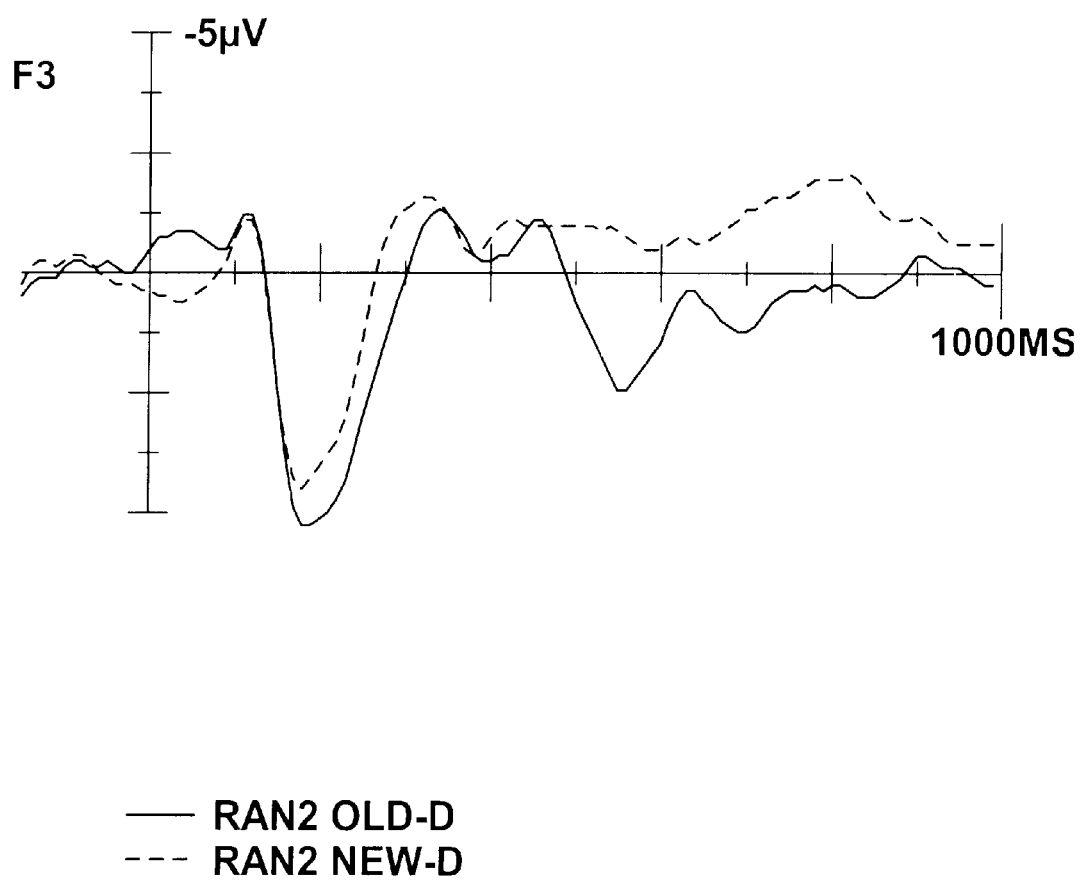

Most unexpected was the finding that, in contrast to the other conditions, within the Random condition, neither Stimulus (Old, New) [F<1] (FIGS. 15 and 21) nor Response type (Random-Truthful, Random-Deceptive) [F<1] had any differential effect on ERN amplitude (FIGS. 17, 19, 25D). Further, there were no apparent differences in brain activity responsible for the ERNs elicited on Random-Truthful and Random-Deceptive trials since the ANOVA on the normalized ERN amplitudes was not significant. The data in FIG. 25D show that, when engaged in long-term monitoring of responses, differential ERN responses as a function of response compatibility or memory status disappear.

Stimulus-Locked Averages

The P300s elicited at Pz in the control and memory conditions are shown in FIG. 30A. In accord with the RT data in Table 2 and the results of previous studies with perceptually-driven conflicts, these waveforms show that P300 latency increased from 415 ms in the Control conditions to 596 ms in the memory conditions [F(1,15)=358.0, p<0.00001]. Also in accord with previous results, the requirement to make a response that conflicted with the stimulus had little effect on P300 latency (Table 4). P300 latency was only 13 ms longer for incompatible responses than for compatible responses, an insignificant increase [F(1,15)=3.2, p=0.095]. P300 amplitude also varied as a function of condition. A 3-way ANOVA using the factors Response (Compatible, Incompatible), Condition

TABLE 4

Mean P300 Latency (in ms) and (SD)
for both Test Repetitions as a Function of Condition
(N = 16)

|  | Control | | | Recognition | | | |
|---|---|---|---|---|---|---|---|
|  | Compatible | Incompatible |  | Truthful | Opposite | Random-Truthful | Random-Deceptive |
| First Repetition |  |  |  |  |  |  |  |
| Left/Right | 407 (25) | 423 (61) | Old | 608 (49) | 628 (59) | 629 (68) | 671 (54) |
|  |  |  | New | 659 (73) | 678 (44) | 606 (55) | 659 (54) |
| Second Repetition |  |  |  |  |  |  |  |
|  |  |  | Old | 591 (33) | 602 (52) | 638 (69) | 649 (49) |
|  |  |  | New | 618 (47) | 642 (35) | 636 (62) | 645 (67) |

(Control, Memory) and Electrode (Cz, Cp1, Cp2, P3, Pz, P4, O1, O2) revealed that significantly smaller P300s were elicited for incompatible responses compared to for compatible responses [F(1,15)=9.7, p<0.01] while larger P300s were elicited in the memory conditions [F(1,15)=13.8, p<0.005]. However, as with the behavioral measures, there was no Response×Condition interaction (F<1) indicating that the P300 amplitude reduction associated with making an incompatible response was independent of task difficulty.

The fact that RTs were more variable in the incompatible response conditions raised the possibility that the smaller P300s in these conditions were an artifact of increased latency variability across trials. Therefore the same analyses were done on the P300 areas (−100 to +300 ms) derived from response-locked averages (FIG. 30, right column). These analyses revealed that, even after removing any latency variability due to response variability, the P300 results remained unchanged; the P300 was still significantly smaller for incompatible responses than for compatible responses [F(1,15)=7.3, p<0.05] and larger P300s were elicited in the memory conditions [F(1,15)=14.2, p<0.005], again with no Response×Task interaction (F<1).

Truthful Versus Opposite Recognition Responses

The ERPs elicited by the old and new words in the Truthful and Opposite conditions are superimposed in the left and right columns of FIG. 31, respectively. It is evident from these data that the effect of making a deceptive response on P300 amplitude was about the same regardless of the memory status of the words. An ANOVA using the Response and Stimulus factors above, plus electrode (Cz, Cp1, Cp2, P3, Pz, P4, O1, O2) confirmed that smaller P300s were elicited in the Opposite condition when subjects made deceptive responses [F(1,15)=5.2, p<0.05] and that old words elicited larger P300s than new words in both conditions [F(1,15)=68.8, p<0.00001]. The Response×Stimulus interaction was not significant (F<1). Thus, although P300 amplitude was decreased for deceptive responses, consistent with the behavioral results, the effect of making a deceptive response, as indexed by P300 amplitude, was independent of both the truthfulness of the subjects'responses and the memory status of the words. P300 latency at Pz was also quantified and the results showed that P300s were, on average, 17 ms later for the deceptive responses compared to truthful responses (Table 4). This difference only approached significance [F(1,15)=4.1, p=0.06]. However, P300 latencies were significantly longer for new words compared to old words (630 ms vs 597 ms, respectively) [F(1,15)=16.6, p<0.001], although there was no Response× Stimulus interaction (F<1).

To ensure that the significant P300 amplitude differences were not due to differences in RT variability across conditions, the response-locked ERPs were quantified and analyzed as above. The ANOVA revealed that P300 remained significantly smaller for deceptive responses compared to truthful responses [F(1,15)=6.1, p<0.05] and that old words still elicited larger P300s than new words [F(1, 15)=56.7, p<0.00001]. As before, the Response×Stimulus interaction was not significant (F<1).

Taken together, both the three behavioral measures and the ERN and P300 results consistently showed that the changes associated with making incompatible responses were independent of whether the response conflict was driven by perceptual or conceptual information. These results were obtained despite differences in both across- and within-task differences in difficulty. The data show, therefore, that the altered behavioral and P300 responses associated with making incompatible/deceptive responses were independent of, and additive to, the effects of stimulus and task difficulty on these measures.

The Effects of Strategic Monitoring

Opposite Versus Random-Deceptive Responses

The stimulus-locked P300s elicited at Pz in the Opposite and Random-Deceptive trials by the old and new words are shown in FIG. 32. It is evident from these waveforms that the additional processing demands imposed by the strategic monitoring task produced large reductions in P300 amplitude compared to those elicited in the Opposite condition for both word categories. Subjects retrieved the identical items, at least for the old words, and made the identical deceptive responses in both conditions, so the amplitude reductions observed n the Random Condition could not be attributed to these aspects of the task. An 3-way ANOVA using the same design and electrode sites as above, confirmed that P300s were significantly smaller in the Random condition [F(1, 15)=29.5, p<0.0001] and that smaller P300s were elicited by the new words in both conditions [F(1,15)=50.5, p<0.00001]. However, because the amplitude difference was greater for old words than for new words, Condition× Stimulus interaction did attain significance [F(1,15)=4.7, p<0.05]. A comparison of the P300 latencies obtained for the Opposite and Random-Deceptive trials revealed that they also varied as a function of Response and Stimulus (Table 4). These results showed that P300s were, on average, 17 ms later for the deceptive responses compared to truthful responses, an amount that only approached significance [F(1,15)=4.1, p=0.06]. However, P300 latency was significantly longer for new words compared to old words (630 ms vs 597 ms, respectively) [F(1,15)=16.6, p<0.001], although there was no Response×Stimulus interaction (F<1).

The fact that RTs were more variable in the Random condition than in the Opposite condition raised the possibility that the P300s in the Random condition were smaller as a result of increased latency variability across trials. Therefore the same analyses were done on the P300 areas (−100 to +300 ms) derived from response-locked averages. These analyses revealed that, even after removing any latency variability due to response variability, the P300 results remained unchanged; P300 remained significantly smaller when subjects had to monitor the pattern of their responses [F(1,15)=61.4, p<0.00001] and old words still elicited larger P300s than new words [F(1,15)=18.3, p<0.001]. In this comparison, Condition×Stimulus interaction was significant [F(1,15)=10.0, p<0.01].

Random-Truthful Versus Random-Deceptive Responses

The stimulus-locked P300s for the truthful and deceptive Random trials are displayed in FIG. 32. It is evident from these waveforms that there was little difference in the P300s elicited by the truthful and deceptive responses while subjects were engaged in the monitoring task. A 3-way ANOVA was done on the P300 area data from the Random condition using the factors Response (truthful, deceptive), Stimulus (old, new) and Electrode (same sites as above). This analysis confirmed a lack of differences between the two response types (F<1), although old words were again found to elicit significantly larger P300s than new words [F(1,15)=15.3, p<0.002]. The absence of any Response×Stimulus interaction (F<1) confirmed what could be seen in the waveforms, that there were no differences as a function of response type. As evident from the data in Table 4, P300 latency did not vary as a function of either type of response made or the memory status of the words.

Guilty Knowledge Measures

One direct way to assess the presence of guilty knowledge is to look for the presence of the different aspects of the episodic memory (EM) effect (also referred to as the "old/new" effect) since they have been shown to be related a variety of memory-retrieval processes. Three subcomponents of the EM effect were evaluated in each of the recognition series: the left posterior, left frontal and occipital subcomponents by comparing the data from the relevant and irrelevant stimuli in the Truthful condition with the data from the two deception conditions using the factors Condition, Stimulus (old, new) and Electrode.

Left Posterior Episodic Memory Effect

This aspect of the episodic memory effect is largest over left parietal-occipital scalp and thus the ERPs elicited by the old and new words in all three conditions are shown for the parietal, P3 electrode site (FIG. 27). As already described above, old words elicited significantly larger P300s than new words in all comparisons (i.e., Truthful vs Opposite, Opposite vs Random-Deceptive and Random-Truthful vs Random-Deceptive). Although the Condition×Stimulus interactions were significant at the 0.05 level for the two comparisons involving the data from the Random condition, this was most likely due to the large amplitude difference between the Opposite and Random conditions. Thus, the data indicate that the magnitude of the left posterior EM effect is largely unaffected by variables such as whether the subject accurately classified the items as known or unknown, response speed, and the variability of response speed.

Left Frontal Episodic Memory Effect

The ERPs elicited by the old and new words at the left frontal site (F3) are shown for old and new words in FIG. 28. These data revealed that new words elicited more frontal negativity in the 300 to 500 ms interval than did old words in both the Truthful and Opposite conditions, but not in the Random condition. Using the area data from the four frontal sites (F3, Fz, Fc5, Fc1), the Truthful versus Opposite comparison, new words produced significantly more negativity than old words [$F(1,15)=18.2$, $p<0.001$] and there was no Condition×Stimulus interaction ($F<1$). For the Truthful vs Random-Truthful comparison, new words again produced significantly more negativity [$F(1,15)=11.8$, $p<0.005$] but, due to the lesser difference between the old and new ERPs on the Random-Truthful trials, the Condition×Stimulus interaction approached significance ($p=0.09$). Finally, for the Truthful vs Random-Deceptive comparison, new words produced significantly more negativity [$F(1,15)=16.9$, $p<0.001$] but, due to the lack of an old-new difference in the Random-Deceptive condition, the Condition×Stimulus interaction was significant [$F(1,15)=4.6$, $p<0.05$]. The presence of a much smaller left frontal effect may be due to the presence of increased negativity, apparent in the response locked averages, around this time.

Occipital Episodic Memory Effect

The occipital episodic memory effect was characterized by an increased negativity for new words in the 300 to 500 ms interval that is maximal over visual areas (FIG. 29). These waveforms revealed that although new words elicited a larger negativity than old words in the Truthful and Opposite conditions, this was not the case in the Random condition. The ANOVAs used to test these effects used the same factors above with the data from five parietal and occipital sites (P3, Pz, P4, O1, O2). The Truthful versus Opposite comparison revealed that new words elicited significantly more negativity than old words [$F(1,15)=29.8$, $p<0.0001$] in both conditions as the Condition×Stimulus interaction was not significant ($F<1$). When Truthful ERPs were compared with those for the Random-Truthful trials, new words again elicited more negativity [$F(1,15)=19.8$, $p<0.0005$], but only in the Truthful condition [Condition×Stimulus: $F(1,15)=12.6$, $p<0.005$]. Similarly, the Truthful versus Random-Deceptive comparison also showed that new words elicited greater negativities than old words [$F(1,15)=20.5$, $p<0.0005$], but only in the Truthful condition [Condition×Stimulus: $F(1,15)=16.9$, $p<0.001$].

Catch-Trial Performance

The primary rationale for including the catch trials in each recognition condition was to discourage subjects from re-assigning the stimulus-response button assignments in the Opposite condition. For example, if the left button was assigned for old words, a subject could eliminate any conflicting response information by simply thinking that the right button would be for old words. If subjects performed this re-assignment they would effectively eliminate the intended conflict between stimulus and response. Therefore, catch trials were included in each recognition in sufficient numbers to discourage subjects from re-assigning the stimulus-response pairings and to provide a method for detecting any reassignment, which would be indicated by decreased accuracy and slower responses.

However, subjects' performance in the catch trials demonstrated an accuracy ranging from 92% to 97% correct across conditions (Table 5).

TABLE 5

Performance Accuracy (in %) and Reaction Time (in ms) for the Catch Trials as a Function of Condition
Mean and Standard Deviation (in parentheses)
(N = 16)

|  | Truthful | Opposite | Random |
| --- | --- | --- | --- |
| % Correct |  |  |  |
| Old | 97.5% (4.1) | 95.9% (5.3) | 92.6% (8.4) |
| New | 95.8% (7.9) | 95.5% (4.4) | 96.0% (7.4) |
| Reaction Time (ms) |  |  |  |
| Old | 576 (111) | 672 (141) | 657 (116) |
| New | 596 (103) | 665 (138) | 660 (123) |

A 2-way ANOVA using the factors Condition (Recognition, Opposite, Random) and Stimulus (old, new) on percent correct revealed no significant differences in accuracy as a function of either condition [$F(1,23)=1.5$, $p=0.23$] or stimulus ($F<1$). Moreover, as evident from comparing the values in Tables 2 and 5, while catch trial RTs were roughly the same as those on the regular trials in the Truthful [$F(1,15)=2.1$, $p=0.17$] and Opposite ($F<1$) conditions. In contrast, in the Random condition, subjects responded significantly more quickly on the catch trials than they did on the regular trials [$F(1,15)=12.1$, $p<0.005$]. Taken together, the speed and accuracy results indicated that subjects did not alter the stimulus-response assignments in the Opposite condition.

In the Guilty Knowledge Test, the left parietal-occipital "old/new effect" was not elicited in the ERP when old words were miscategorized as new or when new words were miscategorized as old. The left parietal-occipital subcomponent has been shown to reflect the recollection (i.e., retrieval) of the item automatically; the fact that it is exclusively elicited by items in memory indicates that it would be difficult to be faked or suppressed by a subject. Responding deceptively produced no significant diminution in the magnitude of the left parietal-occipital old/new effect (between 500 and 800 ms in the stimulus-locked averages (see FIGS. 4, 5, 12, 13, 14 and 27). Consequently, the left parietal-occipital old/new effect can be used as a direct marker of guilty knowledge.

Discussion

The deception-related alterations in behavioral and electrophysiological indices described herein form the basis of the method for detecting when subjects make deceptive responses. The data from the Opposite condition indicate clearly that any attempt to respond deceptively about whether information resides in one's memory, even with a rapid and/or well-practiced response requiring no special planning or monitoring, produces significant changes in RT, ERN amplitude and ERN scalp distribution, among others. In addition, the results of the Random condition show that, if a subject attempts to deliberately monitor the pattern of their behavior during deceptive responding, the magnitude of the differences between the patterns of truthful and deceptive marker activity is enhanced (even slower responses and greater ERN activity).

REFERENCES

Barch, D. M., Braver, T. S., Sabb, F. W. & Noll, D. C. Anterior cingulate and the monitoring of response conflict: evidence from an fMRI study of overt verb generation. Journal of Cognitive Neuroscience 12, 298–309 (2000).

Botvinick, M., Nystrom, L. E., Fissell, K., Carter, C. S. & Cohen, J. D. Conflict monitoring versus selection-for-action in anterior cingulate cortex. Nature 402, 179–181 (1999).

Bush, G., Luu, P. & Posner, M. I. Cognitive and emotional influences in anterior cingulate cortex. Trends in Cognitive Science 4, 215–222 (2000).

Carter, C. S. et al. Parsing executive processes: strategic vs. evaluative functions of the anterior cingulate cortex. Proceedings of the National Academy of Sciences USA 97, 1944–1948 (2000).

Carter, C. S. et al. Anterior cingulate cortex, error detection, and the online monitoring of performance. Science 280, 747–749 (1998).

Casey, B. J. et al. Dissociation of response conflict, attentional selection, and expectancy with functional magnetic resonance imaging. Proceedings of the National Academy of Sciences USA 97, 8728–8733 (2000).

Dehaene, S., Posner, M. I. & Tucker, D. M. Localization of a neural system for error detection and compensation. Psychological Science 5, 303–305 (1994).

Devinsky, O., Morrell, M. J. & Vogt, B. A. Contributions of anterior cingulate cortex to behaviour. Brain 118, 279–306 (1995).

Falkenstein, M., Hohnsbein, J., & Hoormann, J. Effects of crossmodal divided attention on late ERP components II. Error processing in choice reaction tasks. Electroencephalography and Clinical Neurophysiology. 78, 447–455 (1991).

Falkenstein, M., Hoormann, J., Christ, S. & Hohnsbein, J. ERP components on reaction errors and their functional significance: a tutorial. Biological Psychology 51, 87–107 (2000).

Fredrikson, M. et al. Functional neuroanatomical correlates of electrodermal activity: a positron emission tomographic study. Psychophysiology 35, 179–185 (1998).

Friedman, D. & Johnson, R., Jr. Event-related potential (ERP) studies of memory encoding and retrieval: A selective review. Microscopy Research and Technique, 51, 6–28 (2000).

Gehring, W. J., Goss, B., Coles, M. G. H., Meyer, D. E., & Donchin, E. A neural system for error detection and compensation. Psychological Science 4, 385–390 (1993).

Gehring, W. J. & Knight, R. T. Prefrontal-cingulate interactions in action monitoring. Nature Neurosci. 3, 516–520 (2000).

Gehring, W. J., Himle, J. & Nisenson, L. G. Action-monitoring dysfunction in obsessive-compulsive disorder. Psychological. Science 11, (2000).

Johnson, R., Jr. Event-related potential insights into the neurobiology of memory systems. In: F. Boller and J.Grafman (Eds.), Handbook of Neuropsychology, Volume 10. Amsterdam: Elsevier, 135–163 (1995A)

Johnson R Jr. et al., International Journal of Psychophysiology, 1998, 29:83–104

Johnson R Jr et al., Psychophysiology, 1985, 22:497–507

Johnson R, Jr. In: G. Karmos, M. Molnar, V. Csepe, I. Czigler and J. E. Desmedt (Eds.), Perspectives of Event-Related Potentials Research. Electroencephalography and Clinical Neurophysiology. Supplement 44:110–129, 1995B;

Johnson, R., Jr. On the neural generators of the P300 component of the event-related potential. Psychophysiol. 30, 90–97 (1993).

Luu, P., Flaisch, T. & Tucker, D. M. Medial frontal cortex in action monitoring. Journal of Neuroscience. 20, 464–469 (2000).

McCarthy, G., & Woods, C. C. (1985). Scalp distributions of event-related potentials: An ambiguity associated with analysis of variance models. Electroencephalography and clinical Neurophysiology, 62:203–208.

MacDonald, A. W. III, Cohen, J. D., Stenger, V. A. & Carter, C. S. Dissociating the role of the dorsolateral prefrontal and anterior cingulate cortex in cognitive control. Science 288, 1835–1838 (2000).

Miltner, W. H. R., Braun, C. H. & Coles, M. G. H. Event-related brain potentials following incorrect feedback in a time-estimation task: evidence for a "generic" neural system for error detection. Journal of Cognitive Neuroscience 9, 788–798 (1997).

Peterson, B. S. et al. An fMRI study of Stroop word-color interference: evidence for cingulate subregions subserving multiple distributed attentional systems. Biological Psychiatry 45, 1237–1258 (1999).

Picton, T. W.

Ruchkin, D. S., Johnson, R., Jr. & Friedman, D. Scaling is necessary when making comparisons between shapes of event-related potential topographies: A reply to Haig. et al. Psychophysiology 36, 832–834 (1999).

Scheffers, M. K. & Coles, M. G. H. Performance monitoring in a confusing world: error-related brain activity, judgments of response accuracy, and types of errors. Journal of Experimental Psychology: Human Perception and Performance 26, 141–151 (2000).

Turken, A. U. & Swick, D. Response selection in the human anterior cingulate cortex. Nature Neuroscience 2, 920–924 (1999).

Vidal, F., Hasbroucq, T., Grapperon, J. & Bonnet, M. Is the 'error negativity' specific to errors? Biological Psychology 51, 109–128 (2000).

Whalen, P. J. et al. The emotional counting Stroop paradigm: a functional magnetic resonance imaging probe of the anterior cingulate affective division. Biological Psychiatry 44, 1219–1228 (1998).

What is claimed is:

1. A method for determining whether a subject responds deceptively comprising
   a) presenting the subject with a test series of stimuli;
   b) presenting the subject with a control series of stimuli;
   c) monitoring the subject's electrophysiological activity, behavioral activity, or both, associated with the subject's response to the test series and control series of stimuli;

d) comparing the subject's electrophysiological activity, behavioral activity, or both, obtained from the responses to the test series and control series of stimuli; wherein a difference in the activity between the test and control stimuli indicates that the subject is responding deceptively, wherein the electrophysiological activity comprises event-related brain potential (ERP), and wherein a smaller maximal amplitude over parietal-central scalp between 400–800 ms after stimulus in stimulus-locked averages to the test series compared to the control series, or a smaller maximal amplitude between −100 before response and +300 ms after response in response-locked averages to the test series compared to the control series indicates that the subject is responding deceptively.

2. The method of claim 1, wherein the test series of stimuli comprises an equal number of relevant and irrelevant items, and the control series of stimuli comprises an equal number of relevant and irrelevant items.

3. A method for determining whether a subject responds deceptively comprising
   a) presenting the subject with a test series of stimuli;
   b) presenting the subject with a control series of stimuli;
   c) monitoring the subject's electrophysiological activity, behavioral activity, or both, associated with the subject's response to the test series and control series of stimuli;
   d) comparing the subject's electrophysiological activity, behavioral activity, or both, obtained from the responses to the test series and control series of stimuli;
wherein a difference in the activity between the test and control stimuli indicates that the subject is responding deceptively, wherein behavioral activity comprises at least one of variability in response speed and accuracy of response.

4. The method of claim 3 wherein a smaller response accuracy to the test series compared to the control series indicates that the subject is responding deceptively.

5. A method for determining whether a subject responds deceptively comprising
   a) presenting the subject with a test series of stimuli;
   b) presenting the subject with a control series of stimuli;
   c) monitoring the subject's electrophysiological activity, behavioral activity, or both, associated with the subject's response to the test series and control series of stimuli;
   d) comparing the subject's electrophysiological activity, behavioral activity, or both, obtained from the responses to the test series and control series of stimuli;
wherein a difference in the activity between the test and control stimuli indicates that the subject is responding deceptively, wherein the electrophysiological activity comprises event-related brain potential (ERP), and wherein a larger maximal amplitude between 0 and 100 ms after response over central-frontal scalp in response-locked ERP averages to the test series compared to the control series indicates that the subject is responding deceptively.

6. The method of claim 5, wherein the test series of stimuli comprises an equal number of relevant and irrelevant items, and the control series of stimuli comprises an equal number of relevant and irrelevant items.

7. A method for determining whether a subject responds deceptively comprising
   a) presenting the subject with a test series of stimuli;
   b) presenting the subject with a control series of stimuli;
   c) monitoring the subject's electrophysiological activity, behavioral activity, or both, associated with the subject's response to the test series and control series of stimuli;
   d) comparing the subject's electrophysiological activity, behavioral activity, or both, obtained from the responses to the test series and control series of stimuli;
wherein a difference in the activity between the test and control stimuli indicates that the subject is responding deceptively, wherein the electrophysiological activity comprises event-related brain potential (ERP), and wherein a larger negativity maximal over occipital and inferior temporal scalp between 300 and 500 ms after stimulus in stimulus-locked ERP averages to the test series compared to the control series indicates that the subject is responding deceptively.

8. The method of claim 7, wherein the test series of stimuli comprises an equal number of relevant and irrelevant items, and the control series of stimuli comprises an equal number of relevant and irrelevant items.

9. A method for determining whether a subject responds deceptively comprising
   a) presenting the subject with a test series of stimuli;
   b) presenting the subject with a control series of stimuli;
   c) monitoring the subject's electrophysiological activity, behavioral activity, or both, associated with the subject's response to the test series and control series of stimuli;
   d) comparing the subject's electrophysiological activity, behavioral activity, or both, obtained from the responses to the test series and control series of stimuli;
wherein a difference in the activity between the test and control stimuli indicates that the subject is responding deceptively, wherein the electrophysiological activity comprises event-related brain potential (ERP), and wherein a smaller medical frontal-central scalp maximal positivity between 100 and 200 ms after response in response-locked ERP averages to the test series compared to the control series indicates that the subject is responding deceptively.

10. The method of claim 9, wherein the test series of stimuli comprises an equal number of relevant and irrelevant items, and the control series of stimuli comprises an equal number of relevant and irrelevant items.

11. A method of determining whether a subject responds deceptively comprising
   a) presenting the subject with a test series of stimuli;
   b) presenting the subject with a control series of stimuli;
   c) monitoring the subject's electrophysiological activity, behavioral activity, or both, associated with the subject's response to the test series and control series of stimuli;
   d) comparing the subject's electrophysiological activity, behavioral activity, or both, obtained from the responses to the test series and control series of stimuli;
wherein a difference in the activity between the test and control stimuli indicates that the subject is responding deceptively, wherein the electrophysiological activity comprises event-related brain potential (ERP), and wherein a smaller medial frontal-central scalp maximal positivity between −100 and 0 ms before response in response-locked ERP averages to the test series compared to the control series indicates that the subject is responding deceptively.

12. The method of claim 11 wherein the test series of stimuli comprises an equal number of relevant and irrelevant items, and the control series of stimuli comprises an equal number of relevant and irrelevant items.

13. A method for determining whether a subject responds deceptively comprising
   a) presenting the subject with a test series of stimuli;
   b) presenting the subject with a control series of stimuli;

c) monitoring the subject's electrophysiological activity, behavioral activity, or both, associated with the subject's response to the test series and control series of stimuli;

d) comparing the subject's electrophysiological activity, behavioral activity, or both, obtained from the responses to the test series and control series of stimuli; wherein a difference in the activity between the test and control stimuli indicates that the subject is responding deceptively, wherein the electrophysiological activity comprises event-related brain potential (ERP), and wherein a larger negative shift between −100 before and +200 ms after response maximal over medial central-frontal scalp in response-locked ERP averages to the test series compared to the control series indicates that the subject is responding deceptively.

14. The method of claim 13, wherein the test series of stimuli comprises an equal number of relevant and irrelevant items, and the control series of stimuli comprises an equal number of relevant and irrelevant items.

15. A method for determining whether a subject responds deceptively comprising
a) presenting the subject with a test series of stimuli;
b) presenting the subject with a control series of stimuli;
c) monitoring the subject's electrophysiological activity, behavioral activity, or both, associated with the subject's response to the test series and control series of stimuli;
d) comparing the subject's electrophysiological activity, behavioral activity; or both, obtained from the responses to the test series and control series of stimuli; wherein a difference in the activity between the test and control stimuli indicates that the subject is responding deceptively, wherein the electrophysiological activity comprises event-related brain potential (ERP), and wherein the difference in activity is a difference in ERN scalp distribution.

16. A method for determining whether a subject responds deceptively comprising
a) presenting the subject with the test series of stimuli;
b) presenting the subject with a control series of stimuli;
c) monitoring the subject's electrophysiological activity, behavioral activity, or both, associated with the subject's response to the test series and control series of stimuli;
d) comparing the subject's electrophysiological activity, behavioral activity, or both, obtained from the responses to the test series and control series of stimuli; wherein a difference in the activity between the test and control stimuli indicates that the subject is responding deceptively, wherein the electrophysiological activity comprises event-related brain potential (ERP), and wherein an increased P300 latency to the test series compared to the control series indicates that the subject is responding deceptively.

17. A method for determining whether a subject responds deceptively comprising
a) presenting the subject with two or more sets of stimuli, each set comprising a test series of stimuli and a control series of stimuli;
b) monitoring the subject's electrophysiological activity, behavioral activity, or both, associated with the subject's response to each set of stimuli; and
c) comparing the subject's electrophysiological activity, behavioral activity, or both, obtained from the responses to one set of stimuli to the activity from another set of stimuli;
wherein a difference in the activity between the sets of stimuli indicates that the subject is responding deceptively, and wherein behavioral activity comprises at least one of variably in response speed and accuracy of response.

18. A method for determining whether a subject responds deceptively comprising
a) presenting the subject with two or more sets of stimuli, each set comprising a test series of stimuli and a control series of stimuli;
b) monitoring the subject's electrophysiological activity, behavioral activity, or both, associated with the subject's response to each set of stimuli; and
c) comparing the subject's electrophysiological activity, behavioral activity, or both, obtained from the responses to one set of stimuli to the activity from another set of stimuli;
wherein a difference in the activity between the sets of stimuli indicates that the subject is responding deceptively, wherein the electrophysiological activity comprises event-related brain potentials (ERPs), and wherein a smaller positive shift maximal over medial central-frontal scalp between −100 before and +200 ms after in response-locked ERP averages to the test series compared to the control series indicates that the subject is responding deceptively.

19. A method for determining whether a subject responds deceptively comprising
a) presenting the subject with two or more sets of stimuli, each set comprising a test series of stimuli and a control series of stimuli;
b) monitoring the subject's electrophysiological activity, behavioral activity, or both, associated with the subject's response to each set of stimuli; and
c) comparing the subject's electrophysiological activity, behavioral activity, or both, obtained from the responses to one set of stimuli to the activity from another set of stimuli;
wherein a difference in the activity between the sets of stimuli indicates that the subject is responding deceptively, wherein the electrophysiological activity comprises event-related brain potentials (ERPs), and wherein a smaller P300 amplitude increase over parietal scalp between 400 and 800 ms after stimulus in stimulus-locked ERP averages and between −100 before to +300ms after response in response-locked ERP averages to the test series compared to the control series indicates that the subject is responding deceptively.

20. A method for determining whether a subject responds deceptively comprising
a) presenting the subject with two or more sets of stimuli, each set comprising a test series of stimuli and a control series of stimuli;
b) monitoring the subject's electrophysiological activity, behavioral activity, or both, associated with the subject's response to each set of stimuli; and
c) comparing the subject's electrophysiological activity, behavioral activity, or both, obtained from the responses to one set of stimuli to the activity from another set of stimuli;
wherein a difference in the activity between the sets of stimuli indicates that the subject is responding deceptively, wherein the electrophysiological activity comprises event-related brain potentials (ERPs), and wherein a smaller decrease in maximal negativity over occipital scalp between 300 and 500 ms after stimulus in stimulus-locked ERP averages to the test series compared to the control series indicates that the subject is responding deceptively.

21. A method for determining whether a subject responds deceptively comprising
   a) presenting the subject with two or more sets of stimuli, each set comprising a test series of stimuli and a control series of stimuli;
   b) monitoring the subject's electrophysiological activity, behavioral activity, or both, associated with the subject's response to each set of stimuli; and
   c) comparing the subject's electrophysiological activity, behavioral activity, or both, obtained from the responses to one set of stimuli to the activity from another set of stimuli;
wherein a difference in the activity between the sets of stimuli indicates that the subject is responding deceptively, wherein the electrophysiological activity comprises event-related brain potentials (ERPs), and wherein a smaller increase in positivity over medial frontal-central scalp between −100 and 0 ms before response in response-locked ERP averages to the test series compared to the control series indicates that the subject is responding deceptively.

22. A method for determining whether a subject responds deceptively comprising
   a) presenting the subject with two or more sets of stimuli, each set comprising a test series of stimuli and a control series of stimuli;
   b) monitoring the subject's electrophysiological activity, behavioral activity, or both, associated with the subject's response to each set of stimuli; and
   c) comparing the subject's electrophysiological activity, behavioral activity, or both, obtained from the responses to one set of stimuli to the activity from another set of stimuli;
wherein a difference in the activity between the sets of stimuli indicates that the subject is responding deceptively, wherein the electrophysiological activity comprises event-related brain potentials (ERPs), and wherein a smaller decrease in ERN over medial central-frontal scalp between 0 and 100 ms after response in response-locked ERP averages to the test series compared to the control series indicates that the subject is responding deceptively.

23. A method for determining whether a subject responds deceptively comprising
   a) presenting the subject with two or more sets of stimuli, each set comprising a test series of stimuli and a control series of stimuli;
   b) monitoring the subject's electrophysiological activity, behavioral activity, or both, associated with the subject's response to each set of stimuli; and
   c) comparing the subject's electrophysiological activity, behavioral activity, or both, obtained from the responses to one set of stimuli to the activity from another set of stimuli;
wherein a difference in the activity between the sets of stimuli indicates that the subject is responding deceptively, wherein the electrophysiological activity comprises event-related brain potentials (ERPs), and wherein a smaller increase positivity over medial central-frontal scalp between 100 and 200 ms after response in response-locked ERP averages to the test series compared to the control series indicates that the subject is responding deceptively.

24. A method for determining whether a subject responds deceptively comprising
   a) presenting the subject with two or more sets of stimuli, each set comprising a test series of stimuli and a control series of stimuli, wherein both the test series and control series include catch trials;
   b) monitoring the subject's electrophysiological activity, behavioral activity, or both, associated with the subject's response to each set of stimuli; and
   c) comparing the subject's electrophysiological activity, behavioral activity, or both, obtained from the responses to one set of stimuli to the activity from another set of stimuli;
wherein a difference in the activity between the sets of stimuli indicates that the subject is responding deceptively.

25. The method of claim 24 wherein a smaller decrease in speed of responses to the test series compared to the control series indicates that the subject is responding deceptively.

26. The method of claim 24 wherein a smaller decrease in variability in speed of responses to the test series compared to the control series indicates that the subject is responding deceptively.

27. The method of claim 18, wherein a slower speed of response in catch trials in the test series compared to the control series indicates that the subject is responding deceptively.

28. The method of claim 24, wherein a larger variability of speed of response in catch trials in the test series compared to the control series indicates that the subject is responding deceptively.

29. The method of claim 24, wherein a smaller response accuracy in catch trials in the test series compared to the control series indicates that the subject is responding deceptively.

30. The method of claim 24, wherein an equal number of catch trials were presented in the control series in the test series.

31. The method of claim 30, wherein the test series of stimuli comprises an equal number of relevant and irrelevant items, and the control series of stimuli comprises an equal number of relevant and irrelevant items.

32. A method for determining whether a subject possesses guilty knowledge comprising
   a) presenting the subject with a test series of stimuli wherein the test series of stimuli comprises an equal number of relevant and irrelevant items;
   b) presenting the subject with a control series of stimuli wherein the control series of stimuli comprises an equal number of relevant and irrelevant items;
   c) monitoring the subject's electrophysiological activity, behavioral activity, or both, associated with the subject's response to the test series and control series of stimuli;
   d) comparing the subject's electrophysiological activity, behavioral activity, or both, obtained from the responses to the test series and control series of stimuli;
wherein a difference in the activity between the relevant and irrelevant items indicates that the subject posses guilty knowledge.

33. The method of claim 32 wherein the difference in activity is a smaller negativity maximal over left central-frontal scalp between 300 and 500 ms after stimulus in stimulus-locked ERP averages for relevant than for irrelevant items.

34. The method of claim 32 wherein the difference in activity is a larger positivity maximal over left-parietal occipital scalp between 500 and 800 ms after stimulus in stimulus-locked ERP averages for relevant than for irrelevant items.

35. The method of claim 32 wherein the difference in activity is a smaller negativity maximal over occipital and inferior lateral scalp between 300 and 500 ms after stimulus in stimulus-locked ERP averages for relevant than for irrelevant items.

36. The method of claim 32, wherein the electrophysiological activity comprises event-related brain potential (ERP).

37. A method for determining whether a subject responds deceptively comprising
   a) presenting the subject with a test series of stimuli, the test series including catch trials;
   b) presenting the subject with a control series of stimuli, the control series including catch trials;
   c) monitoring the subject's electrophysiological activity, behavior activity, or both, associated with the subject's response to the test series and control series of stimuli;
   d) comparing the subject's electrophysiological activity, behavioral activity, or both, obtained from the responses to the test series and control series of stimuli;
wherein a difference in the activity between the test and control stimuli indicates that the subject is responding deceptively.

38. The method of claim 37 wherein a larger variability of speed of response to the test series compared to the control series indicates that the subject is responding deceptively.

39. The method of claim 37, wherein a smaller response accuracy in catch trials in the test series compared to the control series indicates that the subject is responding deceptively.

40. The method of claim 37, wherein an equal number of catch trials were presented in the control series as in the test series.

41. The method of claim 40, wherein the test series of stimuli comprises an equal number of relevant and irrelevant items, and the control series of stimuli comprises an equal number of relevant and irrelevant items.

42. The method of claim 37, wherein the slower speed of response in catch trials in the test series compared to the control series indicates that the subject is responding deceptively.

43. The method of claim 37, wherein a larger variability of speed of response in catch trials in the test series compared to the control series indicates that the subject is responding deceptively.

* * * * *